United States Patent
Florjancic et al.

(10) Patent No.: US 9,006,275 B2
(45) Date of Patent: *Apr. 14, 2015

(54) COMPOUNDS AS CANNABINOID RECEPTOR LIGANDS AND USES THEREOF

(75) Inventors: Alan S. Florjancic, Kenosha, WI (US); Michael J. Dart, Highland Park, IL (US); Keith B. Ryther, Evansville, IN (US); Arturo Perez-Medrano, Grayslake, IL (US); William A. Carroll, Evanston, IL (US); Meena V. Patel, Green Oaks, IL (US); Karin Rosemarie Tietje, Mundelein, IL (US); Tongmei Li, Lake Bluff, IL (US); Teodozyj Kolasa, Lake Villa, IL (US); Megan E. Gallagher, Highland Park, IL (US); Sridhar Peddi, Grayslake, IL (US); Jennifer M. Frost, Gurnee, IL (US); Derek W. Nelson, Highland Park, IL (US)

(73) Assignee: AbbVie Inc., North Chicago, IL (US)

( * ) Notice: Subject to any disclaimer, the term of this patent is extended or adjusted under 35 U.S.C. 154(b) by 860 days.

This patent is subject to a terminal disclaimer.

(21) Appl. No.: 12/970,480

(22) Filed: Dec. 16, 2010

(65) Prior Publication Data

US 2011/0086855 A1 Apr. 14, 2011

Related U.S. Application Data

(62) Division of application No. 11/755,884, filed on May 31, 2007, now Pat. No. 7,875,639.

(60) Provisional application No. 60/809,615, filed on May 31, 2006.

(51) Int. Cl.
| | |
|---|---|
| A61K 31/429 | (2006.01) |
| C07D 513/04 | (2006.01) |
| C07D 277/46 | (2006.01) |
| C07D 277/48 | (2006.01) |
| C07D 277/82 | (2006.01) |
| C07D 417/04 | (2006.01) |
| C07D 417/06 | (2006.01) |
| C07D 417/12 | (2006.01) |
| C07D 493/08 | (2006.01) |

(52) U.S. Cl.
CPC ............ *C07D 277/46* (2013.01); *C07D 513/04* (2013.01); *A61K 31/429* (2013.01); *C07D 277/48* (2013.01); *C07D 277/82* (2013.01); *C07D 417/04* (2013.01); *C07D 417/06* (2013.01); *C07D 417/12* (2013.01); *C07D 493/08* (2013.01)

(58) Field of Classification Search
CPC .................... A61K 31/429; C07D 513/04
USPC .......................................... 514/367; 548/153
See application file for complete search history.

(56) References Cited

U.S. PATENT DOCUMENTS

| | | | |
|---|---|---|---|
| 3,843,683 A | 10/1974 | Bell | |
| 3,928,327 A | 12/1975 | Takamizawa et al. | |
| 4,885,295 A | 12/1989 | Bell | |
| 4,966,828 A | 10/1990 | Doenges et al. | |
| 4,973,587 A | 11/1990 | Ward et al. | |
| 4,978,664 A | 12/1990 | Bell | |
| 5,013,837 A | 5/1991 | Ward et al. | |
| 5,055,579 A | 10/1991 | Pawlowski et al. | |
| 5,250,498 A | 10/1993 | Andree et al. | |
| 5,468,722 A | 11/1995 | Shibata et al. | |
| 5,530,019 A | 6/1996 | Okada et al. | |
| 5,654,322 A | 8/1997 | Hirata et al. | |
| 6,323,214 B1 * | 11/2001 | Baraldi ........................ | 514/301 |
| 6,358,992 B1 | 3/2002 | Pamukcu et al. | |

(Continued)

FOREIGN PATENT DOCUMENTS

| | | |
|---|---|---|
| CA | 2587667 A1 | 5/2006 |
| DE | 1522361 A1 | 7/1969 |

(Continued)

OTHER PUBLICATIONS

Atwood et al. "CB2: Therapeutic target-in-waiting" Progress in Neuro-Psychopharmacology & Biological Psychiatry 2012, 38, 16-20.*
Campbell et al. British Journal of Pharmacology 2007, 152, 655-662.*
Mayo clinic, Alzheimer's disease, obtained from http://www.mayoclinic.com/health/alzheimers-disease/DS00161/DSECTION=prevention on Nov. 3, 2013.*
Mucke, L. Nature, 2009, 461, 895-897.*
Alfaro, et al., "Dihydroaromatic Compounds in the Diels-Alder Reaction III: In Situ Generation and Diels-Alder Reaction of Cyclohexa-1,3-Dienes," Tetrahedron, 1970, vol. 26, pp. 201-218.

(Continued)

*Primary Examiner* — Joseph Kosack
*Assistant Examiner* — Matthew Coughlin
(74) *Attorney, Agent, or Firm* — Lisa V. Mueller; Michael Best & Friedrich LLP

(57) ABSTRACT

The present invention relates to compounds of formula (I), or pharmaceutically acceptable salts, prodrugs, salts of prodrugs, or combinations thereof,

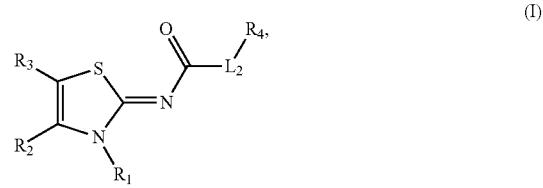

wherein $R_1$, $R_2$, $R_3$, $R_4$, and $L_2$, are defined in the specification, compositions comprising such compounds, and methods of treating conditions and disorders using such compounds and compositions.

2 Claims, No Drawings

(56) References Cited

U.S. PATENT DOCUMENTS

| | | | |
|---|---|---|---|
| 6,369,052 B1* | 4/2002 | Kellar et al. | 514/221 |
| 6,559,186 B1 | 5/2003 | Campbell | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 7,560,456 B2 | 7/2009 | Araki et al. | |
| 7,560,481 B2 | 7/2009 | Frost et al. | |
| 7,674,912 B2 | 3/2010 | Sams et al. | |
| 7,683,084 B2 | 3/2010 | Faghih et al. | |
| 7,750,039 B2 | 7/2010 | Frost et al. | |
| 7,868,038 B2 | 1/2011 | Nelson et al. | |
| 7,872,006 B2 | 1/2011 | Moritani et al. | |
| 7,872,033 B2 | 1/2011 | Carroll et al. | |
| 7,875,639 B2* | 1/2011 | Florjancic et al. | 514/367 |
| 7,875,640 B2 | 1/2011 | Kolasa et al. | |
| 7,985,768 B2 | 7/2011 | Nelson et al. | |
| 8,044,071 B2 | 10/2011 | Carroll | |
| 8,058,293 B2 | 11/2011 | Kolasa et al. | |
| 8,158,663 B2 | 4/2012 | Carroll et al. | |
| 8,173,687 B2 | 5/2012 | Carroll et al. | |
| 8,236,822 B2 | 8/2012 | Wang et al. | |
| 8,288,428 B2 | 10/2012 | Wang et al. | |
| 8,338,467 B2 | 12/2012 | Kolasa et al. | |
| 8,481,574 B2 | 7/2013 | Meyer et al. | |
| 8,492,371 B2 | 7/2013 | Carroll et al. | |
| 8,501,794 B2 | 8/2013 | Carroll et al. | |
| 8,586,596 B2 | 11/2013 | Dart et al. | |
| 2004/0023862 A1* | 2/2004 | Smart et al. | 514/12 |
| 2004/0029040 A1 | 2/2004 | Watanabe et al. | |
| 2004/0034090 A1 | 2/2004 | Barth et al. | |
| 2004/0077617 A1 | 4/2004 | Bennani et al. | |
| 2004/0166539 A1 | 8/2004 | Akhavan-Tafti et al. | |
| 2004/0259912 A1 | 12/2004 | Matsumoto et al. | |
| 2005/0176713 A1* | 8/2005 | Freyne et al. | 514/247 |
| 2006/0199817 A1 | 9/2006 | Tasker et al. | |
| 2007/0061360 A1 | 3/2007 | Holcombe et al. | |
| 2007/0155738 A1 | 7/2007 | Steeneck et al. | |
| 2008/0058335 A1 | 3/2008 | Florjancic et al. | |
| 2008/0058355 A1 | 3/2008 | Westheim et al. | |
| 2008/0139635 A1 | 6/2008 | Martin et al. | |
| 2008/0242654 A1 | 10/2008 | Kolasa et al. | |
| 2008/0287510 A1 | 11/2008 | Carroll et al. | |
| 2008/0312435 A1 | 12/2008 | Saito et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105305 A1 | 4/2009 | Butlin et al. | |
| 2009/0105306 A1 | 4/2009 | Carroll et al. | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2010/0041720 A1 | 2/2010 | Carroll et al. | |
| 2010/0063022 A1 | 3/2010 | Carroll et al. | |
| 2010/0069348 A1 | 3/2010 | Carroll et al. | |
| 2010/0069349 A1 | 3/2010 | Carroll et al. | |
| 2010/0093814 A1 | 4/2010 | Florjancic et al. | |
| 2010/0216760 A1 | 8/2010 | Frost et al. | |
| 2011/0065685 A1 | 3/2011 | Frost et al. | |
| 2011/0082116 A1 | 4/2011 | Carroll et al. | |
| 2011/0086832 A1 | 4/2011 | Kolasa et al. | |
| 2011/0086838 A1 | 4/2011 | Nelson et al. | |

FOREIGN PATENT DOCUMENTS

| | | |
|---|---|---|
| DE | 1772867 A1 | 6/1971 |
| DE | 2458933 A1 | 6/1975 |
| DE | 3533331 A1 | 3/1987 |
| EP | 412404 A2 | 2/1991 |
| EP | 568096 A1 | 11/1993 |
| EP | 0619316 A1 | 10/1994 |
| EP | 0639569 A1 | 2/1995 |
| EP | 1060734 A2 | 12/2000 |
| EP | 1219612 A1 | 7/2002 |
| EP | 1300401 A1 | 4/2003 |
| EP | 1640369 A1 | 3/2006 |
| EP | 1820504 A1 | 8/2007 |
| FR | 2796643 A1 | 1/2001 |
| JP | 557171986 A | 10/1982 |
| JP | 6345736 A | 12/1994 |
| WO | WO-9507271 A1 | 3/1995 |
| WO | WO-9531448 A1 | 11/1995 |
| WO | WO-9601591 A1 | 1/1996 |
| WO | WO-9700860 A1 | 1/1997 |
| WO | WO-9710223 A1 | 3/1997 |
| WO | WO-0063207 A1 | 10/2000 |
| WO | WO0116138 A1 | 3/2001 |
| WO | WO-0128557 A1 | 4/2001 |
| WO | WO-0155139 A1 | 8/2001 |
| WO | WO-0155140 A1 | 8/2001 |
| WO | WO-0183422 A1 | 11/2001 |
| WO | WO-0242269 A1 | 5/2002 |
| WO | WO-02060447 A1 | 8/2002 |
| WO | WO-02102232 A2 | 12/2002 |
| WO | WO03049741 A1 | 6/2003 |
| WO | WO-03097605 A1 | 11/2003 |
| WO | WO-2004050086 A1 | 6/2004 |
| WO | WO-2004110453 A1 | 12/2004 |
| WO | WO-2005023818 A2 | 3/2005 |
| WO | WO-2005058887 A1 | 6/2005 |
| WO | WO-2005075464 A1 | 8/2005 |
| WO | WO-2005099353 A2 | 10/2005 |
| WO | WO-2005099353 A3 | 10/2005 |
| WO | WO-2005115972 A1 | 12/2005 |
| WO | WO-2005115986 A1 | 12/2005 |
| WO | WO-2006008754 A1 | 1/2006 |
| WO | WO-2006051704 A1 | 5/2006 |
| WO | WO2006051704 A1 | 5/2006 |
| WO | WO-2006070106 A1 | 7/2006 |
| WO | WO-2006100208 A1 | 9/2006 |
| WO | WO-2007061360 A2 | 5/2007 |
| WO | WO-2007140385 A2 | 12/2007 |
| WO | WO-2007140439 A2 | 12/2007 |
| WO | WO-2007140439 A3 | 1/2008 |
| WO | WO-2007140385 A3 | 2/2008 |
| WO | WO-2008063781 A2 | 5/2008 |
| WO | WO-2008079687 A1 | 7/2008 |
| WO | WO-2008121558 A1 | 10/2008 |
| WO | WO-2008130953 A2 | 10/2008 |
| WO | WO-2008144360 A1 | 11/2008 |
| WO | WO-2009009550 A1 | 1/2009 |
| WO | WO-2009048936 A1 | 4/2009 |
| WO | WO-2009067613 A1 | 5/2009 |
| WO | WO-2009114566 A1 | 9/2009 |
| WO | WO-2010019547 A1 | 2/2010 |
| WO | WO-2010033543 A1 | 3/2010 |
| WO | WO-2010054024 A2 | 5/2010 |
| WO | WO-2010071783 A1 | 6/2010 |
| WO | WO-2010111573 A1 | 9/2010 |
| WO | WO-2010111574 A1 | 9/2010 |

OTHER PUBLICATIONS

Arevalo-Martin, et al., "Therapeutic Action of Cannabinoids in a Murine Model of Multiple Sclerosis," Journal of Neuroscience, 2003, vol. 23 (7), pp. 2511-2516.

Baker, et al., "Regiospecific Vinyl Phosphate/β-Keto Phosphonate Rearrangements Initiated by Halogen-Metal Exchange," Journal of Organic Chemistry, 1998, vol. 63 (8), pp. 2613-2618.

Benito, et al., "A Glial Endogenous Cannabinoid System is Upregulated in the Brains of Macaques with Simian

(56) References Cited

OTHER PUBLICATIONS

Immunodeficiency Virus-Induced Encephalitis," Journal of Neuroscience, 2005, vol. 25 (10), pp. 2530-2536.
Benito, et al., "Cannabinoid CB2 Receptors and Fatty Acid Amide Hydrolase are Selectively Overexpressed in Neuritic Plaque-Associated Glia in Alzheimer's Disease Brains," Journal of Neuroscience, 2003, vol. 23 (35), pp. 11136-11141.
Bermudez-Silva, et al., "Role of Cannabinoid $CB_2$ Receptors in Gluscose Homeostasis in Rats," Eur. Journal of Pharm., vol. 565, pp. 207-211, 2007.
Bouchard, et al., "Contribution of Endocannabinoids in the Endothelial Protection Afforded by Ischemic Preconditioning in the Isolated Rat Heart," Life Sciences, 2003, vol. 72 (16), pp. 1859-1870.
Boyle, et al., "Osteoclast Differentiation and Activation," Nature, 2003, vol. 423 (6937), pp. 337-342.
Brennan, et al., "Characterization of a Rat Model of Incisional Pain," Pain, 1996, vol. 64, pp. 493-450.
Buckley, et al, "Immunomodulation by Cannabinoids is Absent in Mice Deficient for the Cannabinoid CB2 Receptor," European Journal of Pharmacology, 2000, vol. 396, pp. 141-149.
Carlisle, et al., "Differential Expression of the CB2 Cannabinoid Receptor by Rodent Macrophages and Macrophage-like Cells in Relation to Cell Activation," International Immunopharmacology, 2002, vol. 2, pp. 69.
Carrier, et al., "Endocannabinoids in Neuroimmunology and Stress," Current Drug Targets CNS and Neurological Disorders, 2005, vol. 4, pp. 657-665.
Casanova, et al , "Inhibition of Skin Tumor Growth and Angiogenesis in vivo by Activation of Cannabinoid Receptors," Journal of Clinical Investigation, 2003, vol. 111 (1), pp. 43-50.
Castejon, et al., "A Convenient, Stereodivergent Approach to the Enantioselective Synthesis of N-Boc-Aminoalkyl Epoxides," Tetrahedron Letters, 1995, vol. 36 (17), pp. 3019-3022.
Chaplan, et al., "Quantitative Assessment of Tactile Allodynia in the Rat Paw," Journal of Neuroscience Methods, 1994, vol. 53, pp. 55-63.
Cichewicz, D., "Synergistic Interactions Between Cannabinoid and Opioid Analgesics," Life Sciences, 2004, vol. 74 (11), pp. 1317-1324.
Clayton, et al., "CB1 and CB2 Cannabinoid Receptors are Implicated in Inflammatory Pain," Pain, 2002, vol. 96 (3), pp. 253-260.
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Dauben, et al., "Organic Reactions at High Pressure Cycloadditions with Furans," Journal of the American Chemical Society, 1976, vol. 98 (7), pp. 1992-1993.
Dixon, W., "Efficient Analysis of Experimental Observations," Annual Review of Pharmacology and Toxicology, 1980, vol. 20, pp. 441-462.
Filippo, et al., "Cannabinoid CB2 Receptor Activation Reduces Mouse Myocardial Ischemia-Reperfusion Injury: Involvement of Cytokine/Chemokines and PMN," Journal of Leukocyte Biology, 2004, vol. 75 (3), pp. 453-459.
Galiegue, et al., "Expression of Central and Peripheral Cannabinoid Receptors in Human Immune Tissues and Leukocyte Subpopulations," European Journal of Biochemistry, 1995, vol. 232 (1), pp. 54-61.
Golech, et al., "Human Brain Endothelium: Coexpression and Function of Vannilloid and Endocannabinoid Receptors," Molecular Brain Research, 2004, vol. 132 (1), pp. 87-92.
Greene, et al., Protective Groups in Organic Synthesis, 3rd Edition, John Wiley and Sons, Inc., 1999, Table of Contents.
Grotenhermen, et al., "IACM 2nd Conference on Cannabinoids in Medicine," Expert Opinion in Pharmacotherapy, 1976, vol. 4 (12), pp. 2367-2371.
Hanus, et al., "HU-308: A Specific Agonist for CB 2, a Peripheral Cannabinoid Receptor," Proceedings of the National Academy of Science, 1999, vol. 96, pp. 14228-14233.

Hargreaves, et al., "A New and Sensitive Method for Measuring Thermal Nociception in Cutaneous Hyperalgesia," Pain, 1988. 32 (1), pp. 77-88.
Hohmann, et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.
Ibrahim, et al., "Activation of CB2 Cannabinoid Receptors by AM1241 Inhibits Experimental Neuropathic Pain: Pain Inhibition by Receptors not Present in the CNS," Proceedings of the National Academy of Science, 2003, vol. 100 (18), pp. 10529-10533.
Ibrahim, et al., "CB2 Cannabinoid Receptor Activation Produces Antinociception by Stimulating Peripheral Release of Endogenous Opioids," Proceedings of the National Academy of Science, 2005, vol. 102 (8), pp. 3093-3098.
Ihenetu, et al., "Inhibition of Interleukin-8 Release in the Human Colonic Epithelial Cell Line HT-29 by Cannabinoids," European Journal of Pharmacology, 2003, vol. 458 (1-2), pp. 207-215.
International Search Report for Application No. PCT/US2007/070029, mailed on Nov. 30, 2007, 12 pages.
Jasys, et al., "Preparation of Fluoroadamantane Acids and Amines. Impact of Bridgehead Fluorine Substitution on the Solution- and Solid-State Properties of Functionalized Adamantanes," Journal of the American Chemical Society, 2000, vol. 122, pp. 466-473.
Julien, et al., "Antifibrogenic Role of the Cannabinoid Receptor CB2 in the Liver," Gastroenterology, 2005, vol. 128, pp. 742-755.
Karsak, et al., "Cannabinoid Receptor Type 2 Gene is Associated with Human Osteoporosis," Human Molecular Genetics, 2005, vol. 14 (22), pp. 3389-3396.
Kim, et al., "An Experimental Model for Peripheral Neuropathy Produced by Segmental Spinal Nerve Ligation in the Rat," Pain, 1992, vol. 50 (3), pp. 355-363.
Kreutzberg, et al., "Microglia: A Sensor for Pathological Events in the CNS," Trends in Neuroscience, 1996, vol. 19, pp. 312-318.
Lepicier, et al., "Endocannabinoids Protect the Rat Isolated Heart Against Ischaemia," British Journal of Pharmacology, 2003, vol. 139, pp. 805-815.
Lotersztajn, et al., "Hepatic Fibrosis: Molecular Mechanisms and Drug Targets," Annual Review of Pharmacology and Toxicology, 2005, vol. 45, pp. 605-628.
Malan, et al., "CB2 Cannabinoid Receptor-Mediated Peripheral Antinociception," Pain, 2001, vol. 93, pp. 239-245.
Maresz, et al., "Modulation of the Cannabinoid CB2 Receptor in Microglial Cells in Response to Inflammatory Stimuli," Journal of Neurochemistry, 2005, vol. 95, pp. 437-445.
Masciadri, et al., "Regioselective Friedel Crafts Alkylation of Anilines and Amino-Substituted Heteroarenes with Hexafluoroacetone Sesquihydrate," European Journal of Organic Chemistry, 2003, vol. 2003 (21), pp. 4286-4291.
Mathison, et al., "Effects of Cannabinoid Receptor-2 Activation on Accelerated Gastrointestinal Transit in Lipopolysaccharide-Treated Rats," British Journal of Pharmacology, 2004, vol. 142, pp. 1247-1254.
McKallip, et al., "Targeting CB2 Cannabinoid Receptors as a Novel Therapy to Treat Malignant Lymphoblastic Disease," Blood, 2002, vol. 15 (2), pp. 627-634.
Molina-Holgado, et al., "Endogenous Interleukin-1 Receptor Antagonist Mediates Anti-Inflammatory and Neuroprotective Actions of Cannabinoids in Neurons and Glia," Journal of Neuroscience, 2003, vol. 23 (16), pp. 6470-6474.
Nackley, et al., "Selective Activation of Cannabinoid CB2 Receptors Suppresses Spinal for Protein Expression and Pain Behavior in a Rat Model of Inflammation," Neuroscience, 2003, vol. 119, pp. 747-757.
Ni, et al., "Win 55212-2, a Cannabinoid Receptor Agonist, Attenuates Leukocyte/Endothelial Interactions in an Experimental Autoimmune Encephalomyelitis Model," Multiple Sclerosis, 2004, vol. 10, pp. 158-164.
Nunez, et al., "Cannabinoid CB2 Receptors Are Expressed by Perivascular Microglial Cells in the Human Brain: An Immunohistochemical Study," Synapse, 2004, vol. 53, pp. 208-213.

(56) References Cited

OTHER PUBLICATIONS

Partch, et al., "2-Oxaadamantane-1-N,N,N-trimethylmethanaminium Iodide: 1 Synthesis and Potential for Muscarinic Activity," Croatia Chemical Acta, 1985, vol. 58 (4), pp. 661-669.
Patel, et al, "Inhibition of Guinea-Pig and Human Sensory Nerve Activity and the Cough Reflex in Guinea-Pigs by Cannabinoid (CB2) Receptor Activation," British Journal of Pharmacology, 2003, vol. 140 (2), pp. 261-268.
Pertwee. R., "Cannabinoids and Multiple Sclerosis," Pharmacology & Therapeutics, 2002, vol. 95, pp. 165-174.
Poste, et al., "Lipid Vesicles as Carriers for Introducing Biologically Active Materials into Cells," Methods in Cell Biology, 1976, vol. 14, pp. 33-71.
Quartilho, et al , "Inhibition of Inflammatory Hyperalgesia by Activation of Peripheral CB2 Cannabinoid Receptors," Anesthesiology, 2003, vol. 99, pp. 955-960.
Ralston, S., "Genetic Determinants of Susceptibility to Osteoporosis," Current Opinion in Pharmacology, 2003, vol. 3, pp. 286-290.
Ralston, S., "Regulation of Bone Mass, Bone Loss and Osteoclast Activity by Cannabinoid Receptors," Nature Medicine, 2005, vol. 11 (7), pp. 774-779.
Ramirez, et al., "Prevention of Alzheimers Disease Pathology by Cannabinoids: Neuroprotection Mediated by Blockade of Microglial Activation," Journal of Neuroscience, 2005, vol. 25 (8), pp. 1904-1913.
Rautio, et al, "Prodrugs: Design and Clinical Applications," Nature Reviews Drug Discovery, 2008, vol. 7 (3), pp. 255-270.
Rezoni, et al., "Synthesis of 7-Carboxytricyclo[33103,7]nonan-3-ol," Journal of Organic Chemistry, 1983, vol. 48, pp. 5231-5236.
Sanchez, et al , "Inhibition of Glioma Growth in Vivo by Selective Activation of the CB2 Cannabinoid Receptor1," Cancer Research, 2001, vol. 61, pp. 5784-5789.
Shultz, et al., "Synthesis of Bis(semiquinone)s and their Electrochemical and Electron Paramagnetic Resonance Spectral Characterization," Journal of Organic Chemistry, 1998, vol. 63(25), pp. 9462-9469.
Smith, D., "Do Prodrugs Deliver?" Current Opinion in Drug Discovery and Development, 2007, vol. 10 (5), 550-559.
Steffens, et al., "Low Dose Oral Cannabinoid Therapy Reduces Progression of Atherosclerosis in Mice," Nature, 2005, vol. 434, pp. 782-786.
Testa, B., "Prodrugs: Bridging Pharmacodynamic/Pharmacokinetic Gaps," Current Opinion in Chemical Biology, 2009, vol. 13 (3), pp. 338-344.
Valenzano, et al., "Pharmacological and Pharmacokinetic Characterization of the Cannabinoid Receptor 2 Agonist, Gw405833, Utilizing Rodent Models of Acute and Chronic Pain, Anxiety, Ataxia and Catalepsy," Neuropharmacology, 2005, vol. 48, pp. 658-672.
Walter, et al., "Cannabinoids and Neuroinflammation," British Journal of Pharmacology, 2004, vol. 141 (5), pp. 775-785.
Wang, et al., Drug Delivery: Principles and Applications, John Wiley & Sons, Inc., 2005, pp. 136-137.
Warhurst, et al., "Interferon Gamma Induces Differential Upregulation of Alpha and Beta Chemokine Secretion in Colonic Epithelial Cell Lines," Gut, 1998, vol. 42 (2), pp. 208-213.
Watkins, et al., "Glial Activation: A Driving Force for Pathological Pain," Trends in Neuroscience, 2001, vol. 24 (8), pp. 450-455.
Williams, et al., "Central Nervous System Perivascular Cells Are Immunoregulatory Cells that Connect the CNS with the Peripheral mune System," Journal of Glia, 2001, vol. 36 (2), pp. 156-164.
Wright, et al., "Differential Expression of Cannabinoid Receptors in the Human Colon: Cannabinoids Promote Epithelial Wound Healing," Gastroenterology, 2005, vol. 129 (2), pp. 437-453.
Yoshihara, et al., "Cannabinoid Receptor Agonists Inhibit Sensory Nerve Activation in Guinea Pig Airways," American Journal of Respiratory and Critical Care Medicine, 2004, vol. 170 (9), pp. 941-946.
Yoshihara, et al., "Endogenous Cannabinoid Receptor Agonists Inhibit Neurogenic Inflammations in Guinea Pig Airways," Allergy and Immunology, 2005, vol. 138, pp. 80-87.
Yoshihara, et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.
Zimmer, et al., "Increased Mortality, Hypoactivity, and Hypoalgesia in Cannabinoid CB1 Receptor Knockout Mice," Proceedings of the National Academy of Science, 1999, vol. 96 (10), pp. 5780-5785.
Abreo M.A., et al., "Novel 3-Pyridyl Ethers with Subnanomolar Affinity for Central Neuronal Nicotonic Acetylcholine Receptors," Journal of Medicinal Chemistry, 1996, vol. 39 (4), pp. 817-825.
Ambartsumova R.F., et al., "Effect of Various Factors on the Reaction of 2-Aminobenzothiazoles with Propylene Oxide," Chemistry of Heterocyclic Compounds, 2002, vol. 38 (8), pp. 994-999.
Andreani, et al., "Ring-opened, etc.," Collection of Czechoslovak Chemical Communications, 1999, vol. 64, pp. 299-312.
Ansell M.F., et al., "The Synthesis of (+/−)-10a-Homo-11a-CarbathromboxaneA1, a Stable Thromboxane A Analogue," Journal of Chemical Society Perkin Trans, 1984, pp. 1061-1068.
Araki, et al., (2003): STN International Hcaplus database, (Columbus, OH). Accession No. 2003-931334.
Bacon E.R., et al., "Synthesis of 7-Ethyl-4, 7-dihydro-4-oxo-2-(4-pyridinyl)thieno[2,3-b]pyridine-5-carboxylic Acid," Journal of Heterocyclic Chemistry, 1991, vol. 28, pp. 1953-1955.
Bartlett P.A., et al., "Chorismate Mutase Inhibitors: Synthesis and Evaluation of Some Potential Transition-State Analogues," Journal of Organic Chemistry , 1988, vol. 53, pp. 3195-3210.
Bennett G.J., et al., "A Peripheral Mononeuropathy in Rat that Produces Disorders of Pain Sensation like those Seen in Man," Pain, 1988, vol. 33 (1), pp. 87-107.
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Bozidar K., et al., "Transformations of 1,2,4-Thiadiazolo/2,3-X/Azines," Heterocycles, 1987, vol. 26 (3), pp. 689-697.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Bruson H.A., et al., "Action of Sulfuric Acid upon Unsaturated Isothiocyanates: Mercaptothiazolines ," Journal of American Chemical Society, 2011, vol. 59 (10), pp. 2011-2013.
Cai, et al., Ex Parte Appeal No. 2011005302, decided Jul. 12, 2011.
Caplus Entry for International Application Publication No. WO2008130953, Accessed Aug. 14, 2012, with Structures Relevant to Claim 25 as Filed Aug. 11, 2011.
Caplus Entry for International Application Publication No. WO2008130953, Accessed Aug. 14, 2012, with Structures Relevant to Claim 35 as Filed Aug. 11, 2011.
"Caplus Record of U.S. Patent Application Publication No. 2008/0058335 by Westheim et al., 2007,".
"Caplus Record of U.S. Patent Application Publication No. 2008/0242654 by Kolasa et al., 2008,".
CAS Registry No. 1061668-81-2, which entered STN on Oct. 15, 2008.
Chauhan M.S., "The Reaction of Some Heterocyclic Thiones with Ethyl Azidoformate," Canadian Journal of Chemistry, 1976, vol. 54 (24), pp. 3879-3883.
Chemical Abstracts Accession No. 1030770638, Jun. 26, 2008.
Cotarca L., et al., "Bis (trichloromethyl) Carbonate in Organic Synthesis," 1996, vol. 6, pp. 553-576.
Cross., et al., "Rules for the Nomenclature of Organic Chemistry, Section E: Stereochemistry," International Union of Pure and Applied Chemistry, 1976, vol. 45, pp. 11-30.

(56) References Cited

OTHER PUBLICATIONS

Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Dart et al (2007): STN International HCAPLUS database, Columbus (OH), Accession No. 2007:1396538.
Database Registry [Online] Chemical Abstracts Service, Columbus, Ohio, US, Mar. 2, 2008, XP002687516, Database Accession No. 1006022-43-0.
Database Registry [Online] Chemical Abstracts Service, Columbus, Ohio, US, Mar. 2, 2008, XP002687517, Database Accession No. 1005993-02-1.
Database Registry [Online] Chemical Abstracts Service, Columbus, Ohio, US, Mar. 6, 2008, XP002687515, Database Accession No. 1006758-59-3.
Database Registry [Online6] Chemical Abstracts Service, Columbus, Ohio, US, Mar. 7, 2008, XP002687514, Database Accession No. 1007004-94-5.
Database Registry [Online] Chemical Abstracts Service, Columbus, Ohio, US, Mar. 10, 2008, XP002687513, Database Accession No. 1007244-89-4.
Database Registry [Online] Chemical Abstracts Service, Columbus, Ohio, US, Feb. 29, 2008, XP002687518, Database Accession No. 1005931-81-6.
Dawood K.M., et al., "Synthesis, Anticonvulsant, and Anti-Inflammatory Evaluation of Some New Benzotriazole and Benzofuran-Based Heterocycles," Bioorganic & Medicinal Chemistry, 2006, vol. 14 (11), pp. 3672-3680.
Dellemijn P.L., et al., "Randomised Double-Blind Active-Placebo-Controlled Crossover Trial of Intravenous Fentanyl in Neuropathic Pain," Lancet, 1997, vol. 349 (9054), pp. 753-758.
DeWolfe R.H., "Reactions of Aromatic Amines with Aliphatic Ortho Esters. A Convenient Synthesis of Alkyl N-Arylimidic Esters," Journal of Organic Chemistry, 1962, vol. 27, pp. 490-493.
Dorsch J.B., et al., "The Preparation of Benzoylacetic Ester and Some of its Homologs," Journal of the American Chemical Society, 1932, vol. 54, pp. 2960-2964.
Ebata et al., "Synthesis of Both Enantiomers of 4-Hexanolide and 4-Dodecanolide," Agriculture Biochemical, 1991, vol. 55 (6), pp. 1685-1686.
Eckert H., et al., "Triphosgene, a Crystalline Phosgene Substitute," Angewandte Chemie International Edition in English, 1987, vol. 26 (9), pp. 894-895.
European Search Report for Application No. EP12187944, mailed on Nov. 20, 2012, 7 pages.
Ex Parte Quayle Action mailed Oct. 12, 2012 for U.S. Appl. No. 13/160,952, filed Jun. 15, 2011.
Fattori D., et al. "The Demjanov and Tiffeneau-Demjanov One-Carbon Ring Enlargements of 2-Aminomethyl-7-Oxabicyclo[2.2.1]Heptane derivatives. The Stereo- and Regioselective Additions of 8-Oxabicyclo[3.2.1]Oct-6-en-2-One to Soft Electrophiles," Tetrahedron, 1993, vol. 49 (8), pp. 1649-1664.
Final Office Action mailed Oct. 3, 2013 for U.S. Appl. No. 12/246,808, filed Oct. 7, 2008.
Final Office Action mailed Mar. 10, 2010 for U.S. Appl. No. 11/755,434, filed May 30, 2007.
Final Office Action mailed Jul. 14, 2011 for U.S. Appl. No. 12/246,808, filed Oct. 7, 2008.
Final Office Action mailed Sep. 14, 2011 for U.S. Appl. No. 12/274,105, filed Nov. 19, 2008.
Final Office Action mailed Feb. 15, 2011 for U.S. Appl. No. 12/120,969, filed May 15, 2008.
Final Office Action mailed Nov. 16, 2011 for U.S. Appl. No. 12/554,445, filed Sep. 4, 2009.
Final Office Action mailed Nov. 16, 2011 for U.S. Appl. No. 12/560,897, filed Sep. 16, 2009.
Final Office Action mailed Apr. 19, 2011 for U.S. Appl. No. 12/539,120, filed Aug. 11, 2009.
Final Office Action mailed Oct. 19, 2011 for U.S. Appl. No. 12/560,893, filed Sep. 16, 2009.
Final Office Action mailed Nov. 21, 2012 for U.S. Appl. No. 12/120,969, filed May 15, 2008.
Final Office Action mailed Apr. 23, 2013 for U.S. Appl. No. 12/967,275, filed Dec. 14, 2010.
Final Office Action mailed Mar. 24, 2011 for U.S. Appl. No. 11/755,434, filed May 30, 2007.
Final Office Action mailed Dec. 28, 2011 for U.S. Appl. No. 12/639,173, filed Dec. 16, 2009.
Florjancic A., et al (2009): Caplus Entry for WO2009067613, Accession No. 2009:649814.
Florjancic et al (2010): STN International HCAPLUS database, Columbus (OH), Accession No. 2010:478868.
Foster, A. B. et al., "Deuterium Isotope Effects in the Metabolism of Drugs and Xenobiotics: Implications for Drug Design," Advances in Drug Research, 1985, vol. 14, pp. 2-36.
Giron D., "Applications of Thermal Analysis and Coupled Techniques in Pharmaceutical Industry," Journal of Thermal Analysis and Calorimetry, 2002, vol. 68, pp. 335-357.
Giron D., "Investigations of Polymorphism and Pseudo-Polymorphism in Pharmaceuticals by Combined Thermoanalytical Techniques," The Journal of Thermal Analysis and Calorimetry, 2001, vol. 64, pp. 37-60.
Goerdeler J., et al., "Uber Isothiazole, VIII. Synthese von Sulfonylamino-isothiazolen und Sulfonyliminoisothiazolinen aus Sulfonylsenfolen ," Chemische Berichte, 1969, vol. 102 (7), pp. 2273-2284.
Golub T.R., et al., "Molecular Classification of Cancer: Class Discovery and Class Prediction by Gene Expression Monitoring," Science, 1999, vol. 286 (5439), pp. 531-537.
Goodman A.J., et al., "CB2 Selective Sulfamoyl Benzamides; Optimization of the Amide Functionality," Bioorganic & Medicinal Chemistry Letters , 2009, vol. 19 (2), pp. 309-313.
Gouldson P., et al., "Mutational Analysis and Molecular Modelling of the Antagonist SR144528 Binding Site on the Human Cannabinoid CB2 Receptor," European Journal of Pharmacology, 2000, vol. 401 (1), pp. 17-25.
Greene T.W., et al., "Protection for the Amino group," Protective Groups in Organic Synthesis, 1999, Third Edition, pp. 494-653.
Hamuro Y., et al., "Solid-Phase Synthesis of Acyclic and Cyclic Amino Acid Derived Urea Peptidomimetics Using Phoxime Resin," The Journal of Combinatorial Chemistry, 1999, vol. 1, pp. 163-172.
Horig H., et al., "From Bench to Clinic and Back: Perspective on the 1st IQPC Translational Research conference," Journal of Translational Medicine, 2004, vol. 2 (44).
Hutchins S.M., et al., "A General Method for the Solid Phase Synthesis of Ureas," Tetrahedron Letters, 1994, vol. 35 (24), pp. 4055-4058.
Hutchins S.M., et al., "A Strategy for Urea Linked Diamine Libraries," Tetrahedron Letters, 1995, vol. 36 (15), pp. 2583-2586.
International Preliminary Report on Patentability and Written Opinion for Application No. PCT/US07/081263, mailed on Apr. 15, 2010, 8 pages.
International Preliminary Report on Patentability and Written Opinion for Application No. PCT/US08/069453, mailed on Jan. 12, 2010, 6 pages.
International Preliminary Report on Patentability and Written Opinion for Application No. PCT/US08/079182, mailed on Apr. 13, 2010, 5 pages.
International Preliminary Report on Patentability and Written Opinion for Application No. PCT/US08/080253, mailed on Apr. 20, 2010, 6 pages.
International Preliminary Report on Patentability and Written Opinion for Application No. PCT/US2005/046480, mailed on Jun. 26, 2007, 8 pages.
International Preliminary Report on Patentability and Written Opinion for Application No. PCT/US2007/087175, mailed on Jun. 23, 2009, 8 pages.
International Preliminary Report on Patentability and Written Opinion for Application No. PCT/US2007/069921, mailed on Dec. 3, 2008, 10 pages.

(56) References Cited

OTHER PUBLICATIONS

International Preliminary Report on Patentability and Written Opinion for Application No. PCT/US2007/070029, mailed on Dec. 3, 2008, 8 pages.
International Preliminary Report on Patentability and Written Opinion for Application No. PCT/US2007/077321, mailed on Mar. 3, 2009, 7 pages.
International Preliminary Report on Patentability and Written Opinion for Application No. PCT/US2008/057460, mailed on Sep. 29, 2009, 11 pages.
International Preliminary Report on Patentability and Written Opinion for Application No. PCT/US2008/060400, mailed on Oct. 20, 2009, 11 pages.
International Preliminary Report on Patentability and Written Opinion for Application No. PCT/US2008/063648, mailed on Nov. 24, 2009, 7 pages.
International Preliminary Report on Patentability and Written Opinion for Application No. PCT/US2008/084216, mailed on May 25, 2010, 5 pages.
International Preliminary Report on Patentability and Written Opinion for Application No. PCT/US2009/053369, mailed on Feb. 15, 2011, 6 pages.
International Preliminary Report on Patentability and Written Opinion for Application No. PCT/US2009/056179, mailed on Mar. 8, 2011, 9 pages.
International Preliminary Report on Patentability and Written Opinion for Application No. PCT/US2009/063318, mailed on May 10, 2011, 5 pages.
International Preliminary Report on Patentability and Written Opinion for Application No. PCT/US2009/068173, mailed on Jun. 21, 2011, 8 pages.
International Preliminary Report on Patentability and Written Opinion for Application No. PCT/US2010/028790, mailed on Sep. 27, 2008, 5 pages.
International Preliminary Report on Patentability for Application No. PCT/US2007/077320, mailed on Mar. 3, 2009, 1 page.
International Preliminary Report on Patentability for Application No. PCT/US2009/036715, mailed on Sep. 14, 2010, 1 page.
International Search Report and Written Opinion for Application No. PCT/US2007/077320, mailed on Feb. 7, 2008, 12 pages.
International Search Report and Written Opinion for Application No. PCT/US2009/036715, mailed on Jun. 10, 2009, 9 pages.
International Search Report for Application No. PCT/US07/069921, mailed on Nov. 27, 2007, 4 pages.
International Search Report for Application No. PCT/US07/081263, mailed on Nov. 27, 2008, 3 pages.
International Search Report for Application No. PCT/US08/057460, mailed on Aug. 20, 2008, 3 pages.
International Search Report for Application No. PCT/US08/060400, mailed on Oct. 17, 2008, 3 pages.
International Search Report for Application No. PCT/US08/063648, mailed on Aug. 13, 2008, 3 pages.
International Search Report for Application No. PCT/US08/069453, mailed on Sep. 25, 2008, 2 pages.
International Search Report for Application No. PCT/US08/079182, mailed on Dec. 15, 2008, 2 pages.
International Search Report for Application No. PCT/US08/080253, mailed on Mar. 3, 2009, 3 pages.
International Search Report for Application No. PCT/US2005/0046480, mailed on Apr. 18, 2006, 5 pages.
International Search Report for Application No. PCT/US2007/0077321, mailed on Feb. 1, 2008, 3 pages.
International Search Report for Application No. PCT/US2007/0087175, mailed on Apr. 8, 2008, 4 pages.
International Search Report for Application No. PCT/US2008/084216, mailed on Feb. 19, 2009, 1 page.
International Search Report for Application No. PCT/US2009/053369, mailed on Oct. 22, 2009, 3 pages.
International Search Report for Application No. PCT/US2009/056179, mailed on Jun. 9, 2010, 4 pages.
International Search Report for Application No. PCT/US2009/057088, mailed on Oct. 5, 2010, 4 pages.
International Search Report for Application No. PCT/US2009/063318, mailed on May 6, 2010, 3 pages.
International Search Report for Application No. PCT/US2009/068173, mailed on Feb. 5, 2010, 3 pages.
International Search Report for Application No. PCT/US2010/028790, mailed Jul. 19, 2010, 3 pages.
International Search Report for Application No. PCT/US2010/028794, mailed Jul. 20, 2010, 3 pages.
International Search Report for Application No. PCT/US2010/028796, mailed Jul. 16, 2010, 4 pages.
International Search Report for Application No. PCT/US2011/040501, mailed on Oct. 24, 2011, 2 pages.
Izdebski J., et al., "A New Convenient Method for the Synthesis of Symmetrical and Unsymmetrical N,N'-Disubstituted Ureas," Synthesis, 1989, pp. 423-425.
Jain S., et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.
Jhaveri M.D., et al., "Cannabinoid CB2 Receptor-Mediated Anti-Nociception in Models of Acute and Chronic Pain," Molecular Neurobiology, 2007, vol. 36 (1), pp. 26-35.
Josh S. K., et al., "Comparison of Antinociceptive Actoins of Standard Analgesics in Attenuating Capsaicin and Nerve-Injury-Induced Mechanical Hypersensitivty ," Neuroscience, 2006, vol. 143, pp. 587-596.
Kato, S. et al., "Synthesis of Deuterated Mosapride Citrate," Journal of Labelled Compounds and Radiopharmaceuticals, 1995, vol. 36 (10), pp. 927-932.
Katritzky A.R., et al., "A General Synthesis of Unsymmetrical Tetrasubstituted Ureas," Journal of Organic Chemistry, 1997, vol. 62 (11), pp. 4155-4158.
Kherjee S., et al., "Species Comparison and Pharmacological Characterization of Rat and Human Cb2 Cannabinoid Receptors," European Journal of Pharmacology, 2004, vol. 505 (1-3), pp. 1-9.
Khusnutdinov R.I., et al., "Chlorination of Adamantane and its Derivatives by Carbon Tetrachloride in the Presence of Manganese-, Vanadium-, and molybdenum-Containing Catalysts," Neftekhimiya, 2004, vol. 44 (2), pp. 148-155.
Knolker H.J., et al., "A Novel Method for the Synthesis of Isocyanates Under Mild Conditions," Angewandte Chemie International Edition in English, 1995, vol. 34 (22), pp. 2497-2500.
Knolker H.J., et al., "Synthesis of Symmetrical and Unsymmetrical Ureas by DMAP-Catalyzed Reaction of Alkyl- and Arylamines with Di-tert-butyldicarbonate," Synlett, 1996, pp. 502-504.
Kolasa., "Thiazolylidene Derivatives as Cannabinoid Receptor Ligands and Their Preparation" Accession No. 2008:1184581, Mar. 22, 2011.
Koren B., et al., "Transformations of 1-(2-Chloropyridyl-3)-4-ethoxycarbonyl and 1-(2-Chloropyridyl-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.
Kruijtzer J., et al., "Approaches to the Synthesis of Ureapeptoid Peptidomimetics," Tetrahedron Letters, 1997, vol. 38 (30), pp. 5335-5338.
Kubinyi, "3D QSAR in Drug Design: Ligand Protein Interactions & Molecular Similarity, 800 pages," Springer, 1998, vol. 2-3, pp. 243-244.
Kushner, et al., "Pharmacological uses and perspectives of heavy water and deuterated compounds," Canadian Journal of Physiology and Pharmacology, 1999, vol. 77 (2), pp. 79-88.
Lamothe M., et al., "A Simple One-Pot Preparation of N,N'-unsymmetrical ureas from N-Boc Protected Primary Anilines and Amines," Synlett, 1996, vol. 6, pp. 507-508.
Lemoucheux L., et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," Journal of Organic Chemistry, 2003, vol. 68 (19), pp. 7289-7297.

(56) References Cited

OTHER PUBLICATIONS

Leung M.K., et al., "S,S-Dimethyl Dithiocarbonate: A Convenient Reagent for the Synthesis of Symmetrical and Unsymmetrical Ureas," Journal of Organic Chemistry, 1996, vol. 61 (12), pp. 4175-4179.
Li, W., et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.
Linn, et al., Journal of American Chemistry Society, 1963, 2032, vol. 85.
Lizondo, J. et al., "Linezolid: Oxazolidinone antibacterial," Drugs of the Future, 1996, vol. 21 (11), pp. 1116-1123.
MacLennan S.J., et al., "Evidence for Inverse Agonism of SR141716A at Human Recombinant Cannabinoid CB1 and CB2 Receptors," British Journal of Pharmacology, 1998, vol. 124 (4), pp. 619-622.
Majer P., et al., "A Safe and Efficient Method for Preparation of N,-Unsymmetrically Disubstituted Ureas Utilizing Triphosgene," Journal of Organic Chemistry, 1994, vol. 59, pp. 1937-1938.
Malan T.P., et al., "Inhibition of Pain Responses by Activation of CB(2) Cannabinoid Receptors," Chemistry and Physics of Lipids, 2002, vol. 121 (1-2), pp. 191-200.
Maligres, P.E., et al., "Stereocontrolled Preparation of a Nonpeptidal (-)-Spirobicyclic NK-1 Receptor Antagonist," Journal of Organic Chemistry, 2002, vol. 67 (4), pp. 1093-1101.
Mallat A., et al., "Cannabinoid Receptors as New Targets of Antifibrosing Strategies during Chronic Liver Diseases," Expert Opinion on Therapeutic Targets, 2007, vol. 11 (3), pp. 403-409.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Manaka A., et al., "2-Acylimino-3H-thiazoline Derivatives: A Novel Template for Platelet GPIIb/IIIa Receptor Antagonists," Bioorganic & Medicinal Chemistry Letters, 2001, vol. 11, pp. 1031-1035.
Meyers A.I., et al., "Oxazolines. XX. Synthesis of Achiral and Chiral Thiiranes and Olefins by Reaction of Carbonyl Compounds with 2-(Alkylthio)-2-oxazolines ," Journal of Organic Chemistry, 1976, vol. 41 (10), pp. 1735-1742.
Miyaura N., et al., ed., Topics in Current Chemistry: Cross-Coupling Reactions, Springer, 2002, Table of Contents.
Morii T., et al., "A General Strategy to Determine a Target DNA Sequence of a Short Peptide: Application to a [D]-Peptide," Journal American Chemical Society, 2002, vol. 124 (2), pp. 180-181.
Morissette S.L., et al., "High-throughput Crystallization: Polymorphs, Salts, Co-crystals and Solvates of Pharmaceutical Solids.," Advanced Drug Delivery Reviews, 2004, vol. 56 (3), pp. 275-300.
Negishi E., et al., eds., Handbook of Organopalladium Chemistry for Organic Synthesis, vol. 1, John Wiley & Sons, 2002, Table of Contents.
Nieuwenhuijzen J.W., et al., "Solid and Solution Phase Combinatorial Synthesis of Ureas," Tetrahedron Letters, 1998, vol. 39, pp. 7811-7814.
Non-Final Office Action mailed Jun. 1, 2011 for U.S. Appl. No. 12/554,445, filed Sep. 4, 2009.
Non-Final Office Action mailed Jun. 1, 2011 for U.S. Appl. No. 12/560,897, filed Sep. 16, 2009.
Non-Final Office Action mailed Jun. 2, 2009 for U.S. Appl. No. 11/755,434, filed May 30, 2007.
Non-Final Office Action mailed Sep. 7, 2010 for U.S. Appl. No. 12/120,969, filed May 15, 2008.
Non-Final Office Action mailed Mar. 9, 2012 for U.S. Appl. No. 12/732,428, filed Mar. 26, 2010.
Non-Final Office Action mailed Jan. 12, 2010 for U.S. Appl. No. 12/120,969, filed May 15, 2008.
Non-Final Office Action mailed May 17, 2011 for U.S. Appl. No. 12/560,893, filed Sep. 16, 2009.
Non-Final Office Action mailed Aug. 23, 2011 for U.S. Appl. No. 12/639,173, filed Dec. 16, 2009.
Non-Final Office Action mailed Jan. 27, 2011 for US. Appl. No. 12/274,105, filed Nov. 19, 2008.
Non-Final Office Action mailed Jun. 29, 2010 for U.S. Appl. No. 11/755,434, filed May 30, 2007.
Non-Final Office Action mailed Nov. 30, 2010 for U.S. Appl. No. 11/755,434, filed May 30, 2007.
Ohta H., et al., "Imine Derivatives as new Potent and Selective CB2 Cannabinoid Receptor agonist with an Analgesic Action," Bioorganic and Medicinal Chemistry, 2007, vol. 16 (3), pp. 1111-1124.
Ohta H., et al., "N-Alkyidenearylcarboxamides as a new Potent and Selective CB2 Cannabinoid Receptor Agonist with an Analgesic Action," Bioorganic and Medicinal Chemistry Letters, 2007, vol. 17 (22), pp. 6299-6304.
Opposition filed by "Asociacion de Industries Farmaceuticas Dominicanas Inc" for the Dominican Patent application Nr P2008-0060, received on Apr. 1, 2009, 8 pages.
Ozaki S., et al., "Recent Advances in Isocyanate Chemistry," Chemical Reviews, 1972, vol. 72 (5), pp. 457-496.
Padgett L.W., et al., "Recent Developments in Cannabinoid Ligands," Life Sciences, 2005, vol. 77 (14), pp. 1767-1798.
Radulescu C., et al., "Actes Du Colloque Franco-Roumain De Chimie Appliquee, 3Rd, Bacau, Romania," 2004, pp. 117-120.
Radulescu C., et al., "The Comparative Study on the Synthesis Methods of a Heterocyclic System 2-Aminothiazolo[4,5-13]Pyridine," Revista de Chemie, 2004, vol. 56 (6), pp. 659-662.
Radulescu C., et al., "Synthesis and Characteristics of Compact Condensed Heterocyclic System 2-Aminothiazole[5,4-c]Pyridine," Revista de Chemie, 2004, vol. 55 (11), pp. 889-893.
Ralston S.H., et al., "Regulation of Bone Mass, Bone Loss and Osteoclast Activity by Cannabinoid Receptors," Nature Medicine, 2005, vol. 11 (7), pp. 774-779.
Rodriquez-Spong B., et al., "General Principles of Pharmaceutical Solid Polymorphism: A Supramolecular Perspective," Advanced Drug Delivery Reviews, 2004, vol. 56 (3), pp. 241-274.
Ross W.J., et al., "Antianaphylactic agents. 1. 2-(Acylamino)oxazoles," Journal of Medicinal Chemistry, 1979, vol. 22(4), pp. 412-417.
Sabnis R.W., et al., "2-Aminothiophenes by the Gewald Reaction," Journal of Heterocyclic Chemistry, 1999, vol. 36, pp. 333-345.
Schafer S., et al., "Failure is an Option: Learning from Unsuccessful Proof-of-concept Trials," Drug Discovery Today, 2008, vol. 13 (21-22), pp. 913-916.
Schuart J., et al., "2-aminooxazoles and 2-iminooxazolines. 3. Selected Examples of a Homolog Series of 3 Substituted 2-imino-4-methyl-5-phenyloxazolines," Die Pharmazie, 1974, vol. 29 (3), pp. 170-172.
Scialdone M.A., et al., "Phosgenated p-nitrophenyl(polystyrene)ketoxime or phoxime resin. A new resin for the solid-phase synthesis of ureas via thermolytic cleavage of oxime-carbamates", Journal of Organic Chemistry, 1998, vol. 63, pp. 4802-4807.
Souillac P., et al, "Characterization of Delivery Systems, Differential Scanning Calorimetry," Encyclopedia of Controlled Drug Delivery, 1999, pp. 217-218.
STN International HCAPLUS database Accession No. 2008:1184581, Columbus, Ohio, Lolasa et al, 2008.
Supplementary European Search Report for Application No. EP08837396, mailed on Jan. 16, 2012, 2 pages.
Supplementary European Search Report for Application No. EP08852528, mailed on Nov. 8, 2010, 2 pages.
Takeda K., et al., "Convenient Methods for Syntheses of Active Carbamates, Ureas and Nitrosoureas Using N,N-disuccinimido Carbonate (DSC)," Tetrahedron Letters, 1983, vol. 24, pp. 4569-4572.
Thomson, J.F., "Physiological Effects of D20 in Mammals," Annals of the New York Academy of Sciences, 1960, vol. 84, pp. 736-744.
Vasil'Eva V.F., et al., "Synthesis and Properties of 2-imino-3-benzyl-5-phenyl-1,3,4-oxadiazoline,"Caplus, 1970.
Viallet, et al., "2-Aminothiazoline, etc," 1980, CA 93:8074.
Vippagunta S.R., et al., "Crystalline Solids," Advanced Drug Delivery Reviews, 2001, vol. 48.(1), pp. 3-26.

(56) References Cited

OTHER PUBLICATIONS

Werbel L.M., et al., "1-Alkyl-3-(3-alkyl-5-nitro-4-thiazolin-2-ylidene)ureas nd Related Compounds as Schistosomicides," Journal of Medicinal Chemistry, 1972, vol. 15 (9), pp. 955-963.
Wermuth, "The practice of Medicinal chemistry," 2003, Chapters 9-10, 2nd edition, 768 pages.
Weyer V.R., et al., "Blutzuckersenkende Chinolin-8-Carboxamidoalkyl-Benzol Sulfonamid Derivate," Arzneimittel-Forschung, 1974, vol. 24 (3), pp. 269-275.
Whiteside G.T., et al., "The Role of the Cannabinoid Cb2 Receptor in Pain Transmission and Therapeutic Potential of Small Molecule CB2 Receptor Agonists," Current medicinal chemistry, 2007, vol. 14 (8), pp. 917-936.
Widdowson D.A., et al., "Palladium Catalysed Suzuki Reactions of Fluoroarenes," Chemical Communication (Camb), 2003, vol. 5, pp. 578-579.
Williams P.D., et al., "Renin Inhibitors Containing Conformationally Restricted P1-P1 Dipeptide Mimetics," Journal of Medicinal Chemistry, 1991, vol. 34 (3), pp. 887-900.
Wu K.M., et al., "Regulatory Perspectives of Type II Prodrug Development and Time-Dependent Toxicity Management: Nonclinical Pharm/Tox Analysis and the Role of Comparative Toxicology," Toxicology, 2007, vol. 236 (1-2), pp. 1-6.
Yao B.B., et al., "In Vitro Pharmacological Characterization of Am1241: A Protean Agonist At the Cannabinoid Cb2 Receptor," British Journal of Pharmacology, 2006, vol. 149 (2), pp. 145-154.
Non-Final Rejection mailed Dec. 5, 2013 for U.S. Appl. No. 12/967,282, filed Dec. 14, 2010.
Office Action mailed Nov. 15, 2013 for European Application No. 05855099.7 filed Dec. 21, 2005.
Notice of Allowance mailed Jan. 17, 2014 for U.S. Appl. No. 12/120,969, filed May 15, 2008.
Notice of Allowance mailed Apr. 14, 2014 for U.S. Appl. No. 12/967,282, filed Dec. 14, 2010.
Final Office Action mailed May 23, 2014 for U.S. Appl. No. 12/246,808, filed Oct. 7, 2008.
Notice of Allowance mailed Jun. 2, 2014 for U.S. Appl. No. 12/554,445, filed Sep. 4, 2009.
Notice of Allowance mailed Jun. 9, 2014 for U.S. Appl. No. 12/560,893, filed Sep. 16, 2009.
Notice of Allowance mailed Jun. 9, 2014 for U.S. Appl. No. 12/639,173, filed Dec. 16, 2009.
Notice of Allowance mailed Jun. 9, 2014 for U.S. Appl. No. 12/970,435, filed Dec. 16, 2010.
Notice of Allowance mailed May 14, 2014 for U.S. Appl. No. 12/274,105, filed Nov. 19, 2008.
United States Patent Office Action for U.S. Appl. No. 12/246,808 dated Sep. 29, 2014 (61 pages).

* cited by examiner

COMPOUNDS AS CANNABINOID RECEPTOR LIGANDS AND USES THEREOF

CROSS REFERENCE TO RELATED APPLICATIONS

This is a divisional of U.S. patent application Ser. No. 11/755,884, filed on May 31, 2007, now U.S. Pat. No. 7,875,639, which claims priority to U.S. Provisional Patent Application No. 60/809,615, filed on May 31, 2006, the entire contents of all of which are fully incorporated herein by reference.

TECHNICAL FIELD

The present invention relates to compounds that are cannabinoid receptor ligands, compositions comprising such compounds, and methods of treating conditions and disorders using such compounds and compositions.

BACKGROUND (−)-$\Delta^9$-Tetrahydrocannabinol ($\Delta^9$-THC), the major psychoactive constituent of marijuana, exerts a broad range of biological effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY

In the principal embodiment, the present invention provides compounds of formula (I), or pharmaceutically acceptable salts, prodrugs, salts of prodrugs, or combinations thereof,

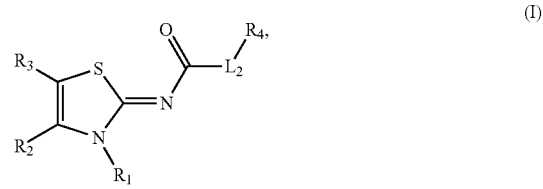

(I)

wherein $R_1$ is alkyl, alkenyl, alkoxyalkyl, alkoxyalkoxyalkyl, alkoxycarbonylalkyl, alkynyl, arylalkoxyalkyl, arylalkyl, aryloxyalkyl, carboxyalkyl, cycloalkyl, cycloalkylalkyl, haloalkyl, haloalkoxyalkyl, heteroarylalkyl, heteroaryloxyalkyl, heterocycle, heterocyclealkyl, heterocycleoxyalkyl, hydroxyalkyl, or $R_aR_bN$-alkylene-;

$R_2$ and $R_3$ are the same or different, and are each independently hydrogen, alkoxy, alkoxycarbonyl, alkoxycarbonylalkyl, azidoalkyl, alkyl, alkylcarbonyl, alkylsulfonyl, aryl, arylalkyl, arylalkenyl, cyano, cycloalkyl, cycloalkenyl, halo, haloalkyl, heteroaryl, heterocycle, —$(CR_jR_k)_n$—$OR_p$, —C(O)H, $R_cR_dN$—, $R_cR_dN$-alkylene-, $R_eR_fNC(O)$—, or $R_8$-$R_7$; or $R_2$ and $R_3$, together with the carbon atoms to which they are attached, form a 4-, 5-, 6-, or 7-membered monocyclic ring, optionally fused to a benzo or a monocyclic heteroaryl, said monocyclic ring contains zero, one, or two additional double bonds, zero or one oxygen atom, and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, alkylsulfonyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl;

with the proviso that when $R_1$ is cycloalkylalkyl, and $L_2$ is a single bond, then $R_2$ and $R_3$ are not both alkyl;

$R_4$ is a bridged cycloalkyl or a bridged heterocycle; optionally substituted with 1, 2, 3, 4, 5, or 6 substituents selected from the group consisting of alkyl, —$OR_p$, —$NR_cR_d$, oxo, halo, haloalkyl, carboxy and =$CH_2$;

$R_7$ and $R_8$, are independently aryl, cycloalkyl, cycloalkenyl, heteroaryl, or heterocycle;

$R_a$ and $R_b$ are each independently hydrogen, alkyl, alkylcarbonyl, alkylsulfonyl, aryl, arylalkyl, arylcarbonyl, arylsulfonyl, cycloalkylalkyl, heteroaryl, heteroarylalkyl, heteroarylcarbonyl, heteroarylsulfonyl, heterocycle, heterocyclealkyl, heterocyclecarbonyl or heterocyclesulfonyl;

$R_c$ and $R_d$, at each occurrence, are each independently hydrogen, alkoxycarbonyl, alkyl, alkylcarbonyl, alkylsulfonyl or arylalkyl;

$R_e$ and $R_f$, at each occurrence, are each independently hydrogen or alkyl;

$L_2$ is a single bond, alkylene, —$NR_g$— or —$NR_g$-alkylene- wherein the alkylene moiety is attached to $R_4$ of formula (I);

$R_g$ is hydrogen or alkyl,

The aryl, cycloalkyl, cycloalkenyl, heterocycle, and heteroaryl moieties, as substituents or part of a substituent, represented by $R_1$, $R_2$, $R_3$, $R_a$, $R_b$, $R_c$, $R_d$, $R_7$, and $R_8$, are each independently unsubstituted or substituted with 1, 2, 3, 4, 5, or 6 substituents independently selected from the group consisting of alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halo, haloalkyl, haloalkoxy, oxo, hydroxy, hydroxyalkyl, —SH, —$NO_2$, —$NZ_1Z_2$, and ($NZ_3Z_4$)carbonyl;

$Z_1$ and $Z_2$ are each independently hydrogen, alkyl, haloalkyl, alkylcarbonyl, or formyl;

$Z_3$ and $Z_4$ are each independently hydrogen, alkyl, or haloalkyl;

$R_j$ and $R_k$, at each occurrence, are each independently hydrogen, halo, alkyl or haloalkyl;

$R_p$, at each occurrence, is independently hydrogen, alkyl, or haloalkyl; and n is 1, 2, 3, 4, or 5.

In another embodiment, the present invention provides a pharmaceutical composition comprising a therapeutically effective amount of a compound of the invention or a pharmaceutically acceptable salt thereof in combination with a pharmaceutically acceptable carrier.

In another embodiment of the present invention, there is disclosed a method of treating pain, nociceptive pain, and neuropathic pain, comprising administration to a mammal a therapeutically effective amount of a compound of the invention, or a pharmaceutically acceptable salt thereof in combination with a pharmaceutically acceptable carrier.

In another embodiment, the present invention provides a method of treating a disorder selected from the group consisting of inflammatory disorders, immune disorders, neurological disorders, cancers of the immune system, respiratory disorders, and cardiovascular disorders in a mammal in need of such treatment comprising administering to the mammal a therapeutically effective amount of a compound of the invention or a pharmaceutically acceptable salt thereof.

In another embodiment, the present invention provides a method of neuroprotection in a mammal in need thereof, comprising administering to the mammal a therapeutically effective amount of a compound of the invention or a pharmaceutically acceptable salt thereof.

Definition of Terms

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds that can be isolated from a reaction mixture.

All patents, patent applications, and literature references cited in the specification are herein incorporated by reference in their entirety. In the case of inconsistencies, the present disclosure, including definitions, will prevail.

As used throughout this specification and the appended claims, the following terms have the following meanings:

The term "alkenyl" as used herein, means a straight or branched chain hydrocarbon containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2, 3, or 4 carbon atoms and contains at least one carbon-carbon double. Representative examples of alkylene include, but are not limited to, —CH=CH— and —$CH_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, methoxymethyl, and 3-methoxypropyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, 4-methylpentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, $-CH_2-$, $-CH(CH_3)-$, $-C(CH_3)_2-$, $-CH_2CH_2-$, $-CH_2CH_2CH_2-$, $-CH_2CH_2CH_2CH_2-$, and $-CH_2CH(CH_3)CH_2-$.

The term "-alkylene-$NR_g$-" as used herein, means an alkylene group, as defined herein, appended to the parent molecular moiety through a $-NR_g-$ group, as defined herein.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkylene group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkylene group, as defined herein. Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited to, methylthio, ethylthio, tert-butylthio, and hexylthio.

The term "alkylthioalkyl" as used herein, means an alkylthio group, as defined herein, appended to the parent molecular moiety through an alkylene group, as defined herein. Representative examples of alkylthioalkyl include, but are not limited to, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl," as used herein, means phenyl, a bicyclic aryl or a tricyclic aryl. The bicyclic aryl is naphthyl, or a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryl ring include, but are not limited to, anthracene, phenanthrene, dihydroanthracenyl, fluorenyl, 1,2-dihydroacenaphthylenyl, and tetrahydrophenanthrenyl. The phenyl, bicyclic and tricyclic aryls are attached to the parent molecular moiety through any carbon atom contained within the phenyl, bicyclic and tricyclic aryls, respectively.

The term "arylalkoxy" as used herein, means an aryl group, as defined herein, appended to the parent molecular moiety through an alkoxy group, as defined herein. Representative examples of arylalkoxy include, but are not limited to, benzyloxy, 2-phenylethoxy, 3-naphth-2-ylpropoxy, and 5-phenylpentyloxy.

The term "arylalkoxyalkyl" as used herein, means an arylalkoxy group, as defined herein, appended to the parent molecular moiety through an alkylene group, as defined herein. Representative examples of arylalkoxyalkyl include, but are not limited to, 2-(benzyloxy)ethyl and 3-(benzyloxy)propyl.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, 2-naphthylethyl, and 1-phenylethyl.

The term "arylalkenyl" as used herein, means an aryl group, as defined herein, appended to the parent molecular moiety through an alkenylene group, as defined herein. An example of arylalkenyl is 2-phenylvinyl.

The term "arylalkylthio" as used herein, means an arylalkyl group, as defined herein, appended to the parent molecular moiety through a sulfur atom. Representative examples of arylalkylthio include, but are not limited to, 2-phenylethylthio, 3-naphth-2-ylpropylthio, and 5-phenylpentylthio.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" as used herein, means an aryloxy group, as defined herein, appended to the parent molecular moiety through an alkylene group, as defined herein. Representative examples of aryloxyalkyl include, but are not limited to, 2-phenoxyethyl, 3-naphth-2-yloxypropyl and 3-bromophenoxymethyl.

The term "arylsulfonyl," as used herein, means an aryl group, as defined herein appended to the parent moiety through a sulfonyl group, as defined herein.

The term "azido" as used herein, means an —$N_3$ group.

The term "azidoalkyl, as used herein, means an azido group, as defined herein, appended to the parent moiety, through an alkylene group, as defined herein.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or a bicyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic ring systems include, but are not limited to, cyclohexenyl such as 2-cyclohexen-1-yl, 3-cyclohexen-1-yl, cyclohex-1-en-1-yl, and the like, 2,4-cyclohexadien-1-yl and 3-cyclopenten-1-yl. Bicyclic ring systems are exemplified by a monocyclic cycloalkenyl ring fused to a monocyclic cycloalkyl ring, or a monocyclic cycloalkenyl ring fused to a monocyclic cycloalkenyl ring. Representative examples of bicyclic ring systems include, but are not limited to, 3a,4,5,6,7,7a-hexahydro-1H-indenyl, 4,5,6,7-tetrahydro-3aH-indene, and octahydronaphthalenyl. The monocyclic or the bicyclic cycloalkenyl ring can be appended to the parent molecular moiety through any carbon atom that can be substituted within the monocyclic or the bicyclic cycloalkenyl.

The term "cycloalkenylalkyl" as used herein, means a cycloalkenyl group as defined herein, appended to the parent molecular moiety through an alkylene group, as defined herein.

The term "cycloalkyl" as used herein, means a monocyclic, a bicyclic, a tricyclic, a spirocyclic, or a bridged ring system. The monocyclic cycloalkyl is a carbocyclic ring system containing 3, 4, 5, 6, 7, or 8 carbon atoms, zero heteroatoms and zero double bonds. Examples of monocyclic ring systems include cyclopropyl, cyclobutyl, cyclopentyl, cyclohexyl, cycloheptyl, and cyclooctyl. Bicyclic ring systems are exemplified by a monocyclic cycloalkyl ring fused to a monocyclic cycloalkyl ring. Representative examples of bicyclic ring systems include, but are not limited to, bicyclo[4.1.0]heptane, bicyclo[6.1.0]nonane, octahydroindene, and decahydronaphthalene. The tricyclic cycloalkyl is exemplified by a bicyclic cycloalkyl fused a monocyclic cycloalkyl ring. An example of a tricyclic cycloalkyl is decahydrocyclopropa[f]indene. Spirocyclic cycloalkyl is exemplified by a monocyclic cycloalkyl ring wherein two of the substituents on the same carbon atom of the ring, form a 3-, 4-, 5-, or 6-membered monocyclic cycloalkyl. An example of a spirocyclic cycloalkyl is spiro[2.5]octane. Bridged cycloalkyl is exemplified by a monocyclic cycloalkyl, a bicyclic cycloalkyl or a tricyclic cycloalkyl, wherein two non adjacent carbon atoms of the group are linked by an alkylene bridge of 1, 2, 3, or 4 carbon atoms, or linked by an alkenylene bridge of 2, 3, or 4 carbon atoms. The bridged monocyclic cycloalkyl can also contain an additional alkylene bridge of 1, 2, 3, or 4 carbon atoms, linking two non adjacent carbon toms of the group. Representative examples of bicyclic ring systems include, but are not limited to, bicyclo [3.1.1]heptane, bicyclo[2.2.1]heptane, bicyclo[2.2.2]octane, bicyclo[3.2.2]nonane, bicyclo[3.3.1]nonane, and bicyclo [4.2.1]nonane, tricycle[$2.2.1.0^{2,6}$]heptane, tricyclo[$3.3.1.0^{3,7}$]nonane (noradamantane or octahydro-2,5-methanopentalene), and tricyclo[$3.3.1.1^{3,7}$]decane (adamantane). The monocyclic, bicyclic, tricyclic, spirocyclic and bridged cycloalkyl groups of the present invention can be appended to the parent molecular moiety through any substitutable carbon atom of the groups.

The term "cycloalkylalkyl" as used herein, means a cycloalkyl group, as defined herein, appended to the parent molecular moiety through an alkylene group, as defined herein. Representative examples of cycloalkylalkyl include, but are not limited to, cyclobutylmethyl, 2-cyclohexylethyl, cyclopentylmethyl, cyclohexylmethyl, cyclopropylmethyl, and 1-cyclopropylethyl.

The term "formyl" as used herein, means a —C(O)H group.

The term "formylalkyl" as used herein, means a formyl group, as defined herein, appended to the parent molecular moiety through an alkylene group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means an alkoxy group, as defined herein, in which one, two, three, four, five or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkyl" as used herein, means an haloalkoxy group, as defined herein, appended to the parent molecular moiety through an alkylene group, as defined herein. An example of haloalkoxyalkyl is 2-(2,2,2-trifluoroethoxy)ethyl.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, trifluoromethyl, 2,2,2-trifluoroethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring containing at least one heteroatom independently selected from the group consisting of O, N, and S. The 5-membered ring contains two double bonds and one, two, three, or four heteroatoms. The 6 membered ring contains three double bonds and one, two, three or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl, thienopyridine and thienopyridinyl. The monocyclic and the bicyclic heteroaryl groups are connected to the parent molecular moiety through any substitutable carbon atom or any substitutable nitrogen atom contained within the groups.

The term "heteroarylalkyl" as used herein, means a heteroaryl, as defined herein, appended to the parent molecular moiety through an alkylene group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, thien-3-ylmethyl, 3-thienylpropyl, pyridinylmethyl, and 2-(1H-indolyl)ethyl.

The term "heteroarylcarbonyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heteroaryloxy" as used herein, means a heteroaryl group, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy, and thien-3-yloxy.

The term "heteroaryloxyalkyl" as used herein, means a heteroaryloxy group, as defined herein, appended to the parent molecular moiety through an alkylene group, as defined herein. Representative examples of heteroaryloxyalkyl include, but are not limited to, pyridin-3-yloxymethyl and 2-quinolin-3-yloxyethyl.

The term "heteroarylsulfonyl," as used herein, means a heteroaryl group, as defined herein, appended to the parent molecular moiety through a sulfonyl group, as defined herein.

The term "heterocycle" or "heterocyclic" as used herein, refers to a monocyclic, a bicyclic, a tricyclic, a spirocyclic or a bridged ring system which contains at least one heteroatom. The monocyclic heterocycle is a 3, 4, 5, 6, 7, or 8-membered ring containing at least one heteroatom independently selected from the group consisting of O, N, and S. The 3 or 4 membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6, 7, or 8-membered ring contains zero, one, or two double bonds, and one, two, or three heteroatoms in the ring selected from the group consisting of O, N and S. Representative examples of monocyclic heterocycle include, but are not limited to, azetidinyl, azepanyl, aziridinyl, diazepanyl, 1,3-dioxanyl, 1,4-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle of the present invention is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle means a 4,5-, 6-, 7-, or 8-membered monocyclic heterocycle ring wherein two of the substituents on the same carbon atom form a 4-, 5-, or 6-membered monocyclic cycloalkyl, wherein the cycloalkyl is optionally substituted with 1, 2, 3, 4, or 5 alkyl groups. One example of a spiroheterocycle is 5-oxaspiro[3,4]octane. The tricyclic heterocycle is a bicyclic heterocycle fused to a phenyl, or a bicyclic heterocycle fused to a monocyclic cycloalkyl, or a bicyclic heterocycle fused to a monocyclic cycloalkenyl, or a bicyclic heterocycle fused to a monocyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl. Bridged heterocycle is exemplified by a monocyclic heterocycle, a bicyclic heterocycle or a tricyclic heterocycle, wherein two non adjacent carbon atoms of the group are linked by an alkylene bridge of 1, 2, 3, or 4 carbon atoms, or linked by an alkenylene bridge of 2, 3, or 4 carbon atoms. The bridged monocyclic heterocycle can also contain an additional alkylene bridge of 1, 2, 3, or 4 carbon atoms, linking two non adjacent carbon toms of the group. Representative examples of bridged heterocycle include, but are not limited to, 2-oxatricyclo[3.3.1.1$^{3,7}$]decane, octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane. The monocyclic, bicyclic, tricyclic, spirocyclic and bridged heterocycle groups are connected to the parent molecular moiety through any substitutable carbon atom or any substitutable nitrogen atom contained within the group.

The term "heterocyclealkyl" as used herein, means a heterocycle, as defined herein, appended to the parent molecular moiety through an alkylene group, as defined herein. Representative examples of heterocyclealkyl include, but are not limited to, tetrahydropyranylmethyl, 2-morpholinylethyl, and tetrahydrofuranylmethyl.

The term "heterocyclecarbonyl" as used herein, means a heterocycle, as defined herein, appended to the parent molecular moiety through a carbonyl group, as defined herein.

The term "heterocyclecarbonylalkyl" as used herein, means a heterocyclecarbonyl, as defined herein, appended to the parent molecular moiety through an alkylene group, as defined herein.

The term "heterocycleoxy" as used herein, means a heterocycle group, as defined herein, appended to the parent molecular moiety through an oxygen atom. Representative examples of heterocycleoxy include, but are not limited to, 2,3-dihydro-1,4-benzodioxinyloxy, pyridin-3-yloxy and quinolin-3-yloxy.

The term "heterocycleoxyalkyl" as used herein, means a heterocycleoxy group, as defined herein, appended to the parent molecular moiety through an alkylene group, as defined herein. An example of heterocycleoxyalkyl is 2-(2,3-dihydro-1,4-benzodioxinyloxy)ethyl.

The term "heterocyclesulfonyl," as used herein, means a heterocycle group, as defined herein, appended to the parent molecular moiety through a sulfonyl group, as defined herein.

The term "hydroxy" or "hydroxyl," as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, 2-ethyl-4-hydroxyheptyl and 2-methyl-propanol.

The term "hydroxy-protecting group" or "O-protecting group" means a substituent which protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "oxo" as used herein, means a =O moiety.

The term "sulfinyl" as used herein, means a —S(O)— group.

The term "sulfonyl" as used herein, means a —SO$_2$— group.

The term "tautomer" as used herein means a proton shift from one atom of a compound to another atom of the same compound wherein two or more structurally distinct compounds are in equilibrium with each other.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like. Prodrugs of the present invention may be rapidly transformed in vivo to compounds of the invention, for example, by hydrolysis in blood.

DETAILED DESCRIPTION

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

In compounds of formula (I), $R_1$ is alkyl, alkenyl, alkoxyalkyl, alkoxyalkoxyalkyl, alkoxycarbonylalkyl, alkynyl, arylalkoxyalkyl, arylalkyl, aryloxyalkyl, carboxyalkyl, cycloalkyl, cycloalkylalkyl, haloalkyl, haloalkoxyalkyl, heteroarylalkyl, heteroaryloxyalkyl, heterocycle, heterocyclealkyl, heterocycleoxyalkyl, hydroxyalkyl, or $R_aR_bN$-alkylene-; wherein $R_a$, $R_b$, and the optional substituents of the aryl, cycloalkyl, heteroaryl, and heterocycle moieties are as described in the Summary. In one embodiment, $R_1$ is alkyl, alkenyl, alkoxyalkyl, alkoxyalkoxyalkyl, alkoxycarbonylalkyl, alkynyl, arylalkoxyalkyl, arylalkyl, aryloxyalkyl, carboxyalkyl, haloalkyl, haloalkoxyalkyl, hydroxyalkyl, or $R_aR_bN$-alkylene-, wherein $R_a$, $R_b$, and the optional substituents of the aryl moiety are as described in the Summary. Examples of aryl moiety include, but are not limited to, phenyl and naphthyl, each of which is optionally substituted as described in the Summary. Other examples of compounds of formula (I) are those wherein $R_1$ is cycloalkyl or cycloalkylalkyl wherein the cycloalkyl moiety is optionally substituted as described in the Summary. Examples of the cycloalkyl moiety include, but are not limited to, cyclobutyl, cyclopentyl, and cyclohexyl, each of which is independently unsubstituted or substituted as described in the Summary. Yet other examples of compounds of formula (I) include those wherein $R_1$ is heteroarylalkyl, heteroaryloxyalkyl, heterocycle, heterocyclealkyl, or heterocycleoxyalkyl, wherein the heteroaryl and heterocycle moieties are independently unsubstituted or substituted as described in the Summary. Embodiments of the present invention include, but are not limited to, those wherein $R_1$ is heteroarylalkyl, heterocyclealkyl, or heterocycleoxyalkyl, wherein the heteroaryl and heterocycle moieties are independently unsubstituted or substituted as described in the Summary. Examples of the heteroaryl moiety include, but are not limited to, indolyl and pyridinyl, each of which is independently unsubstituted or substituted as described in the Summary. Examples of the heterocycle moiety include, but are not limited to, tetrahydrofuranyl, tetrahydropyranyl, 1,4-dioxanyl, morpholinyl, and 1,4-benzodioxinyl, each of which is independently unsubstituted or substituted as described in the Summary. Optional substituents of the aryl, heteroaryl, cycloalkyl, and heterocycle moieties are, for example, alkoxy, alkyl, cyano, halo, haloalkoxy, hydroxy, and —$NZ_1Z_2$ wherein $Z_1$ and $Z_2$ are as described in the Summary.

$R_2$ and $R_3$ can be the same of different, and are as described in the Summary. In one embodiment, $R_2$ and $R_3$ are independently hydrogen, alkoxy, alkoxycarbonyl, alkoxycarbonylalkyl, azidoalkyl, alkyl, alkylcarbonyl, alkylsulfonyl, aryl, arylalkyl, arylalkenyl, cyano, cycloalkyl, cycloalkenyl, halo, haloalkyl, heteroaryl, heterocycle, —$(CR_jR_k)_n$—$OR_p$, —C(O)H, $R_cR_dN$—, $R_cR_dN$-alkylene-, $R_eR_fNC(O)$—, or $R_8$-$R_7$, with the proviso that when $R_1$ is cycloalkylalkyl, and $L_2$ is a single bond, then $R_2$ and $R_3$ are not both alkyl, and wherein n, $R_j$, $R_k$, $R_p$, $R_c$, $R_d$, $R_e$, $R_f$, and the optional substituents of aryl, cycloalkyl, cycloalkenyl, heteroaryl, and heterocycle moieties are as described in the Summary. Examples of the optional substituents of the aryl, cycloalkyl, cycloalkenyl, heteroaryl, and heterocycle moieties include, but are not limited to, alkoxy, alkyl, cyano, halo, haloalkoxy, hydroxy, and —NZ$_1$Z$_2$ wherein Z$_1$ and Z$_2$ are as described in the Summary. Examples of the aryl moiety include, but are not limited to, phenyl and naphthyl. Examples of the cycloalkyl moiety include, but are not limited to, cyclopropyl and cyclohexyl. Examples of the heteroaryl moiety include, but are not limited to, furanyl, pyridinyl, quinolinyl, benzothienyl, indolyl, pyrimidinyl, pyrazolyl. Examples of the heterocycle moiety include, but are not limited to, 1,3-benzodioxolyl. The cycloalkenyl moiety is, for example, cyclohexenyl. R$_7$ and R$_8$ are, for example, phenyl. R$_j$ and R$_k$ are the same or different and are, for example, hydrogen, alkyl such as C$_{1-6}$ alkyl (for example, methyl), or haloalkyl (for example, trifluoromethyl). m is, for example, 1.

In another embodiment, R$_2$ and R$_3$, together with the carbon atoms to which they are attached, form a 4-, 5-, 6-, or 7-membered monocyclic ring as described in the Summary. Embodiments of the present invention include compounds of formula (I) wherein R$_2$ and R$_3$, together with the carbon atoms to which they are attached, form a monocyclic ring as described in the Summary, containing zero heteroatoms in the ring. Non-limiting examples of such monocyclic ring are as represented by formulae (i), (ii), (iii), (iv), (v), (vi), and (vii).

Embodiments of the present invention include those wherein R$_2$ and R$_3$, together with the carbon atoms to which they are attached, form a monocyclic ring as described in the Summary, containing zero or one additional double bond, zero oxygen atom and zero nitrogen atom as ring atoms; and two non-adjacent atoms of said monocyclic ring are linked by an alkenylene bridge of 2, 3, or 4 carbon atoms, or linked by an alkylene bridge of 1, 2, 3, or 4 carbon atoms. Examples include, but are not limited to, (v), (vi) and (vii).

Embodiments of the present invention include those wherein R$_2$ and R$_3$, together with the carbon atoms to which they are attached, form a monocyclic ring as described in the Summary, containing zero or one additional double bond, and one oxygen atom and zero or one nitrogen atom as ring atoms. Examples of such monocyclic ring include, but are not limited to, formula (viii)-(xxii).

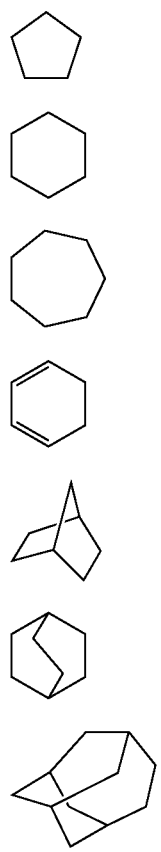

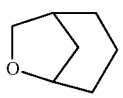
(xx)

(xxi)

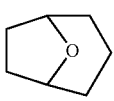
(xxii)

Each monocyclic ring formed by $R_2$, $R_3$, and the carbon atoms to which they are attached is independently unsubstituted or substituted as described in the Summary, and two substituents on the same carbon atom, together with the carbon atom to which they are attached optionally form a monocyclic cycloalkyl as described in the Summary. Such rings are optionally fused with a benzo or a monocyclic heteroaryl (for example, 1,3,4-oxadiazole, pyrrole, furan, and the like).

$R_4$ is a bridged cycloalkyl or a bridged heterocycle, optionally substituted as described in the Summary.

In one embodiment, $R_4$ is a bridged cycloalkyl, optionally substituted as described in the Summary. Examples of some of these bridged cycloalkyls include, but are not limited to, those that are represented by formulae (xxiii)-(xxxi):

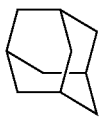
(xxiii)

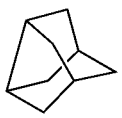
(xxiv)

(xxv)

(xxvi)

(xxvii)

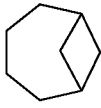
(xxviii)

(xxix)

(xxx)

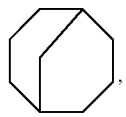
(xxxi)

each of which is independently unsubstituted or substituted as described in the Summary.

In another embodiment $R_4$ is a bridged heterocycle optionally substituted as described in the Summary. Examples of some of these bridged heterocycles include, but are not limited to, those that are represented by formula (xxxii), (xxxiii), (xxxiv), (xxxv), (xxxvi) or (xxxvii):

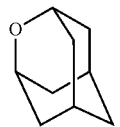
(xxxii)

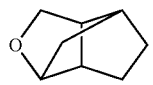
(xxxiii)

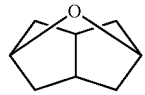
(xxxiv)

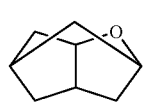
(xxxv)

(xxxvi)

(xxxvii)

each of which is independently unsubstituted or substituted as described in the Summary.

$L_2$ is a single bond, alkylene, $-NR_g-$ or $-NR_g-$alkylene- wherein the alkylene moiety is attached to $R_4$ of formula (I) and $R_g$ is hydrogen or alkyl. Examples of compounds include those wherein $L_2$ is a single bond. Other examples include those wherein $L_2$ is $-NR_g-$. Yet other examples include those wherein $L_2$ is $-NR_g-$alkylene-. Further examples are those wherein $L_2$ is alkylene. Embodiments of compounds of the invention include those wherein $R_g$ is hydrogen.

It is appreciated that the present invention contemplates compounds of formula (I) with combinations of the above embodiments, including particular, more particular and preferred embodiments.

Accordingly, one aspect of the invention relates to a group of compounds of formula (I), or pharmaceutically acceptable salts thereof, wherein $R_4$ is an optionally substituted bridged heterocycle, and $R_1$ is alkyl, alkenyl, alkoxyalkyl, alkoxyalkoxyalkyl, alkoxycarbonylalkyl, alkynyl, arylalkoxyalkyl, arylalkyl, aryloxyalkyl, carboxyalkyl, haloalkyl, haloalkoxyalkyl, hydroxyalkyl, or $R_aR_bN$-alkylene-, wherein $R_2$, $R_3$, $L_2$, $R_a$, $R_b$, and the optional substituents of the bridged heterocycle and the aryl moiety are as disclosed in the Summary. Examples of the aryl moiety include, but are not limited to, phenyl and naphthyl.

Yet another aspect of the invention relates to a group of compounds of formula (I), or pharmaceutically acceptable salts thereof, wherein $R_4$ is an optionally substituted bridged heterocycle, and $R_1$ is cycloalkyl or cycloalkylalkyl wherein $R_2$, $R_3$, $L_2$, and the optional substituents of the bridged heterocycle and the cycloalkyl moiety are as described in the Summary. Examples of the cycloalkyl moiety include, but are not limited to, cyclobutyl, cyclopentyl, and cyclohexyl.

Yet another aspect of the invention relates to a group of compounds of formula (I), or pharmaceutically acceptable salts thereof, wherein $R_4$ is an optionally substituted bridged heterocycle, and $R_1$ is heteroarylalkyl, heterocyclealkyl, or heterocycleoxyalkyl, and $R_2$, $R_3$, $L_2$, the optional substituents of the bridged heterocycle, and the optional substituents of the heteroaryl and heterocycle moieties are as described in the Summary. Examples of the heteroaryl include, but are not limited to, indolyl and pyridinyl. Examples of the heterocycle moiety of the heterocyclealkyl and the heterocycleoxyalkyl as represented by $R_1$ include, but are not limited to, tetrahydrofuranyl, tetrahydropyranyl, 1,4-dioxanyl, morpholinyl, and 1,4-benzodioxinyl.

Examples of the optionally substituted bridged heterocycle of $R_4$ include, but are not limited to, formulae (xxxii), (xxxiii), (xxxiv), (xxxv), (xxxvi) and (xxxvii), each of which is optionally substituted as described in the Summary.

Yet another aspect of the invention relates to a group of compounds of formula (I), or pharmaceutically acceptable salts thereof, wherein $R_4$ is an optionally substituted bridged cycloalkyl, and $R_1$ is alkyl, alkenyl, alkoxyalkyl, alkoxyalkoxyalkyl, alkoxycarbonylalkyl, alkynyl, arylalkoxyalkyl, arylalkyl, aryloxyalkyl, carboxyalkyl, haloalkyl, haloalkoxyalkyl, hydroxyalkyl, or $R_aR_bN$-alkylene-, wherein $R_2$, $R_3$, $L_2$, $R_a$, $R_b$, and the optional substituents of the bridged cycloalkyl and the aryl moiety are as disclosed in the Summary. Examples of the aryl moiety include, but are not limited to, phenyl and naphthyl.

Yet another aspect of the invention relates to a group of compounds of formula (I), or pharmaceutically acceptable salts thereof, wherein $R_4$ is an optionally substituted bridged cycloalkyl, and $R_1$ is cycloalkyl or cycloalkylalkyl wherein $R_2$, $R_3$, $L_2$, and the optional substituents of the bridged cycloalkyl and the cycloalkyl moiety are as described in the Summary. Examples of the cycloalkyl moiety of $R_1$ include, but are not limited to, cyclobutyl, cyclopentyl, and cyclohexyl.

A further aspect of the invention relates to a group of compounds of formula (I), or pharmaceutically acceptable salts thereof, wherein $R_4$ is an optionally substituted bridged cycloalkyl, and $R_1$ is heteroarylalkyl, heterocyclealkyl, or heterocycleoxyalkyl, and $R_2$, $R_3$, $L_2$, the optional substituents of the bridged cycloalkyl, and the optional substituents of the heteroaryl and the heterocycle moieties are as described in the Summary. Examples of heteroaryl moiety include, but are not limited to, indolyl and pyridinyl. Examples of heterocycle moiety include, but are not limited to, tetrahydrofuranyl, tetrahydropyranyl, 1,4-dioxanyl, morpholinyl, and 1,4-benzodioxinyl.

Examples of the optionally substituted bridged cycloalkyl of $R_4$ include, but are not limited to, formulae (xxiii)-(xxxi), each of which is optionally substituted as described in the Summary.

For all the above embodiments, examples of a subgroup include those wherein $R_2$ and $R_3$ are the same or different, and are independently hydrogen, alkoxy, alkoxycarbonyl, alkoxycarbonylalkyl, azidoalkyl, alkyl, alkylcarbonyl, alkylsulfonyl, aryl, arylalkyl, arylalkenyl, cyano, cycloalkyl, cycloalkenyl, halo, haloalkyl, heteroaryl, heterocycle, $-(CR_jR_k)_n-OR_p$, $-C(O)H$, $R_cR_dN-$, $R_cR_dN$-alkylene-, $R_eR_fNC(O)-$, or $R_8$-$R_7$, with the proviso that when $R_1$ is cycloalkylalkyl, and $L_2$ is a single bond, then $R_2$ and $R_3$ are not both alkyl, and wherein n, $R_j$, $R_k$, $R_p$, $R_c$, $R_d$, $R_e$, $R_f$ and the optional substituents of the aryl, the cycloalkyl, the cycloalkenyl, the heteroaryl, and the heterocycle moieties are as described in the Summary.

Other examples of a subgroup include those wherein $R_2$ and $R_3$, together with the carbon atoms to which they are attached, form a 4-, 5-, 6-, or 7-membered monocyclic ring as described in the Summary. Examples of the monocyclic ring include, but are not limited, to formulae (i)-(xxii), each of which is optionally substituted as described in the Summary, and two substituents on the same carbon atom, together with the carbon atoms to which they are attached, optionally form a monocyclic cycloalkyl as described in the Summary. Each of the formulae (i)-(xxii) is optionally fused to a benzo group or a monocyclic heteroaryl (for example, oxadiazole, pyrrole, or furan).

Yet other examples of a subgroup include those wherein $R_2$ and $R_3$, together with the carbon atoms to which they are attached, form a monocyclic ring as described in the Summary, containing zero heteroatoms in the ring. Non-limiting examples of such monocyclic ring are as represented by formulae (i), (ii), (iii), (iv), (v), (vi), and (vii), each of which is optionally fused to a benzo or a monocyclic heteroaryl ring such as, but are not limited to, pyrrole, furan or oxadiazole, and each of which is independently unsubstituted or substituted as described in the Summary, and two substituents on the same carbon atom, together with the carbon atoms to which they are attached, optionally form a monocyclic cycloalkyl as described in the Summary.

Further examples of a subgroup include those wherein $R_2$ and $R_3$, together with the carbon atoms to which they are attached, form a monocyclic ring as described in the Summary, containing zero or one additional double bond, zero oxygen atom and zero nitrogen atom as ring atoms; and two non-adjacent atoms of said monocyclic ring are linked by an alkenylene bridge of 2, 3, or 4 carbon atoms, or linked by an alkylene bridge of 1, 2, 3, or 4 carbon atoms. Examples include, but are not limited to, (v), (vi) and (vii), each of which is optionally fused to a benzo or a monocyclic heteroaryl ring such as, but are not limited to, pyrrole, furan or oxadiazole, and each of which is independently unsubstituted or substituted as described in the Summary, and two substituents on the same carbon atom, together with the carbon atoms to which they are attached, optionally form a monocyclic cycloalkyl as described in the Summary.

Further examples of a subgroup include those wherein $R_2$ and $R_3$, together with the carbon atoms to which they are attached, form a monocyclic ring as described in the Summary, containing zero or one additional double bond, and one oxygen atom and zero or one nitrogen atom as ring atoms. Examples of such monocyclic ring include, but are not limited to, formula (viii)-(xxii), each of which is optionally fused to a benzo or a monocyclic heteroaryl ring such as, but are not limited to, pyrrole, furan or oxadiazole, and each of which is independently unsubstituted or substituted as described in the Summary, and two substituents on the same carbon atom, together with the carbon atoms to which they are attached, optionally form a monocyclic cycloalkyl as described in the Summary.

For all the above embodiments, examples of the optional substituents of the aryl, the heteroaryl, the cycloalkyl, and the heterocycle moieties are, for example, alkoxy, alkyl, cyano, halo, haloalkoxy, hydroxy, and —$NZ_1Z_2$ wherein $Z_1$ and $Z_2$ are as described in the Summary.

For all the above embodiments, examples include those wherein $L_2$ is a single bond. Yet other examples are those wherein $L_2$ is —$NR_g$— wherein $R_g$ is hydrogen or alkyl. Further examples are those wherein $L_2$ is —$NR_g$-alkylene- and $R_g$ is hydrogen or alkyl. Yet further examples are those wherein $L_2$ is alkylene. Particularly, $R_g$ is hydrogen.

For all the foregoing embodiments, the aryl, the heteroaryl, the heterocycle, the cycloalkyl, and the cycloalkenyl moieties, as represented by $R_2$ and $R_3$, have the meanings as discussed herein above.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers and mixtures of various ratio thereof and are included within the scope of this invention. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or heterocycle are designated as being of cis or trans configuration.

Within the present invention it is to be understood that compounds disclosed herein may exhibit the phenomenon of tautomerism Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Abbreviations

Abbreviations which have been used in the descriptions of the Schemes and the Examples that follow are: DME for dimethoxyethane, DMF for N,N-dimethylformamide; EtOAc for ethyl acetate, EtOH for ethanol, HATU for O-(7-azabenzotriazol-1-yl)-N,N,N',N'-tetramethyluronium hexafluorophosphate, $Et_2O$ for diethyl ether, $Et_3N$ for triethylamine, HPLC for high pressure liquid chromatography, MeOH for methanol, min for minute or minutes DMSO for dimethylsulfoxide; TFA for trifluoroacetic acid, THF for tetrahydrofuran; Ts for p-$CH_3PhS(O)_2O$—; Tf or triflate for $CF_3S(O)_2O$—, and HOBt. for 1-hydroxybenzotriazole hydrate.

Methods for Preparing Compounds

This invention is intended to encompass compounds of the invention when prepared by synthetic processes or by metabolic processes. Preparation of the compounds of the invention by metabolic processes include those occurring in the human or animal body (in vivo) or processes occurring in vitro.

The compounds and processes of the present invention will be better understood in connection with the following synthetic Schemes and Examples which illustrate a means by which the compounds of the present invention can be prepared.

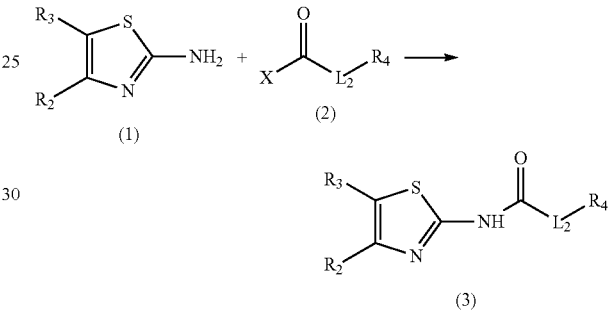

Scheme 1

As shown in Scheme 1, compounds of formula (1), containing an amine group, which are either commercially available or are made according to the Schemes and procedures described within the scope of this document or publications incorporated by reference, when treated with compounds of formula (2), wherein X is chloro or —OH under acid coupling conditions known to one skilled in the art, will provide compounds of formula (3). Typical conditions for the reaction of compounds of formula (2) wherein X is chloro and compounds of formula (1) include, but are not limited to, stirring an equimolar mixture of the compounds in solvents such as chloroform, dichloromethane, or THF in the presence of a base such as, but not limited to, diisopropylethylamine at 0-30° C. for 8-24 hours. Examples of coupling of compounds of formula (2), where X is —OH, and compounds of formula (1), include stirring an equimolar mixture of the compounds with a coupling reagent such as but not limited to bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU) along with a coupling auxiliary such as but not limited to 1-hydroxy-7-azabenzotriazole (HOAT) or 1-hydroxybenzotriazole hydrate (HOBT) in the presence or absence of a base such as but not limited to N-methyl morpholine, diisopropylethylamine in solvents such as, but not limited to, THF, N,N-dimethylacetamide, N,N-dimethylformamide, pyridine and chloroform. Typical reactions can be carried out between 0-65° C. or may be carried out in a microwave reactor to facilitate the coupling.

Scheme 2

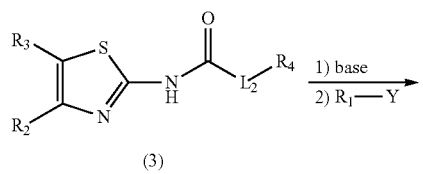

(3)

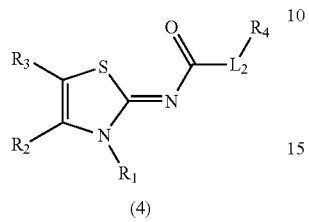

(4)

As shown in Scheme 2, compounds of formula (3) may be converted into compounds of formula (4) which are representative compounds of the present invention. Typical conditions include, but are not limited to, the treatment of compounds of formula (3) with sodium hydride in DMF at 0° C., followed by the addition of reagents such as $R_1$—Y, wherein $R_1$ is as defined in formula (I) and Y is chloro, bromo, iodo, mesyl, triflate or tosyl. Alternatively, other bases such as potassium hydroxide or potassium tert-butoxide in a mixture of THF and DMF, followed by treatment with $R_1$—Y will also provide compounds of formula (4).

Scheme 3

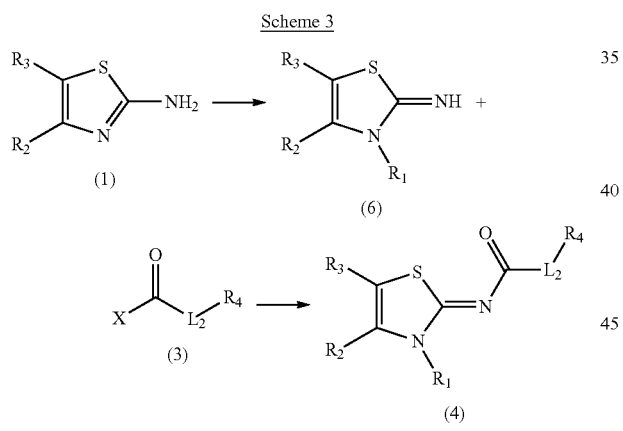

Alternatively, compounds of formula (4) may also be prepared according to the methods outlined in Scheme 3. Compounds of formula (1) when treated with sodium hydride in DMF at 0° C., followed by the addition of reagents such as $R_1$—Y, wherein $R_1$ is as defined in formula (I) and Y is chloro, bromo, iodo, tosyl, mesyl or triflate will provide compounds of formula (6). Alternatively, compounds of formula (1) may be heated neat or in the presence of a minimal amount of solvent to facilitate mixing with compounds of formula $R_1$—Y to obtain compounds of formula (6). Compounds of formula (6) may be isolated as a salt or a free base. The treatment of compounds of formula (6) with compounds of formula (3), wherein X is chloro or —OH, under coupling conditions according to conditions outlined in Scheme 1 will generate compounds of formula (4), which are representative of compounds of the present invention.

Scheme 4

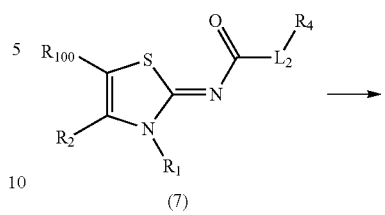

(7)

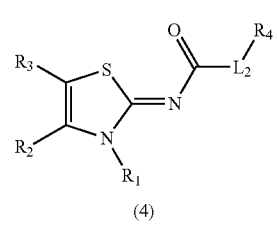

(4)

As outlined in Scheme 4, compounds of formula (7) wherein $R_{100}$ is halide or triflate, which are prepared according to the methods outlined in Schemes 1-3, when treated with a boronic acid of formula $R_3B(OH)_2$, wherein $R_3$ is alkenyl, aryl, arylalkenyl, cycloalkyl, cycloalkenyl, heterocycle, or heteroaryl, a palladium catalyst such as dichlorobis(triphenyl)phosphine)palladium (II) and sodium carbonate in solvents which include but are not limited to DME, ethanol, water or mixtures thereof, under heated conditions will provide compounds of formula (4) which contain alkenyl, aryl, arylalkenyl, cycloalkyl, cycloalkenyl, heterocycle, or heteroaryl substituents in the $R_3$ position.

Scheme 5

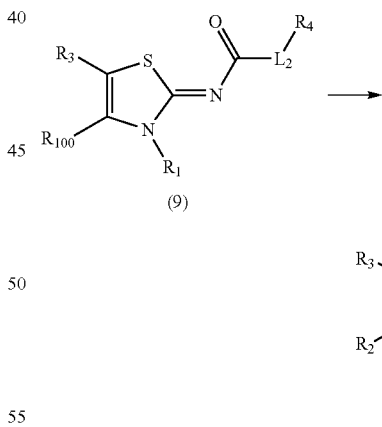

(9)

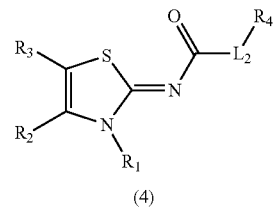

(4)

As outlined in Scheme 5, compounds of formula (9), wherein $R_{100}$ is halide or triflate, which can be prepared according to the methods outlined in Schemes 1-3, when treated with a boronic acid of formula $R_2B(OH)_2$, wherein $R_2$ is alkenyl, aryl, arylalkenyl, cycloalkyl, cycloalkenyl, heterocycle, or heteroaryl and a palladium catalyst according to the methods outlined as Scheme 4 will provide compounds of formula (4) which contain the alkenyl, aryl, arylalkenyl, cycloalkyl, cycloalkenyl, heterocycle, or heteroaryl in the $R_2$ position.

Scheme 6

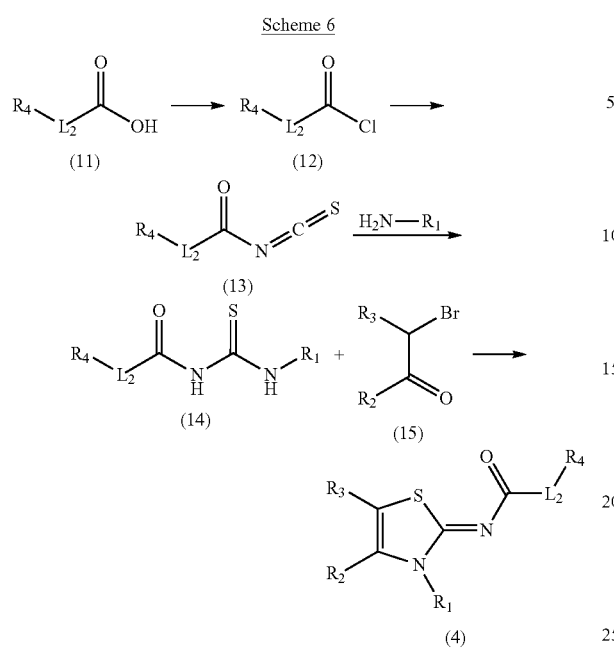

Scheme 6 describes another method of preparation of compounds of formula (4) wherein L₂ is a single bond or alkylene. Compounds of formula (11) when treated with oxalyl chloride in dichloromethane containing a catalytic amount of DMF will provide the acid chloride of formula (12). The acid chloride of formula (12) when treated with potassium thiocyanate in acetone will provide compounds of formula (13). Compounds of formula (13) when treated with an amine of formula R₁—NH₂ in solvents such as, but not limited to, THF will provide compounds of formula (14). Compounds of formula (14) when treated with substituted alpha-bromo-ketones of formula (15) in a solvent such as but not limited to ethanol or mixtures of ethanol and toluene under heated conditions will provide compounds of formula (4).

Scheme 7

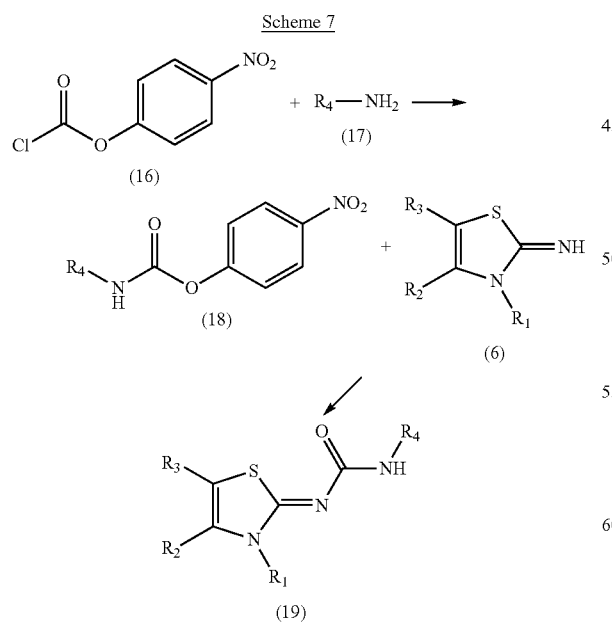

Compounds of formula (I) containing a L₂ group that is —NH—, may be prepared as outlined in Scheme 7. Compounds of formula (16) when treated with an amine of formula (17), wherein R₄ is defined in formula (I), will provide compounds of formula (18). Compounds of formula (18) when treated with compounds of formula (6) will provide compounds of formula (19) which are representative of compounds of formula (I).

Scheme 8

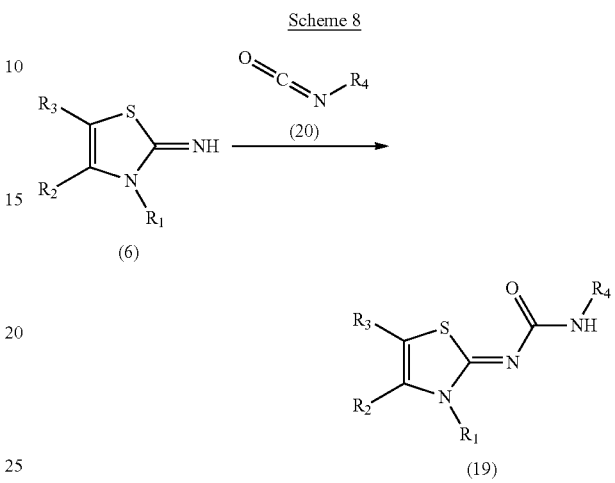

Alternatively, compounds of formula (6) when treated with an isocyanate of formula (20) wherein R₄ is defined in formula (I), will provide compounds of formula (19).

Scheme 9

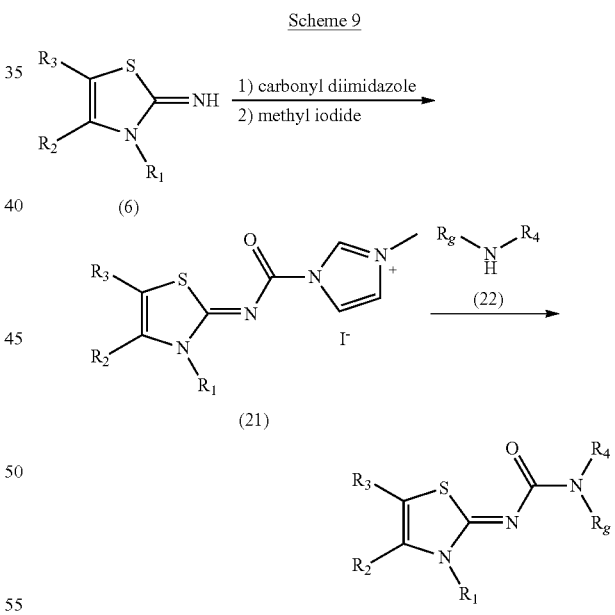

Similarly, compounds of formula (6) when treated with carbonyl diimidazole, followed by treatment with methyl iodide, will provide the imidazolide compounds of formula (21). Compounds of formula (21) when treated with an amine of formula (22), wherein R₄ and R_g are defined in formula (I), will provide compounds of formula (2) which are representative of compounds of formula (I).

Scheme 10

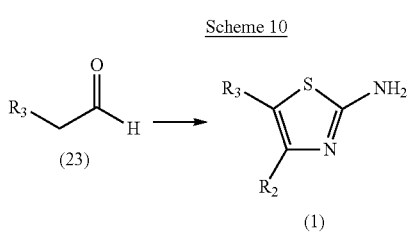

As shown in Scheme 10, compounds of formula (23) wherein $R_3$ is as defined in Formula (I), when treated with pyrrolidine and p-toluenesulfonic acid monohydrate in a solvent such as but not limited to cyclohexane at reflux followed by treatment with sulfur and cyanamide in a solvent such as methanol, will provide compounds of formula (1) wherein $R_2$ is hydrogen.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

EXAMPLES

Example 1

N-[(2Z)-3-(2-methoxyethyl)-1,3-thiazol-2(3H)-ylidene]adamantane-1-carboxamide

Example 1A

N-1,3-thiazol-2-yladamantane-1-carboxamide

To a solution of 2-aminothiazole (6.1 g, 61 mmol) in 250 mL of THF at 0° C. was added a solution of adamantane-1-carbonyl chloride (11 g, 55 mmol) in 25 mL of THF, followed by triethylamine (17 mL, 0.12 mol). The mixture was warmed to 65° C., stirred for 4 hours, and then allowed to cool to ambient temperature. The mixture was diluted with ethyl acetate and washed twice with water and brine. The aqueous washings were combined and extracted with ethyl acetate. The combined organic extracts were dried over magnesium sulfate, filtered and concentrated under reduced pressure. Purification by column chromatography ($SiO_2$, 20-40% ethyl acetate/hexanes gradient) afforded 11 g (78%) of the title compound. $^1$H NMR ($CDCl_3$, 300 MHz) δ ppm 1.68-1.85 (m, 6H), 1.97 (d, J=3.1 Hz, 6H), 2.12 (s, 3H), 6.96 (d, J=3.7 Hz, 1H), 7.44 (d, J=3.4 Hz, 1H), 8.92 (s, 1H); MS (DCI/$NH_3$) m/z 263 (M+H)$^+$.

Example 1B

N-[(2Z)-3-(2-methoxyethyl)-1,3-thiazol-2(3H)-ylidene]adamantane-1-carboxamide

To a solution of Example 1A (0.20 g, 0.76 mmol) in 4 mL of dimethylformamide at 0° C. was added 95% sodium hydride (20 mg, 0.84 mmol). The mixture was stirred at 0° C. for 10 minutes and then warmed to ambient temperature and allowed to stir for an additional 30 minutes. The mixture was cooled to 0° C. and 2-bromoethyl methyl ether (70 μL, 0.68 mmol), (commercially available from Aldrich) was added dropwise. The mixture was warmed to 80° C. and stirred 18 hours. The mixture was quenched with water and diluted with ethyl acetate. The layers were separated and the organic phase was washed twice with water and then brine. The organic extract was dried over magnesium sulfate, filtered, and concentrated under reduced pressure. Purification by column chromatography ($SiO_2$, 50-75% ethyl acetate/hexanes gradient) afforded 34 mg (14%) of the title compound. $^1$H NMR ($CDCl_3$, 300 MHz) δ ppm 1.74 (m, 6H), 1.96-1.97 (m, 6H), 2.03 (br s, 3H), 3.34 (s, 3H), 3.72 (d, J=5.0 Hz, 2H), 4.34 (d, J=5.0 Hz, 2H), 6.52 (d, J=4.7 Hz, 1H), 7.02 (d, J=4.7 Hz, 1H); MS (DCI/$NH_3$) m/z 321 (M+H)$^+$. Anal. Calculated for $C_{17}H_{24}N_2O_2S$: C, 63.72; H, 7.55; N, 8.74. Found: C, 63.49; H, 7.40; N, 8.59.

Example 2

2-(1-adamantyl)-N-[(2E)-3-(2-methoxyethyl)-1,3-thiazol-2(3H)-ylidene]acetamide

Example 2A 3-(2-methoxyethyl)-1,3-thiazol-2(3H)-imine hydrobromide

A mixture of 2-aminothiazole (15 g, 0.15 mol) and 2-bromoethyl methyl ether (17 mL, 0.18 mol) were heated at 85° C. for 16 hours. After cooling to ambient temperature the resulting solid was triturated twice with isopropyl alcohol and collected by filtration to afford 26 g (72%) of the title compound. $^1$H NMR (DMSO-$d_6$, 300 MHz) δ ppm 3.27 (s, 3H), 3.63 (t, J=5.1 Hz, 2H), 4.23 (t, J=4.9 Hz, 2H), 7.02 (d, J=4.7 Hz, 1H), 7.38 (d, J=4.4 Hz, 1H), 9.52 (s, 1H); MS (DCI/NH$_3$) m/z 159 (M+H)$^+$.

Example 2B 2-(1-adamantyl)-N-[(2E)-3-(2-methoxyethyl)-1,3-thiazol-2(3H)-ylidene]acetamide Adamantan-1-yl-acetic acid (39 mg, 0.20 mmol), 3 equivalents of polymer bound dicyclohexylcarbodiimide (PS-DCC), 1-hydroxybenzotriazole hydrate (HOBT, 22 mg, 0.16 mmol), N,N-diisopropylethylamine (62 mg, 0.50 mmol), and the product of Example 2A (39 mg, 0.16 mmol) were combined in dimethylacetamide (DMA, 2.8 mL) and heated in a microwave at 100° C. for 420 seconds. The mixture was filtered through Si-Carbonate (6 mL–1 g cartridge from Silicycle Chemical Division) and then concentrated to dryness). The residue was dissolved in 1:1 DMSO/MeOH and purified by reverse phase HPLC to provide the title compound. $^1$H NMR (500 MHz, DMSO-$d_6$) δ ppm 1.52-1.71 (m, 12H) 1.87-1.94 (m, 3H) 2.15-2.19 (m, 2H) 3.23-3.25 (m, 3H) 3.66 (t, 2H) 4.28 (t, 2H) 6.87 (d, 1H) 7.39 (d, 1H); MS (ESI) m/z 335 (M+H)$^+$.

Example 3

N-[(2Z)-3-(3-methoxypropyl)-1,3-thiazol-2(3H)-ylidene]adamantane-1-carboxamide

Example 3A 3-(3-methoxypropyl)-1,3-thiazol-2(3H)-imine hydrobromide

A mixture of 2-aminothiazole (1.0 g, 10 mmol) and 1-bromo-3-methoxypropane (1.8 g, 12 mmol, commercially available from Aldrich) were heated at 85° C. for 16 hours. The solid was cooled to ambient temperature, triturated with ethanol, and then collected by filtration to afford 1.2 g (48%) of the title compound. MS (DCI/NH$_3$) m/z 173 (M+H)$^+$.

Example 3B

N-[(2Z)-3-(3-methoxypropyl)-1,3-thiazol-2(3H)-ylidene]adamantane-1-carboxamide

To a solution of the product of Example 3A (0.60 g, 2.4 mmol) and 1-adamantanecarboxylic acid (0.43 g, 2.4 mmol) in 12 mL of THF at 0° C. was added O-(7-azabenzotriazol-1-yl)-N,N,N',N'-tetramethyluronium hexafluorophosphate (0.989 g, 2.6 mmol) and diisopropylethylamine (0.836 mL, 4.8 mmol). The mixture was heated to 65° C. for 2.5 hours, cooled to ambient temperature and then diluted with ethyl acetate. The mixture was washed twice with water, saturated aqueous sodium bicarbonate, and brine. The organic phase was dried over magnesium sulfate, and concentrated under reduced pressure. Purification by column chromatography (SiO$_2$, 20-50% ethyl acetate/hexanes gradient) afforded 0.57 g (71%) of the title compound. $^1$H NMR (CDCl$_3$, 300 MHz) δ ppm 1.74 (t, J=2.9 Hz, 6H), 1.97 (d, J=3.1 Hz, 6H), 2.02 (s, 3H), 2.06-2.14 (m, 2H), 3.31-3.37 (m, 2H), 3.33 (s, 3H), 4.26 (t, J=6.6 Hz, 2H), 6.56 (d, J=4.7 Hz, 1H), 6.93 (d, J=4.7 Hz, 1H); MS (DCI/NH$_3$) m/z 335 (M+H)$^+$. Anal. Calculated for $C_{18}H_{26}N_2O_2S$: C, 64.64; H, 7.83; N, 8.38. Found: C, 64.46; H, 8.06; N, 7.99.

Example 4

N-[(2Z)-3-(2-methoxyethyl)-1,3-thiazol-2(3H)-ylidene]hexahydro-2,5-methanopentalene-3a(1H)-carboxamide The product of Example 2A (0.40 g, 2.5 mmol) and hexahydro-2,5-methanopentalene-3a-carboxylic acid (0.45 g, 2.7 mmol) were processed as described in Example 3B. Purification by column chromatography (SiO$_2$, 30-60% ethyl acetate/hexanes gradient) afforded 0.53 g (69%) of the titled compound. $^1$H NMR (CDCl$_3$, 300 MHz) δ ppm 1.58-1.66 (m, 4H), 1.81-1.90 (m, 4H), 2.21 (dd, J=9.5, 2.0 Hz, 2H), 2.31 (s, 2H), 2.70 (t, J=6.6 Hz, 1H), 3.33 (s, 3H), 3.68-3.75 (m, 2H), 4.37 (s, 2H), 6.56 (d, J=4.7 Hz, 1H), 7.06 (d, J=4.7 Hz, 1H); MS (DCI/NH$_3$) m/z 307 (M+H)$^+$. Anal. Calculated for $C_{16}H_{22}N_2O_2S \cdot 0.2H_2O$: C, 62.27; H, 7.34; N, 8.64. Found: C, 62.47; H, 7.54; N, 8.48.

Example 5

3-chloro-N-[(2Z)-3-(2-methoxyethyl)-1,3-thiazol-2(3H)-ylidene]adamantane-1-carboxamide The product of Example 2A (0.40 g, 2.5 mmol) and 3-chloro-adamantane-1-carboxylic acid (0.59 g, 2.8 mmol) were processed as described in Example 3B. Purification by column chromatography (SiO$_2$, 20-40% ethyl acetate/hexanes gradient) afforded 0.36 g (41%) of the title compound. $^1$H NMR (CDCl$_3$, 300 MHz) δ ppm 1.67 (s, 2H), 1.91 (d, J=2.71 Hz, 4H), 2.14 (d, J=3.05 Hz, 4H), 2.21-2.31 (m, 2H), 2.36 (s, 2H), 3.34 (s, 3H), 3.69-3.74 (m, 2H), 4.32-4.39 (m, 2H), 6.57 (d, J=4.75 Hz, 1H), 7.07 (d, J=4.75 Hz, 1H); MS (DCI/NH$_3$) m/z 355 (M+H)$^+$. Anal. Calculated for $C_{17}H_{23}ClN_2O_2S$: C, 57.53; H, 6.53; N, 7.89. Found: C, 57.43; H, 6.40; N, 7.81.

Example 6

N-[(2Z)-3-(2-methoxyethyl)-4-methyl-1,3-thiazol-2(3H)-ylidene]adamantane-1-carboxamide

Example 6A 3-(2-methoxyethyl)-4-methyl-1,3-thiazol-2(3H)-imine hydrobromide

A mixture of 4-methylthiazol-2-ylamine (0.75 g, 6.5 mmol) and 2-bromoethyl methyl ether (73 μL, 7.8 mmol) was heated at 85° C. for 15 hours. The mixture was cooled to ambient temperature and the resulting solid was triturated with isopropanol. Recrystallization from ethanol afforded 0.56 g (34%) of the title compound. $^1$H NMR (DMSO-$d_6$, 300 MHz) δ ppm 2.25 (d, J=1.4 Hz, 3H) 3.25 (s, 3H) 3.57 (t, J=5.1 Hz, 2H) 4.15 (t, J=5.1 Hz, 2H) 6.68 (d, J=1.4 Hz, 1H) 9.40 (s, 1H); MS (DCI/NH$_3$) m/z 173 (M+H)$^+$.

Example 6B

N-[(2Z)-3-(2-methoxyethyl)-4-methyl-1,3-thiazol-2 (3H)-ylidene]adamantane-1-carboxamide The product of Example 6A (0.25 g, 0.99 mmol) and adamantane-1-carboxylic acid (0.20 g, 1.1 mmol) were processed as described in Example 3B. Purification by column chromatography (SiO$_2$, 30-60% ethyl acetate/hexanes gradient) afforded 0.23 g (69%) of the title compound. $^1$H NMR (CDCl$_3$, 300 MHz) δ ppm 1.74 (t, J=2.88 Hz, 6H), 1.98 (d, J=2.37 Hz, 6H), 2.03 (s, 3H), 2.32 (s, 3H), 3.30 (s, 3H), 3.73 (t, J=5.26 Hz, 2H), 4.34 (s, 2H), 6.19 (s, 1H); MS (DCI/NH$_3$) m/z 335 (M+H)$^+$. Anal. Calculated for $C_{18}H_{26}N_2O_2S$: C, 64.64; H, 7.83; N, 8.38. Found: C, 64.48; H, 8.05; N, 8.53.

Example 7 ethyl(2Z)-2-[(1-adamantylcarbonyl)imino]-3-(2-methoxyethyl)-2,3-dihydro-1,3-thiazole-4-carboxylate Example 7A ethyl 2-imino-3-(2-methoxyethyl)-2,3-dihydro-1,3-thiazole-4-carboxylate hydrobromide 2-Aminothiazole-4-carboxylic acid ethyl ester (17.2 g, 100 mmol) and 2-bromoethyl methyl ether (15.3 g, 110 mmol) were processed as described as described in Example 2A to afford 17.1 g (83%) of the title compound. $^1$H NMR (300 MHz, DMSO-$d_6$) δ ppm 1.30 (t, J=7 Hz, 3H) 3.22 (s, 3H) 3.60 (t, J=5 Hz, 2H) 4.32 (t, J=7 Hz, 2H) 4.35-4.61 (m, 2H) 7.84 (s, 1H) 9.76 (s, 1H); MS (DCI/NH$_3$) m/z 231 (M+H)$^+$.

Example 7B ethyl(2Z)-2-[1-adamantylcarbonyl)imino]-3-(2-methoxyethyl)-2,3-dihydro-1,3-thiazole-4-carboxylate The product of Example 7A (6.3 g 27.5 mmol) and 1-adamantanecarboxylic acid (5.45 g, 30.0 mmol) were processed as described in Example 3B to afford 5.8 g (54%) of the title compound. $^1$H NMR (300 MHz, DMSO-$d_6$) δ ppm 1.31 (t, J=7 Hz, 3H) 1.58-1.79 (m, 6H) 1.86 (d, J=2 Hz, 6H) 1.99 (s, 3H) 3.22 (s, 3H) 3.61 (t, J=6 Hz, 2H) 4.31 (q, J=7 Hz, 2H) 4.74 (t, J=6 Hz, 2H) 7.82 (s, 1H); MS (DCI/NH$_3$) m/z 393 (M+H)$^+$. Anal. Calculated for $C_{20}H_{28}N_2O_4S$: C, 61.20; H, 7.19; N, 7.09. Found: C, 61.13; H, 7.26; N, 7.09.

Example 8

N-[(2Z)-4-(hydroxymethyl)-3-(2-methoxyethyl)-1,3-thiazol-2(3H)-ylidene]adamantane-1-carboxamide To a solution of the product of Example 7B (3.68 g, 10.0 mmol) in 100 mL of THF at 0° C. was added lithium borohydride (10 mL of a 2.0 M solution in THF) and the resulting solution was allowed to warm to ambient temperature and stirred overnight. The mixture was quenched with 100 mL of saturated aqueous Na$_2$CO$_3$ and diluted with ethyl acetate (200 mL). The layers were separated and the aqueous phase was extracted with 50 mL ethyl acetate. The combined organic extracts were dried over anhydrous Na$_2$SO$_4$, filtered, and concentrated. Purification by column chromatography (SiO$_2$, 0-50% ethyl acetate/hexanes gradient) afforded 2.6 g (74%) of the title compound. $^1$H NMR (300 MHz, DMSO-$d_6$) δ ppm 1.60-1.76 (m, 6H) 1.85 (d, J=3 Hz, 6H) 1.98 (s, 3H) 3.31 (s, 3H) 3.57-3.72 (m, 2H) 4.32 (t, J=6 Hz, 2H) 4.50 (d, J=5 Hz, 2H) 6.73 (s, 1H); MS (DCI/NH$_3$) m/z 351 (M+H)$^+$.

Example 9

N-[(2Z)-4-(azidomethyl)-3-(2-methoxyethyl)-1,3-thiazol-2(3H)-ylidene]adamantane-1-carboxamide To a solution of Et$_3$N (0.085 mL, 0.60 mmol) in 50 mL THF was added methanesulfonyl chloride (0.044 mL, 0.55 mmol). After 10 minutes, a solution of the product of Example 8 (0.18 g, 0.51 mmol) in 10 mL THF was added and the resulting mixture was stirred for 1 hour at ambient temperature. Sodium azide (0.39 g 6.0 mmol) was added and the mixture was heated to reflux for 2 hours. After cooling to ambient temperature the mixture was diluted with ethyl acetate and was washed twice with water, and brine. The organic phase was dried over magnesium sulfate and concentrated under reduced pressure. Purification by column chromatography (SiO$_2$, 0-50% ethyl acetate/hexanes gradient) afforded 0.148 g (79%) of the title compound. $^1$H NMR (300 MHz, DMSO-$d_6$) δ ppm 1.61-1.76 (m, 6H) 1.85 (d, J=3 Hz, 6H) 1.99 (s, 3H) 3.24 (s, 3H) 3.67 (t, J=5 Hz, 2H) 4.27 (t, J=5 Hz, 2H) 4.59 (s, 2H) 6.99 (s, 1H); MS (DCI/NH$_3$) m/z 365 (M+H)$^+$.

Example 10

N-[(2Z)-4-(aminomethyl)-3-(2-methoxyethyl)-1,3-thiazol-2(3H)-ylidene]adamantane-1-carboxamide To a solution of the product of Example 9 (0.11 g, 0.30 mmol) in 5 mL THF was added triphenylphosphine (0.21 g, 0.60 mmol). The mixture was stirred for 2 hours, water (0.5 mL) was added, and the mixture was heated to reflux for 3 hours. After cooling to ambient temperature the mixture was diluted with ethyl acetate washed twice with water and brine. The organic phase was dried over magnesium sulfate and concentrated under reduced pressure. Purification by column chromatography (SiO$_2$, 0-70% ethyl acetate/hexanes gradient) afforded 0.079 g (76%) of the title compound. $^1$H NMR (300 MHz, DMSO-$d_6$) δ ppm 1.62-1.76 (m, 6H) 1.85 (d, J=2 Hz, 6H) 1.99 (s, 3H) 3.57 (s, 3H) 3.66 (t, J=5 Hz, 2H) 4.12-4.25 (m, 2H) 4.34 (t, J=5 Hz, 2H) 6.94 (s, 1H) 8.42 (s, 2H); MS (DCI/NH$_3$) m/z 350 (M+H)$^+$. Anal. Calculated for $C_{18}H_{27}N_3O_2S$: C, 61.86; H, 7.79; N, 12.02. Found: C, 61.66; H, 7.94; N, 11.68.

Example 11

(2Z)-2-[(1-adamantylcarbonyl)imino]-3-(2-methoxyethyl)-2,3-dihydro-1,3-thiazole-4-carboxamide Example 11A (2Z)-2-[(1-adamantylcarbonyl)imino]-3-(2-methoxyethyl)-2,3-dihydro-1,3-thiazole-4-carboxylic acid To a solution of the product of Example 7 (0.39 g, 10 mmol) in 20 mL of ethanol was added sodium carbonate (0.32 g, 30 mmol) and the mixture was heated at 70° C. overnight. The mixture has diluted with water and the pH was adjusted to 2 with 2 N aqueous HCl and extracted with ethyl acetate. The organic extract was dried over magnesium sulfate and concentrated under reduced pressure. Purification by column chromatography (SiO$_2$, 30-100% ethyl acetate/hexanes gradient) afforded 0.320 g (88%) of the title compound. $^1$H NMR (300 MHz, DMSO-d$_6$) δ ppm 1.62-1.77 (m, 6H) 1.86 (d, J=3 Hz, 6H) 1.99 (s, 3H) 3.24 (s, 3H) 3.58-3.65 (m, 2H) 4.77 (t, J=6 Hz, 2H) 7.77 (s, 1H) 13.67-13.77 (m, 1H); MS (DCI/NH$_3$) m/z 365 (M+H)$^+$.

Example 11B (2Z)-2-[(1-adamantylcarbonyl)imino]-3-(2-methoxyethyl)-2,3-dihydro-1,3-thiazole-4-carboxamide To a solution of the product of Example 11A (0.36 g, 1.0 mmol) in THF (10 mL) was added oxalyl chloride (0.095 mL 1.1 mmol) and a catalytic amount of DMF (2 drops). The solution was stirred for 3 hours then concentrated under reduced pressure. The residue was diluted with THF (10 mL) and concentrated aqueous ammonia (10 mL) was added. After stirring for 1 hour the volatile components were removed under reduced pressure and the mixture was partitioned between EtOAc and water. The phases were separated and the organic extract was washed with brine, dried over anhydrous Na$_2$SO$_4$, filtered, and concentrated. Purification by column chromatography (SiO$_2$, 0-100% ethyl acetate/hexanes gradient) afforded 0.123 g (34%) of the title compound. $^1$H NMR (300 MHz, DMSO-d$_6$) δ ppm 1.60-1.76 (m, 6H) 1.85 (d, J=3 Hz, 6H) 1.99 (s, 3H) 3.22 (s, 3H) 3.60 (t, J=6 Hz, 2H) 4.70 (t, J=6 Hz, 2H) 7.36 (s, 1H) 7.68 (s, 1H) 8.18 (s, 1H); MS (DCI/NH$_3$) m/z 364 (M+H).

Example 12

N-[(2Z)-3-(2-methoxyethyl)-4-{[(methylsulfonyl)amino]methyl}-1,3-thiazol-2(3H)-ylidene]adamantane-1-carboxamide To a solution of the product of Example 10 (0.050 g, 0.14 mmol) in 5 mL of THF and 5.0 mL of triethylamine was added methanesulfonyl chloride (0.035 g, 0.28 mmol) and the resulting mixture was stirred for 16 hours. The mixture was diluted with ethyl acetate and washed twice with water and brine. The organic extract was dried over magnesium sulfate and concentrated under reduced pressure. Purification by column chromatography (SiO$_2$, 0-50% ethyl acetate/hexanes gradient) afforded 0.043 g (70%) of the title compound. $^1$H NMR (300 MHz, DMSO-d$_6$) δ ppm 1.59-1.75 (m, 6H) 1.85 (d, J=3 Hz, 6H) 1.99 (s, 3H) 2.95 (s, 3H) 3.20-3.26 (m, 3H) 3.67 (t, J=5 Hz, 2H) 4.27 (d, J=6 Hz, 2H) 4.31 (t, J=5 Hz, 2H) 6.77 (s, 1H) 7.59-7.64 (m, 1H); MS (DCI/NH$_3$) m/z 364 (M+H)$^+$.

Example 13

N-[(2Z)-3-(2-methoxyethyl)-4-(trifluoromethyl)-1,3-thiazol-2(3H)-ylidene]adamantane-1-carboxamide

Example 13A

N-[(2Z)-4-(trifluoromethyl)-1,3-thiazol-2(3H)-ylidene]adamantane-1-carboxamide

4-Trifluoromethyl-thiazol-2-ylamine (1.0 g, 6.0 mmol) and 1-adamantanecarboxylic acid (1.0 g, 5.5 mmol) were processed as described in Example 3B to afford 0.932 g (51%) of the title compound. $^1$H NMR (300 MHz, DMSO-d$_6$) δ ppm 1.65-1.73 (m, 6H) 1.93 (d, J=3 Hz, 6H) 2.02 (d, 3H) 7.93 (s, 1H); MS (DCI/NH$_3$) m/z 331 (M+H).

Example 13B

N-[(2Z)-3-(2-methoxyethyl)-4-(trifluoromethyl)-1,3-thiazol-2(3H)-ylidene]adamantane-1-carboxamide To a solution of the product of Example 13A (0.33 g, 1.0 mmol) in 5 mL DMF was added NaH (60% dispersion in mineral oil, 0.085 g, 2.1 mmol). After 10 minutes 2-bromoethyl methyl ether (0.15 g, 11 mmol) was added and mixture was heated at 100° C. for 30 minutes. The mixture was cooled to ambient temperature, diluted with ether, and washed with brine (10×10 mL). The combined ether extract was dried over magnesium sulfate, filtered and concentrated under reduced pressure. Purification by column chromatography (SiO$_2$, 0-60% ethyl acetate/hexanes gradient) afforded 0.061 g (16%) of the title compound. $^1$H NMR (300 MHz, DMSO-d$_6$) δ ppm 1.70 (s, 6H) 1.87 (d, J=3 Hz, 6H) 2.00 (s, 3H) 3.26 (s, 3H) 3.73 (t, J=6 Hz, 2H) 4.30 (t, J=6 Hz, 2H) 7.83 (s, 1H); MS (DCI/NH$_3$) m/z 389 (M+H)$^+$.

Example 14

N-[(2Z)-4-(2,4-difluorophenyl)-3-(2-methoxyethyl)-1,3-thiazol-2(3H)-ylidene]hexahydro-2,5-methano-pentalene-3a(1H)-carboxamide

Example 14A

Hexahydro-2,5-methano-pentalene-3a-carbonyl chloride

To a solution of commercially available hexahydro-2,5-methano-pentalene-3a-carboxylic acid (10 g, 0.06 mol) in dichloromethane (200 mL) was added oxalyl chloride (8.7 g, 0.066 mol). The mixture was stirred overnight and then concentrated under reduced pressure to afford the title compound as a colorless oil (11 g, 99%). MS (DCI/NH$_3$) m/z 184 (M+H)$^+$.

Example 14B 1-(Hexahydro-2,5-methano-pentalene-3a-carbonyl)-3-(2-methoxyethyl)-thiourea To a solution of example 14A (2.0 g, 10.8 mmol) in dry acetone was added potassium thiocyanate (1.05 g, 10.8 mmol). The mixture was stirred overnight at room temperature, then filtered, and concentrated under reduced pressure. The residue was dissolved in THF (50 mL) and 2-methoxyethylamine (0.81 g, 10.8 mmol) was added. The mixture was stirred for 8 hours at room temperature and then concentrated. Purification by column chromatography (SiO$_2$, 25% ethyl acetate: 75% hexanes) afforded 0.60 g (20%) of the title compound. MS (ESI$^+$) m/z 283 (M+H)$^+$.

Example 14C

Hexahydro-2,5-methano-pentalene-3a-carboxylic acid[4-(2,4-difluoro-phenyl)-3-(2-methoxyethyl)-3H-thiazol-2-ylidene]-amide To a solution of example 14B (0.21 g, 0.75 mmol) in ethanol (10 mL) was added 2-bromo-1-(2,4-difluorophenyl)

ethanone (0.18 g, 0.75 mmol). The mixture was heated to reflux for 3 hours and then concentrated under reduced pressure. The residue was dissolved in ethyl acetate, washed with 1 M aqueous NaHCO$_3$, dried (Na$_2$SO$_4$), filtered and concentrated. Purification by preparative HPLC on a Waters Symmetry C8 column (40 mm×100 mm, 7 μm particle size) using a gradient of 10% to 100% acetonitrile:ammonium acetate (10 mM) over 15 minutes at a flow rate of 70 mL/minutes provided 65 mg (20%) of the title compound. $^1$H NMR (300 MHz, DMSO-d$_6$) δ ppm 1.47-1.64 (m, 4H), 1.68-1.84 (m, 4H), 2.05-2.20 (m, J=11.5 Hz, 2H), 2.27 (s, 2H), 2.58 (t, J=6.6 Hz, 1H), 3.03 (s, 3H), 3.52 (t, J=5.6 Hz, 2H), 4.07 (t, J=5.4 Hz, 2H), 6.99 (s, 1H), 7.18-7.34 (m, 1H), 7.48 (td, J=9.7, 2.5 Hz, 1H), 7.60 (td, J=8.6, 6.6 Hz, 1H); MS (ESI$^+$) m/z 419 (M+H)$^+$; Anal. Calculated for C$_{22}$H$_{24}$F$_2$N$_2$O$_2$S: C, 63.14; H, 5.78; N, 6.69. Found: C, 63.18; H, 5.80; N, 6.72.

Example 15

N-[(2Z)-3-(2-methoxyethyl)-5-methyl-1,3-thiazol-2 (3H)-ylidene]adamantane-1-carboxamide Example 15A 3-(2-Methoxyethyl)-5-methyl-3H-thiazol-2-ylidene-amine hydrobromide A mixture of 5-methyl-thiazol-2-ylamine (1.0 g, 8.8 mmol) and 2-bromoethyl methyl ether (1.0 mL, 11 mmol) were heated at 85° C. for 16 hours. The mixture was cooled to ambient temperature, triturated with ethanol and the solid was collected by filtration to afford 0.90 g (40%) of the title compound. $^1$H NMR (CDCl$_3$, 300 MHz) δ ppm 2.25 (d, J=1.4 Hz, 3H), 3.36 (s, 3H), 3.72-3.81 (m, 2H), 4.36-4.43 (m, 2H), 6.61 (d, J=1.7 Hz, 1H), 9.54 (s, 1H); MS (DCI/NH$_3$) m/z 173 (M+H)$^+$.

Example 15B

Adamantane-1-carboxylic acid[3-(2-methoxyethyl)-5-methyl-3H-thiazol-2-ylidene]-amide The product of Example 15A (0.21 g, 0.85 mmol) and adamantane-1-carboxylic acid (0.17 g, 0.94 mmol) were processed as described in Example 3B. Purification by column chromatography (SiO$_2$, 30-45% ethyl acetate/hexanes gradient) afforded 0.14 g (48%) of the title compound. $^1$H NMR (CDCl$_3$, 300 MHz) δ ppm 1.73 (t, J=3.0 Hz, 6H), 1.96 (d, J=3.0 Hz, 6H), 1.99-2.08 (m, 3H), 2.24 (d, J=1.36 Hz, 3H), 3.34 (s, 3H), 3.66-3.74 (m, 2H), 4.24-4.30 (m, 2H), 6.69 (s, 1H); MS (DCI/NH$_3$) m/z 335 (M+H)$^+$. Anal. Calculated for C$_{18}$H$_{26}$N$_2$O$_2$S.0.3H$_2$O: C, 64.64; H, 7.83; N, 8.38. Found: C, 63.41; H, 7.74; N, 8.04.

Example 16 methyl (2Z)-2-[(1-adamantylcarbonyl)imino]-3-(2-methoxyethyl)-2,3-dihydro-1,3-thiazole-5-carboxylate Example 16A 2-(Adamantane-1-carbonylimino)-2,3-dihydro-thiazole-5-carboxylic acid methyl ester 2-Amino-thiazole-5-carboxylic acid methyl ester (1.58 g, 10.0 mmole) and 1-adamantanecarboxylic acid (1.98 g, 1.1 mmol) were processed as described in Example 3B to afford 1.26 g (49%) of the title compound. $^1$H NMR (300 MHz, DMSO-d$_6$) δ ppm 1.62-1.79 (m, 6H) 1.86 (d, J=3 Hz, 6H) 1.99 (s, 3H) 3.26 (s, 3H) 3.64-3.81 (s, 3H) 8.30 (s, 1H); MS (DCI/NH$_3$) m/z 321 (M+H).

Example 16B 2-(Adamantane-1-carbonylimino)-3-(2-methoxyethyl)-2,3-dihydro-thiazole-5-carboxylic acid methyl ester The product of Example 16A (0.32 g, 1.0 mmol) and 2-bromoethyl methyl ether (0.15 g, 1.1 mmol) were processed as described in Example 1B to afford 0.097 g (26%) of the title compound. $^1$H NMR (300 MHz, DMSO-d$_6$) δ ppm 1.62-1.79 (m, 6H) 1.86 (d, J=3 Hz, 6H) 1.99 (s, 3H) 3.26 (s, 3H) 3.64-3.75 (m, 2H) 3.81 (s, 3H) 4.37 (t, J=5 Hz, 2H) 8.30 (s, 1H); MS (DCI/NH$_3$) m/z 378 (M+H)$^+$.

Example 17

N-[(2Z)-3-(2-methoxyethyl)-5-phenyl-1,3-thiazol-2 (3H)-ylidene]adamantane-1-carboxamide Example 17A Adamantane-1-carboxylic acid (5-bromothiazol-2-yl)-amide A mixture of 2-amino-5-bromothiazole monohydrobromide (3.00 g, 11.5 mmol), 1-adamantanecarbonyl chloride (2.74 g, 13.8 mmol), 4-dimethylaminopyridine (1.10 g, 0.90 mmol) and triethylamine (3.20 mL, 23.0 mmol) in 100 mL of THF was stirred at 80° C. for 48 hours. The mixture was cooled to ambient temperature, diluted with 100 mL of ethyl acetate and washed with brine. The layers were separated and the aqueous phase was extracted with 2×50 mL ethyl acetate. The combined organic extracts were dried over anhydrous Na$_2$SO$_4$, filtered, and concentrated. Purification by column chromatography (SiO$_2$, 20% ethyl acetate: 80% hexane) afforded 2.55 g of the title compound. $^1$H NMR (400 MHz, DMSO-d$_6$) δ 1.67-1.72 (m, 6H) 1.92 (d, J=2.8 Hz, 6H) 1.97-2.04 (m, 3H) 7.55 (s, 1H) 11.50 (br m, 1H); MS (DCI/NH$_3$) m/z 341 (M)$^+$, 343 (M+2)$^+$.

Example 17B

Adamantane-1-carboxylic acid[5-bromo-3-(2-methoxyethyl)-3H-thiazol-2-ylidene]-amide To a solution of the product of Example 17A (2.55 g, 7.43 mmol) in 60 mL of THF/DMF (2/1) at 0° C. was added NaH (60% dispersion in mineral oil, 386 mg, 9.66 mmol). This mixture was stirred at 0° C. for 10 minutes then warmed to ambient temperature and allowed to stir for 30 minutes. The mixture was cooled to 0° C. and 2-bromoethyl methyl ether (0.77 mL, 8.18 mmol) was added. The ice-bath was removed and the mixture was heated to 65° C. for 12 hours. The mixture was cooled to ambient temperature, diluted with 100 mL of ethyl acetate and washed with brine. The layers were separated and the aqueous phase was extracted with 2×50 mL ethyl acetate. The combined organic extracts were dried over anhydrous Na$_2$SO$_4$, filtered, and concentrated. Purification by column chromatography (SiO$_2$, dichloromethane) afforded 2.55 g of the title compound. $^1$H NMR (500 MHz, DMSO-d$_6$) δ 1.63-1.73 (m, 6H) 1.84 (d, J=2.44 Hz, 6H)

1.96-2.01 (m, 3H) 3.26 (s, 3H) 3.69 (t, J=5.34 Hz, 2H) 4.29 (t, J=5.19 Hz, 2H) 7.70 (s, 1H); MS (DCI/NH$_3$) m/z 399 (M)$^+$, 401 (M+2)$^+$

Example 17C

N-[(2Z)-3-(2-methoxyethyl)-5-phenyl-1,3-thiazol-2(3H)-ylidene]adamantane-1-carboxamide A flask was charged with the product from Example 17B (65.0 mg, 0.16 mmol), phenylboronic acid (24.4 mg, 0.20 mmol), Na$_2$CO$_3$ (2M) (0.24 mL, 0.48 mmol) and PdCl$_2$(PPh$_3$)$_2$ (5.6 mg, 0.008 mmol) in 5 mL of DME/H$_2$O/ethanol (7:3:2). The mixture was heated at 85° C. for 16 hours. After cooling to room temperature, the mixture was diluted with ethyl acetate and washed with water. The organic extract was dried (MgSO$_4$), filtered and concentrated. The residue was purified by preparative HPLC on a Waters Symmetry C8 column (40 mm×100 mm, 7 μm particle size) using a gradient of 10% to 100% acetonitrile:ammonium acetate (10 mM) over 15 minutes at a flow rate of 70 mL/minutes to yield 28.6 mg (45%) of the title product: $^1$H NMR (500 MHz, DMSO-d$_6$) δ 1.64-1.75 (m, 6H) 1.85-1.89 (m, 6H) 1.97-2.03 (m, 3H) 3.28 (s, 3H) 3.77 (t, J=5.3 Hz, 2H) 4.35 (t, J=5.3 Hz, 2H) 7.30-7.35 (m, 1H) 7.44 (t, J=7.8 Hz, 2H) 7.53-7.57 (m, 2H) 7.94 (s, 1H); MS (DCI/NH$_3$) m/z 397 (M+H)$^+$.

Example 18

N-[(2Z)-3-(2-methoxyethyl)-5-pyridin-3-yl-1,3-thiazol-2(3H)-ylidene]adamantane-1-carboxamide The product of Example 17B (65.0 mg, 0.16 mmol), pyridine-3-boronic acid (24.6 mg, 0.20 mmol), Na$_2$CO$_3$ (2 M) (0.24 mL, 0.48 mmol) and PdCl$_2$(PPh$_3$)$_2$ (5.60 mg, 0.008 mmol) in 5 mL of DME/H$_2$O/ethanol (7:3:2) were processed according to the method of Example 17C to afford the title compound. $^1$H NMR (500 MHz, DMSO-d$_6$) δ 1.65-1.75 (m, 6H) 1.88 (d, J=2.4 Hz, 6H) 1.98-2.03 (m, 3H) 3.29 (s, 3H) 3.78 (t, J=5.3 Hz, 2H) 4.36 (t, J=5.3 Hz, 2H) 7.47 (dd, J=7.9, 4.9 Hz, 1H) 7.93-7.96 (m, 1H) 8.09 (s, 1H) 8.51 (dd, J=4.7, 1.4 Hz, 1H) 8.80 (d, J=2.4 Hz, 1H); MS (DCI/NH$_3$) m/z 398 (M+H)$^+$.

Example 19

N-[(2Z)-5-[(E)-2-(4-fluorophenyl)vinyl]-3-(2-methoxyethyl)-1,3-thiazol-2(3H)-ylidene]adamantane-1-carboxamide The product of Example 17B (85.0 mg, 0.21 mmol), trans-β-styreneboronic acid (37.0 mg, 0.25 mmol), Na$_2$CO$_3$ (2M) (0.32 mL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.63-1.75 (m, 6H) 1.87 (d, J=2.45 Hz, 6H) 1.97-2.02 (m, 3H) 3.28 (s, 3H) 3.71 (t, J=5.2 Hz, 2H) 4.31 (t, J=5.2 Hz, 2H) 6.73 (d, J=16.3 Hz, 1H) 7.19 (t, J=8.9 Hz, 2H) 7.27 (d, J=16.3 Hz, 1H) 7.50 (s, 1H) 7.57-7.63 (m, 2H); MS (DCI/NH$_3$) m/z 441 (M+H)$^+$.

Example 20

N-[(2Z)-5-(1-benzothien-2-yl)-3-(2-methoxyethyl)-1,3-thiazol-2(3H)-ylidene]adamantane-1-carboxamide The product of Example 17B (85.0 mg, 0.21 mmol), benzo[b]thiophene-2-boronic acid (44.5 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.65-1.75 (m, 6H) 1.89 (d, J=2.5 Hz, 6H) 1.98-2.03 (m, 3H) 3.29 (s, 3H) 3.77 (t, J=5.4 Hz, 2H) 4.37 (t, J=5.4 Hz, 2H) 7.32-7.42 (m, 2H) 7.55 (s, 1H) 7.84 (dd, J=6.9, 1.7 Hz, 1H) 7.91 (s, 1H) 7.96 (dd, J=8.3, 0.9 Hz, 1H); MS (DCI/NH$_3$) m/z 453 (M+H)$^+$ Example 21

N-[(2Z)-5-(2-fluoro-1,1'-biphenyl-4-yl)-3-(2-methoxyethyl)-1,3-thiazol-2(3H)-ylidene]adamantane-1-carboxamide The product of Example 17B (85.0 mg, 0.21 mmol), 2-fluorobiphenyl-4-boronic acid (54.0 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.64-1.76 (m, 6H) 1.89 (d, J=2.5 Hz, 6H) 1.98-2.03 (m, 3H) 3.30 (s, 3H) 3.79 (t, J=5.4 Hz, 2H) 4.36 (t, J=5.4 Hz, 2H) 7.39-7.53 (m, 4H) 7.54-7.64 (m, 4H) 8.10 (s, 1H); MS (DCI/NH$_3$) m/z 491 (M+H)$^+$ Example 22

N-[(2Z)-5-(4-hydroxyphenyl)-3-(2-methoxyethyl)-1,3-thiazol-2(3H)-ylidene]adamantane-1-carboxamide The product of Example 17B (85.0 mg, 0.21 mmol), 4-(4,4,5,5-tetramethyl-1,3,2-dioxoborolan-2-yl)phenol (55.0 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.63-1.76 (m, 6H) 1.87 (d, J=2.2 Hz, 6H) 1.96-2.02 (m, 3H) 3.28 (s, 3H) 3.75 (t, J=5.4 Hz, 2H) 4.32 (t, J=5.4 Hz, 2H) 6.82 (d, J=8.9 Hz, 2H) 7.35 (d, J=8.6 Hz, 2H) 7.68 (s, 1H) 9.68 (br s, 1H); MS (DCI/NH$_3$) m/z 413 (M+H)$^+$ Example 23

N-[(2Z)-3-(2-methoxyethyl)-5-[3-(trifluoromethoxy)phenyl]-1,3-thiazol-2(3H)-ylidene]adamantane-1-carboxamide The product of Example 17B (85.0 mg, 0.21 mmol), 3-(trifluoromethoxy)benzeneboronic acid (51.5 mg, 0.25 mmol), Na$_2$CO$_3$ (2 M) (315 mL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.64-1.75 (m, 6H) 1.88 (d, J=2.5 Hz, 6H) 1.97-2.03 (m, 3H) 3.28 (s, 3H) 3.78 (t, J=5.4 Hz, 2H) 4.35 (t, J=5.4 Hz, 2H) 7.29-7.34 (m, 1H) 7.53-7.60 (m, 3H) 8.11 (s, 1H); MS (DCI/NH$_3$) m/z 481 (M+H)$^+$ Example 24

N-[(2Z)-5-(2,4-difluorophenyl)-3-(2-methoxyethyl)-1,3-thiazol-2(3H)-ylidene]adamantane-1-carboxamide The product of Example 17B (85.0 mg, 0.21 mmol), 2,4-difluorophenylboronic acid (39.5 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.64-1.75 (m, 6H) 1.88 (d, J=2.5 Hz, 6H) 1.97-2.02 (m, 3H) 3.28 (s, 3H) 3.75 (t, J=5.2 Hz, 2H) 4.38 (t, J=5.4 Hz, 2H) 7.17-7.24 (m, 1H) 7.38-7.46 (m, 1H) 7.63-7.70 (m, 1H) 7.87 (s, 1H); MS (DCI/NH$_3$) m/z 433 (M+H)$^+$; Anal. Calculated for C$_{23}$H$_{26}$F$_2$N$_2$O$_2$S: C, 63.87; H, 6.06; N, 6.48. Found: C, 63.82; H, 6.03; N, 6.48.

Example 25

N-[(2Z)-5-(3-furyl)-3-(2-methoxyethyl)-1,3-thiazol-2(3H)-ylidene]adamantane-1-carboxamide The product of Example 17B (85.0 mg, 0.21 mmol), furan-3-boronic acid (28.0 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.64-1.75 (m, 6H) 1.86 (d, J=2.5 Hz, 6H) 1.96-2.02 (m, 3H) 3.28 (s, 3H) 3.74 (t, J=5.2 Hz, 2H) 4.31 (t, J=5.4 Hz, 2H) 6.83 (dd, J=1.8, 0.9 Hz, 1H) 7.68 (s, 1H) 7.76 (t, J=1.7 Hz, 1H) 8.00 (s, 1H); MS (DCI/NH$_3$) m/z 387 (M+H)$^+$.

Example 26

N-[(2Z)-5-(3-aminophenyl)-3-(2-methoxyethyl)-1,3-thiazol-2(3H)-ylidene]adamantane-1-carboxamide The product of Example 17B (85.0 mg, 0.21 mmol), 3-aminophenylboronic acid (34.2 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.63-1.75 (m, 6H) 1.87 (d, J=2.5 Hz, 6H) 1.96-2.02 (m, 3H) 3.28 (s, 3H) 3.75 (t, J=5.4 Hz, 2H) 4.34 (t, J=5.4 Hz, 2H) 5.23 (s, 2H) 6.50-6.54 (m, 1H) 6.67-6.72 (m, 2H) 7.06 (t, J=8.0 Hz, 1H) 7.72 (s, 1H); MS (DCI/NH$_3$) m/z 412 (M+H)$^+$.

Example 27

N-[(2Z)-5-(2-fluorophenyl)-3-(2-methoxyethyl)-1,3-thiazol-2(3H)-ylidene]adamantane-1-carboxamide The product of Example 17B (85.0 mg, 0.21 mmol), 2-fluorophenylboronic acid (39.5 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.64-1.75 (m, 6H) 1.88 (d, J=2.5 Hz, 6H) 1.97-2.02 (m, 3H) 3.28 (s, 3H) 3.76 (t, J=5.4 Hz, 2H) 4.39 (t, J=5.4 Hz, 2H) 7.27-7.33 (m, 1H) 7.33-7.42 (m, 2H) 7.59-7.65 (m, 1H); MS (DCI/NH$_3$) m/z 415 (M+H)$^+$.

Example 28

N-[(2Z)-5-(3-fluorophenyl)-3-(2-methoxyethyl)-1,3-thiazol-2(3H)-ylidene]adamantane-1-carboxamide The product of Example 17B (85.0 mg, 0.21 mmol), 3-fluorophenylboronic acid (39.5 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.64-1.75 (m, 6H) 1.88 (d, J=2.5 Hz, 6H) 1.97-2.02 (m, 3H) 3.28 (s, 3H) 3.77 (t, J=5.2 Hz, 2H) 4.34 (t, J=5.4 Hz, 2H) 7.12-7.19 (m, 1H) 7.34-7.38 (m, 1H) 7.41-7.51 (m, 2H) 8.04 (s, 1H); MS (DCI/NH$_3$) m/z 415 (M+H)$^+$; Anal. Calculated for C$_{23}$H$_{27}$FN$_2$O$_2$S: C, 66.64; H, 6.56; N, 6.76. Found: C, 66.71; H, 6.71; N, 6.82.

Example 29

N-[(2Z)-5-(4-fluorophenyl)-3-(2-methoxyethyl)-1,3-thiazol-2(3H)-ylidene]adamantane-1-carboxamide The product of Example 17B (85.0 mg, 0.21 mmol), 4-fluorophenylboronic acid (39.5 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.64-1.75 (m, 6H) 1.87 (d, J=2.5 Hz, 6H) 1.97-2.02 (m, 3H) 3.28 (s, 3H) 3.76 (t, J=5.4 Hz, 2H) 4.34 (t, J=5.4 Hz, 2H) 7.29 (t, J=8.8 Hz, 2H) 7.56-7.62 (m, 2H) 7.90 (s, 1H); MS (DCI/NH$_3$) m/z 415 (M+H)$^+$.

Example 30

N-[(2Z)-5-(3-cyanophenyl)-3-(2-methoxyethyl)-1,3-thiazol-2(3H)-ylidene]adamantane-1-carboxamide The product of Example 17B (85.0 mg, 0.21 mmol), 3-cyanophenylboronic acid (36.8 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.64-1.75 (m, 6H) 1.88 (d, J=2.5 Hz, 6H) 1.97-2.03 (m, 3H) 3.29 (s, 3H) 3.78 (t, J=5.4 Hz, 2H) 4.35 (t, J=5.4 Hz, 2H) 7.64 (t, J=7.8 Hz, 1H) 7.75-7.78 (m, 1H) 7.82-7.86 (m, 1H) 8.09 (t, J=1.4 Hz, 1H) 8.14 (s, 1H); MS (DCI/NH$_3$) m/z 422 (M+H)$^+$.

Example 31

N-[(2Z)-5-(4-cyanophenyl)-3-(2-methoxyethyl)-1,3-thiazol-2(3H)-ylidene]adamantane-1-carboxamide The product of Example 17B (85.0 mg, 0.21 mmol), 4-cyanophenylboronic acid (36.8 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H$_2$O/ethanol (7:3:2) were processed according to the method of Example 17C to afford the title compound. $^1$H NMR (400 MHz, DMSO-d$_6$) δ 1.64-1.76 (m, 6H) 1.88 (d, J=2.5 Hz, 6H) 1.97-2.03 (m, 3H) 3.28 (s, 3H) 3.77 (t, J=5.4 Hz, 2H) 4.36 (t, J=5.4 Hz, 2H) 7.74 (d, J=8.6 Hz, 2H) 7.88 (d, J=8.6 Hz, 2H) 8.20 (s, 1H); MS (DCI/NH$_3$) m/z 422 (M+H)$^+$.

Example 32

N-[(2Z)-5-(1,3-benzodioxol-5-yl)-3-(2-methoxyethyl)-1,3-thiazol-2(3H)-ylidene]adamantane-1-carboxamide The product of Example 17B (85.0 mg, 0.21 mmol), 3,4-methylenedioxobenzeneboronic acid (41.5 mg, 0.25 mmol), Na$_2$CO$_3$ (2 M) (315 μL, 0.63 mmol) and PdCl$_2$(PPh$_3$)$_2$ (7.00 mg, 0.01 mmol) in 5 mL of DME/H₂O/ethanol (7:3:2) were processed according to the method of Example 17C to afford the title compound. ¹H NMR (400 MHz, DMSO-d₆) δ 1.63-1.75 (m, 6H) 1.87 (d, J=2.5 Hz, 6H) 1.96-2.02 (m, 3H) 3.28 (s, 3H) 3.76 (t, J=5.4 Hz, 2H) 4.32 (t, J=5.4 Hz, 2H) 6.06 (s, 2H) 6.97 (d, J=0.9 Hz, 2H) 7.18 (s, 1H) 7.80 (s, 1H); MS (DCI/NH₃) m/z 441 (M+H)⁺.

Example 33

N-[(2Z)-3-(2-methoxyethyl)-5-pyridin-4-yl-1,3-thiazol-2(3H)-ylidene]adamantane-1-carboxamide The product of Example 17B (85.0 mg, 0.21 mmol), pyridine-4-boronic acid (30.7 mg, 0.25 mmol), Na₂CO₃ (2 M) (315 μL, 0.63 mmol) and PdCl₂(PPh₃)₂ (7.00 mg, 0.01 mmol) in 5 mL of DME/H₂O/ethanol (7:3:2) were processed according to the method of Example 17C to afford the title compound. ¹H NMR (400 MHz, DMSO-d₆) δ 1.65-1.75 (m, 6H) 1.88 (d, J=2.4 Hz, 6H) 1.97-2.03 (m, 3H) 3.28 (s, 3H) 3.78 (t, J=5.3 Hz, 2H) 4.37 (t, J=5.3 Hz, 3H) 7.53 (dd, J=4.6, 1.5 Hz, 2H) 8.29 (s, 1H) 8.58 (dd, J=4.6, 1.5 Hz, 2H); MS (DCI/NH₃) m/z 398 (M+H)⁺.

Example 34

N-[(2Z)-3-(2-methoxyethyl)-5-quinolin-4-yl-1,3-thiazol-2(3H)-ylidene]adamantane-1-carboxamide The product of Example 17B (85.0 mg, 0.21 mmol), quinoline-4-boronic acid (43.3 mg, 0.25 mmol), Na₂CO₃ (2 M) (315 μL, 0.63 mmol) and PdCl₂(PPh₃)₂ (7.00 mg, 0.01 mmol) in 5 mL of DME/H₂O/ethanol (7:3:2) were processed according to the method of Example 17C to afford the title compound. ¹H NMR (400 MHz, DMSO-d₆) δ 1.67-1.75 (m, 6H) 1.90 (d, J=2.4 Hz, 6H) 1.99-2.03 (m, 3H) 3.30 (s, 3H) 3.80 (t, J=5.3 Hz, 2H) 4.39 (t, J=5.3 Hz, 2H) 7.56 (dd, J=8.2, 4.3 Hz, 1H) 8.04-8.09 (m, 3H) 8.16 (s, 1H) 8.42 (dd, J=8.2, 1.5 Hz, 1H) 8.88 (dd, J=4.1, 1.7 Hz, 1H); MS (DCI/NH₃) m/z 348 (M+H)⁺.

Example 35

N-[(2Z)-5-(2,3-dichlorophenyl)-3-(2-methoxyethyl)-1,3-thiazol-2(3H)-ylidene]adamantane-1-carboxamide The product of Example 17B (85.0 mg, 0.21 mmol), 2,3-dichlorophenylboronic acid (47.7 mg, 0.25 mmol), Na₂CO₃ (2 M) (315 μL, 0.63 mmol) and PdCl₂(PPh₃)₂ (7.00 mg, 0.01 mmol) in 5 mL of DME/H₂O/ethanol (7:3:2) were processed according to the method of Example 17C to afford the title compound. ¹H NMR (400 MHz, DMSO-d₆) δ 1.64-1.75 (m, 6H) 1.88 (d, J=2.5 Hz, 6H) 1.97-2.03 (m, 3H) 3.29 (s, 3H) 3.76 (t, J=5.4 Hz, 2H) 4.39 (t, J=5.4 Hz, 2H) 7.45 (t, J=8.0 Hz, 1H) 7.54 (dd, J=7.8, 1.5 Hz, 1H) 7.68 (dd, J=8.0, 1.5 Hz, 1H) 7.86 (s, 1H); MS (DCI/NH₃) m/z 466 (M+H)⁺.

Example 36

N-[(2Z)-5-(4-chlorophenyl)-3-(2-methoxyethyl)-1,3-thiazol-2(3H)-ylidene]adamantane-1-carboxamide The product of Example 17B (85.0 mg, 0.21 mmol), 4-chlorophenylboronic acid 39.4 mg, 0.25 mmol), Na₂CO₃ (2 M) (315 μL, 0.63 mmol) and PdCl₂(PPh₃)₂ (7.00 mg, 0.01 mmol) in 5 mL of DME/H₂O/ethanol (7:3:2) were processed according to the method of Example 17C to afford the title compound. ¹H NMR (500 MHz, MeOH-d₄) δ 1.74-1.83 (m, 6H) 1.98 (d, J=2.4 Hz, 6H) 2.01-2.05 (m, 3H) 3.36 (s, 3H) 3.80 (t, J=5.2 Hz, 2H) 4.44 (t, J=5.2 Hz, 2H) 7.42 (d, J=8.5 Hz, 2H) 7.53 (d, J=8.5 Hz, 2H) 7.67 (s, 1H); MS (DCI/NH₃) m/z 431 (M+H)⁺.

Example 37

N-[(2Z)-5-(2-chlorophenyl)-3-(2-methoxyethyl)-1,3-thiazol-2(3H)-ylidene]adamantane-1-carboxamide The product of Example 17B (180 mg, 0.52 mmol), 2-chlorophenylboronic acid (97.7 mg, 0.62 mmol), Na₂CO₃ (2 M) (780 μL, 1.56 mmol) and PdCl₂(PPh₃)₂ (18.0 mg, 0.03 mmol) in 10 mL of DME/H₂O/ethanol (7:3:2) were processed according to the method of Example 17C to afford the title compound: ¹H NMR (400 MHz, DMSO-d₆) δ 1.65-1.75 (m, 6H) 1.88 (d, J=2.8 Hz, 6H) 1.97-2.02 (m, 3H) 3.29 (s, 3H) 3.76 (t, J=5.2 Hz, 2H) 4.39 (t, J=5.4 Hz, 2H) 7.37-7.46 (m, 2H) 7.55-7.60 (m, 2H) 7.82 (s, 1H); MS (DCI/NH₃) m/z 431 (M+H)⁺.

Example 38

N-[(2Z)-5-(1H-indol-3-yl)-3-(2-methoxyethyl)-1,3-thiazol-2(3H)-ylidene]adamantane-1-carboxamide The product of Example 17B (85.0 mg, 0.21 mmol), 1H-indol-3-yl-boronic acid (Akhavan-Tafti, Hashem; Eickholt, Robert A.; Lauwers, Kenneth S.; Handley, Richard S. US 2004166539) (40.2 mg, 0.25 mmol), Na₂CO₃ (2 M) (315 μL, 0.63 mmol) and PdCl₂(PPh₃)₂ (7.00 mg, 0.01 mmol) in 5 mL of DME/H₂O/ethanol (7:3:2) were processed according to the method of Example 17C to afford the title compound: ¹H NMR (500 MHz, MeOH-d₄) δ 1.74-1.84 (m, 6H) 1.99 (d, J=2.4 Hz, 6H) 2.01-2.06 (m, 3H) 3.39 (s, 3H) 3.82 (t, J=5.3 Hz, 2H) 4.45 (t, J=5.2 Hz, 2H) 6.48 (d, J=3.1 Hz, 1H) 7.27 (d, J=3.4 Hz, 1H) 7.31 (dd, J=8.4, 1.7 Hz, 1H) 7.42 (d, J=8.2 Hz, 1H) 7.49 (s, 1H) 7.71 (d, J=1.5 Hz, 1H) 7.73-7.77 (m, 1H); MS (DCI/NH₃) m/z 436 (M+H)⁺.

Example 39

N-[(2Z)-5-(3-fluoropyridin-4-yl)-3-(2-methoxyethyl)-1,3-thiazol-2(3H)-ylidene]adamantane-1-carboxamide The product of Example 17B (85.0 mg, 0.21 mmol), 3-fluoropyridine-4-boronic acid (35.2 mg, 0.25 mmol), Na₂CO₃ (2 M) (315 μL, 0.63 mmol) and PdCl₂(PPh₃)₂ (7.00 mg, 0.01 mmol) in 5 mL of DME/H₂O/ethanol (7:3:2) were processed according to the method of Example 17C to afford the title compound: ¹H NMR (400 MHz, DMSO-d₆) δ 1.64-1.76 (m, 6H) 1.88 (d, J=2.8 Hz, 6H) 1.97-2.03 (m, 3H) 3.28 (s, 3H) 3.77 (t, J=5.2 Hz, 2H) 4.42 (t, J=5.4 Hz, 2H) 7.66 (dd, J=6.9, 5.1 Hz, 1H) 8.22 (s, 1H) 8.45 (dd, J=5.2, 0.9 Hz, 1H) 8.65 (d, J=2.8 Hz, 1H); MS (DCI/NH₃) m/z 416 (M+H)⁺.

Example 40

N-[(2Z)-3-(2-methoxyethyl)-5-pyrimidin-5-yl-1,3-thiazol-2(3H)-ylidene]adamantane-1-carboxamide The product of Example 17B (85.0 mg, 0.21 mmol), pyrimidine-5-boronic acid (31.0 mg, 0.25 mmol), Na₂CO₃ (2 M) (315 μL, 0.63 mmol) and PdCl₂(PPh₃)₂ (7.00 mg, 0.01 mmol)

in 5 mL of DME/H₂O/ethanol (7:3:2) were processed according to the method of Example 17C to afford the title compound: ¹H NMR (400 MHz, DMSO-d₆) δ 1.64-1.76 (m, 6H) 1.88 (d, J=2.8 Hz, 6H) 1.97-2.03 (m, 3H) 3.28 (s, 3H) 3.77 (t, J=5.2 Hz, 2H) 4.42 (t, J=5.4 Hz, 2H) 7.66 (dd, J=6.9, 5.1 Hz, 1H) 8.22 (s, 1H) 8.45 (dd, J=5.2, 0.9 Hz, 1H) 8.65 (d, J=2.8 Hz, 1H); MS (DCI/NH₃) m/z 399 (M+H)⁺.

Example 41

N-[(2Z)-3-(2-methoxyethyl)-5-(1H-pyrazol-3-yl)-1,3-thiazol-2(3H)-ylidene]adamantane-1-carboxamide The product of Example 17B (85.0 mg, 0.21 mmol), 1H-pyrazol-3-ylboronic acid (28.0 mg, 0.25 mmol), Na₂CO₃ (2 M) (315 μL, 0.63 mmol) and PdCl₂(PPh₃)₂ (7.00 mg, 0.01 mmol) in 5 mL of DME/H₂O/ethanol (7:3:2) were processed according to the method of Example 17C to afford the title compound: ¹H NMR (400 MHz, MeOH-d₄) δ 1.72-1.83 (m, 6H) 1.97 (d, J=2.8 Hz, 6H) 1.99-2.05 (m, 3H) 3.36 (s, 3H) 3.78 (t, J=5.2 Hz, 2H) 4.40 (t, J=5.2 Hz, 2H) 7.40 (s, 1H) 7.83 (s, 1H); MS (DCI/NH₃) m/z 387 (M+H)⁺.

Example 42

N-[(2Z)-5-(2-fluoropyridin-3-yl)-3-(2-methoxyethyl)-1,3-thiazol-2(3H)-ylidene]adamantane-1-carboxamide The product of Example 17B (85.0 mg, 0.21 mmol), 2-fluoropyridine-3-boronic acid (35.2 mg, 0.25 mmol), Na₂CO₃ (2 M) (315 μL, 0.63 mmol) and PdCl₂(PPh₃)₂ (7.00 mg, 0.01 mmol) in 5 mL of DME/H₂O/ethanol (7:3:2) were processed according to the method of Example 17C to afford the title compound: ¹H NMR (500 MHz, DMSO-d₆) δ 1.65-1.74 (m, 6H) 1.88 (d, J=2.1 Hz, 6H) 1.98-2.02 (m, 3H) 3.28 (s, 3H) 3.76 (t, J=5.2 Hz, 2H) 4.40 (t, J=5.3 Hz, 2H) 7.44-7.48 (m, 1H) 8.02 (s, 1H) 8.14-8.19 (m, 2H); MS (DCI/NH₃) m/z 416 (M+H)⁺.

Example 43

N-[(2Z)-5-(4-fluorobenzyl)-3-(2-methoxyethyl)-1,3-thiazol-2(3H)-ylidene]hexahydro-2,5-methanopentalene-3a(1H)-carboxamide

Example 43A 5-(4-fluoro-benzyl)-3-(2-methoxyethyl)-3H-thiazol-2-ylidene-amine A mixture of 5-(4-fluoro-benzyl)-thiazol-2-ylamine (330 mg, 1.59 mmol) and 2-bromoethyl methyl ether (0.50 mL, 5.34 mmol) was heated to 85° C. and stirred for 12 hours. The mixture was cooled to ambient temperature, diluted with 20 mL of ethyl acetate and washed with saturated aqueous NaHCO₃. The layers were separated and the aqueous phase was extracted with 2×20 mL ethyl acetate and the combined organic extracts were dried over anhydrous Na₂SO₄, filtered, and concentrated. Purification by column chromatography (SiO₂, 50% ethyl acetate in dichloromethane containing 0.5% Et₃N) afforded 342 mg of the title compound: MS (LC/MS) m/z 267 (M+H)⁺.

Example 43B

Hexahydro-2,5-methano-pentalene-3a-carboxylic acid[5-(4-fluoro-benzyl)-3-(2-methoxyethyl)-3H-thiazol-2-ylidene]-amide A mixture of the product of Example 43A (342 mg, 1.29 mmol), hexahydro-2,5-methano-pentalene-3a-carboxylic acid (256 mg, 1.54 mmol), HATU (737 mg, 1.24 mmol) and triethylamine (1.08 mL, 7.74 mmol) in 20 mL of DMF was stirred at room temperature for overnight. The mixture was diluted with ethyl acetate and washed with water. The organic extract was dried (MgSO₄), filtered and concentrated. The residue was purified by preparative HPLC on a Waters Symmetry C8 column (40 mm×100 mm, 7 μm particle size) using a gradient of 10% to 100% acetonitrile:ammonium acetate (10 mM) over 15 minutes at a flow rate of 70 mL/minutes to afford the title compound: ¹H NMR (500 MHz, DMSO-d₆) δ 1.51-1.61 (m, 4H) 1.64-1.75 (m, 4H) 2.06 (d, J=9.2 Hz, 2H) 2.22-2.27 (m, 2H) 2.51-2.53 (m, 1H) 3.25 (s, 3H) 3.67 (t, J=5.3 Hz, 2H) 3.95 (s, 2H) 4.23 (t, J=5.2 Hz, 2H) 7.15 (t, J=8.8 Hz, 2H) 7.23 (s, 1H) 7.29 (dd, J=8.4, 5.6 Hz, 2H); MS (DCI/NH₃) m/z 415 (M+H)⁺.

Example 44

N-[(2Z)-5-(2-fluorobenzyl)-3-(2-methoxyethyl)-1,3-thiazol-2(3H)-ylidene]hexahydro-2,5-methanopentalene-3a(1H)-carboxamide

Example 44A 5-(4-fluoro-benzyl)-3-(2-methoxy-ethyl)-3H-thiazol-2-ylidene-amine A mixture of 5-(2-fluoro-benzyl)-thiazol-2-ylamine (330 mg, 1.59 mmol) and 2-bromoethyl methyl ether (0.50 mL, 5.34 mmol) was processed according to the method of Example 43A to afford the title compound: MS (LC/MS) m/z 267 (M+H)⁺.

Example 44B

N-[(2Z)-5-(2-fluorobenzyl)-3-(2-methoxyethyl)-1,3-thiazol-2(3H)-ylidene]hexahydro-2,5-methanopentalene-3a(1H)-carboxamide A mixture of the product of Example 44A (342 mg, 1.29 mmol), hexahydro-2,5-methano-pentalene-3a-carboxylic acid (256 mg, 1.54 mmol), HATU (737 mg, 1.24 mmol) and triethylamine (1.08 mL, 7.74 mmol) in 20 mL of DMF was processed according to the method of Example 43B to afford the title compound: ¹H NMR (500 MHz, DMSO-d₆) δ 1.51-1.61 (m, 4H) 1.65-1.74 (m, 4H) 2.07 (d, J=9.2 Hz, 2H) 2.22-2.26 (m, 2H) 2.51-2.53 (m, 1H) 3.24 (s, 3H) 3.66 (t, J=5.3 Hz, 2H) 3.98 (s, 2H) 4.23 (t, J=5.3 Hz, 2H) 7.16-7.22 (m, 3H) 7.23 (s, 1H) 7.29-7.38 (m, 2H); MS (DCI/NH₃) m/z 415 (M+H)⁺.

Example 45

N-[(2Z)-5-(3-fluorobenzyl)-3-(2-methoxyethyl)-1,3-thiazol-2(3H)-ylidene]hexahydro-2,5-methanopentalene-3a(1H)-carboxamide

Example 45A 5-(3-fluoro-benzyl)-3-(2-methoxyethyl)-3H-thiazol-2-ylidene-amine A mixture of 5-(3-fluoro-benzyl)-thiazol-2-ylamine (330 mg, 1.59 mmol) and 2-bromoethyl methyl ether (0.50 mL, 5.34 mmol) was processed according to the method of Example 43A to afford the title compound: MS (LC/MS) m/z 267 (M+H)+.

Example 45B

Hexahydro-2,5-methano-pentalene-3a-carboxylic acid[5-(3-fluoro-benzyl)-3-(2-methoxyethyl)-3H-thiazol-2-ylidene]-amide A mixture of the product of Example 45A (342 mg, 1.29 mmol), hexahydro-2,5-methano-pentalene-3a-carboxylic acid (256 mg, 1.54 mmol), HATU (737 mg, 1.24 mmol) and triethylamine (1.08 mL, 7.74 mmol) in 20 mL of DMF was processed according to the method of Example 43B to afford the title compound: $^1$H NMR (400 MHz, DMSO-d$_6$) δ 1.50-1.61 (m, 4H), 1.65-1.76 (m, 4H), 2.03-2.11 (m, 2H), 2.21-2.26 (m, 2H), 2.48-2.55 (m, 1H), 3.25 (s, 3H), 3.68 (t, J=5.4 Hz, 2H), 3.99 (s, 2H), 4.25 (t, J=5.4 Hz, 2H), 7.03-7.13 (m, 3H), 7.26 (s, 1H), 7.33-7.41 (m, 1H); MS (DCI/NH$_3$) m/z 415 (M+H)+.

Example 46

N-[(2Z)-3-(2-methoxyethyl)-4,5-dimethyl-1,3-thiazol-2(3H)-ylidene]adamantane-1-carboxamide

Example 46A 3-(2-Methoxyethyl)-4,5-dimethyl-3H-thiazol-2-ylideneamine hydrobromide A mixture of 4,5-dimethylthiazol-2-ylamine (9.0 g, 70 mmol) and 2-bromoethyl methyl ether (7.9 mL, 84 mmol) was heated at 85° C. for 12 hours. The mixture was cooled to ambient temperature and then triturated with isopropanol. The solid was collected by filtration and dried under vacuum to afford 10 g (56%) of the title compound. $^1$H NMR (DMSO-d$_6$, 300 MHz) δ ppm 2.17 (s, 3H), 2.19 (s, 3H), 3.25 (s, 3H) 3.56 (t, J=5.1 Hz, 2H) 4.16 (t, J=5.1 Hz, 2H) 9.41 (s, 1H); MS (DCI/NH$_3$) m/z 129 (M+H)+.

Example 46B

N-[(2Z)-3-(2-methoxyethyl)-4,5-dimethyl-1,3-thiazol-2(3H)-ylidene]adamantane-1-carboxamide The product of 46A (0.5 g, 1.9 mmol) and adamantane-1-carboxylic acid (0.67 g, 3.7 mmol) were processed as described in Example 3B to afford title compound. $^1$H NMR (CDCl$_3$, 300 MHz) δ ppm 1.74 (s, 6H), 1.99 (s, 6H), 2.03 (s, 3H), 2.19 (s, 3H), 2.22 (s, 3H), 3.30 (s, 3H), 3.72 (t, J=5.3 Hz, 2H), 4.20-4.53 (m, 2H); MS (DCI/NH$_3$) m/z 349 (M+H)+. Anal. Calculated for $C_{19}H_{28}N_2O_2S \cdot 0.7H_2O$: C, 63.19; H, 8.21; N, 7.76. Found: C, 62.92; H, 8.01; N, 7.52.

Example 47

N-[(2Z)-3-[2-(2-methoxyethoxy)ethyl]-4,5-dimethyl-1,3-thiazol-2(3H)-ylidene]adamantane-1-carboxamide A mixture of 4,5-Dimethylthiazol-2-ylamine (20 mg, 0.16 mmol) and 1-bromo-2-(2-methoxyethoxy)ethane (0.20 mmol) was heated at 80° C. overnight to afford 3-[2-(2-methoxyethoxy)-ethyl]-4,5-dimethyl-1,3-thiazol-2(3H)-ylideneamine hydrobromide, which was used without purification. The alkylated thiazolylidene hydrobromide (1.25 equiv), 1-adamantane carboxylic acid (1.0 equiv), polymer-bound dicyclohexylcarbodiimide (PS-DCC, 3 equiv), 1-hydroxybenzotriazole hydrate (HOBT, 1 equiv), N,N-diisopropylethylamine (3 equiv), were combined in dimethylacetamide (DMA, 2.8 mL) and heated in a microwave to 100° C. for 420 seconds. The mixture was filtered through Si-Carbonate (6 mL-1 g cartridge from Silicycle Chemical Division, MeOH wash) and then concentrated to dryness. Purification by reverse phase HPLC afforded the title compound. $^1$H NMR (DMSO-d$_6$, 500 MHz) δ ppm 11.68 (q, J=12.27 Hz, 6H) 1.84 (d, J=2.50 Hz, 6H) 1.94-2.02 (m, 3H) 2.16 (s, 3H) 2.22 (s, 3H) 3.19 (s, 3H) 3.39 (dd, J=5.62, 3.74 Hz, 2H) 3.51 (dd, J=5.62, 3.74 Hz, 2H) 3.73-3.77 (m, 2H) 4.25 (t, J=5.46 Hz, 2H); MS (ESI) m/z 393 (M=H)+.

Example 48

N-[(2Z)-3-(2-ethoxyethyl)-4,5-dimethyl-1,3-thiazol-2(3H)-ylidene]adamantane-1-carboxamide 4,5-Dimethylthiazol-2-ylamine, 1-bromo-2-ethoxyethane and 1-adamantane carboxylic acid were processed as described in Example 47 to afford the title compound. $^1$H NMR (CDCl$_3$, 500 MHz) δ ppm 1.05 (t, J=7.02 Hz, 3H) 1.61-1.76 (m, 6H) 1.84 (d, J=2.50 Hz, 6H) 1.95-2.03 (m, 3H) 2.16 (s, 3H) 2.21 (s, 3H) 3.43 (q, J=7.07 Hz, 2H) 3.69 (t, J=5.46 Hz, 2H) 4.24 (t, J=5.46 Hz, 2H); MS (ESI) m/z 363 (M=H)+.

Example 49

3-hydroxy-N-[(2Z)-3-(2-methoxyethyl)-4,5-dimethyl-1,3-thiazol-2(3H)-ylidene]adamantane-1-carboxamide A mixture of 3-hydroxyadamantane-1-carboxylic acid (1000 mg, 5.10 mmol) and 1,1'-carbonyldiimidazole (992 mg, 6.12 mmol) in EtOAc (25 mL) were stirred at ambient temperature for 4 hours. The mixture was treated with water (5 mL) and the product of Example 46A (13620 mg, 5.10 mmol), then heated at reflux for 14 hours. The mixture was diluted with water and EtOAc and then the phases were separated. The organic extract was washed with water (2×) and brine, dried over MgSO$_4$, and concentrated. The solid was crystallized from hot EtOAc to afford 1430 mg (77%) of the title compound. MS (DCI/NH$_3$) m/z 365 (M+H)+. Anal. Calculated for $C_{19}H_{26}N_2O_3S$: C, 62.61; H, 7.74; N, 7.69. Found: C, 62.35; H, 8.08; N, 7.77.

Example 50

N-[(2Z)-3-[2-(benzyloxy)ethyl]-4,5-dimethyl-1,3-thiazol-2(3H)-ylidene]adamantane-1-carboxamide 4,5-Dimethylthiazol-2-ylamine, (2-Bromoethoxymethyl)-benzene and 1-adamantane carboxylic acid were processed as described in Example 47 to afford the title compound. $^1$H NMR (CDCl$_3$, 300 MHz) δ ppm 1.58-1.73 (m, 6H) 1.79 (d, J=2.50 Hz, 6H) 1.91-2.02 (m, 3H) 2.15 (s, 3H) 2.22 (s, 3H) 3.77 (t, J=5.46 Hz, 2H) 4.29 (t, J=5.46 Hz, 2H) 4.47 (s, 2H) 7.19 (d, J=6.55 Hz, 2H) 7.22-7.33 (m, 3H); MS (ESI) m/z 425 (M=H)+.

Example 51

3-chloro-N-[(2Z)-3-(2-methoxyethyl)-4,5-dimethyl-1,3-thiazol-2(3H)-ylidene]adamantane-1-carboxamide The product of Example 46A (267 mg, 1.00 mmol) and 3-chloroadamantane-1-carboxylic acid (215 mg, 1.00 mmol) were processed as described in Example 49 to afford the title compound (221 mg, 58%). MS (DCI/NH$_3$) m/z 383, 385 (M+H)$^+$. Anal. Calculated for C$_{19}$H$_{27}$ClN$_2$O$_2$S: C, 59.59; H, 7.11; N, 7.32. Found: C, 59.37; H, 7.26; N, 7.37.

Example 53

(1R,4S)—N-[(2Z)-3-(2-methoxyethyl)-4,5-dimethyl-1,3-thiazol-2(3H)-ylidene]-4,7,7-trimethyl-3-oxo-2-oxabicyclo[2.2.1]heptane-1-carboxamide A mixture of the product of Example 46A (150 mg, 0.56 mmol), (+)-(1R,4S)-camphanic acid chloride (111 mg, 0.56 mmol) and triethylamine (312 µL, 2.24 mmol) in 5 ml of THF was processed according to the method of Example 1A to afford the title compound: $^1$H NMR (300 MHz, DMSO-d$_6$) δ 0.79 (s, 3H) 1.00 (s, 3H) 1.05 (s, 3H) 1.47-1.59 (m, 1H) 1.78-1.89 (m, 1H) 1.90-2.01 (m, 1H) 2.21 (s, 3H) 2.24 (s, 3H) 2.52-2.56 (m, 1H) 3.23 (s, 3H) 3.63 (t, J=5.3 Hz, 2H) 4.24-4.31 (m, 2H); MS (ESI$^+$) m/z 367 (M+H)$^+$.

Example 54

(1S,4R)—N-[(2Z)-3-(2-methoxyethyl)-4,5-dimethyl-1,3-thiazol-2(3H)-ylidene]-4,7,7-trimethyl-3-oxo-2-oxabicyclo[2.2.1]heptane-1-carboxamide A mixture of the product of Example 46A (150 mg, 0.56 mmol), (−)-(1S,4R)-camphanic acid chloride (111 mg, 0.56 mmol) and triethylamine (312 µL, 2.24 mmol) in 5 mL of THF was processed according to the method of Example 1A to afford the title compound: $^1$H NMR (300 MHz, DMSO-d$_6$) δ 0.79 (s, 3H) 1.00 (s, 3H) 1.05 (m, 3H) 1.47-1.58 (m, 1H) 1.78-1.89 (m, 1H) 1.89-2.01 (m, 1H) 2.21 (s, 3H) 2.24 (s, 3H) 2.52-2.57 (m, 1H) 3.23 (s, 3H) 3.63 (t, J=5.3 Hz, 2H) 4.24-4.32 (m, 2H); MS (ESI$^+$) m/z 367 (M+H)$^+$.

Example 55

3-({[(2Z)-3-(2-methoxyethyl)-4,5-dimethyl-1,3-thiazol-2(3H)-ylidene]amino}carbonyl)adamantane-1-carboxylic acid Adamantane-1,3-dicarboxylic acid (1.0 g, 4.4 mmol) was dissolved in 5 mL thionyl chloride and heated to reflux for 1.5 hours. The mixture was cooled to ambient temperature and then concentrated under reduced pressure. To a solution of the unpurified acid chloride and the product of Example 46A (0.82 g, 4.4 mmol) in 20 ml of THF at 0° C. was added triethylamine (1.4 mL, 9.7 mmol). The mixture was warmed to 65° C. and stirred for 6 hours. The mixture was diluted with ethyl acetate and washed with saturated potassium carbonate, water and brine. The aqueous washings were combined and extracted with ethyl acetate. The combined organic extracts were dried over magnesium sulfate and concentrated under reduced pressure. Purification by column chromatography (SiO$_2$, 20-40% ethyl acetate/hexanes gradient) afforded the title compound. $^1$H NMR (DMSO-d$_6$, 300 MHz) δ ppm 1.62 (s, 2H), 1.69-1.92 (m, 10H), 2.08 (s, 2H), 2.15 (s, 3H), 2.20 (s, 3H), 3.24 (s, 3H), 3.64 (t, J=5.4 Hz, 2H), 4.24 (t, J=5.4 Hz, 2H), 12.01 (br s, 1H); MS (DCI/NH$_3$) m/z 393 (M+H)$^+$. Anal. Calculated for C$_{20}$H$_{28}$N$_2$O$_4$S.0.3H$_2$O: C, 60.37; H, 7.24; N, 7.04. Found: C, 60.21; H, 7.15; N, 7.11.

Example 56

N-[(2Z)-3-(2-methoxyethyl)-4,5-dimethyl-1,3-thiazol-2(3H)-ylidene]-2-oxatricyclo[3.3.1.1$^{3,7}$]decane-1-carboxamide

Example 56A

2-Oxa-tricyclo[3.3.1.1$^{3,7}$]decane-1-carboxylic acid methyl ester

The title compound was prepared according to the procedure as described in Partch, R.; Brewster W.; Stokes, B. *Croatia Chemical Acta* (1986), 58(4), 661-669. MS (ESI$^+$) m/z 197 (M+H)$^+$.

Example 56B

2-Oxa-tricyclo[3.3.1.1$^{3,7}$]decane-1-carboxylic acid

To a solution of Example 56A (2.5 g, 12.6 mmol) in methanol/water (1:1, 100 mL) was added 5 N aqueous NaOH (3.8 mL, 19 mmol). The mixture was stirred at room temperature for 3 hours and then extracted with methylene chloride to remove unreacted starting material. The aqueous layer was acidified (pH~2) with 6 N aqueous HCl and then extracted with methylene chloride. The combined acidic extracts were dried (Na$_2$SO$_4$), filtered and concentrated to afford 1.92 g of the title compound. MS (ESI$^+$) m/z 183 (M+H)$^+$.

Example 56C

2-Oxa-tricyclo[3.3.1.1$^{3,7}$]decane-1-carboxylic acid [3-(2-methoxyethyl)-4,5-dimethyl-3H-thiazol-2-ylidene]-amide To a solution of Example 46A (0.22 g, 0.8 mmol) in THF (10 mL) was added N-(3-dimethylaminopropyl)-N-ethylcarbodiimide hydrochloride (0.19 g, 1.0 mmol), 1-hydroxybenzotriazole (0.14 g, 1.0 mmol), triethylamine (0.45 mL, 3.2 mmol), and the product of Example 56B (0.15 g, 0.8 mmol). The mixture was stirred overnight at room temperature and then diluted with ethyl acetate, washed with 1 M aqueous NaHCO$_3$, dried (Na$_2$SO$_4$), filtered and concentrated. Purification by preparative HPLC on a Waters Symmetry C8 column (40 mm×100 mm, 7 µm particle size) using a gradient of 10% to 100% acetonitrile:ammonium acetate (10 mM) over 15 minutes at a flow rate of 70 mL/minutes afforded 110 mg of the title compound. $^1$H NMR (300 MHz, DMSO-d$_6$) δ ppm 1.53-1.69 (m, 2H), 1.80-1.90 (m, 6H), 1.91-2.02 (m, 2H), 2.10-2.16 (m, 2H), 2.16 (s, 3H), 2.21 (s, 3H), 3.24 (s, 3H), 3.63 (t, J=5.4 Hz, 2H), 4.03 (s, 1H), 4.24 (t, J=5.3 Hz, 2H); MS (ESI$^+$) m/z 351 (M+H)$^+$; Anal. Calculated for C$_{18}$H$_{26}$N$_2$O$_3$S: 0.03H$_2$O: C, 61.58; H, 7.64; N, 7.98. Found: C, 61.20; H, 7.45; N, 8.00.

Example 57

N-[(2Z)-3-(3-methoxypropyl)-4,5-dimethyl-1,3-thiazol-2(3H)-ylidene]adamantane-1-carboxamide A mixture of 4,5-dimethyl-thiazol-2-ylamine (0.20 g, 1.6 mmol) and 1-bromo-3-methoxypropane (0.28 g, 1.7 mmol)

was heated at 85° C. for 14 hours. After cooling to ambient temperature, the unpurified residue (0.31 g, 1.1 mmol) and adamantane-1-carboxylic acid (0.22 g, 1.2 mmol) were processed as described in Example 3B. Purification by column chromatography (SiO$_2$, 20-40% ethyl acetate/hexanes gradient) afforded 0.20 g (50%) of the title compound. $^1$H NMR (CDCl$_3$, 300 MHz) δ ppm 1.69-1.79 (m, 6H), 1.90-2.00 (m, 6H), 2.00-2.10 (m, 5H), 2.18 (s, 3H), 2.19 (s, 3H), 3.33 (s, 3H), 3.40 (t, J=5.9 Hz, 2H), 4.22 (s, 2H); MS (DCI/NH$_3$) m/z 363 (M+H)$^+$. Anal. Calculated for C$_{20}$H$_{30}$N$_2$O$_2$S: C, 66.26; H, 8.34; N, 7.73. Found: C, 66.00; H, 8.60; N, 7.37.

Example 58

N-[(2Z)-4,5-dimethyl-3-(tetrahydro-2H-pyran-4-ylmethyl)-1,3-thiazol-2(3H)-ylidene]adamantane-1-carboxamide Example 58A 4,5-Dimethyl-3-(tetrahydro-pyran-4-ylmethyl)-3H-thiazol-2-ylideneamine A mixture of 4,5-dimethyl-thiazol-2-ylamine (0.36 g, 2.8 mmol) and 4-bromomethyltetrahydropyran (0.75 g, 4.2 mmol) was heated at 85° C. for 16 hours. The residue purified by preparative HPLC to afford 80 mg (13%) of the title compound.

Example 58B

Adamantane-1-carboxylic acid[4,5-dimethyl-3-(tetrahydro-pyran-4-ylmethyl)-3H-thiazol-2-ylidene]-amide The product of Example 58A (0.11 g, 0.49 mmol) and adamantane-1-carboxylic acid (97 mg, 0.54 mmol) were processed as described in Example 3B. Purification by column chromatography (SiO$_2$, 0-20% methanol/methylene chloride gradient) afforded 25 mg (13%) of the title compound. MS (DCI/NH$_3$) m/z 389 (M+H)$^+$. Anal. Calculated for C$_{22}$H$_{32}$N$_2$O$_2$S: C, 68.00; H, 8.30; N, 7.21. Found: C, 67.61; H, 8.67; N, 7.17.

Example 59

N-[(2Z)-3-[3-(benzyloxy)propyl]-4,5-dimethyl-1,3-thiazol-2(3H)-ylidene]adamantane-1-carboxamide 4,5-Dimethylthiazol-2-ylamine, (3-bromo-propoxymethyl)-benzene and 1-adamantane carboxylic acid were processed as described in Example 47 to afford the title compound. $^1$H NMR (CDCl$_3$, 500 MHz) δ ppm 1.57-1.73 (m, 6H) 1.79-1.85 (m, 6H) 1.91-1.96 (m, 3H) 1.96-2.04 (m, 2H) 2.12-2.17 (m, 3H) 2.18-2.22 (m, 3H) 3.51 (t, J=5.93 Hz, 2H) 4.20 (t, 2H) 4.46 (s, 2H) 7.25-7.38 (m, 5H); MS (ESI) m/z 439 (M+H)$^+$.

Example 60

N-[(2Z)-3-(2-methoxyethyl)-1,3-benzothiazol-2 (3H)-ylidene]adamantane-1-carboxamide Example 60A 3-(2-Methoxyethyl)-3H-benzothiazol-2-ylideneamine hydrobromide Benzothiazol-2-ylamine (10.0 g, 66.6 mmol) and 2-bromoethyl methyl ether (9.39 mL, 99.9 mmol) were combined and heated at 85° C. for 6 hours. The dark solid was triturated with EtOH then filtered and dried under vacuum to afford the title compound (15.8 g, 82%). $^1$H NMR (DMSO-d$_6$, 300 MHz) δ ppm 3.23 (s, 3H), 3.69 (t, J=5.1 Hz, 2H), 4.51 (t, J=5.1 Hz, 2H), 7.42 (dt, J=1.0, 8.0 Hz, 1H), 7.56 (m, 1H), 7.72 (d, J=8.0 Hz, 1H), 8.00 (dd, J=1.1, 8.0 Hz, 1H), 10.16 (br s, 2H); MS (DCI/NH$_3$) m/z 209 (M+H)$^+$.

Example 60B

N-[(2Z)-3-(2-methoxyethyl)-1,3-benzothiazol-2 (3H)-ylidene]adamantane-1-carboxamide The product of Example 60A and adamantane-1-carboxylic acid were processed as described in Example 3B. Purification by column chromatography (SiO$_2$, 20-50% ethyl acetate/hexanes gradient) afforded the title compound. $^1$H NMR (CDCl$_3$, 300 MHz) δ ppm 1.76 (s, 6H), 1.95-2.03 (m, 6H), 2.05 (d, J=3.4 Hz, 3H), 3.34 (s, 3H), 3.81 (t, J=5.6 Hz, 2H), 4.55 (t, J=5.8 Hz, 2H), 7.21-7.28 (m, 1H), 7.36-7.47 (m, 2H), 7.62 (d, J=7.8 Hz, 1H); MS (DCI/NH$_3$) m/z 371 (M+H)$^+$. Anal. Calculated for C$_{21}$H$_{26}$N$_2$O$_2$S: C, 68.08; H, 7.07; N, 7.56. Found: C, 68.24; H, 7.16; N, 7.40.

Example 61

N-[(2Z)-3-(3-methoxypropyl)-1,3-benzothiazol-2 (3H)-ylidene]adamantane-1-carboxamide Example 61A 3-(3-Methoxy-propyl)-3H-benzothiazol-2-ylidene-amine hydrobromide Benzothiazol-2-ylamine (1.0 g, 6.6 mmol) and 1-bromo-3-methoxy-propane (1.2 g, 7.9 mmol) were processed as described in Example 2A. Recrystallization from ethyl acetate afforded 1.7 g (89%) of the title compound. $^1$H NMR (DMSO-d$_6$, 300 MHz) δ ppm 1.90-2.02 (m, 2H), 3.18 (s, 3H), 3.39 (t, J=5.9 Hz, 2H), 4.31 (t, J=7.1 Hz, 2H), 7.37-7.48 (m, 1H), 7.53-7.69 (m, 2H), 8.00 (dd, J=8.0, 0.8 Hz, 1H), 10.08 (s, 1H); MS (DCI/NH$_3$) m/z 233 (M+H)$^+$.

Example 61B

N-[(2Z)-3-(3-methoxypropyl)-1,3-benzothiazol-2 (3H)-ylidene]adamantane-1-carboxamide The product of Example 61A (0.40 g, 1.3 mmol) and adamantane-1-carboxylic acid (0.24 g, 1.3 mmol) were processed as described in Example 3B. Purification by column chromatography (SiO$_2$, 30-45% ethyl acetate/hexanes gradient) afforded 0.13 g (26%) of the title compound. $^1$H NMR (CDCl$_3$, 300 MHz) δ ppm 1.76 (t, J=2.9 Hz, 6H), 2.01 (d, J=2.7 Hz, 6H), 2.06 (s, 3H), 2.09-2.19 (m, 2H), 3.32 (s, 3H), 3.40 (t, J=5.8 Hz, 2H), 4.49 (t, J=6.8 Hz, 2H), 7.22-7.28 (m, 1H), 7.36-7.48 (m, 2H), 7.64 (d, J=7.8 Hz, 1H); MS (DCI/NH$_3$) m/z 385 (M+H)$^+$. Anal. Calculated for C$_{22}$H$_{28}$N$_2$O$_2$S: C, 68.72; H, 7.34; N, 7.28. Found: C, 68.75; H, 7.62; N, 7.26.

Example 62

N-[(2Z)-3-(2-methoxyethyl)-6-(methylsulfonyl)-1,3-benzothiazol-2(3H)-ylidene]adamantane-1-carboxamide

Example 62A

Adamantane-1-carboxylic acid (6-methanesulfonyl-benzothiazol-2-yl)-amide

Commercially available 6-methanesulfonyl-benzothiazol-2-ylamine, triethylamine, and adamantane-1-carbonyl chloride were processed as described for Example 17A to afford the title compound. MS (ESI$^+$) m/z 391 (M+H)$^+$;

Example 62B

Adamantane-1-carboxylic acid[6-methanesulfonyl-3-(2-methoxyethyl)-3H-benzothiazol-2-ylidene]-amide The product from Example 62A, sodium hydride (60% solution in mineral oil) and 2-bromoethyl methyl ether were processed as described for Example 17B to afford the title compound. $^1$H NMR (300 MHz, DMSO-$d_6$) δ ppm 1.61-1.80 (m, 6H), 1.87-1.94 (m, 6H), 1.99-2.07 (m, 3H), 3.24 (s, 3H), 3.26 (s, 3H), 3.78 (t, J=5.4 Hz, 2H), 4.63 (t, J=5.3 Hz, 2H), 7.82-7.91 (m, 1H), 7.93-8.03 (m, 1H), 8.46 (d, J=1.7 Hz, 1H); MS (ESI$^+$) m/z 449 (M+H)$^+$; Anal. Calculated for $C_{22}H_{28}N_2O_4S_2$: C, 58.90; H, 6.29; N, 6.24. Found: C, 58.86; H, 6.30; N, 6.25.

Example 63

N-[(2Z)-6-fluoro-3-(2-methoxyethyl)-1,3-benzothiazol-2(3H)-ylidene]hexahydro-2,5-methanopentalene-3a(1H)-carboxamide

Example 63A

6-Fluoro-3-(2-methoxyethyl)-3H-benzothiazol-2-ylideneamine HBr

Commercially available 6-fluoro-benzothiazol-2-ylamine and 2-bromoethyl methyl ether were processed as described for Example 2A to afford the title compound. MS (ESI$^+$) m/z 227 (M+H)$^+$.

Example 63B

Hexahydro-2,5-methano-pentalene-3a-carboxylic acid[6-fluoro-3-(2-methoxyethyl)-3H-benzothiazol-2-ylidene]-amide The product from Example 63A and the product from Example 14A were processed as described for example 17A to afford the title compound. $^1$H NMR (300 MHz, DMSO-$d_6$) δ ppm 1.50-1.90 (m, 8H), 2.07-2.21 (m, 2H), 2.29 (s, 2H), 2.61 (t, J=6.6 Hz, 1H), 3.23 (s, 3H), 3.74 (t, J=5.3 Hz, 2H), 4.55 (t, J=5.4 Hz, 2H), 7.34 (td, J=9.2, 2.7 Hz, 1H), 7.67 (dd, J=8.8, 4.4 Hz, 1H), 7.81 (dd, J=8.5, 2.7 Hz, 1H); MS (ESI$^+$) m/z 375 (M+H)$^+$; Anal. Calculated for $C_{20}H_{23}FN_2O_2S$: C, 64.15; H, 6.19; N, 7.48. Found: C, 64.03; H, 6.24; N, 7.40.

Example 64

N-[(2Z)-5,6-difluoro-3-(2-methoxyethyl)-1,3-benzothiazol-2(3H)-ylidene]hexahydro-2,5-methanopentalene-3a(1H)-carboxamide

Example 64A 5,6-Difluoro-3-(2-methoxyethyl)-3H-benzothiazol-2-ylideneamine hydrobromide Commercially available 5,6-difluoro-benzothiazol-2-ylamine and 2-bromoethyl methyl ether were processed as described for Example 46A to afford the title compound. MS (ESI$^+$) m/z 245 (M+H)$^+$.

Example 64B

Hexahydro-2,5-methano-pentalene-3a-carboxylic acid[5,6-difluoro-3-(2-methoxyethyl)-3H-benzothiazol-2-ylidene]-amide The product of Example 64A and the product of Example 14A were processed as described for Example 17A to afford the title compound. $^1$H NMR (300 MHz, DMSO-$d_6$) δ ppm 1.47-1.67 (m, 4H), 1.71-1.87 (m, 4H), 2.10-2.20 (m, J=1.7 Hz, 2H), 2.29 (s, 2H), 2.61 (t, J=6.4 Hz, 1H), 3.23 (s, 3H), 3.73 (t, J=5.3 Hz, 2H), 4.54 (t, J=5.4 Hz, 2H), 7.88 (dd, J=11.4, 6.6 Hz, 1H), 8.06 (dd, J=10.0, 8.0 Hz, 1H); MS (ESI$^+$) m/z 393 (M+H)$^+$; Anal. Calculated for $C_{20}H_{22}F_2N_2O_2S$: C, 61.21; H, 5.65; N, 7.14. Found: C, 61.24; H, 5.60; N, 7.10.

Example 65

N-[(2Z)-5-fluoro-3-(2-methoxyethyl)-1,3-benzothiazol-2(3H)-ylidene]hexahydro-2,5-methanopentalene-3a(1H)-carboxamide

Example 65A

5-Fluoro-3-(2-methoxyethyl)-3H-benzothiazol-2-ylideneamine

Commercially available 5-fluoro-benzothiazol-2-ylamine and 2-bromoethyl methyl ether were processed as described for Example 46A to afford the title compound. MS (ESI$^+$) m/z 227 (M+H)$^+$.

Example 65B

Hexahydro-2,5-methano-pentalene-3a-carboxylic acid[5-fluoro-3-(2-methoxyethyl)-3H-benzothiazol-2-ylidene]-amide The product of Example 65A and the product of Example 14A were processed according to the method of Example 17A to afford the title compound. $^1$H NMR (300 MHz, DMSO-$d_6$) δ ppm 1.52-1.68 (m, 4H), 1.70-1.86 (m, 4H), 2.09-2.20 (m, 2H), 2.29 (s, 2H), 2.61 (t, J=6.8 Hz, 1H), 3.23 (s, 3H), 3.74 (t, J=5.4 Hz, 2H), 4.55 (t, J=5.4 Hz, 2H), 7.34 (td, J=9.0, 2.7 Hz, 1H), 7.62-7.73 (m, 1H), 7.81 (dd, J=8.3, 2.5 Hz, 1H); MS (ESI$^+$) m/z 375 (M+H)$^+$; Anal. Calculated for $C_{20}H_{23}FN_2O_2S$: C, 64.15; H, 6.19; N, 7.48. Found: C, 64.08; H, 6.11; N, 7.47.

Example 66

N-[(2Z)-5-bromo-3-(2-methoxyethyl)-1,3-thiazol-2 (3H)-ylidene]adamantane-1-carboxamide

Example 66A

Adamantane-1-carboxylic acid (5-bromo-thiazol-2-yl)-amide

A mixture of 2-amino-5-bromothiazole monohydrobromide (3.00 g, 11.5 mmol), 1-adamantanecarbonyl chloride (2.74 g, 13.8 mmol), 4-dimethylaminopyridine (1.10 g, 0.90 mmol) and triethylamine (3.20 mL, 23.0 mmol) in 100 mL of THF was stirred at 80° C. for 48 hours. The mixture was cooled to ambient temperature, diluted with 100 mL of ethyl acetate and washed with brine. The layers were separated and the aqueous phase was extracted twice with 50 mL of ethyl acetate. The combined organic extracts were dried over anhydrous $Na_2SO_4$, filtered, and concentrated. Purification by column chromatography ($SiO_2$, 20% ethyl acetate: 80% hexane) afforded 2.55 g of the title compound: $^1$H NMR (400 MHz, DMSO-$d_6$) δ 1.67-1.72 (m, 6H) 1.92 (d, J=2.8 Hz, 6H) 1.97-2.04 (m, 3H) 7.55 (s, 1H) 11.50 (br m, 1H); MS (DCI/NH$_3$) m/z 341 (M)$^+$, 343 (M+2)$^+$.

Example 66B

Adamantane-1-carboxylic acid[5-bromo-3-(2-methoxyethyl)-3H-thiazol-2-ylidene]-amide To a solution of the product of Example 66A (2.55 g, 7.43 mmol) in 60 mL of THF/DMF (2/1) at 0° C. was added NaH (60% dispersion in mineral oil, 386 mg, 9.66 mmol). The mixture was stirred at 0° C. for 10 minutes then warmed to ambient temperature for 30 minutes. After cooling to 0° C., 2-bromoethyl methyl ether (0.77 mL, 8.18 mmol) was added and the mixture was heated to 65° C. for 12 hours. The mixture was cooled to ambient temperature, diluted with 100 mL of ethyl acetate and washed with brine. The layers were separated and the aqueous phase was extracted twice with 50 mL of ethyl acetate. The combined organic extracts were dried over anhydrous $Na_2SO_4$, filtered, and concentrated. Purification by column chromatography ($SiO_2$, dichloromethane) afforded 2.55 g of the title compound: $^1$H NMR (500 MHz, DMSO-$d_6$) δ 1.63-1.73 (m, 6H) 1.84 (d, J=2.44 Hz, 6H) 1.96-2.01 (m, 3H) 3.26 (s, 3H) 3.69 (t, J=5.34 Hz, 2H) 4.29 (t, J=5.19 Hz, 2H) 7.70 (s, 1H); MS (DCI/NH$_3$) m/z 399 (M)$^+$, 401 (M+2)$^+$

Example 67

N-[(2Z)-5-chloro-3-(2-methoxyethyl)-1,3-thiazol-2 (3H)-ylidene]adamantane-1-carboxamide

Example 67A

Adamantane-1-carboxylic acid (5-chloro-thiazol-2-yl)-amide

A mixture of 2-amino-5-chlorothiazole (2.00 g, 14.9 mmol), 1-adamantanecarbonyl chloride (3.54 g, 17.8 mmol), 4-dimethylaminopyridine (1.10 g, 0.90 mmol) and triethylamine (4.15 mL, 23.0 mmol) in 80 mL of THF was stirred at 80° C. for 48 hours. The mixture was cooled to ambient temperature, diluted with 100 mL of ethyl acetate and washed with brine. The layers were separated and the aqueous phase was extracted twice with 50 mL of ethyl acetate. The combined organic extracts were dried over anhydrous $Na_2SO_4$, filtered, and concentrated. Purification by column chromatography ($SiO_2$, dichloromethane) afforded 2.27 g of the title compound: MS (DCI/NH$_3$) m/z 297 (M+H)$^+$.

Example 67B

Adamantane-1-carboxylic acid[5-chloro-3-(2-methoxyethyl)-3H-thiazol-2-ylidene]-amide To a solution of the product of Example 67A (2.27 g, 7.60 mmol) in 60 mL of THF/DMF (2/1) at 0° C. was added NaH (60% dispersion in mineral oil, 396 mg, 9.90 mmol). This mixture was stirred at 0° C. for 10 minutes then warmed to ambient temperature for 30 minutes. The mixture was cooled to 0° C. and 2-bromoethyl methyl ether (0.79 mL, 8.40 mmol) was added. The ice-bath was removed and the mixture was heated to 75° C. for 12 hours. The mixture was cooled to ambient temperature, diluted with 100 mL ethyl acetate and washed with brine. The layers were separated and the aqueous phase was extracted twice with 50 mL of ethyl acetate. The combined organic extracts were dried over anhydrous $Na_2SO_4$, filtered, and concentrated. Purification by column chromatography ($SiO_2$, dichloromethane) afforded the title compound; $^1$H NMR (400 MHz, DMSO-$d_6$) δ 1.62-1.74 (m, 6H) 1.85 (d, J=2.5 Hz, 6H) 1.96-2.01 (m, 3H) 3.26 (s, 3H) 3.70 (t, J=5.2 Hz, 2H) 4.29 (t, J=5.4 Hz, 2H) 7.67 (s, 1H); MS (DCI/NH$_3$) m/z 355 (M+H)$^+$.

Example 68

N-[(2Z)-3-(2-methoxyethyl)-4,5,6,7-tetrahydro-1,3-benzothiazol-2(3H)-ylidene]hexahydro-2,5-methanopentalene-3a(1H)-carboxamide

Example 68A 3-(2-methoxy-ethy)-4,5,6,7-tetrahydro-3H-benzothiazol-2-ylideneamine hydrobromide A mixture of 4,5,6,7-tetrahydro-benzothiazol-2-ylamine (300 mg, 1.94 mmol) and 2-bromoethyl methyl ether (600 μL, 6.40 mmol) was processed according to the method of Example 2A to afford the title compound: MS (LC/MS) m/z 213 (M+H)$^+$.

Example 68B

N-[(2Z)-3-(2-methoxyethyl)-4,5,6,7-tetrahydro-1,3-benzothiazol-2(3H)-ylidene]hexahydro-2,5-methanopentalene-3a(1H)-carboxamide A mixture of the product of Example 68A (293 mg, 1.00 mmol), hexahydro-2,5-methano-pentalene-3a-carboxylic acid (199 mg, 1.20 mmol), HATU (570 mg, 1.50 mmol) and triethylamine (836 mL, 6.00 mmol) in 15 mL of DMF was processed according to the method of Example 3B to afford the title compound: $^1$H NMR (500 MHz, DMSO-$d_6$) δ 1.53-1.62 (m, 4H) 1.67-1.82 (m, 8H) 2.07-2.12 (m, 2H) 2.23-2.27 (m, 2H) 2.45-2.49 (m, 3H) 2.54-2.59 (m, 2H) 3.23 (s, 3H) 3.63 (t, J=5.3 Hz, 2H) 4.16 (t, J=5.5 Hz, 2H); MS (DCI/NH$_3$) m/z 361 (M+H)$^+$.

Example 69

N-[(2Z)-3-(2-methoxyethyl)-3,4,5,6-tetrahydro-2H-cyclopenta[d][1,3]thiazol-2-ylidene]adamantane-1-carboxamide

Example 69A

Adamantane-1-carboxylic acid (5,6-dihydro-4H-cyclopentathiazol-2-yl)-amide

A mixture of 5,6-dihydro-4H-cyclopentathiazole-2-ylamine hydrochloride (400 mg, 2.27 mmol), 1-adamantanecarbonyl chloride (540 mg, 2.72 mmol), 4-dimethylaminopyridine (100 mg, 0.82 mmol) and triethylamine (632 µL, 4.54 mmol) in 30 mL of THF was processed according to the method of Example 1A to afford the title compound: MS (DCI/NH$_3$) m/z 303 (M+H)$^+$.

Example 69B

Adamantane-1-carboxylic acid[3-(2-methoxy-ethy)-3,4,5,6-tetrahydro-cyclopentathiazol-2-ylidene]-amide A mixture of the product of Example 69A (535 mg, 1.77 mmol), NaH (60% dispersion in mineral oil (92.0 mg, 2.30 mmol) and 2-bromoethyl methyl ether (183 µL, 1.95 mmol) in 30 mL of THF/DMF (2/1) was processed according to the method of Example 1B to afford the title compound: $^1$H NMR (500 MHz, DMSO-d$_6$) δ 1.62-1.72 (m, 6H) 1.84 (d, J=2.1 Hz, 6H) 1.95-2.00 (m, 3H) 2.31-2.39 (m, 2H) 2.73 (t, J=7.0 Hz, 2H) 2.78 (t, J=7.0 Hz, 2H) 3.24 (s, 3H) 3.66 (t, J=5.3 Hz, 2H) 4.17 (t, J=5.2 Hz, 2H); MS (DCI/NH$_3$) m/z 361 (M+H)$^+$.

Example 70

N-[(2Z)-3-(2-methoxyethyl)-3,8-dihydro-2H-indeno[1,2-d][1,3]thiazol-2-ylidene]hexahydro-2,5-methanopentalene-3a(1H)-carboxamide Commercially available 2-bromo-indan-1-one and the product of Example 14B were processed according to the method of Example 14C to afford the title compound. $^1$H NMR (300 MHz, DMSO-d$_6$) δ ppm 1.55-1.70 (m, 4H), 1.70-1.86 (m, 4H), 2.09-2.20 (m, J=9.0, 2.5 Hz, 2H), 2.24-2.34 (m, 2H), 2.60 (t, J=6.6 Hz, 1H), 3.23 (s, 3H), 3.74-3.86 (m, 4H), 4.69 (t, J=5.4 Hz, 2H), 7.29 (td, J=7.4, 0.8 Hz, 1H), 7.39 (td, 1H), 7.58 (d, J=7.1 Hz, 1H), 7.74 (d, J=7.8 Hz, 1H); MS (ESI$^+$) m/z 395 (M+H)$^+$; Anal. Calculated for C$_{23}$H$_{26}$N$_2$O$_2$S: C, 70.02; H, 6.64; N, 7.10. Found: C, 69.83; H, 6.57; N, 6.92.

Example 71

N-[(7Z)-8-(2-methoxyethyl)-5,8-dihydro[1,3]thiazolo[4,5-e][2,1,3]benzoxadiazol-7(4H)-ylidene]hexahydro-2,5-methanopentalene-3a(1H)-carboxamide

Example 71A 4,5-dihydro[1,3]thiazolo[4,5-e][2,1,3]benzoxadiazol-7-amine

To a solution commercially available 5-bromo-6,7-dihydro-5H-benzo[1,2,5]oxadiazol-4-one (1.1 g, 5.1 mmol) in absolute ethanol (60 mL) was added thiourea. The mixture was stirred at 60° C. overnight and then concentrated. The residue was triturated in hexanes and then collected by filtration to afford 1.3 g (90%) of the title compound. MS (ESI$^+$) m/z 195 (M+H)$^+$.

Example 71B

N-4,5-dihydro[1,3]thiazolo[4,5-e][2,1,3]benzoxadiazol-7-ylhexahydro-2,5-methanopentalene-3a(1H)-carboxamide The product of Example 71A and the product of Example 14A were processed as described for Example 17A to afford the title compound. MS (ESI$^+$) m/z 343 (M+H)$^+$.

Example 71C

N-[(7Z)-8-(2-methoxyethyl)-5,8-dihydro[1,3]thiazolo[4,5-e][2,1,3]benzoxadiazol-7(4H)-ylidene]hexahydro-2,5-methanopentalene-3a(1H)-carboxamide The product from Example 71B and 2-bromoethyl methyl ether were processed according to the method of Example 1B to afford the title compound. $^1$H NMR (300 MHz, DMSO-d$_6$) δ ppm 1.44-1.70 (m, 4H), 1.70-1.87 (m, 4H), 2.14 (d, J=11.2 Hz, 2H), 2.29 (s, 2H), 2.59 (t, J=6.8 Hz, 1H), 3.13 (t, J=7.1 Hz, 2H), 3.21-3.30 (m, 5H), 3.63-3.85 (m, 2H), 4.69 (t, J=5.8 Hz, 2H); MS (ESI$^+$) m/z 401 (M+H)$^+$; Anal. Calculated for C$_{20}$H$_{24}$N$_4$O$_3$S: C, 59.98; H, 6.04; N, 13.99. Found: C, 59.90; H, 6.09; N, 13.95.

Example 72

N-[(2Z)-3-(2-methoxyethyl)-4,6-dihydrofuro[3,4-d][1,3]thiazol-2(3H)-ylidene]adamantane-1-carboxamide

Example 72A

4-Bromo-dihydro-furan-3-one

The title compound was prepared according to the procedure as described in Baker, Tracy J, Wiemer, David F, *J. Org. Chem.*, 1998, 63(8), 2613-2618.

Example 72B

3a-Ethoxy-3a,4,6,6a-tetrahydro-furo[3,4-d]thiazol-2-ylamine

The product of Example 72A and thiourea were processed as described for Example 71A to afford the title compound. MS (ESI$^+$) m/z 189 (M+H)$^+$.

Example 72C

Adamantane-1-carboxylic acid (3a-ethoxy-3a,4,6,6a-tetrahydro-furo[3,4-d]thiazol-2-yl)-amide The product of Example 72B, triethylamine, and adamantane-1-carbonyl chloride were processed according to the method of Example 1A to afford the title compound. MS (ESI$^+$) m/z 351 (M+H)$^+$.

Example 72D

N-[(2Z)-3a-ethoxy-3-(2-methoxyethyl)tetrahydro-furo[3,4-d][1,3]thiazol-2(3H)-ylidene]adamantane-1-carboxamide The product of Example 72C and 2-bromoethyl methyl ether were processed according to the method of Example 1B to afford the title compound. MS (ESI⁺) m/z 409 (M+H)⁺.

Example 72E

Adamantane-1-carboxylic acid[3-(2-methoxyethyl)-4,6-dihydro-3H-furo[3,4-d]thiazol-2-ylidene]-amide To a solution the product of Example 72D (15 mg, 0.04 mmol) in toluene (10 mL) was added p-toluenesulfonic acid monohydrate (2 mg). The solution was heated at reflux for 3 hours and then cooled to room temperature, diluted with ethyl acetate, washed with 1M aqueous NaHCO₃, dried (Na₂SO₄), filtered and concentrated. Purification by preparative HPLC on a Waters Symmetry C8 column (40 mm×100 mm, 7 µm particle size) using a gradient of 10% to 100% acetonitrile: ammonium acetate (10 mM) over 15 minutes at a flow rate of 70 mL/minutes afforded 4 mg (30%) of the title compound. $^1$H NMR (500 MHz, DMSO-d₆) δ ppm 1.61-1.76 (m, 6H), 1.82-1.88 (m, 6H), 1.93-2.02 (m, 3H), 3.24 (s, 3H), 3.63 (t, J=5.0 Hz, 2H), 4.18 (t, J=5.0 Hz, 2H), 4.91 (s, 4H); MS (ESI⁺) m/z 363 (M+H)⁺;

Example 73

N-[(2Z)-3-(2-methoxyethyl)-4,6-dihydrofuro[3,4-d][1,3]thiazol-2(3H)-ylidene]hexahydro-2,5-methano-pentalene-3a(1H)-carboxamide Hexahydro-2,5-methano-pentalene-3a-carbonyl chloride (Example 14A), 2-bromoethyl methyl ether and 4-bromo-dihydro-furan-3-one (Baker, Tracy J, Wiemer, David F, *J. Org. Chem.*, 1998, 63(8), 2613-2618) were processed according to the method of Example 72B-E to afford the title compound. $^1$H NMR (300 MHz, DMSO-d₆) δ ppm 1.49-1.66 (m, 4H), 1.67-1.81 (m, 4H), 2.04-2.15 (m, J=11.5 Hz, 2H), 2.27 (s, 2H), 2.55 (t, J=7.0 Hz, 1H), 3.23 (s, 3H), 3.62 (t, J=4.9 Hz, 2H), 4.16 (t, J=4.9 Hz, 2H), 4.91 (s, 4H); MS (ESI⁺) m/z 349 (M+H)⁺; Anal. Calculated for C₁₈H₂₄N₂O₃S: C, 62.04; H, 6.94; N, 8.04. Found: C, 62.09; H, 6.99; N, 7.95.

Example 74

N-[(2Z)-1-(2-methoxyethyl)-1,4,6,7-tetrahydro-2H-pyrano[4,3-d][1,3]thiazol-2-ylidene]hexahydro-2,5-methanopentalene-3a(1H)-carboxamide 3-Bromotetrahydro-4H-pyran-4-one (prepared as described in Kolasa, Teodozyj; Patel, Meena V. WO2001016138) (200 mg, 1.12 mmol), 2-methoxy ethylamine and hexahydro-2,5-methano-pentalene-3a-carbonyl chloride (Example 14A, 316 mg, 1.12 mmol) was processed according to the method of Example 72B-E to afford the title compound: $^1$H NMR (300 MHz, DMSO-d₆) δ 1.55-1.62 (m, 4H) 1.67-1.80 (m, 4H) 2.06-2.14 (m, 2H) 2.23-2.29 (m, 2H) 2.52-2.58 (m, 1H) 2.66-2.73 (m, 2H) 3.23 (s, 3H) 3.64 (t, J=5.3 Hz, 2H) 3.92 (t, J=5.6 Hz, 2H) 4.18 (t, J=5.3 Hz, 2H) 4.52 (t, J=1.9 Hz, 2H); MS (ESI⁺) m/z 363 (M+H)⁺.

Example 75

N-[(2Z)-3-methyl-1,3-thiazol-2(3H)-ylidene]adamantane-1-carboxamide

To a solution of Example 1A (50 mg, 0.19 mmol) in 1 mL of dimethylformamide at 0° C. was added 95% sodium hydride (5.0 mg, 0.21 mmol). The mixture was stirred at 0° C. for 10 minutes, ambient temperature for 1 hour, and then cooled to 0° C. Methyl iodide (10 µL, 0.17 mmol) was added and the mixture was warmed to 80° C. for 14 hours. The mixture was diluted with ethyl acetate and then washed twice with water and then brine. The organic phase was dried over magnesium sulfate, filtered, and concentrated under reduced pressure. Purification by column chromatography (SiO₂, 30-50% ethyl acetate/hexanes gradient) afforded 30 mg (57%) of the title compound. $^1$H NMR (CDCl₃, 300 MHz) δ ppm 1.74-1.75 (m, 6H), 1.99-2.00 (m, 6H), 2.04 (br s, 3H), 3.73 (s, 3H), 6.58 (d, J=4.8 Hz, 1H), 6.91 (d, J=4.8 Hz, 1H); MS (DCI/NH₃) m/z 277 (M+H)⁺.

Example 76

N-[(2Z)-3-butyl-1,3-thiazol-2(3H)-ylidene]adamantane-1-carboxamide

To a solution of Example 1A (0.25 g, 0.95 mmol) in 5 mL of 4:1 tetrahydrofuran:dimethylformamide at 0° C. was added potassium tert-butoxide (0.26 g, 2.3 mmol). The mixture stirred at 0° C. for 30 minutes, ambient temperature for 30 minutes, and then cooled to 0° C. Then 1-iodobutane (0.50 mL, 4.8 mmol) was added and the mixture was heated at 65° C. for 5 hours. The mixture was diluted with EtOAc and washed twice with water and brine. The organic extract was dried over magnesium sulfate, filtered, and concentrated under reduced pressure. Purification by column chromatography (SiO₂, 30-50% ethyl acetate/hexanes gradient) afforded 0.23 g (77%) of the title compound. $^1$H NMR (CDCl₃, 300 MHz) δ ppm 0.97 (t, J=7.3 Hz, 3H), 1.36 (dd, J=14.9, 7.5 Hz, 2H), 1.70-1.76 (m, J=2.9, 2.9 Hz, 6H), 1.76-1.85 (m, 2H), 1.95-2.00 (m, 6H), 2.01-2.06 (m, 3H), 4.18 (t, J=7.1 Hz, 2H), 6.56 (d, J=4.7 Hz, 1H), 6.90 (d, J=4.7 Hz, 1H); MS (DCI/NH₃) m/z 319 (M+H)⁺. Anal. Calculated for C₁₈H₂₆N₂OS.0.5H₂O: C, 66.02; H, 8.31; N, 8.55. Found: C, 65.96; H, 7.93; N, 8.40.

Example 77 ethyl[(2Z)-2-[(1-adamantylcarbonyl)imino]-1,3-thiazol-3(2H)-yl]acetate

Example 77A ethyl(2-imino-1,3-thiazol-3(2H)-yl)acetate hydrobromide

A solution of 2-aminothiazole (27 g, 0.27 mol) and bromoacetic acid ethyl ester (36 mL, 0.32 mol) in 540 mL of acetone was heated at 50° C. for 6 hours. The mixture was concentrated under reduced pressure and the residue was triturated with ethanol. The solid was collected by filtration to provide 58 g (80%) of the title compound. $^1$H NMR (DMSO-d₆, 300 MHz) δ ppm 1.25 (t, J=7.1 Hz, 3H), 4.20 (q, J=7.1 Hz, 2H), 5.00 (s, 2H), 7.04 (d, J=4.7 Hz, 1H), 7.38 (d, J=4.7 Hz, 1H), 9.62 (s, 1H).

Example 77B ethyl[(2Z)-2-[(1-adamantylcarbonyl)imino]-1,3-thiazol-3(2H)-yl]acetate To a solution of the product from Example 77A (0.75 g, 2.8 mmol) and 1-adamantanecarboxylic acid (0.56 g, 3.1 mmol) in 14 mL of THF at 0° C. was added O-(7-azabenzotriazol-1-yl)-N,N,N',N'-tetramethyluronium hexafluorophosphate (1.2 g, 3.1 mmol) and diisopropylethylamine (1.1 mL, 6.2 mmol). The mixture was heated to 65° C. for 2.5 hours, cooled to ambient temperature and then diluted with ethyl acetate. The mixture was washed twice with water, saturated aqueous sodium bicarbonate, and brine. The organic extract was dried over magnesium sulfate, and concentrated under reduced pressure. Purification by column chromatography ($SiO_2$, 30-50% ethyl acetate/hexanes gradient) afforded 0.79 g (81%) of the title compound. $^1$H NMR ($CDCl_3$, 300 MHz) δ ppm 1.29 (t, J=7.1 Hz, 3H), 1.69-1.76 (m, 6H), 1.93-1.94 (m, 6H), 1.99-2.04 (m, 3H), 4.25 (q, J=7.3 Hz, 2H), 4.84 (s, 2H), 6.60 (d, J=5.1 Hz, 1H), 6.93 (d, J=4.7 Hz, 1H); MS (DCI/$NH_3$) m/z 349 (M+H)$^+$. Anal. Calculated for $C_{18}H_{24}N_2O_3S$: C, 62.04; H, 6.94; N, 8.04. Found: C, 62.24; H, 7.08; N, 8.04.

Example 78

N-[(2Z)-3-(2-hydroxyethyl)-1,3-thiazol-2(3H)-ylidene]adamantane-1-carboxamide

To a solution of the product of Example 77B (0.18 g, 0.52 mmol) in 2.5 mL of diethylether at 0° C. was added lithium borohydride (260 μL of a 2.0 M solution in THF). The mixture stirred at 0° C. for 1 hour and then at ambient temperature for 3.5 hours. The mixture was quenched with water and extracted with diethyl ether. The organic phase washed with water and brine. The aqueous washings were combined and extracted with ether. The combined organic extracts were dried over magnesium sulfate and concentrated under reduced pressure. Purification by column chromatography ($SiO_2$, 0-20% methanol/dichloromethane gradient) afforded 0.12 g (77%) of the title compound. $^1$H NMR ($CDCl_3$, 300 MHz) δ ppm 1.75 (t, J=3.1 Hz, 6H), 1.95-2.02 (m, 6H), 2.05 (d, J=4.1 Hz, 3H), 3.98-4.11 (m, 2H), 4.44 (s, 2H), 6.71 (s, 1H), 7.01 (d, J=4.7 Hz, 1H); MS (DCI/$NH_3$) m/z 307 (M+H)$^+$.

Example 79

N-[(2Z)-3-(2-morpholin-4-ylethyl)-1,3-thiazol-2(3H)-ylidene]adamantane-1-carboxamide

Example 79A

2-[(2Z)-2-[(1-adamantylcarbonyl)imino]-1,3-thiazol-3(2H)-yl]ethyl methanesulfonate To a solution of the product from Example 78 (0.95 g, 3.1 mmol) in 15 mL of THF at 0° C. was added triethylamine (1.3 mL, 9.3 mmol) and methanesulfonyl chloride (310 μL, 4.0 mmol). The mixture was stirred at ambient temperature for 15 hours then filtered (EtOAc rinse). The filtrate was concentrated under reduced pressure and purified by column chromatography ($SiO_2$, 20-40% ethyl acetate/hexanes gradient) to afford 0.22 g (18%) of the title compound. $^1$H NMR ($CDCl_3$, 300 MHz) δ ppm 1.95 (d, J=3.1 Hz, 6H), 2.00-2.09 (m, 6H), 2.15 (s, 3H), 2.92 (s, 3H), 4.49 (d, J=5.4 Hz, 2H), 4.64 (d, J=5.4 Hz, 2H), 4.64 (d, J=5.4 Hz, 2H), 6.59 (d, J=4.7 Hz, 1H), 7.01 (d, J=4.7 Hz, 1H).

Example 79B

N-[(2Z)-3-(2-morpholin-4-ylethyl)-1,3-thiazol-2(3H)-ylidene]adamantane-1-carboxamide To a solution of Example 79A (0.22 g, 0.57 mmol) in 3 mL of acetonitrile was added morpholine (50 μL, 0.63 mmol), potassium iodide (0.11 g, 0.63 mmol), and potassium carbonate (0.17 g, 1.3 mmol). The mixture stirred for 16 hours and then diluted with methylene chloride and was washed with water, saturated aqueous potassium carbonate and brine. The organic phase was dried over anhydrous potassium carbonate, filtered and concentrated under reduced pressure. Purification by preparative HPLC afforded 60 mg (28%) of the title compound. $^1$H NMR ($CDCl_3$, 400 MHz) δ ppm 1.69-1.79 (m, 6H), 1.96 (d, J=2.8 Hz, 6H), 2.03 (s, 3H), 2.48-2.58 (m, 4H), 2.75 (t, J=6.3 Hz, 2H), 3.64-3.72 (m, 4H), 4.28 (t, J=6.3 Hz, 2H), 6.55 (d, J=4.6 Hz, 1H), 6.99 (d, J=4.6 Hz, 1H); MS (DCI/$NH_3$) m/z 376 (M+H)$^+$. Anal. Calculated for $C_{20}H_{29}N_3O_2S$: C, 63.97; H, 7.78; N, 11.19. Found: C, 63.85; H, 7.42; N, 10.91.

Example 80

N-[(2Z)-4,5-dimethyl-3-(2-phenoxyethyl)-1,3-thiazol-2(3H)-ylidene]adamantane-1-carboxamide 4,5-Dimethylthiazol-2-ylamine, (2-bromoethoxy)benzene and 1-adamantane carboxylic acid were processed according to the method of Example 47 to afford the title compound. $^1$H NMR ($CDCl_3$, 300 MHz) δ ppm 1.57-1.77 (m, 6H) 1.83 (d, J=2.50 Hz, 6H) 1.93-2.03 (m, 3H) 2.16 (s, 3H) 2.26 (s, 3H) 4.34 (t, J=5.30 Hz, 2H) 4.46 (t, J=5.30 Hz, 2H) 6.83-7.03 (m, 3H) 7.23-7.36 (m, 2H); MS (ESI) m/z 411 (M=H)$^+$.

Example 81

N-[(2Z)-3-[2-(2,3-dihydro-1,4-benzodioxin-5-yloxy)ethyl]-4,5-dimethyl-1,3-thiazol-2(3H)-ylidene]adamantane-1-carboxamide

Example 81A

3-[2-(2,3-Dihydro-benzo[1,4]dioxin-5-yloxy)-ethyl]-4,5-dimethyl-3H-thiazol-2-ylideneamine hydrobromide A mixture of 5-(2-bromoethoxy)-2,3-dihydro-benzo[1,4]dioxine (1.2 g, 4.7 mmol) and 4,5-dimethyl-thiazol-2-ylamine (0.50 g, 3.9 mmol) was heated at 85° C. for 7 hours. The mixture was cooled to ambient temperature and the residue was recrystallized from ethanol to provide 0.18 g (13%) of the title compound.

Example 81B

Adamantane-1-carboxylic acid{3-[2-(2,3-dihydro-benzo[1,4]dioxin-5-yloxy)-ethyl]-4,5-dimethyl-3H-thiazol-2-ylidene}-amide Adamantane-1-carboxylic acid (0.78 g, 0.12 mmol) and the product of Example 81A (0.15 g, 0.39 mmol) were processed according to the method of Example 77B. Purification by column chromatography ($SiO_2$, 0-15% methanol/methylene chloride gradient) afforded 0.11 g (60%) of the title compound. $^1$H NMR (CDCl$_3$, 300 MHz) δ ppm 1.68-1.79 (m, 6H), 1.96 (d, J=2.4 Hz, 6H), 2.04 (d, J=5.4 Hz, 3H), 2.17 (s, 3H), 2.29 (s, 3H), 4.18-4.30 (m, 4H), 4.36 (t, J=5.3 Hz, 2H), 4.51 (s, 2H), 6.44-6.58 (m, 2H), 6.72 (t, J=8.1 Hz, 1H); MS (DCI/NH$_3$) m/z 469 (M+H)$^+$. Anal. Calculated for C$_{26}$H$_{32}$N$_2$O$_4$S: C, 66.64; H, 6.88; N, 5.98. Found: C, 66.36; H, 6.80; N, 5.87.

Example 82 tert-butyl[(2Z)-2-[(1-adamantylcarbonyl)imino]-4,5-dimethyl-1,3-thiazol-3(2H)-yl]acetate

Example 82A tert-butyl-(2-Imino-4,5-dimethyl-thiazol-3-yl)acetate hydrobromide Bromoacetic acid tert-butyl ester (1.4 mL, 9.4 mmol) and 4,5-dimethyl-2-aminothiazole (1.0 g, 7.8 mmol) were heated at 85° C. for 14 hours. The mixture was cooled to ambient temperature and the resulting solid was triturated with ethyl acetate to provide the title compound.

Example 82B

[2-(Adamantane-1-carbonylimino)-4,5-dimethyl-thiazol-3-yl]-acetic acid tert-butyl ester Adamantane-1-carboxylic acid (2.2 g, 12 mmol) and the product of Example 82A (2.9 g, 10 mmol) were processed according to the method of Example 77B. Purification by column chromatography (SiO$_2$, 20-35% ethyl acetate/hexanes gradient) afforded 0.25 g (63%) of the title compound. $^1$H NMR (CDCl$_3$, 300 MHz) δ ppm 1.47 (s, 9H), 1.71-1.75 (m, 6H), 1.96-2.00 (m, 6H), 2.00-2.04 (m, 3H), 2.14 (s, 3H), 2.21 (s, 3H), 4.85-5.02 (m, 2H); MS (DCI/NH$_3$) m/z 405 (M+H)$^+$. Anal. Calculated for C$_{22}$H$_{32}$N$_2$O$_3$S: C, 65.31; H, 7.97; N, 6.92. Found: C, 65.38; H, 7.95; N, 6.84.

Example 83

N-[(2Z)-3-(2-methoxyethyl)-4,5-dimethyl-1,3-thiazol-2(3H)-ylidene]hexahydro-2,5-methanopentalene-3a(1H)-carboxamide Hexahydro-2,5-methano-pentalene-3a-carboxylic acid (0.30 g, 1.8 mmol) and the product of Example 46A (0.37 g, 2.0 mmol) were processed according to the method of Example 77B. Recrystallization from hexanes afforded 0.25 g (70%) of the title compound. $^1$H NMR (CDCl$_3$, 300 MHz) δ ppm 1.59 (d, J=2.7 Hz, 3H), 1.63 (d, J=2.4 Hz, 3H), 1.80-1.91 (m, 4H), 2.19 (s, 3H), 2.21 (s, 3H), 2.30 (d, J=2.0 Hz, 2H), 2.70 (t, J=6.4 Hz, 1H), 3.30 (s, 3H), 3.70 (t, J=5.3 Hz, 2H), 4.20-4.44 (m, 2H); MS (DCI/NH$_3$) m/z 335 (M+H)$^+$. Anal. Calculated for C$_{18}$H$_{26}$N$_2$O$_2$S: C, 64.64; H, 7.83; N, 8.38. Found: C, 64.89; H, 7.64; N, 8.03.

Example 84

N-[(2Z)-3-(2-methoxy ethyl)-4,5-dimethyl-1,3-thiazol-2(3H)-ylidene]-3,5-dimethyladamantane-1-carboxamide The product of Example 46A (0.40 g, 2.2 mmol) and 3,5-dimethyladamantane-1-carboxylic acid (0.54 g, 2.6 mmol) were processed according to the method of Example 77B. Purification by column chromatography (SiO$_2$, 30-50% ethyl acetate/hexanes gradient) afforded 0.27 g (33%) of the title compound. $^1$H NMR (CDCl$_3$, 300 MHz) δ ppm 0.85 (s, 6H), 1.16 (s, 2H), 1.28-1.44 (m, 4H), 1.51-1.65 (m, 4H), 1.79 (d, J=2.4 Hz, 2H), 2.08-2.14 (m, 1H), 2.18 (s, 3H), 2.21 (s, 3H), 3.31 (s, 3H), 3.70 (t, J=5.4 Hz, 2H), 4.19-4.39 (m, 2H). Anal. Calculated for C$_{18}$H$_{26}$N$_2$O$_2$S: C, 64.64; H, 7.83; N, 8.38. Found: C, 64.89; H, 7.64; N, 8.03.

Example 85

N-[(2Z)-4,5-dimethyl-3-[2-(2,2,2-trifluoroethoxy)ethyl]-1,3-thiazol-2(3H)-ylidene]hexahydro-2,5-methanopentalene-3a(1H)-carboxamide

Example 85A 4,5-dimethyl-3-[2-(2,2,2-trifluoro-ethoxy)-ethyl]-3H-thiazol-2-ylideneamine hydrobromide 4,5-Dimethyl-thiazol-2-ylamine and 2-(2-bromo-ethoxy)-1,1,1-trifluoroethane were mixed and heated at 65° C. for 4 hours. The residue was triturated with hexane to afford the title compound. MS (ESI$^+$) m/z 255 (M+H)$^+$.

Example 85B

Adamantane-1-carboxylic acid{4,5-dimethyl-3-[2-(2,2,2-trifluoro-ethoxy)-ethyl]-3H-thiazol-2-ylidene}-amide To a solution of Example 85A (0.20 g, 0.8 mmol) in THF (10 mL) was added triethylamine (0.4 mL) and adamantane-1-carbonyl chloride (0.2 g, 1 mmol). The mixture was heated at reflux overnight and then concentrated under reduced pressure. The residue was diluted with ethyl acetate, washed with 1M aqueous NaHCO$_3$, dried (Na$_2$SO$_4$), filtered, and concentrated. Purification by preparative HPLC on a Waters Symmetry C8 column (40 mm×100 mm, 7 μm particle size) using a gradient of 10% to 100% acetonitrile:ammonium acetate (10 mM) over 15 minutes at a flow rate of 70 mL/minutes afforded 10 mg of the title compound. $^1$H NMR (300 MHz, DMSO-d$_6$) δ ppm 1.60-1.75 (m, J=28.8 Hz, 6H), 1.83 (d, J=2.7 Hz, 6H), 1.93-2.01 (m, 3H), 2.15 (s, 3H), 2.20 (s, 3H), 3.92 (t, J=5.3 Hz, 2H), 4.09 (q, J=9.5 Hz, 2H), 4.28 (t, J=5.3 Hz, 2H); MS (ESI$^+$) m/z 417 (M+H)$^+$; Anal. Calculated for C$_{20}$H$_{17}$F$_3$N$_2$O$_2$S: C, 57.67; H, 6.53; N, 6.73. Found: C, 57.53; H, 6.55; N, 6.69.

Example 86

N-[(2Z)-3-(2-hydroxyethyl)-4,5-dimethyl-1,3-thiazol-2(3H)-ylidene]adamantane-1-carboxamide

Example 86A 2-(2-Imino-4,5-dimethyl-thiazol-3-yl)-ethanol hydrobromide

A mixture of 4,5-dimethyl-thiazol-2-ylamine (1.0 g, 7.8 mmol) and 2-bromoethanol (0.68 mL, 9.4 mmol) were processed as described in Example 8A to provide 0.92 g (47%) of the title compound. $^1$H NMR (DMSO-d$_6$, 300 MHz) δ ppm 2.19 (s, 6H), 3.61-3.68 (m, 2H), 4.03 (t, J=4.9 Hz, 2H), 5.14 (br s, 1H), 9.27 (s, 1H); MS (DCI/NH$_3$) m/z 173 (M+H)$^+$.

Example 86B

N-[(2Z)-3-(2-hydroxyethyl)-4,5-dimethyl-1,3-thiazol-2(3H)-ylidene]adamantane-1-carboxamide The product of Example 86A (0.45 g, 1.8 mmol) and adamantane-1-carboxylic acid (0.32 g, 1.8 mmol) were processed according to the method of Example 77B. Purification by column chromatography (SiO$_2$, 10-20% methanol/methylene chloride gradient) afforded 0.34 g (57%) of the title compound. $^1$H NMR (CDCl$_3$, 300 MHz) δ ppm 1.73 (t, J=3.1 Hz, 6H), 1.95 (d, J=2.7 Hz, 6H), 2.04 (s, 3H), 2.18 (s, 3H), 2.20 (s, 3H), 3.94-4.02 (m, 2H), 4.27-4.37 (m, 2H), 5.17 (s, 1H); MS (DCI/NH$_3$) m/z 335 (M+H)$^+$. Anal. Calculated for C$_{18}$H$_{26}$N$_2$O$_2$S: C, 64.64; H, 7.83; N, 8.38. Found: C, 64.63; H, 7.91; N, 8.28.

Example 87

N-[(2Z)-4,5-dimethyl-3-(2-morpholin-4-ylethyl)-1,3-thiazol-2(3H)-ylidene]adamantane-1-carboxamide hydrochloride

Example 87A 4,5-dimethyl-3-(2-morpholin-4-ylethyl)-1,3-thiazol-2(3H)-ylideneamine A mixture of 4,5-dimethyl-thiazol-2-ylamine (1.0 g, 7.8 mmol), 4-(2-chloroethyl)-morpholine hydrochloride (1.6 g, 8.6 mmol) and triethylamine (2.4 mL, 17.2 mmol) were heated at 80° C. After 3 hours, additional triethylamine (1.1 mL, 7.9 mmol) was added and the mixture was stirred at 80° C. for 14 hours, then cooled to ambient temperature and concentrated. The residue was diluted with methylene chloride and washed with saturated aqueous sodium bicarbonate and water. The organic extract was dried over magnesium sulfate, filtered and concentrated under reduced pressure to provide 0.26 g (14%) of a 3:1 mixture of title compound to 4,5-dimethyl-thiazol-2-ylamine. MS (DCI/NH$_3$) m/z 242 (M+H)$^+$.

Example 87B

N-[(2Z)-4,5-dimethyl-3-(2-morpholin-4-ylethyl)-1,3-thiazol-2(3H)-ylidene]adamantane-1-carboxamide The product of Example 87A (0.19 g, 0.81 mmol, 3:1 mixture) and adamantane-1-carboxylic acid (0.16 g, 0.89 mmol) were processed according to the method of Example 77B to afford the title compound. MS (DCI/NH$_3$) m/z 404 (M+H)$^+$.

Example 87C

Adamantane-1-carboxylic acid[4,5-dimethyl-3-(2-morpholin-4-yl-ethyl)-3H-thiazol-2-ylidene]-amide hydrochloride To a solution of the product of Example 87B (0.12 g, 0.30 mmol) in 10 mL of ethanol was added a 0.1 mL of 4 M solution of HCl in 1,4-dioxane. The mixture was stirred at ambient temperature for 16 hours. The solid was collected by filtration to afford 73 mg (55%) of the title compound. $^1$H NMR (DMSO-d$_6$, 300 MHz) δ ppm 1.65-1.74 (m, 6H), 1.85 (d, J=2.7 Hz, 6H), 1.94-2.04 (m, 3H), 2.17 (s, 3H), 2.27 (s, 3H), 3.37-3.54 (m, 6H), 3.76-3.99 (m, 4H), 4.48-4.59 (m, 2H); MS (DCI/NH$_3$) m/z 404 (M+H)$^+$. Anal. Calculated for C$_{22}$H$_{33}$N$_3$O$_2$S.HCl: C, 60.05; H, 7.79; N, 9.55. Found: C, 60.26; H, 7.87; N, 9.45.

Example 88

N-[(2Z)-3-cyclobutyl-4,5-dimethyl-1,3-thiazol-2(3H)-ylidene]adamantane-1-carboxamide 4,5-Dimethylthiazol-2-ylamine, bromocyclobutane and 1-adamantane carboxylic acid were processed according to the method of Example 47 to afford the title compound. $^1$H NMR (CDCl$_3$, 500 MHz) δ ppm 0.43-0.53 (m, 3H) 1.21-1.29 (m, J=7.18, 7.18 Hz, 1H) 1.60-1.74 (m, J=15.60 Hz, 7H) 1.82 (d, J=2.81 Hz, 6H) 1.94-2.03 (m, 3H) 2.17 (s, 3H) 2.24 (s, 3H) 4.06 (d, J=7.18 Hz, 2H); MS (ESI) m/z 345 (M+H)$^+$.

Example 89

N-[(2Z)-3-but-3-enyl-4,5-dimethyl-1,3-thiazol-2(3H)-ylidene]adamantane-1-carboxamide 4,5-Dimethylthiazol-2-ylamine, 4-bromo-but-1-ene and 1-adamantane carboxylic acid were processed according to the method of Example 47 to afford the title compound. $^1$H NMR (CDCl$_3$, 500 MHz) δ ppm 1.60-1.76 (m, 6H) 1.85 (d, J=2.50 Hz, 6H) 1.94-2.04 (m, 3H) 2.15 (s, 3H) 2.20 (s, 3H) 2.46 (q, J=7.18 Hz, 2H) 4.16 (t, 2H) 4.94-5.13 (m, 2H) 5.75-5.90 (m, 1H); MS (ESI) m/z 345 (M+H)$^+$.

Example 90

N-[(2Z)-4,5-dimethyl-3-pent-4-enyl-1,3-thiazol-2(3H)-ylidene]adamantane-1-carboxamide 4,5-Dimethylthiazol-2-ylamine, 5-bromo-pent-1-ene and 1-adamantane carboxylic acid were processed according to the method of Example 47 to afford the title compound. $^1$H NMR (CDCl$_3$, 500 MHz) δ ppm 1.68 (q, 6H) 1.74-1.81 (m, 2H) 1.84 (d, J=2.50 Hz, 6H) 1.94-2.02 (m, 3H) 2.10 (q, 2H) 2.15 (s, 3H) 2.20 (s, 3H) 4.11 (t, 2H) 4.95-5.13 (m, 2H) 5.80-5.95 (m, 1H); MS (ESI) m/z 359 (M+H)$^+$.

Example 91

N-[(2Z)-3-(cyclobutylmethyl)-4,5-dimethyl-1,3-thiazol-2(3H)-ylidene]adamantane-1-carboxamide 4,5-Dimethylthiazol-2-ylamine, bromomethylcyclobutane and 1-adamantane carboxylic acid were processed according to the method of Example 47 to afford the title compound. $^1$H NMR (CDCl$_3$, 500 MHz) δ ppm 1.60-1.75 (m, 6H) 1.75-1.93 (m, 10H) 1.92-2.06 (m, 5H) 2.15 (s, 3H) 2.18 (s, 3H) 2.64-2.74 (m, 1H) 4.22 (d, J=7.18 Hz, 2H); MS (ESI) m/z 359 (M+H)$^+$.

Example 92

N-[(2Z)-4,5-dimethyl-3-(4-methylpentyl)-1,3-thiazol-2(3H)-ylidene]adamantane-1-carboxamide 4,5-Dimethylthiazol-2-ylamine, 1-bromo-4-methyl-pentane and 1-adamantane carboxylic acid were processed according to the method of Example 47 to afford the title compound. $^1$H NMR (CDCl$_3$, 500 MHz) δ ppm 0.87 (d, J=6.55 Hz, 6H) 1.18-1.27 (m, 2H) 1.54-1.62 (m, 1H) 1.62-

1.76 (m, 8H) 1.84 (d, J=2.50 Hz, 6H) 1.94-2.03 (m, 3H) 2.15 (s, 3H) 2.20 (s, 3H) 3.98-4.11 (m, 2H); MS (ESI) m/z 374 (M=H)$^+$.

Example 93

N-[(2Z)-3-ethyl-4,5-dimethyl-1,3-thiazol-2(3H)-ylidene]adamantane-1-carboxamide 4,5-Dimethylthiazol-2-ylamine, iodoethane and 1-adamantane carboxylic acid were processed according to the method of Example 47 to afford the title compound. $^1$H NMR (CDCl$_3$, 500 MHz) δ ppm 1.20-1.29 (m, 3H) 1.68 (q, J=11.96 Hz, 6H) 1.84 (d, J=2.50 Hz, 6H) 1.94-2.03 (m, 3H) 2.16 (s, 3H) 2.21 (s, 3H) 4.14 (q, J=7.18 Hz, 2H); MS (ESI) m/z 319 (M+H)$^+$.

Example 94

N-[(2Z)-4,5-dimethyl-3-(1-phenylethyl)-1,3-thiazol-2(3H)-ylidene]adamantane-1-carboxamide 4,5-dimethylthiazol-2-ylamine, (1-bromo-ethyl)benzene and 1-adamantane carboxylic acid were processed according to the method of Example 47 to afford the title compound. $^1$H NMR (CDCl$_3$, 500 MHz) δ ppm 1.51-1.75 (m, 12H) 1.91 (d, J=6.86 Hz, 6H) 2.03-2.11 (m, 3H) 2.14 (s, 3H) 5.98-6.31 (m, 1H) 7.21 (d, J=8.11 Hz, 2H) 7.25 (t, J=7.33 Hz, 1H) 7.34 (t, J=7.49 Hz, 2H); MS (ESI) m/z 394 (M+H)$^+$.

Example 95

N-[(2Z)-3-(4-tert-butylbenzyl)-4,5-dimethyl-1,3-thiazol-2(3H)-ylidene]adamantane-1-carboxamide 4,5-Dimethylthiazol-2-ylamine, 1-bromomethyl-4-tert-butylbenzene and 1-adamantane carboxylic acid were processed according to the method of Example 47 to afford the title compound. $^1$H NMR (CDCl$_3$, 500 MHz) δ ppm 1.24 (s, 9H) 1.54-1.73 (m, 6H) 1.82 (d, J=2.50 Hz, 6H) 1.92-2.01 (m, 3H) 2.10 (s, 3H) 2.13 (s, 3H) 5.39 (s, 2H) 7.19 (d, J=8.42 Hz, 2H) 7.36 (d, J=8.42 Hz, 2H); MS (ESI) m/z 437 (M+H)$^+$.

Example 96

N-[(2Z)-4,5-dimethyl-3-(pyridin-3-ylmethyl)-1,3-thiazol-2(3H)-ylidene]adamantane-1-carboxamide 4,5-Dimethylthiazol-2-ylamine, 3-bromomethylpyridine and 1-adamantane carboxylic acid were processed according to the method of Example 47 to afford the title compound. $^1$H NMR (CDCl$_3$, 500 MHz) δ ppm 1.49-1.71 (m, 6H) 1.74 (d, J=2.50 Hz, 6H) 1.85-2.02 (m, 3H) 2.19 (d, J=11.54 Hz, 6H) 5.44 (s, 2H) 7.29 (t, J=7.33 Hz, 2H) 7.69-7.85 (m, 1H) 8.49 (d, J=4.68 Hz, 1H); MS (ESI) m/z 382 (M+H)$^+$.

Example 97

N-[(2Z)-4,5-dimethyl-3-(pyridin-4-ylmethyl)-1,3-thiazol-2(3H)-ylidene]adamantane-1-carboxamide

Example 97A

Adamantane-1-carboxylic acid (4,5-dimethyl-thiazol-2-yl)-amide

To a solution of 4,5-dimethyl-thiazol-2-ylamine hydrochloride (1.65 g, 10.0 mmol) in THF (100 mL) was added triethylamine (4.2 mL, 30 mmol) and adamantane-1-carbonyl chloride (2.2 g, 11 mmol). The mixture was heated at reflux overnight and then concentrated under reduced pressure. The residue was diluted with ethyl acetate, washed with 1M NaHCO$_3$, dried (Na$_2$SO$_4$), filtered and concentrated. Purification by column chromatography (SiO$_2$, 10% ethyl acetate: 90% hexanes) afforded 2.15 g (74%) of the title compound. MS (ESI$^+$) m/z 291 (M+H)$^+$.

Example 97B

Adamantane-1-carboxylic acid(4,5-dimethyl-3-pyridin-4-ylmethyl-3H-thiazol-2-ylidene)-amide To a solution of Example 97A (145 mg, 0.50 mmol) in DMF (5 mL) was added potassium tert-butoxide (120 mg, 1.10 mmol) and the hydrochloride salt of 4-chloromethylpyridine (82 mg, 0.5 mmol). The mixture was heated in a SmithSynthesizer™ microwave at 250° C. for 15 minutes. The mixture was diluted with ethyl acetate, washed with 1M NaHCO$_3$, and layers were separated. The aqueous layer was extracted with methylene chloride (3×). The combined organic extracts were dried (Na$_2$SO$_4$), filtered and concentrated. The residue was recrystallized from ethyl acetate to afford the title compound (70 mg, 36%). $^1$H NMR (300 MHz, DMSO-d$_6$) δ ppm 1.54-1.72 (m, 6H), 1.75 (d, J=2.4 Hz, 6H), 1.91 (s, 3H), 2.09 (d, J=0.7 Hz, 3H), 2.17 (d, J=0.7 Hz, 3H), 5.44 (s, 2H), 7.06-7.20 (m, 2H), 8.50-8.56 (m, J=6.1 Hz, 2H); MS (ESI$^+$) m/z 382 (M+H)$^+$; Anal. Calculated for C$_{22}$H$_{27}$N$_3$OS.0.2H$_2$O: C, 68.61; H, 7.17; N, 10.91. Found: C, 68.56; H, 7.12; N, 10.76.

Example 98

N-[(2Z)-3-(2-cyclohexylethyl)-4,5-dimethyl-1,3-thiazol-2(3H)-ylidene]adamantane-1-carboxamide 4,5-Dimethylthiazol-2-ylamine, (2-bromoethyl)-cyclohexane and 1-adamantane carboxylic acid were processed according to the method of Example 47 to afford the title compound. $^1$H NMR (CDCl$_3$, 500 MHz) δ ppm 0.93-1.05 (m, 2H) 1.10-1.26 (m, 3H) 1.29-1.38 (m, 1H) 1.48-1.57 (m, 2H) 1.58-1.75 (m, 9H) 1.75-1.83 (m, J=12.79 Hz, 2H) 1.85 (d, J=2.50 Hz, 6H) 1.94-2.02 (m, 3H) 2.15 (s, 3H) 2.20 (s, 3H) 4.07-4.18 (m, 2H); MS (ESI) m/z 401 (M+H)$^+$.

Example 99

N-[(2Z)-3-[2-(1H-indol-3-yl)ethyl]-4,5-dimethyl-1,3-thiazol-2(3H)-ylidene]adamantane-1-carboxamide 4,5-Dimethylthiazol-2-ylamine, 3-(2-bromo-ethyl)-1H-indole and 1-adamantane carboxylic acid were processed according to the method of Example 47 to afford the title compound. $^1$H NMR (CDCl$_3$, 500 MHz) δ ppm 1.68-1.75 (m, 6H) 1.91 (d, J=2.50 Hz, 6H) 1.98-2.04 (m, 3H) 2.13 (d, J=4.68 Hz, 6H) 3.04-3.21 (m, 2H) 4.20-4.43 (m, 2H) 6.98 (t, J=7.49 Hz, 1H) 7.09 (t, J=7.64 Hz, 1H) 7.17 (d, J=2.18 Hz, 1H) 7.36 (d, J=8.11 Hz, 1H) 7.68 (d, J=7.80 Hz, 1H) 10.88 (s, 1H); MS (ESI) m/z 434 (M+H)$^+$.

Example 100

N-[(2Z)-4,5-dimethyl-3-pent-2-ynyl-1,3-thiazol-2 (3H)-ylidene]adamantane-1-carboxamide 4,5-Dimethylthiazol-2-ylamine, 1-bromo-pent-2-yne and 1-adamantane carboxylic acid were processed according to the method of Example 47 to afford the title compound. $^1$H NMR (CDCl$_3$, 500 MHz) δ ppm 1.03 (t, J=7.49 Hz, 3H) 1.64-1.75 (m, 6H) 1.84 (d, J=2.50 Hz, 6H) 1.94-2.02 (m, 3H) 2.16 (s, 3H) 2.16-2.22 (m, 2H) 2.28 (s, 3H) 5.00 (t, J=2.18 Hz, 2H); MS (ESI) m/z 357 (M+H)$^+$.

Example 101

N-[(2Z)-4,5-dimethyl-3-[2-(1-naphthyl)ethyl]-1,3-thiazol-2(3H)-ylidene]adamantane-1-carboxamide 4,5-Dimethylthiazol-2-ylamine, 1-(2-bromo-ethyl)-naphthalene and 1-adamantane carboxylic acid were processed according to the method of Example 47 to afford the title compound. $^1$H NMR (CDCl$_3$, 500 MHz) δ ppm 1.61-1.80 (m, 6H) 1.82-1.93 (m, 6H) 1.95-2.05 (m, 3H) 2.13 (d, J=4.06 Hz, 6H) 3.40-3.56 (m, 2H) 4.26-4.52 (m, 2H) 7.34-7.41 (m, 1H) 7.41-7.46 (m, 1H) 7.51-7.60 (m, 2H) 7.78-7.92 (m, 1H) 7.92-8.02 (m, 1H) 8.27-8.44 (m, 1H); MS (ESI) m/z 445 (M+H)$^+$.

Example 102

N-[(2Z)-3-(2-chloro-6-fluorobenzyl)-4,5-dimethyl-1,3-thiazol-2(3H)-ylidene]adamantane-1-carboxamide 4,5-Dimethylthiazol-2-ylamine, 2-bromomethyl-1-chloro-3-fluorobenzene and 1-adamantane carboxylic acid were processed according to the method of Example 47 to afford the title compound. $^1$H NMR (CDCl$_3$, 500 MHz) δ ppm 1.50-1.70 (m, 12H) 1.80-1.93 (m, 3H) 2.17 (s, 3H) 2.22 (s, 3H) 5.42 (s, 2H) 7.11-7.22 (m, 1H) 7.26-7.41 (m, 2H); MS (ESI) m/z 433 (M+H)$^+$.

Example 103

N-[(2Z)-3-(3-hydroxypropyl)-4,5-dimethyl-1,3-thiazol-2(3H)-ylidene]adamantane-1-carboxamide Example 103A 3-(2-Imino-4,5-dimethyl-thiazol-3-yl)-propan-1-ol hydrobromide 4,5-dimethyl-thiazol-2-ylamine (2.0 g, 16 mmol) and 3-bromo-propan-1-ol (1.6 mL, 19 mmol) were processed according to the method of Example 46A to afford the title compound.

Example 103B

N-[(2Z)-3-(3-hydroxypropyl)-4,5-dimethyl-1,3-thiazol-2(3H)-ylidene]adamantane-1-carboxamide The product of 103A (1.0 g, 5.4 mmol) and adamantane-1-carboxylic acid (1.1 g, 5.9 mmol) were processed according to the method of Example 77B. Purification by column chromatography (SiO$_2$, 0-20% methanol/methylene chloride gradient) afforded 0.61 mg (32%) of the title compound. $^1$H NMR (CDCl$_3$, 300 MHz) δ ppm 1.73 (t, J=2.9 Hz, 6H), 1.87-1.95 (m, 2H), 1.97 (d, J=2.7 Hz, 6H), 2.04 (s, 3H), 2.20 (s, 3H), 2.23 (s, 3H), 3.40-3.48 (m, 2H), 4.34-4.41 (m, 2H)); MS (DCI/NH$_3$) m/z 349 (M+H)$^+$. Anal. Calculated for C$_{19}$H$_{28}$N$_2$O$_2$S.0.5H$_2$O: C, 63.83; H, 8.18; N, 7.84. Found: C, 63.79; H, 8.15; N, 7.87.

Example 104

[(2Z)-2-[(1-adamantylcarbonyl)imino]-4,5-dimethyl-1,3-thiazol-3(2H)-yl]acetic acid Example 104A tert-butyl-(2-Imino-4,5-dimethyl-thiazol-3-yl)-acetate hydrobromide A mixture of 4,5-dimethyl-thiazol-2-ylamine (1.0 g, 7.8 mmol) and bromoacetic acid tert-butyl ester (1.4 mL, 9.4 mmol) was heated at 85° C. for 14 hours and then cooled to ambient temperature. Recrystallization of the residue from ethyl acetate provided 2.9 g of a 4:1 mixture of the title compound to starting 4,5-dimethylthiazol-2-ylamine.

Example 104B

[2-(Adamantane-1-carbonylimino)-4,5-dimethyl-1,3-thiazol-3(2H)-yl]acetic acid tert-butyl ester The product of Example 104A (2.9 g, 10 mmol, 4:1 mixture) and adamantane-1-carboxylic acid (2.2 g, 12 mmol) were processed according to the method of Example 77B to afford 2.5 g (63%) of the title compound. $^1$H NMR (CDCl$_3$, 300 MHz) δ ppm 1.47 (s, 9H), 1.70-1.75 (m, 6H), 1.96 (d, J=2.4 Hz, 6H), 1.99-2.05 (m, 3H), 2.13 (s, 3H), 2.19 (s, 3H), 4.84 (s, 2H); MS (DCI/NH$_3$) m/z 405 (M+H)$^+$.

Example 104C

[(2Z)-2-[(1-adamantylcarbonyl)imino]-4,5-dimethyl-1,3-thiazol-3(2H)-yl]acetic acid To a solution of the product of Example 104B (2.5 g, 6.2 mmol) in 2 mL of methylene chloride was added 2 mL of trifluoroacetic acid. The solution stirred for 16 hours and then concentrated under reduced pressure. The residue was diluted with methylene chloride and washed twice with water and then brine. The organic extract was dried over magnesium sulfate, filtered and concentrated under reduced pressure to afford 1.8 g (83%) of the title compound. $^1$H NMR (CDCl$_3$, 300 MHz) δ ppm 1.60-1.73 (m, 6H), 1.80 (d, J=2.7 Hz, 6H), 1.91-2.00 (m, 3H), 2.13 (s, 3H), 2.16 (s, 3H), 4.86 (s, 2H), 13.14 (s, 1H); MS (DCI/NH$_3$) m/z 349 (M+H)$^+$. Anal. Calculated for C$_{18}$H$_{24}$N$_2$O$_3$S.0.1H$_2$O: C, 58.99; H, 7.15; N, 7.64. Found: C, 58.74; H, 7.14; N, 7.54.

Example 105

N-[(2Z)-3-butyl-1,3-benzothiazol-2(3H)-ylidene]adamantane-1-carboxamide

Example 105A

3-Butyl-3H-benzothiazol-2-ylideneamine hydroiodide

Benzothiazol-2-ylamine (1.0 g, 6.6 mmol) and 1-iodobutane (0.90 mL, 7.9 mmol) were processed as described in Example 46A. Recrystallization from ethyl acetate provided 1.4 g (63%) of the title compound. $^1$H NMR (DMSO-d$_6$, 300

MHz) δ ppm 0.92 (t, J=7.3 Hz, 3H), 1.32-1.46 (m, 2H), 1.60-1.73 (m, 2H), 4.19-4.28 (m, 2H), 7.40-7.47 (m, 1H), 7.54-7.62 (m, 1H), 7.73 (d, J=7.8 Hz, 1H), 8.00 (dd, J=7.8, 1.0 Hz, 1H), 10.00-10.13 (m, 1H); MS (DCI/NH$_3$) m/z 207 (M+H)$^+$.

Example 105B

N-[(2Z)-3-butyl-1,3-benzothiazol-2(3H)-ylidene]adamantane-1-carboxamide

The product of Example 105A (0.35 g, 1.1 mmol) and adamantane-1-carboxylic acid (0.19 g, 1.1 mmol) were processed according to the method of Example 77B. Purification by column chromatography (SiO$_2$, 20-30% ethyl acetate/hexanes gradient) afforded 95 mg (25%) of the title compound. $^1$H NMR (CDCl$_3$, 300 MHz) δ ppm 1.00 (t, J=7.5 Hz, 3H), 1.43-1.49 (m, 2H), 1.76 (t, J=3.1 Hz, 6H), 1.79-1.87 (m, 2H), 2.02 (d, J=2.7 Hz, 6H), 2.07 (s, 3H), 4.44 (t, J=7.3 Hz, 2H), 7.28-7.36 (m, 2H), 7.41-7.49 (m, 1H), 7.67 (d, J=7.8 Hz, 1H); MS (DCI/NH$_3$) m/z 369 (M+H)$^+$. Anal. Calculated for C$_{22}$H$_{28}$N$_2$OS: C, 71.70; H, 7.66; N, 7.60. Found: C, 71.79; H, 7.63; N, 7.49.

Example 106 ethyl[(2Z)-2-[(1-adamantylcarbonyl)imino]-1,3-benzothiazol-3(2H)-yl]acetate

Example 106A (2-Iminobenzothiazol-3-yl)-acetic acid ethyl ester hydrobromide A mixture of benzothiazol-2-ylamine (1.0 g, 6.6 mmol) and bromoacetic acid ethyl ester (0.86 mL, 7.9 mmol) in 30 mL of acetone was heated at 50° C. for 6 hours. The mixture was cooled to ambient temperature and the solid was triturated with ethanol, collected by filtration, and dried under vacuum to provide 1.8 g (86%) of the title compound. $^1$H NMR (DMSO-d$_6$, 300 MHz) δ ppm 1.25 (t, J=7.1 Hz, 3H), 4.22 (q, J=7.1 Hz, 2H), 5.28 (s, 2H), 7.44 (td, J=7.6, 1.0 Hz, 1H), 7.55 (td, J=7.8, 1.4 Hz, 1H), 7.68 (d, J=7.8 Hz, 1H), 8.01 (dd, J=8.1, 1.0 Hz, 1H), 10.3 (s, 1H); MS (DCI/NH$_3$) m/z 237 (M+H)$^+$.

Example 106B

[2-(Adamantane-1-carbonylimino)-benzothiazol-3-yl]-acetic acid ethyl ester

The product of Example 106A (1.0 g, 3.2 mmol) and adamantane-1-carboxylic acid (0.57 g, 3.2 mmol) were processed according to the method of Example 77B. Purification by column chromatography (SiO$_2$, 20-30% ethyl acetate/hexanes gradient) afforded 0.47 g (37%) of the title compound. $^1$H NMR (CDCl$_3$, 300 MHz) δ ppm 1.26 (t, J=7.1 Hz, 3H), 1.74 (s, 6H), 1.97 (d, J=3.1 Hz, 6H), 2.04 (s, 3H), 4.25 (q, J=7.1 Hz, 2H), 5.08 (s, 2H), 7.17 (d, J=8.1 Hz, 1H), 7.24-7.31 (m, 1H), 7.37-7.44 (m, 1H), 7.65 (d, J=7.8 Hz, 1H); MS (DCI/NH$_3$) m/z 399 (M+H)$^+$. Anal. Calculated for C$_{22}$H$_{26}$N$_2$O$_3$S.0.2H$_2$O: C, 65.71; H, 6.62; N, 6.97. Found: C, 65.77; H, 6.62; N, 6.86.

Example 107

N-[(2Z)-3-methyl-1,3-benzothiazol-2(3H)-ylidene]adamantane-1-carboxamide

Example 107A

3-Methyl-1,3-benzothiazol-2(3H)-ylideneamine hydroiodide

Benzothiazol-2-ylamine (1.0 g, 6.6 mmol) and methyl iodide (0.48 mL, 7.9 mmol) were processed as described in Example 46A to provide 1.2 g (60%) of the title compound. $^1$H NMR (DMSO-d$_6$, 300 MHz) δ ppm 3.73 (s, 3H), 7.39-7.47 (m, 1H), 7.59 dt, J=7.8, 1.0 Hz, 1H), 7.65-7.71 (m, 1H), 7.99 (d, J=8.1 Hz, 1H), 9.99 (s, 2H); MS (DCI/NH$_3$) m/z 165 (M+H)$^+$.

Example 107B

N-[(2Z)-3-methyl-1,3-benzothiazol-2(3H)-ylidene]adamantane-1-carboxamide

The product of Example 107A (0.4 g, 1.4 mmol) and adamantane-1-carboxylic acid (0.25 g, 1.4 mmol) were processed according to the method of Example 77B. Purification by column chromatography (SiO$_2$, 30-45% ethyl acetate/hexanes gradient) afforded 0.14 g (31%) of the title compound. $^1$H NMR (CDCl$_3$, 300 MHz) δ ppm 1.76 (t, J=3.1 Hz, 6H), 2.00-2.03 (m, 6H), 2.04-2.09 (m, 3H), 3.87 (s, 3H), 7.24-7.32 (m, 2H), 7.43 (ddd, J=8.2, 7.2, 1.2 Hz, 1H), 7.64 (dt, J=7.9, 0.8 Hz, 1H); MS (DCI/NH$_3$) m/z 327 (M+H)$^+$. Anal. Calculated for C$_{19}$H$_{22}$N$_2$OS: C, 69.90; H, 6.79; N, 8.58. Found: C, 69.76; H, 7.00; N, 8.61.

Example 108

N-[(2Z)-3-(2-morpholin-4-ylethyl)-1,3-benzothiazol-2(3H)-ylidene]adamantane-1-carboxamide

Example 108A 3-(2-Morpholin-4-yl-ethyl)-1,3-benzothiazol-2(3H)-ylideneamine

Benzothiazol-2-ylamine (1.0 g, 6.6 mmol), 4-(2-chloroethyl)-morpholine hydrochloride (1.2 g, 6.6 mmol) and triethylamine (2.8 mL, 20 mmol) were heated at 80° C. for 16 hours. The solid was recrystallized from ethyl acetate, collected by filtration, dried under vacuum to provide 0.45 g (26%) of the title compound. MS (DCI/NH$_3$) m/z 264 (M+H)$^+$.

Example 108B

N-[(2Z)-3-(2-morpholin-4-ylethyl)-1,3-benzothiazol-2(3H)-ylidene]adamantane-1-carboxamide The product of Example 108A (0.20 g, 0.76 mmol) and adamantane-1-carboxylic acid (0.15 g, 0.84 mmol) were processed according to the method of Example 77B. Purification by column chromatography (SiO$_2$, 0-30% methanol/methylene gradient) afforded 82 mg (25%) of the title compound. $^1$H NMR (CDCl$_3$, 300 MHz) δ ppm 1.67-1.82 (m, 6H), 1.99 (d, J=2.7 Hz, 6H), 2.06 (s, 3H), 2.62 (s, 4H), 2.78 (s, 2H), 3.70 (s, 4H), 4.53 (s, 2H), 7.22-7.37 (m, 2H), 7.43 (t, J=7.6 Hz, 1H), 7.65 (d, J=7.8 Hz, 1H); MS (DCI/NH$_3$) m/z 426 (M+H)$^+$.

Anal. Calculated for $C_{24}H_{31}N_3O_2S \cdot 0.2H_2O$: C, 67.16; H, 7.37; N, 9.79. Found: C, 66.92; H, 7.59; N, 9.83.

Example 109

1-Adamantan-2-yl-3-[(2Z)-3-(2-methoxyethyl)-4,5-dimethyl-1,3-thiazol-2(3H)-ylidene]urea To a solution of adamantan-2-ylamine (167 mg, 1.00 mmol) in 19 mL of THF and 1 mL of N,N-diisopropylethylamine was added 4-nitrophenyl chloroformate (403 mg, 2.00 mmol). The solution was irradiated in a sealed tube placed in a single node microwave at 70° C. for 300 sec (maximum power 300 W) with stirring. The resulting solution was cooled to room temperature and the product of Example 46A (300 mg, 1.10 mmol) was added. The sealed tube was irradiated at 120° C. for 1800 sec with stirring. The mixture was cooled to ambient temperature and the solvent removed under reduced pressure. The residue was partitioned between water and ethyl acetate and the phases were separated. The organic extract was washed with brine, dried over anhydrous $Na_2SO_4$, filtered, and concentrated. Purification by column chromatography ($SiO_2$, 0-70% ethyl acetate/hexanes gradient) afforded 153 mg (39%) of the title compound. $^1$H NMR (300 MHz, DMSO-$d_6$) δ ppm 1.46 (d, J=14 Hz, 2H), 1.68 (s, 2H), 1.73-1.85 (m, 8H), 2.00 (d, J=13 Hz, 2H), 2.07 (s, 3H), 2.12 (s, 3H), 3.24 (s, 3H), 3.57 (t, J=6 Hz, 2H), 3.74 (d, J=4 Hz, 1H), 4.07-4.13 (m, 2H), 6.59 (d, J=7 Hz, 1H); MS (DCI/NH$_3$) m/z 364 (M+H)$^+$.

Example 110

1-Adamantan-2-yl-3-[(2Z)-3-(2-methoxyethyl)-1,3-thiazol-2(3H)-ylidene]urea

The product of Example 2A and adamantan-2-ylamine were processed according to the method in Example 109 to afford the title compound. $^1$H NMR (300 MHz, DMSO-$d_6$) δ ppm 1.54 (d, J=13 Hz, 2H), 1.71 (s, 2H), 1.82 (d, J=12 Hz, 8H), 1.99 (t, J=7 Hz, 2H), 3.57 (s, 3H), 3.69 (t, J=5 Hz, 2H), 3.85 (s, 1H), 4.46 (s, 2H), 7.19 (s, 1H), 7.54 (s, 1H); MS (DCI/NH$_3$) m/z 336 (M+H)$^+$.

Example 111

1-Adamantan-2-yl-3-[(2Z)-3-(2-methoxyethyl)-1,3-benzothiazol-2(3H)-ylidene]urea

The product of Example 60A and adamantan-2-ylamine were processed according to the method in Example 109 to afford the title compound. MS (DCI/NH$_3$) m/z 364 (M+H)$^+$.

Example 112

1-Adamantan-1-yl-3-[(2Z)-3-(2-methoxyethyl)-4,5-dimethyl-1,3-thiazol-2(3H)-ylidene]urea The product of Example 46A and adamantan-1-ylamine were processed according to the method in Example 109 to afford the title compound. $^1$H NMR (300 MHz, DMSO-$d_6$) δ ppm 1.62 (s, 6H), 1.93 (s, 6H), 2.00 (s, 3H), 2.06 (s, 3H), 2.12 (s, 3H), 3.23 (s, 3H), 3.54 (t, J=5 Hz, 2H), 4.05 (t, J=5 Hz, 2H), 6.18 (s, 1H); MS (DCI/NH$_3$) m/z 364 (M+H)$^+$. Anal. Calculated for $C_{19}H_{29}N_3O_2S$: C, 63.79; H, 8.04; N, 11.56. Found: C, 62.93; H, 8.04; N, 11.56.

Example 113

1-(Hexahydro-2,5-methanopentalen-3a-yl)-3-[(2Z)-3-(2-methoxyethyl)-4,5-dimethyl-1,3-thiazol-2(3H)-ylidene]urea The product of Example 46A and hexahydro-2,5-methanopentalen-3a-ylamine were processed according to the method in Example 109 to afford the title compound., $^1$H NMR (300 MHz, DMSO-$d_6$) δ ppm 1.43-1.61 (m, 4H), 1.77 (d, J=9 Hz, 2H), 1.87-1.98 (m, 3H), 2.03 (s, 1H), 2.07 (s, 3H), 2.12 (s, 3H), 2.19 (s, 2H), 2.35 (t, J=6 Hz, 1H), 3.24 (s, 3H), 3.53-3.59 (m, 2H), 4.06 (t, J=5 Hz, 2H), 6.77 (s, 1H); MS (DCI/NH$_3$) m/z 350 (M+H)$^+$. Anal. Calculated for $C_{18}H_{27}N_3O_2S \cdot 0.4CH_2Cl_2$: C, 57.63; H, 7.31; N, 10.96. Found: C, 58.02; H, 7.20; N, 11.18.

Example 114

1-Adamantan-2-yl-3-[(2Z)-3-(2-methoxyethyl)-4-methyl-1,3-thiazol-2(3H)-ylidene]urea The product of Example 6A and adamantan-2-ylamine were processed according to the method in Example 109 to afford the title compound. $^1$H NMR (300 MHz, DMSO-$d_6$) δ ppm 1.46 (d, J=12 Hz, 2H), 1.69 (s, 2H), 1.73-1.86 (m, 8H), 2.00 (d, J=12 Hz, 2H), 2.21 (s, 3H), 3.24 (s, 3H), 3.59 (t, J=5 Hz, 2H), 3.75 (d, J=7 Hz, 1H), 4.11 (t, J=5 Hz, 2H), 6.23 (s, 1H), 6.65 (d, J=8 Hz, 1H); MS (DCI/NH$_3$) m/z 350 (M+H)$^+$. Anal. Calculated for $C_{18}H_{27}N_3O_2S$: C, 61.86; H, 7.79; N, 12.02. Found: C, 61.49; H, 7.65; N, 11.90.

Example 115

1-Adamantan-2-yl-3-[(2Z)-3-(2-methoxyethyl)-5-methyl-1,3-thiazol-2(3H)-ylidene]urea The product of Example 15A and adamantan-2-ylamine were processed according to the method in Example 109 to afford the title compound. $^1$H NMR (300 MHz, DMSO-$d_6$) δ ppm 1.45 (d, J=12 Hz, 2H), 1.68 (s, 2H), 1.79 (d, J=13 Hz, 8H), 1.98 (d, J=3 Hz, 2H), 2.13 (d, J=1 Hz, 3H), 3.25 (s, 3H), 3.59 (t, J=5 Hz, 2H), 3.75 (d, J=7 Hz, 1H), 4.09 (t, J=5 Hz, 2H), 6.64 (d, J=7 Hz, 1H), 6.85 (d, J=1 Hz, 1H); MS (DCI/NH$_3$) m/z 350 (M+H)$^+$. Anal. Calculated for $C_{18}H_{27}N_3O_2S$ 0.2H$_2$O: C, 61.23; H, 7.82; N, 11.90. Found C, 60.85; H, 7.71; N, 11.69.

Example 116

1-Adamantan-2-yl-3-[(2Z)-4,5-dimethyl-3-(tetrahydropyran-2-ylmethyl)-1,3-thiazol-2(3H)-ylidene]urea

Example 116A 4,5-Dimethyl-3-(tetrahydropyran-2-ylmethyl)-1,3-thiazol-2(3H)-ylideneamine hydrobromide A mixture of 2-amino-4,5-dimethylthiazole and 2-(bromoethyl)tetrahydro-2H-pyran were processed as described in Example 2A to afford the title compound. $^1$H NMR (300 MHz, DMSO-$d_6$) δ ppm 1.13-1.31 (m, 1H), 1.36-1.52 (m, 3H), 1.64-1.85 (m, 2H), 2.18 (d, J=4 Hz, 6H), 3.19-3.33 (m, 1H), 3.49-3.63 (m, 1H), 3.77-3.89 (m, 1H), 3.94-4.02 (m, 2H), 9.34 (s, 2H); MS (DCI/NH$_3$) m/z 227 (M+H)$^+$.

Example 116B

1-Adamantan-2-yl-3-[(2Z)-4,5-dimethyl-3-(tetrahydropyran-2-ylmethyl)-1,3-thiazol-2(3H)-ylidene]urea The product of Example 116A and adamantan-2-ylamine were processed according to the method in Example 109 to afford the title compound. $^1$H NMR (300 MHz, DMSO-d$_6$) δ ppm 1.13-1.29 (m, 1H), 1.39-1.52 (m, 5H), 1.53-1.64 (m, 1H), 1.69 (s, 2H), 1.80 (d, J=13 Hz, 8H), 2.00 (d, J=14 Hz, 3H), 2.07 (s, 4H), 2.12 (s, 3H), 3.17 (d, J=5 Hz, 3H), 3.59-3.69 (m, 1H), 4.09 (q, J=5 Hz, 1H), 6.34 (d, J=7 Hz, 1H); MS (DCI/NH$_3$) m/z 404 (M+H)$^+$. Anal. Calculated for C$_{22}$H$_{33}$N$_3$O$_2$S.0.7H$_2$O: C, 63.49; H, 8.33; N, 10.10. Found C, 63.18; H, 8.55; N, 9.77.

Example 117

1-Adamantan-1-ylmethyl-3-[(2Z)-3-(2-methoxyethyl)-1,3-benzothiazol-2(3H)-ylidene]urea The product of Example 60A and adamantan-1-ylmethylamine were processed according to the method in Example 109 to afford the title compound. MS (DCI/NH$_3$) m/z 400 (M+H)$^+$.

Example 118

1-Adamantan-1-yl-3-[(2Z)-3-(2-methoxyethyl)-1,3-benzothiazol-2(3H)-ylidene]urea

The product of Example 60A and adamantan-1-ylamine were processed according to the method in Example 109 to afford the title compound. MS (DCI/NH$_3$) m/z 386 (M+H)$^+$.

Example 119

(1S,2R,5S)-1-(6,6-Dimethylbicyclo[3.1.1]hept-2-ylmethyl)-3-[(2Z)-3-(2-methoxyethyl)-1,3-benzothiazol-2(3H)-ylidene]urea The product of Example 60A and (−)-cis-myrantylamine (commercially available from Aldrich) were processed according to the method in Example 109 to afford the title compound. MS (DCI/NH$_3$) m/z 388 (M+H)$^+$.

Example 120

1-Adamantan-1-yl-3-[(2Z)-5-(2,4-difluorophenyl)-3-(2-methoxyethyl)-1,3-thiazol-2(3H)-ylidene]urea

Example 120A

N-[5-chloro-3-(2-methoxyethyl)-1,3-thiazol-2(3H)-ylidene]acetamide

A flask was charged with 2-acetamido-5-chlorothiazole (Lancaster, 19.3 g, 110 mmol) in 200 mL of 2:1 THF/DMF. To the solution was added sodium hydride (60% dispersion in mineral oil, 5.44 g, 142 mmol). The mixture was stirred at room temperature for 15 minutes and then 2-bromoethyl methyl ether (18.3 g, 131 mmol) was added. The mixture was warmed to 85° C. and stirred overnight. After cooling to room temperature, the mixture was diluted with ethyl acetate and washed with water. The organic extract was dried (MgSO$_4$), filtered, and concentrated. The residue was purified by flash chromatography on SiO$_2$ using a gradient of 0% to 100% ethyl acetate:hexane to provide 10.3 g (42%) of the title compound as the more polar regioisomer: $^1$H NMR (300 MHz, CDCl$_3$) δ 2.28 (s, 3H) 3.35 (s, 3H) 3.65-3.71 (m, 2H) 4.28-4.36 (m, 2H) 7.00 (s, 1H); MS (ESI$^+$) m/z 235 (M+H)$^+$.

Example 120B

N-[5-(2,4-difluorophenyl)-3-(2-methoxyethyl)-1,3-thiazol-2(3H)-ylidene]acetamide A flask was charged with the product from Example 120A (10.2 g, 42.6 mmol), 2,4-difluorophenylboronic acid (8.08 g, 51.1 mmol), Na$_2$CO$_3$ (64.0 mL of a 2 M aqueous solution, 128 mmol) and PdCl$_2$(PPh$_3$)$_2$ (1.5 g, 2.13 mmol) in 100 mL of DME/H$_2$O/ethanol (7:3:2). The mixture was warmed to 85° C. and stirred overnight. After cooling to room temperature, the mixture was diluted with ethyl acetate and washed with water. The organic extract was dried (MgSO$_4$), filtered and concentrated. The residue was purified by flash chromatography on SiO$_2$ using a gradient of 0% to 100% ethyl acetate:hexane to provide 11.5 g (86%) of the title compound: $^1$H NMR (300 MHz, CDCl$_3$) δ 2.17 (s, 3H) 3.27 (s, 3H) 3.71 (t, J=5.3 Hz, 2H) 4.37 (t, J=5.4 Hz, 2H) 7.17-7.24 (m, 1H) 7.38-7.48 (m, 1H) 7.64-7.74 (m, 1H) 7.88 (s, 1H); MS (ESI$^+$) m/z 313 (M+H)$^+$.

Example 120C

N-5-(2,4-difluoro-phenyl)-3-(2-methoxyethyl)-1,3-thiazol-2(3H)-ylideneamine

To a solution of the product from Example 120B (11.5 g, 36.8 mmol) in 100 mL of THF was added 25 mL of 5 N aqueous HCl. The mixture was warmed to 40° C. and stirred overnight. After cooling to room temperature, the solvent was removed under reduced pressure and the residue diluted with ethyl acetate. The mixture was neutralized to pH 7 with saturated aqueous NaHCO$_3$ and then washed with water. The organic extract was dried (MgSO$_4$), filtered and concentrated. The residue was purified by flash chromatography on SiO$_2$ using a gradient of 0% to 100% ethyl acetate:hexane to provide 8.5 g (85%) of the title compound: $^1$H NMR (300 MHz, DMSO-d$_6$) δ 3.27 (s, 3H) 3.57 (t, J=5.3 Hz, 2H) 3.86 (t, J=5.4 Hz, 2H) 7.06-7.14 (m, Hz, 1H) 7.25 (s, 1H) 7.29 (dd, J=9.2, 2.7 Hz, 2H) 7.34 (dd, J=5.9, 3.2 Hz, 1H) 7.94 (s, 1H); MS (ESI$^+$) m/z 271 (M+H)$^+$.

Example 120D

1-Adamantan-1-yl-3-[(2Z)-5-(2,4-difluorophenyl)-3-(2-methoxyethyl)-1,3-thiazol-2(3H)-ylidene]urea A mixture of Example 120C and adamantan-1-ylamine were processed according to the method in Example 109 to afford the title compound. $^1$H NMR (400 MHz, DMSO-d$_6$) δ ppm 1.64 (m, 6H) 1.99 (m, 9H) 3.27 (s, 3H) 3.65 (t, J=5.22 Hz, 2H) 4.19 (t, J=4.91 Hz, 2H) 6.54 (s, 1H) 7.16 (td, J=8.59, 2.45 Hz, 1H) 7.38 (m, 1H) 7.57 (m, 1H) 7.61 (s, 1H); MS (DCI/NH$_3$) m/z 448 (M+H)$^+$.

Example 121

1-Adamantan-2-yl-3-[(2Z)-5-(2,4-difluorophenyl)-3-(2-methoxyethyl)-1,3-thiazol-2(3H)-ylidene]urea A mixture of the product of Example 120C and adamantan-2-ylamine were processed according to the method in Example 109 to afford the title compound. $^1$H NMR (400 MHz, DMSO-d$_6$) δ ppm 1.47 (m, 2H) 1.69 (m, 2H) 1.81 (m, 9H) 2.03 (m, 2H) 3.28 (s, 3H) 3.68 (t, J=5.22 Hz, 2H) 4.24 (t, J=5.83 Hz, 2H) 6.93 (d, J=7.06 Hz, 1H) 7.18 (td, J=8.29, 2.15 Hz, 1H) 7.38 (m, 1H) 7.56 (m, 1H) 7.63 (brs, 1H); MS (DCI/NH$_3$) m/z 448 (M+H)$^+$.

Example 122

N-[(2Z)-5-tert-butyl-3-(2-methoxyethyl)-4-methyl-1,3-thiazol-2(3H)-ylidene]hexahydro-2,5-methanopentalene-3a(1H)-carboxamide Example 122A 5-tert-butyl-3-(2-methoxyethyl)-4-methylthiazol-2(3H)-imine A mixture of 5-tert-butyl-4-methylthiazole-2-ylamine (Matrix, 1.5 g, 8.8 mmol) and 2-bromoethyl methyl ether (0.91 mL, 9.7 mmol) was warmed to 85° C. and allowed to stir for 24 hours. The mixture was cooled to ambient temperature and material was purified via flash column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 229 (M+H)$^+$.

Example 122B

N-[(2Z)-5-tert-butyl-3-(2-methoxyethyl)-4-methyl-1,3-thiazol-2(3H)-ylidene]hexahydro-2,5-methanopentalene-3a(1H)-carboxamide To a solution of Example 122A (0.2 g, 0.88 mmol) in 15 mL of tetrahydrofuran at ambient temperature was added triethylamine (0.48 mL, 3.4 mmol) followed by a solution of Example 14A (1.1 mmol) in 5 mL of tetrahydrofuran via cannula. This mixture was stirred at ambient temperature for 18 hours then quenched with 10 mL of NH$_4$Cl and 5 mL of H$_2$O. The layers were separated and the aqueous phase was extracted with three 5 mL portions of CH$_2$Cl$_2$. The combined organic extracts were dried over anhydrous Na$_2$SO$_4$, filtered and concentrated under reduced pressure. Purification via flash column chromatography (SiO$_2$, 70% hexanes in ethyl acetate) afforded the title compound. $^1$H NMR (300 MHz, CDCl$_3$) δ ppm 1.38 (s, 9H), 1.53-1.65 (m, 4H), 1.73-1.90 (m, 4H), 2.17-2.25 (m, 2H), 2.26-2.32 (m, 2H), 2.36 (s, 3H), 2.67 (t, J=6.6 Hz, 1H), 3.31 (s, 3H), 3.69 (t, J=5.4 Hz, 2H), 4.17-4.36 (m, 2H); MS (DCI/NH$_3$) m/z 377 (M+H)$^+$. Anal. Calculated for C$_{21}$H$_{32}$N$_2$O$_2$S: C, 66.98; H, 8.57; N, 7.44. Found: C, 67.00; H, 8.88; N, 7.40.

Example 123

N-[(2Z)-5-methyl-3-(tetrahydrofuran-2-ylmethyl)-1,3-thiazol-2(3H)-ylidene]adamantane-1-carboxamide Example 123A 5-methyl-3-((tetrahydrofuran-2-yl)methyl)thiazol-2(3H)-imine A mixture of 2-amino-5-methylthiazole (1.0 g, 8.7 mmol) and 2-(bromomethyl)tetrahydrofuran (1.1 mL, 10 mmol) was warmed to 85° C. and stirred for 24 hours. The mixture was cooled to ambient temperature and purified via column chromatography (SiO$_2$, 10% methanol in ethyl acetate then 9:1: 0.1 CH$_2$Cl$_2$:methanol:NH$_4$OH) to afford the title compound. MS (DCI/NH$_3$) m/z 199 (M+H)$^+$.

Example 123B 1-adamantanecarbonyl chloride

A solution of 1-adamantanecarboxylic acid (0.27 g, 1.5 mmol) in 5 mL of thionyl chloride was warmed to reflux and stirred for 2 hours. The mixture was cooled to ambient temperature and concentrated under reduced pressure. The residue was diluted with 5 mL of toluene and concentrated under reduced pressure three times to afford the title compound, which was used without additional purification or characterization.

Example 123C

N-[(2Z)-5-methyl-3-(tetrahydrofuran-2-ylmethyl)-1,3-thiazol-2(3H)-ylidene]adamantane-1-carboxamide To a solution of Example 123A (0.15 g, 0.76 mmol) in 20 mL of tetrahydrofuran was added triethylamine (0.32 mL, 2.3 mmol) followed by a solution of Example 123B (1.5 mmol) in 5 mL of tetrahydrofuran via cannula. This mixture was warmed to 50° C. and stirred for 4 hours. The mixture was then cooled to ambient temperature, quenched with 10 mL of NH$_4$Cl and diluted with 10 mL of ethyl acetate. The layers were separated and the aqueous layer was extracted with three 5 mL portions of ethyl acetate. The combined organic extracts were dried over Na$_2$SO$_4$, filtered, concentrated under reduced pressure and purified by column chromatography (SiO$_2$, 50% hexanes in ethyl acetate) to afford the title compound. $^1$H NMR (300 MHz, CDCl$_3$) δ ppm 1.59-1.71 (m, 2H), 1.71-1.76 (m, 6H), 1.77-1.90 (m, 2H), 1.94-2.00 (m, 6H), 2.00-2.06 (m, 3H), 2.25 (d, J=1.4 Hz, 3H), 3.71-3.90 (m, 2H), 4.11-4.37 (m, 3H), 6.76 (s, 1H); MS (DCI/NH$_3$) m/z 361 (M+H)$^+$.

Example 124

N-[(2Z)-5-methyl-3-(tetrahydro-2H-pyran-2-ylmethyl)-1,3-thiazol-2(3H)-ylidene]hexahydro-2,5-methanopentalene-3a(1H)-carboxamide Example 124A 5-methyl-3-((tetrahydro-2H-pyran-2-yl)methyl)thiazol-2(3H)-imine A mixture of 2-amino-5-methylthiazole (1.2 g, 11 mmol) and 2-(bromomethyl)tetrahydro-2H-pyran (1.5 mL, 12 mmol) was warmed to 85° C. and stirred for 18 hours. The mixture was cooled to ambient temperature and purified via flash column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 213 (M+H)$^+$.

Example 124B

N-[(2Z)-5-methyl-3-(tetrahydro-2H-pyran-2-ylmethyl)-1,3-thiazol-2(3H)-ylidene]hexahydro-2,5-methanopentalene-3a(1H)-carboxamide Example 124A (0.15 g, 0.71 mmol), triethylamine (0.3 mL, 2.2 mmol) and Example 14A (0.92 mmol) in 10 mL of tetrahydrofuran were processed as described in Example 122B to afford the title compound. $^1$H NMR (300 MHz, CDCl$_3$) δ ppm 1.47-1.54 (m, 3H), 1.59-1.67 (m, 4H), 1.76-1.90 (m, 6H), 2.16-2.33 (m, 8H), 2.61-2.71 (m, 1H), 3.30-3.43 (m, 1H), 3.62-3.74 (m, 1H), 3.90-4.00 (m, 2H), 4.20-4.34 (m, 1H), 6.67-6.77 (m, 1H); MS (DCI/NH$_3$) m/z 361 (M+H)$^+$. Anal. Calculated for C$_{20}$H$_{28}$N$_2$O$_2$S.0.1H$_2$O: C, 66.30; H, 7.84; N, 7.73. Found: C, 66.12; H, 7.69; N, 7.65.

Example 125

N-[(2Z)-3-butyl-5-methyl-1,3-thiazol-2(3H)-ylidene]hexahydro-2,5-methanopentalene-3a(1H)-carboxamide Example 125A 3-butyl-5-methylthiazol-2(3H)-imine A mixture of 2-amino-5-methylthiazole (1.8 g, 16 mmol) and 1-bromobutane (1.9 mL, 17 mmol) was warmed to 85° C. and stirred for 8 hours. The mixture was cooled to ambient temperature and purified via flash column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 171 (M+H)$^+$.

Example 125B

N-[(2Z)-3-butyl-5-methyl-1,3-thiazol-2(3H)-ylidene]hexahydro-2,5-methanopentalene-3a(1H)-carboxamide Example 125A (0.20 g, 1.2 mmol), triethylamine (0.49 mL, 3.5 mmol) and Example 14A (1.5 mmol) in 10 mL of tetrahydrofuran were processed as described in Example 122B to afford the title compound. $^1$H NMR (300 MHz, CDCl$_3$) δ ppm 0.95 (t, J=7.3 Hz, 3H), 1.25-1.41 (m, 2H), 1.61-1.64 (m, 4H), 1.69-1.90 (m, 6H), 2.19-2.26 (m, 2H), 2.25 (d, J=1.4 Hz, 3H), 2.27-2.32 (m, 2H), 2.68 (t, J=6.6 Hz, 1H), 4.07 (t, J=7.1 Hz, 2H), 6.53-6.58 (m, 1H); MS (DCI/NH$_3$) m/z 319 (M+H)$^+$. Anal. Calculated for C$_{18}$H$_{26}$N$_2$OS: C, 67.88; H, 8.23; N, 8.80. Found: C, 67.72; H, 8.17; N, 8.80.

Example 126

N-[(2Z)-3-[2-(2-methoxyethoxy)ethyl]-5-methyl-1,3-thiazol-2(3H)-ylidene]hexahydro-2,5-methanopentalene-3a(1H)-carboxamide Example 126A 3-(2-(2-methoxyethoxy)ethyl)-5-methylthiazol-2(3H)-imine A mixture of 2-amino-5-methylthiazole (1.5 g, 13.0 mmol) and 1-bromo-2-(2-methoxyethoxy)ethane (2.0 mL, 14.5 mmol) was warmed to 85° C. and stirred for 5 hours. The mixture was cooled to ambient temperature and the residue was purified via flash column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 217 (M+H)$^+$.

Example 126B

N-[(2Z)-3-[2-(2-methoxyethoxy)ethyl]-5-methyl-1,3-thiazol-2(3H)-ylidene]hexahydro-2,5-methanopentalene-3a(1H)-carboxamide Example 126A (0.22 g, 1.0 mmol), triethylamine (0.42 mL, 3.0 mmol) and Example 14A (1.3 mmol) in 10 mL of tetrahydrofuran were processed as described in Example 122B to afford the title compound. $^1$H NMR (300 MHz, CD$_3$OD) δ ppm 1.57-1.72 (m, 4H), 1.76-1.91 (m, 4H), 2.14-2.23 (m, 2H), 2.28 (d, J=1.4 Hz, 3H), 2.28-2.33 (m, 2H), 2.60-2.68 (m, 1H), 3.31 (s, 3H), 3.46-3.51 (m, 2H), 3.57-3.62 (m, 2H), 3.82 (t, J=5.3 Hz, 2H), 4.31 (t, J=5.3 Hz, 2H), 7.02 (q, J=1.2 Hz, 1H); MS (DCI/NH$_3$) m/z 365 (M+H)$^+$. Anal. Calculated for C$_{19}$H$_{28}$N$_2$O$_3$S: C, 62.61; H, 7.74; N, 7.69. Found: C, 62.48; H, 7.72; N, 7.59.

Example 127

N-[(2Z)-4-formyl-3-(2-methoxyethyl)-5-methyl-1,3-thiazol-2(3H)-ylidene]hexahydro-2,5-methanopentalene-3a(1H)-carboxamide Example 14B and Example 72A were processed using the method described in Example 14C to obtain a mixture of Example 73 and the title compound, which were separated by column chromatography. $^1$H NMR (300 MHz, dimethylsulfoxide-d$_6$) δ ppm 1.48-1.65 (m, 4H), 1.67-1.85 (m, 4H), 2.04-2.11 (m, 1H), 2.10-2.16 (m, 1H), 2.20-2.34 (m, 2H), 2.56 (t, J=6.6 Hz, 1H), 2.62 (s, 3H), 3.23 (s, 3H), 3.60 (t, J=5.8 Hz, 2H), 4.70 (t, J=5.8 Hz, 2H), 9.90 (s, 1H); MS (ESI m/z 349 (M+H)$^+$.

Example 128

N-[(2Z)-4-(hydroxymethyl)-3-(2-methoxyethyl)-5-methyl-1,3-thiazol-2(3H)-ylidene]hexahydro-2,5-methanopentalene-3a(1H)-carboxamide To a 0° C. solution of Example 127 (47.0 mg, 0.14 mmol) in methanol (3 mL) was added a solution of sodium borohydride (6.0 mg, 0.15 mmol) in methanol (3 mL). The reaction mixture was stirred at 0° C. for 30 minutes and then warmed to reflux for 1 hour. The reaction mixture was then cooled, quenched with aqueous 1 M aqueous HCl, neutralized with saturated aqueous NaHCO$_3$ and extracted with ethyl acetate. The organic extract was dried over anhydrous Na$_2$SO$_4$, filtered and concentrated under reduced pressure to afford the title compound. $^1$H NMR (300 MHz, dimethylsulfoxide-d$_6$) δ ppm 1.48-1.65 (m, 4H), 1.66-1.82 (m, 4H), 2.08 (s, 1H), 2.12 (s, 1H), 2.23 (s, 3H), 2.26 (s, 2H), 2.52-2.59 (m, 1H), 3.24 (s, 3H), 3.66 (t, J=5.6 Hz, 2H), 4.34 (t, J=5.8 Hz, 2H), 4.46 (d, J=4.4 Hz, 2H), 5.29 (t, 1H); MS (ESI$^+$) m/z 351 (M+H)$^+$.

Example 129

N-[(2Z)-3-(2-methoxyethyl)-4-(methoxymethyl)-5-methyl-1,3-thiazol-2(3H)-ylidene]hexahydro-2,5-methanopentalene-3a(1H)-carboxamide To a solution of Example 128 (32.0 mg, 0.09 mmol) in tetrahydrofuran (3 mL) was added sodium hydride (Aldrich, 3.7 mg, 0.15 mmol) and methyl iodide (Aldrich, 15.6 mg, 0.11 mmol). The reaction mixture was stirred at room temperature overnight then quenched with saturated aqueous NaHCO$_3$ and extracted with ethyl acetate. The combined organic extracts were dried over anhydrous Na$_2$SO$_4$, filtered and concentrated under reduced pressure. The residue was purified by preparative high pressure liquid chromatography on a waters Symmetry C8 column (40 mm×100 mm, 7 μm particle size) using a gradient of 10% to 100% acetonitrile:ammonium acetate (10 mM) over 15 minutes at a flow rate of 70 mL/minutes to afford the title compound. $^1$H NMR (300 MHz, dimethylsulfoxide-d$_6$) δ ppm 1.47-1.64 (m, 4H), 1.62-

1.84 (m, 4H), 2.03-2.18 (m, 2H), 2.27 (s, 2H), 2.27 (s, 3H), 2.50-2.62 (m, 1H), 3.24 (d, J=1.4 Hz, 3H), 3.24 (s, 3H), 3.64 (t, J=5.8 Hz, 2H), 4.26 (t, J=5.8 Hz, 2H), 4.45 (s, 2H); MS (ESI$^+$) m/z 365 (M+H)$^+$; Anal. Calculated for $C_{19}H_{28}N_2O_3S$: C, 62.61; H, 7.74; N, 7.69. Found: C, 62.62; H, 7.73; N, 7.85.

Example 130

N-[(2Z)-5-(2,4-difluorophenyl)-3-(2-methoxyethyl)-1,3-thiazol-2(3H)-ylidene]hexahydro-2,5-methanopentalene-3a(1H)-carboxamide

Example 130A

N-(5-bromo-1,3-thiazol-2-yl)hexahydro-2,5-methanopentalene-3a(1H)-carboxamide

A mixture of 2-amino-5-bromothiazole monohydrobromide (14.3 g, 55.1 mmol), Example 14A (11.20 g, 60.65 mmol), 4-dimethylaminopyridine (0.34 g, 2.8 mmol) and triethylamine (20.0 mL, 138 mmol) in 200 mL of tetrahydrofuran was stirred at 22° C. for 48 hours. The mixture was cooled to ambient temperature, diluted with 200 mL of ethyl acetate and washed with brine. The layers were separated and the aqueous phase was extracted twice with 50 mL of ethyl acetate. The combined organic extracts were dried over anhydrous $Na_2SO_4$, filtered, and concentrated. Purification by column chromatography ($SiO_2$, 20% ethyl acetate: 80% hexane) afforded the title compound. MS (DCI/NH$_3$) m/z 327 (M)$^+$, 329 (M+2)$^+$.

Example 130B

N-[(2Z)-5-bromo-3-(2-methoxy ethyl)-1,3-thiazol-2(3H)-ylidene]hexahydro-2,5-methanopentalene-3a(1H)-carboxamide Example 130A (5.0 g, 14.7 mmol) and 2-bromoethyl methyl ether (2.2 g, 16.1 mmol) were processed according to the method of Example 17B to afford the title compound. MS (ESI$^+$) m/z 385 (M)$^+$, 387 (M+2)$^+$.

Example 130C

N-[(2Z)-5-(2,4-difluorophenyl)-3-(2-methoxyethyl)-1,3-thiazol-2(3H)-ylidene]hexahydro-2,5-methanopentalene-3a(1H)-carboxamide Example 130B (150 mg, 0.39 mmol), 2,4-difluorophenylboronic acid (74.0 mg, 0.47 mmol), $Na_2CO_3$ (2 M) (584 μL, 1.17 mmol) and bis(triphenylphosphine)palladium(II) dichloride (14.0 mg, 0.02 mmol) in 10 mL of dimethoxyethane/$H_2O$/ethanol (7:3:2) were processed according to the method of Example 17C to afford the title compound. $^1$H NMR (300 MHz, dimethylsulfoxide-d$_6$) δ 1.53-1.65 (m, 4H), 1.70-1.82 (m, 4H), 2.09-2.17 (m, 2H), 2.24-2.31 (m, 2H), 2.58 (t, J=6.6 Hz, 1H), 3.27 (s, 3H), 3.74 (t, J=5.4 Hz, 2H), 4.36 (t, J=5.4 Hz, 2H), 7.17-7.25 (m, 1H), 7.38-7.48 (m, 1H), 7.62-7.72 (m, 1H), 7.88 (s, 1H); MS (ESI$^+$) m/z 419 (M+H)$^+$. Anal. Calculated for $C_{22}H_{24}F_2N_2O_2S$: C, 63.14; H, 5.78; N, 6.69. Found: C, 62.90; H, 5.75; N, 6.65.

Example 131

N-[(2Z)-5-(4-chlorophenyl)-3-(2-methoxyethyl)-1,3-thiazol-2(3H)-ylidene]adamantane-1-carboxamide

Example 131A

N-(5-bromo-1,3-thiazol-2-yl)adamantane-1-carboxamide

A mixture of 5-bromothiazol-2-amine (3.0 g, 11.5 mmol), adamantane-1-carbonyl chloride (2.74 g, 13.8 mmol), triethylamine (3.2 mL, 23 mmol) and 4-di(methylamino)pyridine (1.1 g) in tetrahydrofuran (100 mL) was heated at 80° C. for 48 hours. The mixture was cooled to ambient temperature, concentrated, diluted with water and extracted with ethyl acetate. The organic extract was dried ($Na_2SO_4$), filtered and concentrated. Purification by flash chromatography (silica gel, 25% ethyl acetate/hexanes) afforded the title compound. MS (ESI) m/z 342 (M+H)$^+$.

Example 131B

N-[(2Z)-5-bromo-3-(2-methoxyethyl)-1,3-thiazol-2(3H)-ylidene]adamantane-1-carboxamide A solution of Example 131A (2.55 g, 7.43 mmol), 1-bromo-2-methoxyethane (0.77 mL, 8.15 mmol) and sodium hydride (60%) (386 mg, 9.66 mmol) in tetrahydrofuran/N,N-dimethylformamide (2:1) (60 mL) was heated at 75° C. for 12 hours. The mixture was cooled to ambient temperature, diluted with water, and extracted with dichloromethane. The organic extract was dried ($Na_2SO_4$), filtered and concentrated. Purification by chromatography (silica gel, 100% dichloromethane) afforded the title compound. MS (ESI) m/z 399 (M+H)$^+$.

Example 131C

N-[(2Z)-5-(4-chlorophenyl)-3-(2-methoxyethyl)-1,3-thiazol-2(3H)-ylidene]adamantane-1-carboxamide A 10 mL microwave vial was charged with Example 131B (85 mg, 0.21 mmol), 4-chlorophenylboronic acid (48 mg, 0.31 mmol) and 2 M aqueous $Na_2CO_3$ (0.5 mL) and bis(triphenylphosphine)palladium(II) dichloride (7 mg, 0.01 mmol) in dimethoxyethane/$H_2O$/ethanol (7:3:2) (4 mL) and the mixture was heated at 85° C. for 12 hours. After cooling to ambient temperature, the mixture was filtered through Celite and extracted with ethyl acetate. The organic extract was dried ($Na_2SO_4$), filtered and concentrated. Purification by preparative high pressure liquid chromatography on a Waters Symmetry C8 column (40 mm×100 mm, 7 μm particle size) using a gradient of 10% to 100% acetonitrile:ammonium acetate (10 mM) over 15 minutes at a flow rate of 70 mL/minutes afforded the title compound. $^1$H NMR (500 MHz, CD$_3$OD) δ ppm 1.73-1.84 (m, 6H) 1.96-1.99 (m, 6H) 2.01-2.05 (m, 3H) 3.36 (s, 3H) 3.80 (t, J=5.19 Hz, 2H) 4.44 (t, J=5.19 Hz, 2H) 7.42 (d, J=8.54 Hz, 2H) 7.53 (d, J=6.71 Hz, 2H) 7.67-7.68 (m, 1H); MS (ESI) m/z 399 (M+H)$^+$.

Example 132

N-[(2Z)-5-cyclopropyl-3-(2-methoxyethyl)-1,3-thiazol-2(3H)-ylidene]hexahydro-2,5-methanopentalene-3a(1H)-carboxamide A flask was charged with the product from Example 130B (150.0 mg, 0.39 mmol), cyclopropylboronic acid (Aldrich) (86 mg, 0.51 mmol), $K_3PO_4$ (212 mg, 1.36 mmol) and dichlorobis(trichlorohexylphosphine)palladium (II) (29 mg, 0.04 mmol) in 5 mL of $H_2O$/toluene (1:1). The mixture was warmed to 100° C. and stirred overnight. After cooling to room temperature, the mixture was diluted with ethyl acetate and washed with water. The organic extract was dried ($MgSO_4$), filtered and concentrated. The residue was purified by flash chromatography on $SiO_2$ using a gradient of 0% to 100% ethyl acetate:hexane to afford the title compound. $^1H$ NMR (300 MHz, dimethylsulfoxide-$d_6$) δ 0.59-0.65 (m, 2H), 0.86-0.95 (m, 2H), 1.53-1.61 (m, 4H), 1.65-1.79 (m, 4H), 1.86-1.97 (m, 1H), 2.04-2.13 (m, 2H), 2.22-2.29 (m, 2H), 2.51-2.56 (m, 1H), 3.24 (s, 3H), 3.66 (t, J=5.3 Hz, 2H), 4.20 (t, J=5.4 Hz, 2H), 7.15 (d, J=1.0 Hz, 1H); MS (ESI$^+$) m/z 347 (M+H)$^+$.

Example 133

3-methoxy-N-[(2Z)-3-(2-methoxyethyl)-4,5-dimethyl-1,3-thiazol-2(3H)-ylidene]adamantane-1-carboxamide To a solution of Example 49 (200 mg, 0.55 mmol) in 10 mL of tetrahydrofuran at 0° C. was added sodium hydride (60% dispersion in mineral oil, 28 mg, 0.71 mmol). This mixture was stirred at 0° C. for 10 minutes then warmed to ambient temperature. Dimethyl sulfate (104 μL, 1.10 mmol) was added. The mixture was heated to 80° C. for 36 hours. The mixture was cooled to ambient temperature, diluted with ethyl acetate and washed with brine. The layers were separated and the aqueous phase was extracted twice with 15 mL of ethyl acetate. The combined organic extracts were dried over anhydrous $Na_2SO_4$, filtered, and concentrated. Purification by column chromatography ($SiO_2$) using a gradient of 0% to 100% ethyl acetate:hexane provided the title compound. $^1H$ NMR (300 MHz, dimethylsulfoxide-$d_6$) δ 1.52-1.57 (m, 2H), 1.61-1.66 (m, 4H), 1.70-1.78 (m, 6H), 2.15 (s, 3H), 2.18-2.23 (m, 5H), 3.12 (s, 3H), 3.24 (s, 3H), 3.54 (t, J=5.4 Hz, 2H), 4.24 (t, J=5.4 Hz, 2H); MS (ESI$^+$) m/z 379 (M+H)$^+$. Anal. Calculated for $C_{20}H_{30}N_2O_3S \cdot 0.25 H_2O$: C, 62.71; H, 8.03; N, 7.31. Found: C, 62.45; H, 7.96; N, 7.03.

Example 134

3-ethyl-5-hydroxy-N-[(2Z)-3-(2-methoxyethyl)-4,5-dimethyl-1,3-thiazol-2(3H)-ylidene]adamantane-1-carboxamide To a solution of Example 46A (230 mg, 0.86 mmol) in tetrahydrofuran (10 mL) was added N-(3-dimethylaminopropyl)-N-ethylcarbodiimide hydrochloride (166 mg, 0.86 mmol), 1-hydroxybenzotriazole (117 mg, 0.86 mmol), triethylamine (300 mL, 2.15 mmol), and 3-ethyl-5-hydroxyadamantane-1-carboxylic acid (Chembridge) (194 mg, 0.86 mmol). The mixture was stirred overnight at 80° C. and then diluted with ethyl acetate, washed with 1 M aqueous sodium carbonate, dried ($Na_2SO_4$), filtered and concentrated. Purification by preparative high pressure liquid chromatography on a Waters Symmetry C8 column (40 mm×100 mm, 7 μm particle size) using a gradient of 10% to 100% acetonitrile: ammonium acetate (10 mM) over 15 minutes at a flow rate of 70 mL/minutes afforded the title compound. $^1H$ NMR (300 MHz, dimethylsulfoxide-$d_6$) δ 0.77 (t, J=7.5 Hz, 3H), 1.17 (q, J=7.6 Hz, 2H), 1.24-1.30 (m, 4H), 1.40-1.44 (m, 2H), 1.47-1.53 (m, 2H), 1.62-1.67 (m, 4H), 2.15 (s, 3H), 2.16-2.19 (m, 1H) 2.20 (s, 3H), 3.24 (s, 3H), 3.64 (t, J=5.4 Hz, 2H), 4.23 (t, J=5.4 Hz, 2H), 4.39 (s, 1H); MS (ESI$^+$) m/z 393 (M+H)$^+$.

Example 135

3-ethoxy-N-[(2Z)-3-(2-methoxyethyl)-4,5-dimethyl-1,3-thiazol-2(3H)-ylidene]adamantane-1-carboxamide Example 49 (200 mg, 0.55 mmol) and diethyl sulfate (144 μL, 1.10 mmol) were processed as described in Example 133 to afford the title compound. $^1H$ NMR (300 MHz, dimethylsulfoxide-$d_6$) δ 1.05 (t, J=7.0 Hz, 3H), 1.51-1.56 (m, 2H), 1.62-1.67 (m, 4H), 1.70-1.74 (m, 4H), 1.75-1.79 (m, 2H), 2.15 (d, J=0.7 Hz, 3H), 2.16-2.19 (m, 2H), 2.20 (s, 3H), 3.24 (s, 3H), 3.41 (q, J=7.1 Hz, 2H), 3.64 (t, J=5.3 Hz, 2H), 4.24 (t, J=5.4 Hz, 2H); MS (ESI$^+$) m/z 393 (M+H)$^+$. Anal. Calculated for $C_{20}H_{30}N_2O_3S$: C, 64.25; H, 8.22; N, 7.14. Found: C, 64.23; H, 8.37; N, 7.09.

Example 136

N-[(2Z)-5-tert-butyl-3-(2-methoxyethyl)-1,3-thiazol-2(3H)-ylidene]hexahydro-2,5-methanopentalene-3a(1H)-carboxamide

Example 136A 5-tert-butylthiazol-2-amine

A mixture of 3,3-dimethylbutanal (Aldrich, 5.0 g, 50 mmol), pyrrolidine (Aldrich, 4.4 mL, 52 mmol) and p-toluenesulfonic acid monohydrate (10 mg) in cyclohexane (70 mL) was heated to reflux for 3 hours under a Dean-Stark trap. The reaction mixture was decanted and concentrated under reduced pressure. The residue was dissolved in methanol (20 mL) and then cooled to 0° C. To this solution was added sulfur (Aldrich, 1.6 g, 50 mmol) and a solution of cyanamide (Aldrich, 2.1 g, 50 mmol) in methanol (5 mL). The reaction mixture was stirred at room temperature for 12 hours and was concentrated under reduced pressure. The residue was purified by column chromatography ($SiO_2$, 2% methanol in dichloromethane to afford the title compound. MS (ESI$^+$) m/z 157 (M+H)$^+$.

Example 136B 5-tert-butyl-3-(2-methoxyethyl)thiazol-2(3H)-imine hydrobromide A mixture of Example 136A and commercially available 2-bromoethyl methyl ether (Aldrich) was processed using the method described in Example 46A to afford the title compound. MS (ESI$^+$) m/z 215 (M+H)$^+$.

Example 136C

N-[(2Z)-5-tert-butyl-3-(2-methoxyethyl)-1,3-thiazol-2(3H)-ylidene]hexahydro-2,5-methanopentalene-3a(1H)-carboxamide Commercially available hexahydro-2,5-methano-pentalene-3a-carboxylic acid and Example 136B were processed using the method described in Example 56C to afford the title compound. $^1$H NMR (300 MHz, dimethylsulfoxide-$d_6$) δ ppm 1.27 (s, 9H), 1.52-1.62 (m, 4H), 1.65-1.80 (m, 4H), 2.03-2.14 (m, 2H), 2.26 (s, 2H), 2.53-2.56 (m, 1H), 3.25 (s, 3H), 3.68 (t, J=5.4 Hz, 2H), 4.23 (t, J=5.6 Hz, 2H), 7.12 (s, 1H); MS (ESI$^+$) m/z 363 (M+H)$^+$.

Example 137

N-[(2Z)-3-(2-methoxyethyl)-4,6-dihydrofuro[3,4-d][1,3]thiazol-2(3H)-ylidene]-2-oxatricyclo[3.3.1.1$^{3,7}$]decane-1-carboxamide Example 137A 2-Oxa-tricyclo[3.3.1.1$^{3,7}$]decane-1-carboxylic acid [3a-ethoxy-3a,4,6,6a-tetrahydrofuro(3,4-d)thiazol-2-yl]-amide The product Example 72B and Example 56B were processed as described in Example 56C to obtain the title compound. MS (ESI$^+$) m/z 353 (M+H)$^+$.

Example 137B

2-Oxa-tricyclo[3.3.1.1$^{3,7}$]decane-1-carboxylic acid [4,6-dihydro-3H-furo(3,4-d)thiazol-2-yl]-amide Example 137A and p-toluenesulfonic acid monohydrate were processed as described for Example 72E to obtain the title compound. MS (ESI$^+$) m/z 307 (M+H)$^+$.

Example 137C

N-[(2Z)-3-(2-methoxyethyl)-4,6-dihydrofuro[3,4-d][1,3]thiazol-2(3H)-ylidene]-2-oxatricyclo[3.3.1.1$^{3,7}$]decane-1-carboxamide Example 137B and commercially available 2-bromoethyl methyl ether (Aldrich) were processed using the method described in Example 76 to afford the title compound. $^1$H NMR (300 MHz, dimethylsulfoxide-$d_6$) δ ppm 1.47-1.69 (m, 2H), 1.79-1.91 (m, 6H), 1.93-2.03 (m, 2H), 2.15 (s, 2H), 3.24 (s, 3H), 3.61 (t, J=5.1 Hz, 2H), 4.05 (s, 1H), 4.19 (t, J=5.1 Hz, 2H), 4.92 (s, 4H); MS (ESI$^+$) m/z 365 (M+H)$^+$; Anal. Calculated for $C_{18}H_{24}N_2O_4S$: C, 59.32; H, 6.64; N, 7.69. Found: C, 59.25; H, 6.65; N, 7.68.

Example 138

N-[(2Z)-3-(2-methoxyethyl)-5-tetrahydro-2H-pyran-4-yl-1,3-thiazol-2(3H)-ylidene]hexahydro-2,5-methanopentalene-3a(1H)-carboxamide Example 138A 5-(tetrahydro-2H-pyran-4-yl)thiazol-2-amine A mixture of (tetrahydro-pyran-4-yl)-acetaldehyde (Pharmacore), pyrrolidine, p-toluenesulfonic acid monohydrate, sulfur and cyanamide were processed using the method described in Example 136A to obtain the title compound. MS (ESI$^+$) m/z 185 (M+H)$^+$.

Example 138B 3-(2-methoxyethyl)-5-(tetrahydro-2H-pyran-4-yl)thiazol-2(3H)-imine hydrobromide A mixture of Example 138A and commercially available 2-bromoethyl methyl ether (Aldrich) was processed using the method described in Example 46A to afford the title compound. MS (ESI$^+$) m/z 243 (M+H)$^+$.

Example 138C

N-[(2Z)-3-(2-methoxyethyl)-5-tetrahydro-2H-pyran-4-yl-1,3-thiazol-2(3H)-ylidene]hexahydro-2,5-methanopentalene-3a(1H)-carboxamide Commercially available hexahydro-2,5-methano-pentalene-3a-carboxylic acid and Example 138B were processed using the method described in Example 56C to afford the title compound. $^1$H NMR (300 MHz, dimethylsulfoxide-$d_6$) δ 1.44-1.66 (m, 6H), 1.64-1.88 (m, 6H), 2.03-2.14 (m, 2H), 2.26 (s, 2H), 2.52-2.58 (m, 1H), 2.78-2.99 (m, 1H), 3.25 (s, 3H), 3.41 (td, J=11.6, 1.9 Hz, 2H), 3.68 (t, J=5.4 Hz, 2H), 3.82-3.96 (m, 2H), 4.23 (t, J=5.4 Hz, 2H), 7.17 (d, J=1.0 Hz, 1H); MS (ESI$^+$) m/z 391 (M+H)$^+$; Anal. Calculated for $C_{21}H_{30}N_2O_3S$: C, 64.58; H, 7.74; N, 7.17. Found: C, 64.11; H, 7.79; N, 7.38.

Example 139

N-[(2Z)-3-(2-methoxyethyl)-5-(2,2,2-trifluoroethyl)-1,3-thiazol-2(3H)-ylidene]hexahydro-2,5-methanopentalene-3a(1H)-carboxamide Example 139A 5-(2,2,2-trifluoroethyl)thiazol-2-amine A mixture of 4,4,4-trifluorobutyraldehyde (Matrix), pyrrolidine, p-toluenesulfonic acid monohydrate, sulfur and cyanamide were processed using the method described in Example 136A to obtain the title compound. MS (ESI$^+$) m/z 183 (M+H)$^+$.

Example 139B 3-(2-methoxyethyl)-5-(2,2,2-trifluoroethyl)thiazol-2(3H)-imine hydrobromide A mixture of Example 139A and commercially available 2-bromoethyl methyl ether (Aldrich) was processed using the method described in Example 46A to afford the title compound. MS (ESI$^+$) m/z 241 (M+H)$^+$.

Example 139C

N-[(2Z)-3-(2-methoxyethyl)-5-(2,2,2-trifluoroethyl)-1,3-thiazol-2(3H)-ylidene]hexahydro-2,5-methanopentalene-3a(1H)-carboxamide Commercially available hexahydro-2,5-methano-pentalene-3a-carboxylic acid and Example 139B were processed using the method described in Example 56C to afford the title compound. ¹H NMR (300 MHz, dimethylsulfoxide-$d_6$) δ ppm 1.58-1.66 (m, 4H), 1.76-1.87 (m, 4H), 2.15-2.25 (m, 2H), 2.30 (s, 2H), 2.67 (t, J=6.8 Hz, 1H), 3.29-3.46 (m, 5H), 3.66-3.73 (m, 2H), 4.24-4.34 (m, 2H), 6.97 (s, 1H); MS (ESI⁺) m/z 389 (M+H)⁺; Anal. Calculated for $C_{21}H_{30}N_2O_3S$: C, 64.58; H, 7.74; N, 7.17. Found: C, 64.11; H, 7.79; N, 7.38.

Example 140

N-[(2Z)-3-(2-methoxyethyl)-5-(methoxymethyl)-1,3-thiazol-2(3H)-ylidene]hexahydro-2,5-methanopentalene-3a(1H)-carboxamide Example 140A Ethyl 2-imino-3-(2-methoxyethyl)-2,3-dihydrothiazole-5-carboxylate hydrobromide A mixture of commercially available ethyl 2-aminothiazole-5-carboxylate (ABCR) and 2-bromoethyl methyl ether (Aldrich) was processed using the method described in Example 46A to afford the title compound. MS (ESI⁺) m/z 231 (M+H)⁺.

Example 140B 2-(Hexahydro-2,5-methano-pentalene-3a-carbonylimino)-3-(2-methoxyethyl)-2,3-dihydro-thiazole-5-carboxylic acid ethyl ester Commercially available hexahydro-2,5-methano-pentalene-3a-carboxylic acid and Example 140A were processed using the method described in Example 56C to afford the title compound. MS (ESI⁺) m/z 379 (M+H)⁺.

Example 140C 2-(Hexahydro-2,5-methano-pentalene-3a-carbonylimino)-3-(1-hydroxymethyl)-2,3-dihydro-thiazole Example 140B and lithium borohydride (Aldrich, 2M in tetrahydrofuran) were processed using the method described in Example 8 to afford the title compound. MS (ESI⁺) m/z 337 (M+H)⁺.

Example 140D

N-[(2Z)-3-(2-methoxyethyl)-5-(methoxymethyl)-1,3-thiazol-2(3H)-ylidene]hexahydro-2,5-methanopentalene-3a(1H)-carboxamide To a solution of Example 140C (120 mg, 0.34 mmol) in tetrahydrofuran (5 mL) were added potassium tert-butoxide (83 mg, 0.75 mmol) and dimethyl sulfate (95 mg. 0.75 mmol). The reaction mixture was stirred at 75° C. for 16 hours, then cooled, quenched with saturated aqueous NaHCO₃ (5 mL) and extracted with ethyl acetate (2×10 mL). The combined organic extracts were dried over anhydrous Na₂SO₄, filtered and concentrated under reduced pressure. The residue was purified by column chromatography using an Analogix® Intelliflash 280™ (SiO₂, 0-100% ethyl acetate in hexanes) to afford the title compound. ¹H NMR (300 MHz, dimethylsulfoxide-$d_6$) δ ppm 1.54-1.70 (m, 4H), 1.73-1.92 (m, 4H), 2.13-2.24 (m, 2H), 2.30 (s, 1H), 2.67 (t, J=6.8 Hz, 2H), 3.33 (s, 3H), 3.36 (s, 3H), 3.64-3.73 (m, 2H), 4.22-4.30 (m, 2H), 4.42 (s, 2H), 6.95 (s, 1H); MS (ESI⁺) m/z 351 (M+H)⁺; Anal. Calculated for $C_{18}H_{26}N_2O_3S$: C, 61.69; H, 7.48; N, 7.99. Found: C, 61.93; H, 7.62; N, 7.68.

Example 141

(1R,3s,5S,7s)-7-hydroxy-N-[(2Z)-3-(2-methoxyethyl)-4,5-dimethyl-1,3-thiazol-2(3H)-ylidene]bicyclo[3.3.1]nonane-3-carboxamide Example 141A (1R,3s,5S,7s)-7-hydroxybicyclo[3.3.1]nonane-3-carboxylic acid The title compound was prepared from commercially available 2-adamantanone (Aldrich) according to the procedure as described in Rezoni, G. E.; Borden, W. T., *J. Org. Chem.* (1983), 48, 5231-5236. MS (ESI⁺) m/z 184 (M+NH₄—H₂O)⁺.

Example 141B (1R,3s,5S,7s)-7-hydroxy-N-[(2Z)-3-(2-methoxyethyl)-4,5-dimethyl-1,3-thiazol-2(3H)-ylidene]bicyclo[3.3.1]nonane-3-carboxamide Example 141A and Example 46A were processed using the method described in Example 56C to afford the title compound. ¹H NMR (300 MHz, dimethylsulfoxide-$d_6$) δ ppm 0.98-1.24 (m, 3H), 1.39-1.61 (m, 3H), 1.65-1.76 (m, 2H), 1.92-2.11 (m, 5H), 2.14 (s, 3H), 2.20 (s, 3H), 3.24 (s, 3H), 3.63 (t, J=5.3 Hz, 2H), 3.69-3.82 (m, 1H), 4.23 (t, J=5.4 Hz, 2H), 4.36 (d, J=4.7 Hz, 1H); MS (ESI⁺) m/z 353 (M+H)⁺.

Example 142

(1R,3s,5S,7s)-7-methoxy-N-[(2Z)-3-(2-methoxyethyl)-4,5-dimethyl-1,3-thiazol-2(3H)-ylidene]bicyclo[3.3.1]nonane-3-carboxamide Example 141B, potassium tert-butoxide and dimethyl sulfate were processed using the method described in Example 140D to afford the title compound. ¹H NMR (300 MHz, dimethylsulfoxide-$d_6$) δ ppm 1.54-1.70 (m, 4H), 1.73-1.92 (m, 4H), 2.13-2.24 (m, 2H), 2.30 (s, 1H), 2.67 (t, J=6.8 Hz, 2H), 3.33 (s, 3H), 3.36 (s, 3H), 3.64-3.73 (m, 2H), 4.22-4.30 (m, 2H), 4.42 (s, 2H), 6.95 (s, 1H); MS (ESI⁺) m/z 367 (M+H)⁺; Anal. Calculated for $C_{19}H_{30}N_2O_3S$: C, 62.26; H, 8.25; N, 7.64. Found: C, 62.18; H, 8.38; N, 7.50.

Example 143

1-methoxy-N-[(2Z)-3-(2-methoxyethyl)-4,5-dimethyl-1,3-thiazol-2(3H)-ylidene]bicyclo[2.2.2]octane-2-carboxamide Example 46A (150.0 mg, 0.56 mmol) and 1-methoxybicyclo[2.2.2]octane-2-carboxylic acid (Alfaro, I.; et al. *Tetrahedron* 1970, 26, 201-218) (103.2 mg, 0.56 mmol) were processed as described in Example 134 to afford the title compound. ¹H NMR (300 MHz, dimethylsulfoxide-$d_6$) δ 1.24-1.43 (m, 2H), 1.52-1.71 (m, 4H), 1.74-1.89 (m, 3H), 1.89-1.99 (m, 1H), 2.01-2.11 (m, 1H), 2.16 (s, 3H), 2.21 (s, 3H), 2.98-3.06 (m, 1H), 3.12 (s, 3H), 3.23 (s, 3H), 3.63 (t, J=5.4 Hz, 2H), 4.23 (t, J=5.4 Hz, 2H); MS (ESI⁺) m/z 353 (M+H)⁺.

Example 144

3-(acetylamino)-N-[(2Z)-3-(2-methoxyethyl)-4,5-dimethyl-1,3-thiazol-2(3H)-ylidene]adamantane-1-carboxamide Example 46A (150.0 mg, 0.56 mmol) and 3-acetylamino-adamantane-1-carboxylic acid (Iflab) (133 mg, 0.56 mmol) were processed as described in Example 134 to afford the title compound. $^1$H NMR (300 MHz, dimethylsulfoxide-$d_6$) δ 1.53-1.60 (m, 2H), 1.71-1.78 (m, 6H), 1.80-1.96 (m, 5H), 1.97-2.01 (m, 2H), 2.06-2.13 (m, 2H), 2.15 (s, 3H), 2.18-2.21 (m, 3H), 3.24 (s, 3H), 3.64 (t, J=5.4 Hz, 2H), 4.24 (t, J=5.4 Hz, 2H); MS (ESI$^+$) m/z 406 (M+H)$^+$.

Example 145

N-[(2Z)-5-cyclohex-1-en-1-yl-3-(2-methoxyethyl)-1,3-thiazol-2(3H)-ylidene]hexahydro-2,5-methanopentalene-3a(1H)-carboxamide Example 130B (150.0 mg, 0.39 mmol), 1-cyclohexenylboronic acid (Combi-Blocks) (59.2 mg, 0.47 mmol), Na$_2$CO$_3$ (2 M) (584 μL, 1.17 mmol) and bis(triphenylphosphine)palladium(II) dichloride (14.0 mg, 0.02 mmol) in 10 mL of dimethoxyethane/H$_2$O/ethanol (7:3:2) were processed according to the method of Example 17C to afford the title compound. $^1$H NMR (300 MHz, dimethylsulfoxide-$d_6$) δ 1.55-1.63 (m, 6H), 1.64-1.79 (m, 6H), 2.07-2.20 (m, 4H), 2.22-2.30 (m, 4H), 2.53-2.58 (m, 1H), 3.25 (s, 3H), 3.69 (t, J=5.4 Hz, 2H), 4.24 (t, J=5.4 Hz, 2H), 5.89 (t, J=4.1 Hz, 1H), 7.32 (s, 1H); MS (ESI$^+$) m/z 387 (M+H)$^+$.

Example 146

N-[(2Z)-3-(2-methoxyethyl)-4,5-dimethyl-1,3-thiazol-2(3H)-ylidene]-1,4-dimethyl-7-oxabicyclo[2.2.1]heptane-2-carboxamide Methyl 1,4-dimethyl-7-oxabicyclo[2.2.1]hept-5-ene-2-carboxylate (Dauben, W. G.; Krabbenhoft, H. O. *J. Am. Chem. Soc.* (1976), 98(7), 1992-1993) was transformed into 1,4-dimethyl-7-oxabicyclo[2.2.1]heptane-2-carboxylic acid by standard hydrogenation of the alkene followed by basic hydrolysis of the ester. A mixture of 1,4-dimethyl-7-oxabicyclo[2.2.1]heptane-2-carboxylic acid and the product of Example 46A were processed as in Example 56C to afford the title compound. $^1$H NMR (400 MHz, dimethylsulfoxide-$d_6$) δ ppm 1.18-1.33 (m, 1H) 1.35 (s, 3H) 1.39-1.51 (m, 1H) 1.53 (s, 3H) 1.58-1.72 (m, 3H) 2.16 (s, 3H) 2.21 (s, 3H) 2.24 (dd, J=11.66, 4.91 Hz, 1H) 2.83 (ddd, J=4.60, 2.15 Hz, 1H) 3.22 (s, 3H) 3.62 (t, J=5.52 Hz, 2H) 4.25 (t, J=5.52 Hz, 2H); MS (ESI) m/z 339 (M+H)$^+$.

Example 147

N-[(2Z)-3-(2-methoxyethyl)-5-methyl-4-(trifluoromethyl)-1,3-thiazol-2(3H)-ylidene]-2-oxatricyclo[3.3.1.1$^{3,7}$]decane-1-carboxamide

Example 147A 5-methyl-4-(trifluoromethyl)thiazol-2-amine 1,1,1-Trifluorobutan-2-one (Aldrich) was processed as in Example 139A to afford the title compound. MS (ESI) m/z 183 (M+H)$^+$.

Example 147B 3-(2-methoxyethyl)-5-methyl-4-(trifluoromethyl)thiazol-2(3H)-imine hydrobromide Example 147A was processed as in Example 46A to afford the title compound. MS (ESI) m/z 241 (M+H)$^+$.

Example 147C

N-[(2Z)-3-(2-methoxyethyl)-5-methyl-4-(trifluoromethyl)-1,3-thiazol-2(3H)-ylidene]-2-oxatricyclo[3.3.1.1$^{3,7}$]decane-1-carboxamide A mixture of Example 147B and Example 56B were processed as in Example 56C to afford the title compound. $^1$H NMR (400 MHz, dimethylsulfoxide-$d_6$) δ ppm 1.59-1.66 (m, 2H) 1.83-1.90 (m, 6H) 1.96-2.03 (m, 2H) 2.13-2.19 (m, 2H) 2.41 (q, J=3.38 Hz, 3H) 3.27 (s, 3H) 3.68 (t, J=6.14 Hz, 2H) 4.04-4.09 (m, 1H) 4.31 (t, J=6.44 Hz, 2H); MS (ESI) m/z 405 (M+H)$^+$.

Example 148

N-[(2Z)-5-(2,4-difluorophenyl)-3-(2-methoxyethyl)-1,3-thiazol-2(3H)-ylidene]-2-oxatricyclo[3.3.1.1$^{3,7}$]decane-1-carboxamide Example 120C (151 mg, 0.56 mmol) and the product from Example 56B (102 mg, 0.56 mmol) were processed as described in Example 134 to afford the title compound. $^1$H NMR (300 MHz, dimethylsulfoxide-$d_6$) δ 1.59-1.67 (m, 2H), 1.83-1.93 (m, 6H), 1.95-2.05 (m, 2H), 2.13-2.21 (m, 2H), 3.28 (s, 3H), 3.74 (t, J=5.3 Hz, 2H), 4.03-4.10 (m, 1H), 4.39 (t, J=5.3 Hz, 2H), 7.17-7.26 (m, 1H), 7.39-7.49 (m, 1H), 7.64-7.74 (m, 1H), 7.91-7.92 (m, 1H); MS (ESI m/z 435 (M+H)$^+$.

Example 149

N-[(2Z)-5-(2,4-difluorophenyl)-3-(2-methoxyethyl)-1,3-thiazol-2(3H)-ylidene]bicyclo[2.2.1]heptane-2-carboxamide Example 120C (151.4 mg, 0.56 mmol) and bicyclo[2,2,1]heptane-2-carboxylic acid (Alfa) (78.5 mg, 0.56 mmol) were processed as described in Example 134 to afford the title compound. $^1$H NMR (300 MHz, dimethylsulfoxide-$d_6$) δ 1.01-1.34 (m, 4H), 1.37-1.53 (m, 2H), 1.55-1.66 (m, 1H), 1.69-1.78 (m, 1H), 2.21-2.29 (m, 1H), 2.52-2.58 (m, 1H), 2.87-2.98 (m, 1H), 3.27 (s, 3H), 3.73 (t, J=5.3 Hz, 2H), 4.37 (t, J=5.4 Hz, 2H), 7.17-7.25 (m, 1H), 7.39-7.48 (m, 1H), 7.61-7.74 (m, 1H), 7.87 (s, 1H); MS (ESI$^+$) m/z 392 (M+H)$^+$.

Example 150

N-[(2Z)-3-(2-methoxy ethyl)-4,5-dimethyl-1,3-thiazol-2(3H)-ylidene]-3a,6a-dimethylhexahydro-1H-1,4-methanocyclopenta[c]furan-1-carboxamide Example 46A (150 mg, 0.56 mmol) and 6,7-dimethyl-4-oxatricyclo[4.3.0.0$^{3,7}$]nonane-3-carboxylic acid (Iflab) (110 mg, 0.56 mmol) were processed as described in Example 134 to afford the title compound. $^1$H NMR (300 MHz, dimethylsulfoxide-$d_6$) δ 0.74 (s, 3H), 0.85 (s, 3H), 1.19-1.35 (m, 2H), 1.62-1.82 (m, 3H), 2.17 (s, 3H), 2.21 (s, 2H), 2.22-2.28 (m, 1H), 3.23 (s, 3H), 3.41 (d, J=7.8 Hz, 1H), 3.62 (d, J=7.8 Hz, 1H), 3.63 (t, J=5.6 Hz, 2H), 4.23 (t, J=5.6 Hz, 2H); MS (ESI⁺) m/z 365 (M+H)⁺. Anal. Calculated for $C_{19}H_{28}N_2O_3S$: C, 62.61; H, 7.74; N, 7.69. Found: C, 62.34; H, 7.80; N, 7.92.

Example 151

2-hydroxy-N-[(2Z)-3-(2-methoxyethyl)-4,5-dimethyl-1,3-thiazol-2(3H)-ylidene]adamantane-2-carboxamide Example 46A (150 mg, 0.56 mmol) and 2-hydroxy-adamantane-2-carboxylic acid (MicroChemistry Ltd.) (110 mg, 0.56 mmol) were processed as described in Example 134 to afford the title compound. ¹H NMR (300 MHz, dimethylsulfoxide-d₆) δ 1.41-1.51 (m, 2H), 1.58-1.76 (m, 8H), 2.17 (s, 3H), 2.19-2.21 (m, 1H), 2.21 (s, 3H), 2.23-2.29 (m, 2H), 3.22 (s, 3H), 3.63 (t, J=5.4 Hz, 2H), 4.24 (t, J=5.3 Hz, 2H), 4.63 (s, 1H); MS (ESI⁺) m/z 365 (M+H)⁺.

Example 152

2-hydroxy-N-[(2Z)-3-(2-methoxyethyl)-5-methyl-1,3-thiazol-2(3H)-ylidene]adamantane-2-carboxamide Example 15A (150 mg, 0.59 mmol) and 2-hydroxyadamantane-2-carboxylic acid (MicroChemistry Ltd.) (116 mg, 0.59 mmol) were processed as described in Example 134 to afford the title compound. ¹H NMR (300 MHz, dimethylsulfoxide-d₆) δ 1.41-1.51 (m, 2H), 1.57-1.76 (m, 8H), 2.15-2.20 (m, 1H), 2.23 (s, 3H), 2.24-2.30 (m, 2H), 3.24 (s, 3H), 3.65 (t, J=5.4 Hz, 2H), 4.24 (t, J=5.3 Hz, 2H), 4.65 (s, 1H), 7.14 (s, 1H); MS (ESI⁺) m/z 351 (M+H)⁺.

Example 153

N-[(2Z)-3-butyl-5-chloro-1,3-thiazol-2(3H)-ylidene]-3-hydroxyadamantane-1-carboxamide Example 153A 3-Hydroxy-adamantane-1-carboxylic acid[5-chloro-3H-thiazol-(2Z)-ylidene]-amide To a suspension of 2-amino-5-chlorothiazole hydrochloride (Aldrich) (1.00 g, 5.84 mmol) in tetrahydrofuran (50 mL) was added N-(3-dimethylaminopropyl)-N-ethylcarbodiimide hydrochloride (1.12 g, 5.84 mmol), 1-hydroxybenzotriazole (0.79 g, 5.84 mmol), triethylamine (2.04 mL, 14.6 mmol), and 3-hydroxyadamantane-1-carboxylic acid (Acros) (1.15 g, 5.84 mmol). The mixture was stirred overnight at room temperature and was diluted with ethyl acetate, washed with 1 M aqueous sodium carbonate, dried ($Na_2SO_4$), filtered and concentrated. Purification by column chromatography ($SiO_2$) using a gradient of 0% to 100% ethyl acetate:hexane provided the title compound. MS (ESI⁺) m/z 313 (M+H)⁺.

Example 153B

N-[(2Z)-3-butyl-5-chloro-1,3-thiazol-2(3H)-ylidene]-3-hydroxyadamantane-1-carboxamide Example 153A (312.8 mg, 1.0 mmol), sodium hydride (60% dispersion in mineral oil, 49.8 mg, 1.3 mmol) and 1-bromobutane (118.1 μL, 1.1 mmol) were processed according to the method of Example 66B. Purification by column chromatography ($SiO_2$, 20-30% ethyl acetate/hexanes gradient) afforded the title compound. ¹H NMR (300 MHz, dimethylsulfoxide-d₆) δ 0.91 (t, J=7.3 Hz, 3H), 1.19-1.31 (m, 2H), 1.47-1.60 (m, 6H), 1.67-1.78 (m, 8H), 2.11-2.20 (m, 2H), 4.13 (t, J=7.0 Hz, 2H), 4.42 (s, 1H), 7.76 (s, 1H); MS (ESI⁺) m/z 369 (M+H)⁺.

Example 154

N-[(2Z)-5-chloro-3-(tetrahydro-2H-pyran-4-ylmethyl)-1,3-thiazol-2(3H)-ylidene]-3-hydroxyadamantane-1-carboxamide Example 153A (313 mg, 1.0 mmol), sodium hydride (60% dispersion in mineral oil, 50 mg, 1.3 mmol) and 4-bromomethyltetrahydropyran (Combi-Blocks) (197 mg, 1.1 mmol) were processed according to the method of Example 66B. Purification by column chromatography ($SiO_2$, 30-50% ethyl acetate/hexanes gradient) afforded the title compound. ¹H NMR (300 MHz, dimethylsulfoxide-d₆) δ ppm 1.19-1.36 (m, 2H), 1.37-1.48 (m, 2H), 1.48-1.60 (m, 6H), 1.66-1.74 (m, 6H), 2.04-2.22 (m, 3H), 3.18-3.28 (m, 2H), 3.80-3.88 (m, 2H), 4.05 (d, J=7.1 Hz, 2H), 4.43 (s, 1H), 7.76 (s, 1H); MS (ESI⁺) m/z 411 (M+H)⁺.

Example 155

(1R,2S,4R)—N-[(2Z)-3-(2-methoxyethyl)-4,5-dimethyl-1,3-thiazol-2(3H)-ylidene]-4,7,7-trimethyl-3-oxobicyclo[2.2.1]heptane-2-carboxamide Example 46A (150 mg, 0.56 mmol) and (+)-camphorcarboxylic acid (Pfaltz-Bauer) (110 mg, 0.56 mmol) were processed as described in Example 134 to afford the title compound. ¹H NMR (300 MHz, dimethylsulfoxide-d₆) δ 0.80-0.83 (m, 6H), 0.94-0.97 (m, 3H), 1.34-1.50 (m, 2H), 1.57-1.75 (m, 2H), 2.17 (s, 3H), 2.21 (s, 3H), 2.34 (t, J=4.1 Hz, 1H), 3.22 (s, 3H), 3.38 (d, J=6.1 Hz, 1H), 3.58 (t, J=3.4 Hz, 2H), 4.18 (t, J=5.4 Hz, 2H); MS (ESI⁺) m/z 365 (M+H)⁺.

Example 156

N-[(2Z)-3-(2-methoxyethyl)-4,5-dimethyl-1,3-thiazol-2(3H)-ylidene]-4,7,7-trimethyl-3-oxobicyclo[2.2.1]heptane-1-carboxamide Example 46A (150 mg, 0.56 mmol) and 4,7,7-trimethyl-3-oxobicyclo[2,2,1]heptane-1-carboxylic acid (Matrix) (110 mg, 0.56 mmol) were processed as described in Example 134 to afford the title compound. ¹H NMR (300 MHz, dimethylsulfoxide-d₆) δ 0.75 (s, 3H), 0.83 (s, 3H), 0.94 (s, 3H), 1.26-1.37 (m, 1H), 1.50-1.62 (m, 1H), 1.68-1.80 (m, 1H), 2.07 (d, J=18.3 Hz, 1H), 2.18 (s, 3H), 2.22 (s, 3H), 2.40-2.48 (m, 1H), 2.87 (dd, J=18.5, 3.2 Hz, 1H), 3.22 (s, 3H), 3.63 (t, J=5.4 Hz, 2H), 4.25 (t, J=5.3 Hz, 2H); MS (ESI⁺) m/z 365 (M+H)⁺.

Example 157

(1S,4R)—N-[(2Z)-3-(2-methoxyethyl)-4,5-dimethyl-1,3-thiazol-2(3H)-ylidene]-7,7-dimethyl-2-oxobicyclo[2.2.1]heptane-1-carboxamide Example 46A (150 mg, 0.56 mmol) and (S)-(+)-ketopinic acid (Aldrich) (102 mg, 0.56 mmol) were processed as described in Example 134 to afford the title compound. ¹H NMR (300 MHz, dimethylsulfoxide-d₆) δ 0.97 (s, 3H), 1.16 (s, 3H), 1.30-1.41 (m, 1H), 1.56-1.68 (m, 1H), 1.83-1.98 (m, 2H), 2.05 (t, J=4.4 Hz, 1H), 2.17 (s, 3H), 2.21 (s, 3H), 2.31-

2.46 (m, 2H), 3.21 (s, 3H), 3.60 (t, J=5.4 Hz, 2H), 4.19 (t, J=5.3 Hz, 2H); MS (ESI) m/z 351 (M+H)+.

Example 158

(1R,3R,4R)—N-[(2Z)-3-(2-methoxyethyl)-4,5-dimethyl-1,3-thiazol-2(3H)-ylidene]-5-oxotricyclo[2.2.1.0$^{3,7}$]heptane-3-carboxamide Example 46A (150 mg, 0.56 mmol) and anti-3-oxotricyclo [2.2.1.0$^{3,7}$]acid (Aldrich) (85.2 mg, 0.56 mmol) were processed as described in Example 134 to afford the title compound. $^1$H NMR (300 MHz, dimethylsulfoxide-d$_6$) δ 1.43-1.48 (m, 1H), 1.66-1.72 (m, 1H), 1.77-1.84 (m, 1H), 2.09 (brs, 1H), 2.08-2.11 (m, 1H), 2.18 (s, 3H), 2.21 (s, 3H), 2.22-2.28 (m, 1H), 2.40-2.45 (m, 1H), 3.02-3.04 (m, J=1.4 Hz, 1H), 3.23 (s, 3H), 3.63 (t, J=5.4 Hz, 2H), 4.25 (t, J=5.4 Hz, 2H); MS (ESI m/z 321 (M+H)+.

Example 159

N-[(2Z)-3-(2-methoxyethyl)-4,5-dimethyl-1,3-thiazol-2(3H)-ylidene]bicyclo[2.2.1]heptane-7-carboxamide A mixture of Example 46A (267 mg, 1.00 mmol), bicyclo[2.2.1]heptane-7-carboxylic acid (prepared by the method of Schultz, et al *J. Org. Chem.* 1998, 63, 9462-9469: 168 mg, 1.20 mmol), and 2-(1H-benzo[d][1,2,3]triazol-1-yl)-1,1,3,3-tetramethylisouronium tetrafluoroborate (Alltech, 385 mg, 1.20 mmol) in anhydrous acetonitrile (5 mL) was prepared. Triethylamine (Aldrich, 669 μL, 486 mg, 4.80 mmol) was added and the resulting mixture was stirred at room temperature for 24 hours. The volatile components were removed by rotary evaporation and the residue was purified by flash chromatography (silica gel: 35% ethyl acetate/65% hexanes) to afford the title compound. $^1$H NMR (300 MHz, dimethylsulfoxide-d$_6$) δ1.13-1.21 (m, 4H), 1.59-1.66 (m, 4H), 2.15 (s, 3H), 2.20 (s, 3H), 2.39 (br s, 2H), 2.47 (br s, 1H), 3.23 (s, 3H), 3.62 (t, J=5.4 Hz, 2H), 4.22 (t, J=5.4 Hz, 2H); MS (ESI) m/z 309 (M+H)+.

Example 160

N-[(2Z)-5-methyl-3-[(2R)-tetrahydrofuran-2-ylmethyl]-1,3-thiazol-2(3H)-ylidene]-2-oxatricyclo[3.3.1.1$^{3,7}$]decane-1-carboxamide Example 160A (R)-(tetrahydrofuran-2-yl)methyl 4-methylbenzenesulfonate To a solution of (R)-tetrahydrofurfuryl alcohol (Lancaster, 1.0 g, 9.8 mmol) in mL of CH$_2$Cl$_2$ and 5 mL of pyridine was added p-toluenesulfonyl chloride (2.8 g, 15 mmol) portionwise over 15 minutes. The mixture stirred at ambient temperature for 3 hours and was quenched with 10 mL of saturated, aqueous NaHCO$_3$. The layers were separated and the aqueous phase was extracted with three 5 mL portions of CH$_2$Cl$_2$. The combined organic extracts were dried over anhydrous Na$_2$SO$_4$, filtered and concentrated under reduced pressure to afford the title compound. MS (DCI/NH$_3$) m/z 257 (M+H)+, 274 (M+NH$_4$)+.

Example 160B (R)-5-methyl-3-((tetrahydrofuran-2-yl)methyl)thiazol-2(3H)-imine

A mixture of Example 160A (1.5 g, 5.9 mmol), 2-amino-5-methylthiazole (0.68 g, 5.9 mmol) and tetrabutylammonium iodide (1.1 g, 3.0 mmol) in 3 mL of N,N-dimethylformamide was warmed to 85° C. and stirred for 48 hours. The mixture was diluted with 10 mL of CH$_2$Cl$_2$, washed with 10 mL of 10% aqueous NaHCO$_3$, dried over anhydrous Na$_2$SO$_4$, filtered and concentrated under reduced pressure. Purification via column chromatography (SiO$_2$, 10% methanol in ethyl acetate then 9:1:0.1 CH$_2$Cl$_2$:methanol:NH$_4$OH) afforded the title compound.

Example 160C 2-oxaadamantane-1-carbonyl chloride

A solution of Example 56B (0.1 g, 0.55 mmol) in 5 mL of thionyl chloride was warmed to reflux and stirred for 2 hours. The mixture was cooled to ambient temperature and concentrated under reduced pressure. The residue was diluted with 5 mL of toluene and concentrated under reduced pressure three times to afford title compound, which was used without additional purification or characterization.

Example 160D

N-[(2Z)-5-methyl-3-[(2R)-tetrahydrofuran-2-ylmethyl]-1,3-thiazol-2(3H)-ylidene]-2-oxatricyclo[3.3.1.1$^{3,7}$]decane-1-carboxamide Example 160B (0.11 g, 0.55 mmol), triethylamine (0.23 mL, 1.6 mmol) and Example 160C (0.55 mmol) were processed as described in Example 123C to afford the title compound. $^1$H NMR (300 MHz, CD$_3$OD) δ ppm 1.60-1.77 (m, 3H), 1.81-2.07 (m, 9H), 2.08-2.22 (m, 4H), 2.29 (d, J=1.4 Hz, 3H), 3.69-3.79 (m, 1H), 3.82-3.91 (m, 1H), 4.15-4.36 (m, 4H), 7.05 (q, J=1.4 Hz, 1H); MS (DCI/NH$_3$) m/z 363 (M+H)+. Anal. Calculated for C$_{19}$H$_{26}$N$_2$O$_3$S.0.2H$_2$O: C, 62.34; H, 7.27; N, 7.65. Found: C, 62.25; H, 7.32; N, 7.67.

Example 161

N-[(2Z)-3-(cyclobutylmethyl)-5-methyl-1,3-thiazol-2(3H)-ylidene]-3-hydroxyadamantane-1-carboxamide Example 161A 3-(cyclobutylmethyl)-5-methylthiazol-2(3H)-imine A mixture of 2-amino-5-methylthiazole (1.0 g, 8.8 mmol) and (bromomethyl)cyclobutane (0.98 mL, 8.8 mmol) was warmed to 85° C. and stirred for 18 hours. The mixture was cooled to ambient temperature and the residue was purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 183 (M+H)+.

Example 161B

N-[(2Z)-3-(cyclobutylmethyl)-5-methyl-1,3-thiazol-2(3H)-ylidene]-3-hydroxyadamantane-1-carboxamide A mixture of 3-hydroxyadamantane-1-carboxylic acid (Acros, 0.22 g, 1.1 mmol) and 1,1'-carbonyldiimidazole (0.21 g, 1.3 mmol) in 10 mL of ethyl acetate was stirred at ambient temperature for 3.5 hours. Example 161A (0.2 g, 1.1 mmol) in 5 mL of N,N-dimethylformamide was added and the mixture was warmed to 75° C. and stirred for 16 hours. The mixture was cooled to ambient temperature then diluted with 5 mL of saturated aqueous $NH_4Cl$ and 10 mL of ethyl acetate. The layers were separated and the aqueous phase was extracted twice with 5 mL of ethyl acetate. The combined organic extracts were dried over anhydrous $Na_2SO_4$, filtered and concentrated under reduced pressure. Purification via column chromatography ($SiO_2$, 5% methanol in ethyl acetate) afforded the title compound. $^1$H NMR (300 MHz, $CD_3OD$) δ ppm 1.61-1.67 (m, 2H), 1.71 (d, J=3.1 Hz, 4H), 1.81-1.95 (m, 9H), 1.96-2.09 (m, 3H), 2.21-2.26 (m, J=3.4 Hz, 2H), 2.27 (d, J=1.4 Hz, 3H), 2.74-2.92 (m, 1H), 4.21 (d, J=7.5 Hz, 2H), 6.97-7.01 (m, 1H); MS (DCI/$NH_3$) m/z 361 (M+H)$^+$. Anal. Calculated for $C_{20}H_{28}N_2O_2S$: C, 66.63; H, 7.83; N, 7.77. Found: C, 66.60; H, 8.04; N, 7.72.

Example 162

N-[(2Z)-3-(cyclobutylmethyl)-5-methyl-1,3-thiazol-2(3H)-ylidene]-2-oxatricyclo[3.3.1.1$^{3,7}$]decane-1-carboxamide Example 161A (0.20 g, 1.1 mmol), triethylamine (0.46 mL, 3.3 mmol) and Example 160C (1.1 mmol) were processed as described in Example 123C to afford the title compound. $^1$H NMR (300 MHz, $CD_3OD$) δ ppm 1.67-1.77 (m, 2H), 1.80-2.10 (m, 12H), 2.11-2.22 (m, 4H), 2.28 (d, J=1.4 Hz, 3H), 2.73-2.91 (m, 1H), 4.13-4.21 (m, 1H), 4.22 (d, J=7.5 Hz, 2H), 7.01 (q, J=1.4 Hz, 1H); MS (DCI/$NH_3$) m/z 347 (M+H)$^+$. Anal. Calculated for $C_{19}H_{26}N_2O_2S$: C, 65.86; H, 7.56; N, 8.08. Found: C, 65.89; H, 7.70; N, 8.05.

Example 163

N-[(2Z)-3-(cyclobutylmethyl)-4,5-dimethyl-1,3-thiazol-2(3H)-ylidene]-3-hydroxyadamantane-1-carboxamide Example 163A 3-(cyclobutylmethyl)-4,5-dimethylthiazol-2(3H)-imine A mixture of 2-amino-4,5-dimethylthiazole (1.0 g, 7.8 mmol) and (bromomethyl)cyclobutane (0.88 mL, 7.8 mmol) was warmed to 85° C. and stirred for 18 hours. The mixture was cooled to ambient temperature and the residue was purified via column chromatography ($SiO_2$, 10% methanol in ethyl acetate then 9:1:0.1 $CH_2Cl_2$:methanol:$NH_4OH$) to afford the title compound. MS (DCI/$NH_3$) m/z 197 (M+H)$^+$.

Example 163B

N-[(2Z)-3-(cyclobutylmethyl)-4,5-dimethyl-1,3-thiazol-2(3H)-ylidene]-3-hydroxyadamantane-1-carboxamide Example 163A (0.20 g, 1.0 mmol), 3-hydroxyadamantane-1-carboxylic acid (Acros, 0.20 g, 1.0 mmol) and 1,1'-carbonyldiimidazole (0.2 g, 1.2 mmol) in 10 mL of ethyl acetate and 5 mL of N,N-dimethylformamide were processed as in Example 161B to afford the title compound. $^1$H NMR (300 MHz, $CD_3OD$) δ ppm 1.64 (t, J=2.9 Hz, 2H), 1.71 (d, J=3.1 Hz, 4H), 1.82-2.08 (m, 12H), 2.19-2.28 (m, 8H), 2.73-2.84 (m, 1H), 4.30 (d, J=7.1 Hz, 2H); MS (DCI/$NH_3$) m/z 375 (M+H)$^+$. Anal. Calculated for $C_{21}H_{30}N_2O_2S$: C, 67.34; H, 8.07; N, 7.48. Found: C, 67.12; H, 7.87; N, 7.40.

Example 164

N-[(2Z)-3-(cyclobutylmethyl)-1,3-thiazol-2(3H)-ylidene]-3-hydroxyadamantane-1-carboxamide Example 164A 3-(cyclobutylmethyl)thiazol-2(3H)-imine A mixture of 2-aminothiazole (1.0 g, 10 mmol) and (bromomethyl)cyclobutane (1.1 mL, 10 mmol) was warmed to 85° C. and stirred for 18 hours. The mixture was cooled to ambient temperature and the residue was purified via column chromatography ($SiO_2$, 10% methanol in ethyl acetate then 9:1:0.1 $CH_2Cl_2$:methanol:$NH_4OH$) to afford the title compound. MS (DCI/$NH_3$) m/z 169 (M+H)$^+$.

Example 164B

N-[(2Z)-3-(cyclobutylmethyl)-1,3-thiazol-2(3H)-ylidene]-3-hydroxyadamantane-1-carboxamide Example 164A (0.20 g, 1.2 mmol), 3-hydroxyadamantane-1-carboxylic acid (Acros, 0.23 g, 1.2 mmol) and 1,1'-carbonyldiimidazole (0.23 g, 1.4 mmol) in 7 mL of ethyl acetate and 5 mL of N,N-dimethylformamide were processed as in Example 161B to afford the title compound. $^1$H NMR (300 MHz, $CD_3OD$) δ ppm 1.61-1.67 (m, 2H), 1.72 (d, J=3.1 Hz, 4H), 1.78-2.10 (m, 12H), 2.21-2.29 (m, 2H), 2.80-2.93 (m, 1H), 4.28 (d, J=7.5 Hz, 2H), 6.84 (d, J=4.7 Hz, 1H), 7.31 (d, J=4.7 Hz, 1H); MS (DCI/$NH_3$) m/z 347 (M+H)$^+$. Anal. Calculated for $C_{19}H_{26}N_2O_2S$: C, 65.86; H, 7.56; N, 8.08. Found: C, 66.00; H, 7.61; N, 8.07.

Example 165

3-hydroxy-N-[(2Z)-5-methyl-3-[(2R)-tetrahydrofuran-2-ylmethyl]-1,3-thiazol-2(3H)-ylidene]adamantane-1-carboxamide Example 160B (0.23 g, 1.2 mmol), 3-hydroxyadamantane-1-carboxylic acid (Acros, 0.23 g, 1.2 mmol) and 1,1'-carbonyldiimidazole (0.23 g, 1.4 mmol) in 10 mL of ethyl acetate and 5 mL of N,N-dimethylformamide were processed as in Example 161B to afford the title compound. $^1$H NMR (300 MHz, $CD_3OD$) δ ppm 1.60-1.66 (m, 2H), 1.66-1.73 (m, 5H), 1.80-1.93 (m, 8H), 1.97-2.10 (m, 1H), 2.21-2.25 (m, 2H), 2.28 (d, J=1.4 Hz, 3H), 3.69-3.79 (m, 1H), 3.80-3.90 (m, 1H), 4.16-4.35 (m, 3H), 7.01-7.04 (m, 1H); MS (DCI/$NH_3$) m/z 377 (M+H)$^+$. Anal. Calculated for $C_{20}H_{28}N_2O_3S \cdot 0.5H_2O$: C, 62.31; H, 7.58; N, 7.27. Found: C, 62.29; H, 7.81; N, 7.17.

Example 166

N-[(2Z)-3-(1,4-dioxan-2-ylmethyl)-5-methyl-1,3-thiazol-2(3H)-ylidene]-3-hydroxyadamantane-1-carboxamide Example 166A 3-((1,4-dioxan-2-yl)methyl)-5-methylthiazol-2(3H)-imine A mixture of 2-amino-5-methylthiazole (0.77 g, 8.8 mmol) and 2-iodo-methyl-1,4-dioxane (Synchem-OHG, 1.5 g, 6.7 mmol) was warmed to 85° C. and stirred for 16 hours. The mixture was cooled to ambient temperature and the residue was purified via column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 215 (M+H)$^+$.

Example 166B

N-[(2Z)-3-(1,4-dioxan-2-ylmethyl)-5-methyl-1,3-thiazol-2(3H)-ylidene]-3-hydroxyadamantane-1-carboxamide Example 166A (0.2 g, 0.93 mmol), 3-hydroxyadamantane-1-carboxylic acid (Acros, 0.18 g, 0.93 mmol) and 1,1'-carbonyldiimidazole (0.18 g, 1.1 mmol) in 7 mL of ethyl acetate and 7 mL of N,N-dimethylformamide were processed as in Example 161B to afford the title compound. $^1$H NMR (300 MHz, CD$_3$OD) δ ppm 1.61-1.79 (m, 7H), 1.81-1.91 (m, 6H), 2.21-2.26 (m, 2H), 2.28 (d, J=1.4 Hz, 3H), 3.55 (dd, J=11.9, 3.1 Hz, 1H), 3.60-3.70 (m, 2H), 3.76-3.84 (m, 2H), 3.91-4.01 (m, 1H), 4.19-4.23 (m, 2H), 6.98 (q, J=1.1 Hz, 1H); MS (DCI/NH$_3$) m/z 393 (M+H)$^+$. Anal. Calculated for C$_{20}$H$_{28}$N$_2$O$_4$S.0.1H$_2$O: C, 60.92; H, 7.21; N, 7.10. Found: C, 60.69; H, 7.16; N, 7.03.

Example 167

N-[(2Z)-5-tert-butyl-3-[(cis)-(3-methoxycyclobutyl)methyl]-1,3-thiazol-2(3H)-ylidene]-2-oxatricyclo[3.3.1.1$^{3,7}$]decane-1-carboxamide

Example 167A cis-3-benzyloxymethylcyclobutanol methyl ether

To a solution of cis-3-benzyloxymethylcyclobutanol (Albany Molecular Research Institute, 1.0 g, 5.2 mmol) in 10 mL of tetrahydrofuran at 0° C. was added NaH (0.62 g, 15.6 mmol). The mixture stirred for 15 minutes then iodomethane (0.49 mL, 7.8 mmol) was added and the mixture was allowed to warm to ambient temperature and stir for 16 hours. Some starting material remained by TLC so additional NaH (0.21, 5.2 mmol) and iodomethane (0.32 mL, 5.2 mmol) were added and the mixture stirred for an additional 2 hours. The mixture was quenched with 10 mL of NH$_4$Cl and diluted with 10 mL of ethyl acetate. The layers were separated and the aqueous layer was extracted 2×5 mL of ethyl acetate. The combined organic extracts were dried over anhydrous Na$_2$SO$_4$, filtered and concentrated under reduced pressure. Purification via column chromatography (SiO$_2$, 75% hexanes in ethyl acetate) afforded the title compound. MS (DCI/NH$_3$) m/z 207 (M+H)$^+$.

Example 167B (cis-3-methoxycyclobutyl)methanol

A solution of Example 167A (1.05 g, 5.2 mmol) in 10 mL of ethanol was degassed and the flask was filled with N$_2$. This was repeated two additional times. Pd/C (0.1 g, 10 wt %) was added and the mixture was degassed again and filled with N$_2$. This was repeated two additional times then the flask was put under 1 atmosphere of H$_2$ and allowed to stir at ambient temperature for 72 hours. The mixture was degassed and the flask was filled with N$_2$ then filtered. The filtrate was concentrated under reduced pressure and purified by column chromatography (SiO$_2$, 25% hexanes in ethyl acetate) to afford the title compound. MS (DCI/NH$_3$) m/z 134 (M+NH$_4$)$^+$.

Example 167C (cis-3-methoxycyclobutyl)methyl 4-methylbenzenesulfonate

Example 167B (0.49 g, 4.2 mmol) and p-toluenesulfonyl chloride (0.80 g, 4.2 mmol) in 5 mL of CH$_2$Cl$_2$ and 5 mL of pyridine were processed as in Example 160A to afford the title compound. MS (DCI/NH$_3$) m/z 288 (M+NH$_4$)$^+$.

Example 167D 5-tert-butyl-3-((cis-3-methoxycyclobutyl)methyl)thiazol-2(3H)-imine Example 136A (0.25 g, 1.6 mmol), Example 167C (0.44 g, 1.6 mmol) and tetrabutylammonium iodide (0.30 g, 0.81 mmol) in 0.5 mL of N,N-dimethylformamide were processed as in Example 160B to afford the title compound. MS (DCI/NH$_3$) m/z 266 (M+H)$^+$.

Example 167E

N-[(2Z)-5-tert-butyl-3-[(cis)-(3-methoxycyclobutyl)methyl]-1,3-thiazol-2(3H)-ylidene]-2-oxatricyclo[3.3.1.1$^{3,7}$]decane-1-carboxamide Example 167D (0.14 g, 0.55 mmol), triethylamine (0.23 mL, 1.6 mmol) and Example 160C (0.55 mmol) were processed as described in Example 123C to afford the title compound. $^1$H NMR (300 MHz, CD$_3$OD) δ ppm 1.34 (s, 9H), 1.68-1.79 (m, 3H), 1.88-2.06 (m, 6H), 2.12-2.24 (m, 4H), 2.26-2.41 (m, 3H), 3.17-3.26 (m, 1H), 3.21 (s, 3H), 3.69-3.81 (m, 1H), 4.17-4.21 (m, 1H), 4.23 (d, J=6.1 Hz, 2H), 7.04 (s, 1H); MS (DCI/NH$_3$) m/z 419 (M+H)$^+$. Anal. Calculated for C$_{19}$H$_{26}$N$_2$O$_2$S.0.3H$_2$O.0.3C$_6$H$_{14}$: C, 66.21; H, 8.69; N, 6.23. Found: C, 66.53; H, 8.87; N, 5.85.

Example 168

3-chloro-N-[(2Z)-5-methyl-3-(tetrahydrofuran-2-ylmethyl)-1,3-thiazol-2(3H)-ylidene]adamantane-1-carboxamide

Example 168A 3-chloroadamantane-1-carbonyl chloride

A solution of 3-hydroxyadamantane-1-carboxylic acid (0.20 g, 1.0 mmol) in 8 mL of thionyl chloride was warmed to reflux and allowed to stir for 2 hours. The mixture was cooled to ambient temperature and concentrated under reduced pressure. The residue was diluted with 5 mL of toluene and concentrated under reduced pressure three times to afford the title compound, which was used without additional purification or characterization.

Example 168B 3-chloro-N-[(2Z)-5-methyl-3-(tetrahydrofuran-2-ylmethyl)-1,3-thiazol-2(3H)-ylidene]adamantane-1-carboxamide Example 123A (0.20 g, 1.0 mmol), triethylamine (0.23 mL, 1.6 mmol) and Example 168A (1.0 mmol) were processed as described in Example 123C to afford the title compound. ¹H NMR (300 MHz, CD₃OD) δ ppm 1.62-1.76 (m, 3H), 1.82-1.96 (m, 6H), 1.99-2.17 (m, 5H), 2.21-2.30 (m, 4H), 2.29 (d, J=1.4 Hz, 3H), 3.70-3.79 (m, 1H), 3.81-3.91 (m, 1H), 4.18-4.36 (m, 3H), 7.04 (q, J=1.4 Hz, 1H); MS (DCI/NH₃) m/z 395 (M+H)⁺. Anal. Calculated for C₂₀H₂₇N₂O₂S.0.2H₂O: C, 60.27; H, 6.93; N, 7.03. Found: C, 60.23; H, 6.80; N, 6.71.

Example 169

3-hydroxy-N-[(2Z)-3-(2-methoxyethyl)-5-methyl-1,3-thiazol-2(3H)-ylidene]adamantane-1-carboxamide Example 169A 3-(2-methoxyethyl)-5-methylthiazol-2(3H)-imine A mixture of 2-amino-5-methylthiazole (10 g, 88 mmol) and 2-bromoethylmethyl ether (9.1 mL, 96 mmol) was warmed to 85° C. and stirred for 4.5 hours. The mixture was cooled to ambient temperature and the residue was purified via flash column chromatography (SiO₂, 10% methanol in ethyl acetate then 9:1:0.1 CH₂Cl₂:methanol:NH₄OH) to afford the title compound. MS (DCI/NH₃) m/z 173 (M+H)⁺.

Example 169B 3-hydroxy-N-[(2Z)-3-(2-methoxyethyl)-5-methyl-1,3-thiazol-2(3H)-ylidene]adamantane-1-carboxamide Example 169A (0.17 g, 1.0 mmol), 3-hydroxyadamantane-1-carboxylic acid (Acros, 0.20 g, 1.0 mmol) and 1,1'-carbonyldiimidazole (0.20 g, 1.2 mmol) in 15 mL of ethyl acetate and 1 mL of N,N-dimethylformamide were processed as in Example 161B to afford the title compound. ¹H NMR (300 MHz, CD₃OD) δ ppm 1.61-1.65 (m, 2H), 1.70 (d, J=3.1 Hz, 4H), 1.77-1.85 (m, 4H), 1.87 (s, 2H), 2.20-2.25 (m, 2H), 2.28 (d, J=1.4 Hz, 3H), 3.33 (s, 3H), 3.72 (t, J=5.1 Hz, 2H), 4.33 (t, J=5.3 Hz, 2H), 6.99 (q, J=1.2 Hz, 1H); MS (DCI/NH₃) m/z 351 (M+H)⁺. Anal. Calculated for C₁₈H₂₆N₂O₃S.0.2H₂O: C, 61.06; H, 7.52; N, 7.91. Found: C, 61.01; H, 7.37; N, 7.80.

Example 170

3-hydroxy-N-[(2Z)-5-methyl-3-(tetrahydrofuran-2-ylmethyl)-1,3-thiazol-2(3H)-ylidene]adamantane-1-carboxamide Example 123A (0.2 g, 1.0 mmol), 3-hydroxyadamantane-1-carboxylic acid (Acros, 0.20 g, 1.0 mmol) and 1,1'-carbonyldiimidazole (0.20 g, 1.2 mmol) in 10 mL of ethyl acetate and 1 mL of N,N-dimethylformamide were processed as in Example 161B to afford the title compound. ¹H NMR (300 MHz, CD₃OD) δ ppm 1.63 (t, J=2.7 Hz, 2H), 1.66-1.75 (m, 5H), 1.79-1.93 (m, 8H), 1.96-2.10 (m, 1H), 2.21-2.25 (m, 2H), 2.28 (d, J=1.4 Hz, 3H), 3.69-3.79 (m, 1H), 3.80-3.91 (m, 1H), 4.16-4.34 (m, 3H), 7.02 (q, J=1.2 Hz, 1H); MS (DCI/NH₃) m/z 377 (M+H)⁺. Anal. Calculated for C₂₀H₂₈N₂O₃S: C, 63.80; H, 7.50; N, 7.44. Found: C, 63.56; H, 7.56; N, 7.43.

Example 171

N-[(2Z)-3-butyl-5-methyl-1,3-thiazol-2(3H)-ylidene]-2-oxatricyclo[3.3.1.1³,⁷]decane-1-carboxamide Example 125A (0.10 g, 0.59 mmol), Example 160C (0.11 mmol) and 1,1'-carbonyldiimidazole (0.11 g, 0.71 mmol) in 10 mL of ethyl acetate and 2 mL of N,N-dimethylformamide were processed as in Example 161B to afford the title compound. ¹H NMR (300 MHz, CD₃OD) δ ppm 0.92-1.02 (m, 3H), 1.27-1.42 (m, 2H), 1.67-1.85 (m, 4H), 1.88-2.07 (m, 6H), 2.10-2.22 (m, 4H), 2.29 (d, J=1.4 Hz, 3H), 4.19 (t, J=7.1 Hz, 2H), 4.17-4.20 (m, 1H), 7.03 (q, J=1.4 Hz, 1H); MS (DCI/NH₃) m/z 335 (M+H)⁺. Anal. Calculated for C₁₈H₂₆N₂O₂S.0.2H₂O: C, 63.95; H, 7.87; N, 8.29. Found: C, 64.07; H, 7.74; N, 8.40.

Example 172

N-[(2Z)-5-methyl-3-(tetrahydro-2H-pyran-2-ylmethyl)-1,3-thiazol-2(3H)-ylidene]-2-oxatricyclo[3.3.1.1³,⁷]decane-1-carboxamide Example 124A (0.10 g, 0.47 mmol), triethylamine (0.2 mL, 1.4 mmol) and Example 160C (0.47 mmol) in 5 mL of tetrahydrofuran were processed as described in Example 122B to afford the title compound. ¹H NMR (300 MHz, CD₃OD) δ ppm 1.17-1.34 (m, 1H), 1.45-1.59 (m, 3H), 1.61-1.77 (m, 3H), 1.82-2.05 (m, 7H), 2.09-2.22 (m, 4H), 2.28 (d, J=1.4 Hz, 3H), 3.33-3.43 (m, 1H), 3.65-3.76 (m, 1H), 3.88-3.99 (m, 1H), 4.06-4.15 (m, 1H), 4.15-4.21 (m, 1H), 4.25-4.35 (m, 1H), 7.00 (q, J=1.4 Hz, 1H); MS (DCI/NH₃) m/z 377 (M+H)⁺. Anal. Calculated for C₂₀H₂₈N₂O₃S: C, 63.80; H, 7.50; N, 7.44. Found: C, 63.12; H, 7.37; N, 7.16.

Example 173

N-[(2Z)-5-methyl-3-(tetrahydro-2H-pyran-4-ylmethyl)-1,3-thiazol-2(3H)-ylidene]-2-oxatricyclo[3.3.1.1³,⁷]decane-1-carboxamide Example 173A (tetrahydro-2H-pyran-4-yl)methyl 4-methylbenzenesulfonate Tetrahydro-2-H-pyran-4-ylmethanol (Combi-Blocks, 2.0 g, 17 mmol) and p-toluenesulfonyl chloride (3.5 g, 18 mmol) in 10 mL of CH₂Cl₂ and 10 mL of pyridine were processed as in Example 160A to afford the title compound. MS (DCI/NH₃) m/z 288 (M+NH₄)⁺.

Example 173B 5-methyl-3-((tetrahydro-2H-pyran-4-yl)methyl)thiazol-2(3H)-imine

Example 173A (1.9 g, 7.0 mmol), 2-amino-5-methylthiazole (0.80 g, 7.0 mmol) and tetrabutylammonium iodide (1.3 g, 3.5 mmol) in 3 mL of N,N-dimethylformamide were processed as in Example 160B to afford the title compound. MS (DCI/NH₃) m/z 213 (M+H)⁺.

Example 173C

N-[(2Z)-5-methyl-3-(tetrahydro-2H-pyran-4-ylmethyl)-1,3-thiazol-2(3H)-ylidene]-2-oxatricyclo[3.3.1.1³,⁷]decane-1-carboxamide Example 173B (0.15 g, 0.71 mmol), triethylamine (0.3 mL, 2.1 mmol) and Example 160C (0.71 mmol) in 15 mL of tetrahydrofuran and 2 mL of N,N-dimethylformamide were processed as described in Example 122C to afford the title compound. ¹H NMR (300 MHz, CD₃OD) δ ppm 1.31-1.56

(m, 4H), 1.72 (dd, J=13.7, 1.5 Hz, 2H), 1.87-2.08 (m, 6H), 2.10-2.24 (m, 5H), 2.29 (d, J=1.4 Hz, 3H), 3.37 (dt, J=11.5, 2.4 Hz, 2H), 3.93 (ddd, J=11.6, 4.2, 2.2 Hz, 2H), 4.10 (d, J=7.5 Hz, 2H), 4.15-4.20 (m, 1H), 7.04 (q, J=1.4 Hz, 1H); MS (DCI/NH$_3$) m/z 377 (M+H)$^+$. Anal. Calculated for C$_{20}$H$_{28}$N$_2$O$_3$S: C, 63.80; H, 7.50; N, 7.44. Found: C, 63.43; H, 7.38; N, 7.33.

Example 174

N-[(2Z)-3-(3-methoxypropyl)-5-methyl-1,3-thiazol-2(3H)-ylidene]-2-oxatricyclo[3.3.1.1$^{3,7}$]decane-1-carboxamide

Example 174A 3-(3-methoxypropyl)-5-methylthiazol-2(3H)-imine

A mixture of 2-amino-5-methylthiazole (0.87 g, 7.6 mmol) and 1-bromo-3-methoxypropane (Matrix, 1.3 g, 8.5 mmol) was warmed to 85° C. and stirred for 5 hours. The mixture was cooled to ambient temperature and the residue was purified via flash column chromatography (SiO$_2$, 10% methanol in ethyl acetate then 9:1:0.1 CH$_2$Cl$_2$:methanol:NH$_4$OH) to provide the title compound. MS (DCI/NH$_3$) m/z 187 (M+H)$^+$.

Example 174B

N-[(2Z)-3-(3-methoxypropyl)-5-methyl-1,3-thiazol-2(3H)-ylidene]-2-oxatricyclo[3.3.1.1$^{3,7}$]decane-1-carboxamide Example 174A (0.11 g, 0.60 mmol), triethylamine (0.25 mL, 1.8 mmol) and Example 160C (0.60 mmol) in 12 mL of tetrahydrofuran and 2 mL of N,N-dimethylformamide were processed as described in Example 122B to afford the title compound. $^1$H NMR (300 MHz, CD$_3$OD) δ ppm 1.66-1.78 (m, 2H), 1.87-2.11 (m, 8H), 2.11-2.22 (m, 4H), 2.29 (d, J=1.4 Hz, 3H), 3.31 (s, 3H), 3.38 (t, J=5.9 Hz, 2H), 4.16-4.20 (m, 1H), 4.25 (t, J=7.0 Hz, 2H), 7.00 (q, J=1.1 Hz, 1H); MS (DCI/NH$_3$) m/z 351 (M+H)$^+$. Anal. Calculated for C$_{18}$H$_{26}$N$_2$O$_3$S: C, 61.69; H, 7.48; N, 7.99. Found: C, 61.46; H, 7.24; N, 7.91.

Example 175

N-[(2Z)-3-butyl-5-tert-butyl-1,3-thiazol-2(3H)-ylidene]-2-oxatricyclo[3.3.1.1$^{3,7}$]decane-1-carboxamide

Example 175A 5-tert-butyl-3-butylthiazol-2(3H)-imine

A mixture of Example 136A (0.6 g, 3.8 mmol) and 1-bromobutane (0.45 mL, 4.2 mmol) was warmed to 85° C. and stirred for 18 hours. The mixture was cooled to ambient temperature and the residue was purified via flash column chromatography (SiO$_2$, 10% methanol in ethyl acetate then 9:1:0.1 CH$_2$Cl$_2$:methanol:NH$_4$OH) to afford the title compound. MS (DCI/NH$_3$) m/z 213 (M+H)$^+$.

Example 175B

N-[(2Z)-3-butyl-5-tert-butyl-1,3-thiazol-2(3H)-ylidene]-2-oxatricyclo[3.3.1.1$^{3,7}$]decane-1-carboxamide Example 175A (0.21 g, 1.0 mmol), triethylamine (0.42 mL, 3.0 mmol) and Example 160C (1.0 mmol) in 12 mL of tetrahydrofuran and were processed as described in Example 122B to afford the title compound. $^1$H NMR (300 MHz, CD$_3$OD) δ ppm 0.97 (t, J=7.3 Hz, 3H), 1.23-1.43 (m, 2H), 1.34 (s, 9H), 1.66-1.85 (m, 4H), 1.89-2.06 (m, 7H), 2.09-2.28 (m, 4H), 4.19 (t, J=7.1 Hz, 2H), 7.05 (s, 1H); MS (DCI/NH$_3$) m/z 376 (M+H)$^+$. Anal. Calculated for C$_{21}$H$_{32}$N$_2$O$_2$S: C, 66.98; H, 8.57; N, 7.44. Found: C, 66.76; H, 8.64; N, 7.37.

Example 176

(1R,4S)-4,7,7-trimethyl-N-[(2Z)-5-methyl-3-[(2R)-tetrahydrofuran-2-ylmethyl]-1,3-thiazol-2(3H)-ylidene]-3-oxo-2-oxabicyclo[2.2.1]heptane-1-carboxamide Example 160B and (1R)-(+)-camphanic acid (Aldrich) were processed as in Example 2B to afford the title compound. MS (DCI/NH$_3$) m/z 379 (M+H)$^+$.

Example 177

(1R,4S)—N-[(2Z)-3-butyl-5-methyl-1,3-thiazol-2(3H)-ylidene]-4,7,7-trimethyl-3-oxo-2-oxabicyclo[2.2.1]heptane-1-carboxamide Example 125A and (1R)-(+)-camphanic acid (Aldrich) were processed as in Example 2B to afford the title compound. MS (DCI/NH$_3$) m/z 351 (M+H)$^+$.

Example 178

N-[(2Z)-4-ethyl-3-(2-methoxyethyl)-1,3-thiazol-2(3H)-ylidene]adamantane-1-carboxamide

Example 178A 4-ethylthiazol-2-amine

A mixture of 1-bromo-butan-2-one and thiourea (0.25 g, 3.3 mmol) in ethanol was processed as in Example 71A to afford the title compound. MS (DCI/NH$_3$) m/z 129 (M+H)$^+$.

Example 178B 4-ethyl-3-(2-methoxyethyl)-1,3-thiazol-2(3H)-imine hydrobromide Example 178A and 1-bromo-2-methoxy ethane were processed as in Example 2A to afford the title compound. MS (DCI/NH$_3$) m/z 187 (M+H)$^+$.

Example 178C

N-[(2Z)-4-ethyl-3-(2-methoxyethyl)-1,3-thiazol-2(3H)-ylidene]adamantane-1-carboxamide Example 178B and adamantane-1-carboxylic acid were processed as in Example 17A to afford the title compound. $^1$H NMR (CDCl$_3$, 500 MHz) δ ppm 1.29 (t, J=7.48 Hz, 3H), 1.69-1.77 (m, 6H), 1.96 (d, J=2.44 Hz, 6H), 2.03 (s, 3H), 2.59-2.70 (m, 2H), 3.30 (s, 3H), 3.73 (t, J=5.34 Hz, 2H), 4.28 (t, J=5.34 Hz, 2H), 6.15 (s, 1H); MS (DCI/NH$_3$) m/z 349

(M+H)⁺. Anal. calculated for $C_{19}H_{28}N_2O_2S$: C, 65.48; H, 8.10; N, 8.04. Found: C, 65.40; H, 7.98; N, 7.90.

Example 179

N-[(2Z)-4-cyclopropyl-3-(2-methoxyethyl)-1,3-thiazol-2(3H)-ylidene]adamantane-1-carboxamide Example 179A 4-cyclopropylthiazol-2-amine A mixture of 2-bromo-1-cyclopropyl-ethanone (0.50 g, 3.0 mmol, Waterstone Technology) and thiourea (0.23 g, 3.1 mmol) were processed as in Example 71A to afford the title compound. MS (DCI/NH₃) m/z 141 (M+H)⁺.

Example 179B

Adamantane-1-carboxylic acid (4-cyclopropylthiazol-2-yl)-amide

The product from Example 179A and adamantane-1-carboxylic acid were processed as described in Example 17A to afford the title compound. MS (DCI/NH₃) m/z 303 (M+H)⁺.

Example 179C

N-[(2Z)-4-cyclopropyl-3-(2-methoxyethyl)-1,3-thiazol-2(3H)-ylidene]adamantane-1-carboxamide A mixture of Example 179B and 1-bromo-2-methoxy ethane was processed as in Example 17B to afford the title compound. ¹H NMR (CDCl₃, 500 MHz) δ ppm 0.63-0.72 (m, 2H), 0.89-0.99 (m, 2H), 1.56 (s, 1H), 1.74 (s, 6H), 1.89-1.98 (m, 6H), 2.03 (s, 3H), 3.33 (s, 3H), 3.78 (t, J=5.49 Hz, 2H), 4.48 (t, J=5.49 Hz, 2H), 6.08 (s, 21H); MS (DCI/NH₃) m/z 361 (M+H)⁺. Anal. calculated for $C_{20}H_{28}N_2O_2S$: C, 66.63; H, 7.83; N, 7.77. Found: C, 66.08; H, 7.81; N, 7.58.

Example 181

N-[(2Z)-4-tert-butyl-3-(2-methoxyethyl)-1,3-thiazol-2(3H)-ylidene]hexahydro-2,5-methanopentalene-3a(1H)-carboxamide A mixture of Example 14B (57 mg, 0.20 mmol) and 1-bromo-3,3-dimethylbutan-2-one (36 mg, 0.027 mL, 0.20 mmol, Aldrich) was processed according to the method described in Example 14C. Purification by column chromatography (SiO₂, 30-45% ethyl acetate/hexanes gradient) afforded title compound. ¹H NMR (dimethylsulfoxide-d₆, 300 MHz) δ 1.37 (s, 9H), 1.56-1.63 (m, 4H), 1.69-1.79 (m, 4H), 2.07-2.18 (m, 2H), 2.24-2.30 (m, 2H), 2.53-2.60 (m, 1H), 3.26 (s, 3H), 3.75 (t, J=6.78 Hz, 2H), 4.40 (t, J=6.95 Hz, 2H), 6.57 (s, 1H); MS (DCI/NH₃) m/z 363 (M+H)⁺.

Example 182

N-[(2Z)-5-cyclohexyl-3-(2-methoxyethyl)-1,3-thiazol-2(3H)-ylidene]-2-oxatricyclo[3.3.1.1³,⁷]decane-1-carboxamide Example 182A 2-cyclohexylacetaldehyde The title compound was prepared from 2-cyclohexylethanol according to the procedure as described Tetrahedron Letters (1995), 36(17), 3019-22. ¹H NMR (300 MHz, chloroform-d) δ ppm 0.87-1.08 (m, 2H), 1.13-1.41 (m, 3H), 1.61-1.80 (m, 5H), 1.81-1.99 (m, 1H), 2.29 (dd, J=6.8, 2.4 Hz, 2H), 9.76 (t, J=2.4 Hz, 1H). Example 182B 5-cyclohexylthiazol-2-amine Example 182A, pyrrolidine, p-toluenesulfonic acid monohydrate, sulfur and cyanamide were processed using the method described in Example 136A to obtain the title compound. MS (ESI⁺) m/z 183 (M+H)⁺.

Example 182C 5-cyclohexyl-3-(2-methoxyethyl)thiazol-2(3H)-imine hydrobromide

A mixture of Example 182B and commercially available 2-bromoethyl methyl ether (Aldrich) was processed using the method described in Example 46A to afford the title compound. MS (ESI⁺) m/z 241 (M+H)⁺.

Example 182D

N-[(2Z)-5-cyclohexyl-3-(2-methoxyethyl)-1,3-thiazol-2(3H)-ylidene]-2-oxatricyclo[3.3.1.1³,⁷]decane-1-carboxamide Example 56B and Example 182C were processed using the method described in Example 56C to afford the title compound. ¹H NMR (300 MHz, dimethylsulfoxide-d₆) δ ppm 1.16-1.32 (m, 1H), 1.31-1.46 (m, 3H), 1.50-1.88 (m, 8H), 1.87-2.15 (m, 10H), 2.15-2.27 (m, 2H), 2.49-2.72 (m, 1H), 3.34 (s, 3H), 3.64-3.77 (m, J=4.4 Hz, 2H), 4.13-4.44 (m, 2H), 5.34 (none, 1H), 6.59-6.82 (m, J=7.1 Hz, 1H); MS (ESI⁺) m/z 405 (M+H)⁺.

Example 183

N-[(2Z)-5-cyano-3-(2-methoxyethyl)-1,3-thiazol-2(3H)-ylidene]adamantane-1-carboxamide Example 183A 2-aminothiazole-5-carbonitrile The title compound was prepared from bromonaldehyde in 3 steps as described in U.S. Pat. No. 4,324,899. ¹H NMR (300 MHz, dimethylsulfoxide-d₆) δ ppm 7.83 (s, 1H), 8.13 (s, 2H).

Example 183B

Adamantane-1-carboxylic acid (5-cyano-1,3-thiazol-2-yl)-amide

Example 183A and commercially available adamantane-1-carbonyl chloride were processed using the method described in Example 1A to afford the title compound. ¹H NMR (300 MHz, dimethylsulfoxide-d₆) δ ppm 1.61-1.75 (m, 6H), 1.91-1.97 (m, 6H), 1.96-2.12 (m, 3H), 8.38 (s, 1H), 12.60 (s, 1H).

Example 183C

N-[(2Z)-5-cyano-3-(2-methoxyethyl)-1,3-thiazol-2(3H)-ylidene]adamantane-1-carboxamide To a solution of Example 183B (240 mg, 0.84 mmol) in N,N-dimethylformamide/tetrahydrofuran (1:4, 10 mL) were added a solution of potassium tert-butoxide (Aldrich, 133 mg, 1.2 mmol) and commercially available, 2-bromoethyl methyl ether (Aldrich, 104 µL, 1.2 mmol). The reaction mixture was stirred at 80° C. for 16 hours, cooled to room temperature, quenched with saturated aqueous NaHCO$_3$ (10 mL) and extracted with ethyl acetate (3×10 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-100% ethyl acetate in hexanes) to afford the title compound. $^1$H NMR (300 MHz, dimethylsulfoxide-d$_6$) δ ppm 1.59-1.77 (m, 6H), 1.84-1.91 (m, 6H), 1.95-2.04 (m, 3H), 3.26 (s, 3H), 3.71 (t, J=5.3 Hz, 2H), 4.36 (t, J=5.1 Hz, 2H), 8.54 (s, 1H); MS (ESI$^+$) m/z 346 (M+H)$^+$; Anal. Calculated for C$_{18}$H$_{23}$N$_3$O$_2$S: C, 62.58; H, 6.71; N, 12.16. Found: C, 62.15; H, 6.89; N, 11.95.

Example 184

N-[(2Z)-5-(4,4-difluorocyclohexyl)-3-(2-methoxyethyl)-1,3-thiazol-2(3H)-ylidene]adamantane-1-carboxamide Example 184A (4,4-difluorocyclohexyl)methanol To a suspension of lithium aluminum hydride (2.6 g, 69 mmol) in diethyl ether (160 mL) was added slowly a solution of commercially available ethyl 4,4-difluorocyclohexanecarboxylate (Matrix, 11.0 g, 57 mmol) in diethyl ether (20 mL). The reaction mixture was refluxed for 4 hours, then cooled in an ice bath, quenched cautiously with sequential addition of water (2.6 mL), 15% NaOH (2.6 mL) and water (7.8 mL) and extracted with ethyl acetate (3×100 mL). The mixture was filtered and concentrated to afford the title compound.

Example 184B (4,4-difluorocyclohexyl)methyl 4-methylbenzenesulfonate

To a solution of Example 184A (8.5 g, 57 mmol) in dichloromethane (100 mL) were added triethylamine (Aldrich, 25 mL, 180 mmol) and tosyl chloride (Aldrich, 11.4 g, 60 mmol). The reaction mixture was stirred at room temperature for 16 hours and washed with water (50 mL) and brine (50 mL). The organic layer was dried over anhydrous Na$_2$SO$_4$, filtered and concentrated under reduced pressure. The residue was purified by column chromatography using an Analogix® Intelliflash280™ (SiO$_2$, 0-50% ethyl acetate in hexanes) to afford the title compound. $^1$H NMR (300 MHz, chloroform-d) δ ppm 1.17-1.42 (m, 2H), 1.57-1.69 (m, 1H), 1.70-1.91 (m, 4H), 1.93-2.18 (m, 2H), 2.46 (s, 3H), 3.86 (d, J=6.4 Hz, 2H), 7.35 (d, J=8.5 Hz, 2H), 7.78 (d, J=8.1 Hz, 2H).

Example 184C 2-(4,4-difluorocyclohexyl)acetonitrile

To a solution of Example 184B (4.5 g, 15 mmol) in dimethylsulfoxide (100 mL) was added sodium cyanide (Aldrich, 2.2 g, 45 mmol). The reaction mixture was stirred at 80° C. for 14 hours, cooled to room temperature, quenched with saturated aqueous NaHCO$_3$ (50 mL) and extracted with diethyl ether (3×50 mL). The combined organic extracts were dried over anhydrous MgSO$_4$, filtered and concentrated under reduced pressure. The residue was purified by column chromatography using an Analogix® Intelliflash280™ (SiO$_2$, 50% pentane in ether) to afford the title compound. MS (ESI$^+$) m/z 177 (M+NH$_4$)$^+$.

Example 184D 2-(4,4-difluorocyclohexyl)acetaldehyde

To a solution of Example 184C (3.8 g, 24 mmol) in dichloromethane (50 mL) was added diisobutylaluminum hydride (1.6M in cyclohexane, 22.5 mL, 36 mmol), dropwise. The reaction mixture was stirred at room temperature for 3 hours. The reaction mixture was quenched with 1M tartaric acid (40 mL), stirred for 1 hour and the layers were separated. The aqueous layer was extracted with dichloromethane (3×50 mL). The combined organic extracts were dried over anhydrous MgSO$_4$, filtered and concentrated under reduced pressure to afford the title compound. MS (ESI$^+$) m/z 162 (M+NH$_4$-H$_2$O)$^+$.

Example 184E 5-(4,4-difluorocyclohexyl)-2,3-dihydrothiazol-2-amine

Example 184D, pyrrolidine, p-toluenesulfonic acid monohydrate, sulfur and cyanamide were processed using the method described in Example 136A to obtain the title compound. MS (ESI$^+$) m/z 219 (M+H)$^+$.

Example 184F 5-(4,4-difluorocyclohexyl)-3-(2-methoxyethyl)thiazol-2(3H)-imine hydrobromide A mixture of Example 184E and commercially available 2-bromoethyl methyl ether (Aldrich) was processed using the method described in Example 46A to afford the title compound. MS (ESI$^+$) m/z 277 (M+H)$^+$.

Example 184G

N-[(2Z)-5-(4,4-difluorocyclohexyl)-3-(2-methoxyethyl)-1,3-thiazol-2(3H)-ylidene]adamantane-1-carboxamide Example 184F and adamantane-1-carbonyl chloride were processed using the method described in Example 1A to afford the title compound: $^1$H NMR (300 MHz, dimethylsulfoxide-d$_6$) δ ppm 1.45-1.77 (m, 8H), 1.75-1.92 (m, 6H), 1.91-2.16 (m, 9H), 2.69-2.94 (m, 1H), 3.25 (s, 3H), 3.69 (t, J=5.4 Hz, 2H), 4.25 (t, J=5.4 Hz, 2H), 7.21 (s, 1H); MS (ESI$^+$) m/z 439 (M+H)$^+$; Anal. Calculated for C$_{23}$H$_{32}$F$_2$N$_2$O$_2$S: C, 62.99; H, 7.35; N, 6.39. Found: C, 62.98; H, 7.36; N, 6.21.

Example 185

N-[(2Z)-5-methoxy-3-(2-methoxyethyl)-1,3-thiazol-2(3H)-ylidene]adamantane-1-carboxamide Example 185A 5-methoxythiazol-2-amine The commercially available HBr salt of 5-bromothiazol-2-amine (Aldrich, 5.0 g, 19 mmol) was converted to its free base. To a solution of 5-bromothiazol-2-amine, in methanol (100 mL) was added sodium methoxide (0.5M in methanol, 36 mL, 18 mmol). The reaction mixture was stirred at 50° C. for 14 hours, cooled and concentrated. The residue was purified by column chromatography using an Analogix® Intelliflash280™ (SiO$_2$, 0-100% ethyl acetate in hexanes) to afford the title compound. MS (ESI$^+$) m/z 131 (M+H)$^+$.

Example 185B 5-methoxy-3-(2-methoxyethyl)thiazol-2(3H)-imine hydrobromide

A mixture of Example 185A and commercially available 2-bromoethyl methyl ether (Aldrich) was processed using the method described in Example 46A to afford the title compound. MS (ESI$^+$) m/z 189 (M+H)$^+$.

Example 185C

N-[(2Z)-5-methoxy-3-(2-methoxyethyl)-1,3-thiazol-2(3H)-ylidene]adamantane-1-carboxamide Example 185B and adamantane-1-carbonyl chloride were processed using the method described in Example 1A to afford the title compound. $^1$H NMR (300 MHz, dimethylsulfoxide-d$_6$) δ ppm 1.55-1.75 (m, 6H), 1.78-1.91 (m, 6H), 1.93-2.05 (m, 3H), 3.27 (s, 3H), 3.70 (t, J=5.4 Hz, 2H), 3.80 (s, 3H), 4.23 (t, J=5.4 Hz, 2H), 6.90 (s, 1H); MS (ESI$^+$) m/z 351 (M+H)$^+$; Anal. Calculated for C$_{18}$H$_{26}$N$_2$O$_3$S: C, 61.69; H, 7.48; N, 7.99. Found: C, 61.63; H, 7.60; N, 7.99.

Example 186

N-[(2Z)-3-(2-methoxyethyl)-5-[2,2,2-trifluoro-1-hydroxy-1-(trifluoromethyl)ethyl]-1,3-thiazol-2(3H)-ylidene]adamantane-1-carboxamide

Example 186A 2-(2-amino-4-methylthiazol-5-yl)-1,1,1,3,3,3-hexafluoropropan-2-ol The title compound was prepared from commercially available of 4-methylthiazol-2-amine (Aldrich) and hexafluoroacetone trihydrate (Aldrich) according to the procedure described in European Journal of Organic Chemistry, (21), 4286-4291; 2003. MS (ESI$^+$) m/z 281 (M+H)$^+$.

Example 186B 1,1,1,3,3,3-hexafluoro-2-(2-imino-3-(2-methoxyethyl)-2,3-dihydrothiazol-5-yl)propan-2-ol hydrobromide A mixture of Example 186A and commercially available 2-bromoethyl methyl ether (Aldrich) was processed using the method described in Example 46A to afford the title compound. MS (ESI$^+$) m/z 325 (M+H)$^+$.

Example 186C

N-[(2Z)-3-(2-methoxyethyl)-5-[2,2,2-trifluoro-1-hydroxy-1-(trifluoromethyl)ethyl]-1,3-thiazol-2(3H)-ylidene]adamantane-1-carboxamide Example 186B and commercially available adamantane-1-carbonyl chloride were processed using the method described in Example 1A to afford the title compound. $^1$H NMR (300 MHz, dimethylsulfoxide-d$_6$) δ ppm 1.53-1.79 (m, 6H), 1.82-1.91 (m, 6H), 1.95-2.06 (m, 3H), 3.25 (s, 3H), 3.71 (t, J=5.3 Hz, 2H), 4.37 (t, J=5.3 Hz, 2H), 7.74 (s, 1H), 9.25 (s, 1H); MS (ESI$^+$) m/z 487 (M+H)$^+$; Anal. Calculated for C$_{20}$H$_{24}$F$_6$N$_2$O$_3$S: C, 49.38; H, 4.97; N, 5.76. Found: C, 49.42; H, 4.76; N, 5.87.

Example 187

N-[(2Z)-5-tert-butyl-3-(2-methoxyethyl)-1,3-thiazol-2(3H)-ylidene]-3-hydroxyadamantane-1-carboxamide

Example 187A

N-(5-tert-butylthiazol-2-yl)-3-hydroxyadamantane-1-carboxamide

Example 136A and 3-hydroxyadamantane-1-carboxylic acid were processed using the method described in Example 56C to afford the title compound. MS (ESI$^+$) m/z 335 (M+H)$^+$.

Example 187B

N-[(2Z)-5-tert-butyl-3-(2-methoxyethyl)-1,3-thiazol-2(3H)-ylidene]-3-hydroxyadamantane-1-carboxamide Example 187A and commercially available 2-bromoethyl methyl ether (Aldrich) were processed using the method described in Example 183C to afford the title compound. $^1$H NMR (300 MHz, dimethylsulfoxide-d$_6$) δ ppm 1.27 (s, 9H), 1.46-1.59 (m, 6H), 1.69 (s, 6H), 2.07-2.18 (m, 2H), 3.26 (s, 3H), 3.69 (t, J=5.4 Hz, 2H), 4.24 (t, J=5.4 Hz, 2H), 4.40 (s, 1H), 7.13 (s, 1H); MS (ESI$^+$) m/z 393 (M+H)$^+$; Anal. Calculated for C$_{21}$H$_{32}$N$_2$O$_3$S: C, 64.25; H, 8.22; N, 7.14. Found: C, 64.50; H, 8.39; N, 6.93.

Example 188

N-[(2Z)-5-tert-butyl-3-(tetrahydro-2H-pyran-4-ylmethyl)-1,3-thiazol-2(3H)-ylidene]-3-hydroxyadamantane-1-carboxamide

Example 188A (tetrahydro-2H-pyran-4-yl)methyl 4-methylbenzenesulfonate

Commercially available (tetrahydro-2H-pyran-4-yl)methanol (Maybridge), tosyl chloride and triethylamine were processed using the method described in Example 184B to afford the title compound. $^1$H NMR (300 MHz, dimethylsulfoxide-d$_6$) δ ppm 1.05-1.25 (m, 2H), 1.40-1.53 (m, 2H), 1.73-1.94 (m, 1H), 2.43 (s, 3H), 3.14-3.28 (m, 2H), 3.71-3.84 (m, 2H), 3.88 (d, J=6.4 Hz, 2H), 7.48 (d, J=8.5 Hz, 2H), 7.79 (d, J=8.5 Hz, 2H).

Example 188B

N-[(2Z)-5-tert-butyl-3-(tetrahydro-2H-pyran-4-ylmethyl)-1,3-thiazol-2(3H)-ylidene]-3-hydroxyadamantane-1-carboxamide Example 187A and Example 188A were processed using the method described in Example 183C to afford the title compound. ¹H NMR (300 MHz, dimethylsulfoxide-$d_6$) δ ppm 1.27 (s, 9H), 1.30-1.59 (m, 8H), 1.65-1.73 (m, 6H), 2.06-2.22 (m, 3H), 3.18-3.28 (m, 4H), 3.76-3.89 (m, 2H), 4.00 (d, J=7.1 Hz, 2H), 4.39 (s, 1H), 7.17 (s, 1H); MS (ESI⁺) m/z 433 (M+H)⁺; Anal. Calculated for $C_{24}H_{36}N_2O_3S$: C, 66.63; H, 8.39; N, 6.48. Found: C, 66.19; H, 8.55; N, 6.38.

Example 189

N-[(2Z)-3-butyl-5-tert-butyl-1,3-thiazol-2(3H)-ylidene]-3-hydroxyadamantane-1-carboxamide Example 187A and 1-bromobutane were processed using the method described in Example 183C to afford the title compound. ¹H NMR (300 MHz, dimethylsulfoxide-$d_6$) δ ppm 0.92 (t, J=7.3 Hz, 3H), 1.18-1.33 (m, 11H), 1.47-1.60 (m, 6H), 1.63-1.79 (m, 8H), 2.05-2.20 (m, 2H), 4.08 (t, J=7.1 Hz, 2H), 4.38 (s, 1H), 7.17 (s, 1H); MS (ESI⁺) m/z 391 (M+H)⁺; Anal. Calculated for $C_{22}H_{34}N_2O_2S$: C, 67.65; H, 8.77; N, 7.17. Found: C, 67.62; H, 9.07; N, 7.13.

Example 190

N-[(2Z)-5-tert-butyl-3-(tetrahydrofuran-2-ylmethyl)-1,3-thiazol-2(3H)-ylidene]-3-hydroxyadamantane-1-carboxamide Example 187A and commercially available tetrahydrofurfuryl bromide (Maybridge) were processed using the method described in Example 183C to afford the title compound. ¹H NMR (300 MHz, dimethylsulfoxide-$d_6$) δ ppm 1.27 (s, 9H), 1.45-1.53 (m, 2H), 1.52-1.59 (m, J=2.7 Hz, 4H), 1.58-1.66 (m, 1H), 1.66-1.72 (m, 6H), 1.73-1.84 (m, 2H), 1.84-1.95 (m, 1H), 2.08-2.20 (m, 2H), 3.58-3.69 (m, 1H), 3.72-3.81 (m, 1H), 4.09-4.17 (m, 2H), 4.19-4.31 (m, 1H), 4.40 (s, 1H), 7.11 (s, 1H); MS (ESI⁺) m/z 419 (M+H)⁺; Anal. Calculated for $C_{23}H_{34}N_2O_3S$: C, 65.99; H, 8.19; N, 6.69. Found: C, 65.71; H, 8.18; N, 6.54.

Example 191

3-hydroxy-N-[(2Z)-3-(2-methoxyethyl)-4,5,6,7-tetrahydro-1,3-benzothiazol-2(3H)-ylidene]adamantane-1-carboxamide Example 191A N-(3-(2-methoxyethyl)-4,5,6,7-tetrahydro-1,3-benzothiazol-2-yl)-3-hydroxyadamantane-1-carboxamide A mixture of 4,5,6,7-tetrahydrobenzo[d]thiazol-2-amine (Aldrich) and 3-hydroxyadamantane-1-carboxylic acid were processed using the method described in Example 56C to afford the title compound. MS (ESI⁺) m/z 333 (M+H)⁺.

Example 191B 3-hydroxy-N-[(2Z)-3-(2-methoxyethyl)-4,5,6,7-tetrahydro-1,3-benzothiazol-2(3H)-ylidene]adamantane-1-carboxamide Example 191A and 2-bromoethyl methyl ether (Aldrich) were processed using the method described in Example 183C to afford the title compound. ¹H NMR (300 MHz, dimethylsulfoxide-$d_6$) δ ppm 1.44-1.60 (m, 6H), 1.66-1.71 (m, 6H), 1.71-1.84 (m, 4H), 2.07-2.20 (m, 2H), 2.43-2.49 (m, 2H), 2.53-2.61 (m, 2H), 3.24 (s, 3H), 3.64 (t, J=5.4 Hz, 2H), 4.18 (t, J=5.4 Hz, 2H), 4.39 (s, 1H); MS (ESI⁺) m/z 391 (M+H)⁺; Anal. Calculated for $C_{21}H_{30}N_2O_3S$: C, 64.58; H, 7.74; N, 7.17. Found: C, 64.29; H, 8.00; N, 6.99.

Example 192

3-hydroxy-N-[(2Z)-3-(tetrahydro-2H-pyran-4-ylmethyl)-4,5,6,7-tetrahydro-1,3-benzothiazol-2(3H)-ylidene]adamantane-1-carboxamide Example 191A and Example 188A were processed using the method described in Example 183C to afford the title compound. ¹H NMR (300 MHz, dimethylsulfoxide-$d_6$) δ ppm 1.27-1.45 (m, 4H), 1.47-1.59 (m, 6H), 1.66-1.71 (m, 6H), 1.72-1.85 (m, 5H), 2.09-2.20 (m, 2H), 2.45-2.49 (m, 2H), 2.53-2.59 (m, 2H), 3.17-3.27 (m, 2H), 3.76-3.88 (m, 2H), 3.97 (d, J=7.5 Hz, 2H), 4.39 (s, 1H); MS (ESI⁺) m/z 431 (M+H)⁺; Anal. Calculated for $C_{24}H_{34}N_2O_3S$: C, 66.94; H, 7.96; N, 6.51. Found: C, 66.87; H, 8.12; N, 6.35.

Example 193

N-[(2Z)-3-butyl-4,5,6,7-tetrahydro-1,3-benzothiazol-2(3H)-ylidene]-3-hydroxyadamantane-1-carboxamide Example 191A and 1-bromobutane (Aldrich) were processed using the method described in Example 183C to afford the title compound. ¹H NMR (300 MHz, dimethylsulfoxide-$d_6$) δ ppm 0.93 (d, J=14.6 Hz, 3H), 1.24-1.40 (m, 2H), 1.46-1.59 (m, 6H), 1.58-1.73 (m, 8H), 1.72-1.86 (m, 4H), 2.14 (s, 2H), 2.43-2.49 (m, 2H), 2.53-2.60 (m, J=5.3, 5.3 Hz, 2H), 3.95-4.11 (m, 2H), 4.37 (s, 1H); MS (ESI⁺) m/z 389 (M+H)⁺; Anal. Calculated for $C_{22}H_{32}N_2O_2S$: C, 68.00; H, 8.30; N, 7.21. Found: C, 68.05; H, 8.23; N, 7.20.

Example 194

3-hydroxy-N-[(2Z)-3-(tetrahydrofuran-2-ylmethyl)-4,5,6,7-tetrahydro-1,3-benzothiazol-2(3H)-ylidene]adamantane-1-carboxamide Example 191A and commercially available tetrahydrofurfuryl bromide (Maybridge) were processed using the method described in Example 183C to afford the title compound. ¹H NMR (300 MHz, dimethylsulfoxide-$d_6$) δ ppm 1.47-1.53 (m, 2H), 1.53-1.59 (m, 4H), 1.62-1.73 (m, 7H), 1.71-2.01 (m, 7H), 2.04-2.26 (m, 2H), 2.42-2.49 (m, 2H), 2.54-2.65 (m, 2H), 3.56-3.67 (m, 1H), 3.71-3.83 (m, 1H), 3.87-4.05 (m, 1H), 4.12-4.31 (m, 2H), 4.39 (s, 1H); MS (ESI⁺) m/z 417 (M+H)⁺; Anal. Calculated for $C_{23}H_{32}N_2O_3S \cdot 0.2H_2O$: C, 65.75; H, 7.77; N, 6.67. Found: C, 65.56; H, 7.98; N, 6.51.

Example 195

(1R,3s,5S,7s)-7-hydroxy-N-[(2Z)-3-(2-methoxyethyl)-5-methyl-1,3-thiazol-2(3H)-ylidene]bicyclo[3.3.1]nonane-3-carboxamide Example 195A (1R,3s,5S,7s)-7-hydroxy-N-(5-methylthiazol-2-yl)bicyclo[3.3.1]nonane-3-carboxamide Example 141A and commercially available 5-methylthiazol-2-amine (Aldrich) were processed using the method described in Example 56C to afford the title compound. MS (ESI⁺) m/z 281 (M+H)⁺.

Example 195B (1R,3s,5S,7s)-7-hydroxy-N-[(2Z)-3-(2-methoxyethyl)-5-methyl-1,3-thiazol-2(3H)-ylidene]bicyclo[3.3.1]nonane-3-carboxamide Example 195A and commercially available 2-bromoethyl methyl ether (Aldrich) were processed using the method described in Example 183C to afford the title compound. $^1$H NMR (300 MHz, dimethylsulfoxide-$d_6$) δ ppm 0.97-1.29 (m, 3H), 1.39-1.61 (m, 3H), 1.64-1.79 (m, 2H), 1.92-2.15 (m, 4H), 2.21 (s, 3H), 3.06-3.21 (m, 1H), 3.25 (s, 3H), 3.66 (t, J=5.3 Hz, 2H), 3.70-3.82 (m, 1H), 4.23 (t, J=5.3 Hz, 2H), 4.37 (d, J=4.7 Hz, 1H), 7.10 (s, 1H); MS (ESI$^+$) m/z 339 (M+H)$^+$; Anal. Calculated for $C_{17}H_{26}N_2O_3S$: C, 60.33; H, 7.74; N, 8.28. Found: C, 60.02; H, 7.91; N, 8.27.

Example 196

(1R,3s,5S,7r)-7-fluoro-N-[(2Z)-3-(2-methoxyethyl)-5-methyl-1,3-thiazol-2(3H)-ylidene]bicyclo[3.3.1]nonane-3-carboxamide To a solution of Example 195B (100 mg, 0.3 mmol) in dichloromethane (3 mL) was added a solution of (diethylamino)sulfur trifluoride (95 mg, 0.6 mmol) in dichloromethane (3 mL) at 0° C. The reaction mixture was stirred at 0° C. for 2 hours and then at room temperature for 2 hours. The reaction mixture was then quenched with saturated aqueous NaHCO$_3$ (5 mL) and extracted with dichloromethane (3×5 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-100% ethyl acetate in hexanes) to afford the title compound. $^1$H NMR (300 MHz, dimethylsulfoxide-$d_6$) δ ppm 1.20-1.76 (m, 6H), 1.75-1.89 (m, 2H), 2.02-2.18 (m, 4H), 2.21 (s, 3H), 3.25 (s, 3H), 3.34-3.42 (m, 1H), 3.66 (t, J=5.3 Hz, 2H), 4.24 (t, J=5.3 Hz, 2H), 4.89-5.50 (m, 1H), 7.12 (s, 1H); MS (ESI$^+$) m/z 340 (M+H)$^+$.

Example 197

(1R,3 s,5S)—N-[(2Z)-3-(2-methoxyethyl)-5-methyl-1,3-thiazol-2(3H)-ylidene]-7-oxobicyclo[3.3.1]nonane-3-carboxamide To a solution of oxalyl chloride (0.28 g, 2.2 mmol) in dichloromethane (20 mL) at −78° C. was slowly added and dimethylsulfoxide (0.31 g, 4.0 mmol). After 5 minutes, a solution of Example 195B (0.68 g, 2 mmol) in dichloromethane (5 mL) was added. The mixture was stirred for 30 minutes at −78° C. then triethylamine (1.1 mL, 8 mmol) was added. The reaction mixture was allowed to warm to ambient temperature then water (10 mL) was added. The layers were separated and the aqueous phase was extracted with ethyl acetate (3×10 mL). The combined organic extracts were washed successively with 1% aqueous HCl (5 mL), water (5 mL), 5% aqueous NaHCO$_3$ (5 mL) and brine (5 mL). The organic extract was dried over anhydrous Na$_2$SO$_4$, filtered and concentrated under reduced pressure. The residue was purified by column chromatography using an Analogix® Intelliflash280™ (SiO$_2$, 0-100% ethyl acetate in hexanes) to afford the title compound. $^1$H NMR (300 MHz, dimethylsulfoxide-$d_6$) δ ppm 1.60-1.75 (m, 3H), 1.76-1.97 (m, 3H), 2.18-2.24 (m, 3H), 2.23-2.29 (m, 2H), 2.31-2.43 (m, 3H), 2.52-2.64 (m, 2H), 3.24 (s, 3H), 3.64 (t, J=5.1 Hz, 2H), 4.22 (t, J=5.3 Hz, 2H), 7.12 (s, 1H); MS (ESI$^+$) m/z 337 (M+H)$^+$; Anal. Calculated for $C_{17}H_{24}N_2O_3S$: C, 60.69; H, 7.19; N, 8.33. Found: C, 60.51; H, 7.37; N, 8.33.

Example 198

(1R,3s,5S,7s)-7-hydroxy-N-[(2Z)-3-(2-methoxyethyl)-5-methyl-1,3-thiazol-2(3H)-ylidene]-7-methylbicyclo[3.3.1]nonane-3-carboxamide To a solution of methyl lithium (Aldrich, 1.6M in diethyl ether, 0.47 mL, 0.75 mmol) in tetrahydrofuran (5 mL) at −78° C. was added slowly a solution of Example 197 (0.10 g, 0.30 mmol) in tetrahydrofuran (3 mL). The reaction mixture was stirred at −78° C. for 2 hours and then allowed to warm to room temperature and stirred overnight. The reaction mixture was quenched with water (5 mL) and extracted with ethyl acetate (2×10 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-5% methanol in dichloromethane) to afford the title compound. $^1$H NMR (300 MHz, dimethylsulfoxide-$d_6$) δ ppm 1.49-1.66 (m, 4H), 1.69 (s, 3H), 1.73-1.95 (m, 4H), 2.12-2.23 (m, 2H), 2.22-2.29 (m, 4H), 2.31-2.47 (m, 1H), 2.59-2.83 (m, 1H), 3.34 (s, 3H), 3.68 (t, J=4.9 Hz, 2H), 4.16-4.36 (m, 2H), 5.48 (d, J=6.4 Hz, 1H), 6.69 (s, 1H); MS (ESI$^+$) m/z 335 (M−OH)$^+$

Example 199

N-[(2Z)-5-(2,4-difluorophenyl)-3-(2-hydroxyethyl)-1,3-thiazol-2(3H)-ylidene]adamantane-1-carboxamide Example 24 (1.3 g, 3.0 mmol) in CH$_2$Cl$_2$ (40 mL) at −78° C. was treated with a 1 M solution of BBr$_3$ in CH$_2$Cl$_2$ (18 mL, 18 mmol). The reaction mixture was allowed to warm up to room temperature and stirred for 5 hours. The mixture was quenched with water and extracted with ethyl acetate. The organic extract was dried (Na$_2$SO$_4$), filtered and concentrated. Purification by preparative high pressure liquid chromotography on a Waters Symmetry C8 column (40 mm×100 mm, 7 μm particle size) using a gradient of 10% to 100% acetonitrile:ammonium acetate (10 mM) over 15 minutes at a flow rate of 70 mL/minute afforded the title compound. $^1$H NMR (400 MHz, dimethylsulfoxide-$d_6$) δ ppm 1.64-1.76 (m, 6H) 1.85-1.90 (m, 6H) 1.96-2.03 (m, 3H) 3.80 (q, J=5.52 Hz, 2H) 4.26 (t, J=5.22 Hz, 2H) 4.97 (t, J=5.22 Hz, 1H) 7.20 (td, J=8.90, 2.76, 0.92 Hz, 1H) 7.38-7.46 (m, 1H) 7.66 (td, J=8.59, 6.14 Hz, 1H) 7.84-7.85 (m, 1H); MS (ESI) m/z 419 (M+H)$^+$.

Example 200

N-[(2Z)-5-(2,4-difluorophenyl)-3-(tetrahydrofuran-2-ylmethyl)-1,3-thiazol-2(3H)-ylidene]adamantane-1-carboxamide

Example 200A

N-[(2Z)-5-bromo-3-{[2-(trimethylsilyl)ethoxy]methyl}-1,3-thiazol-2(3H)-ylidene]adamantane-1-carboxamide Example 131A and 2-(trimethylsilyl)ethoxy]methyl chloride were processed using the method described in Example 131B to afford the title compound. MS (ESI) m/z 472 (M+H)$^+$.

Example 200B

Adamantane-1-carboxylic acid[5-(2,4-difluoro-phenyl)-3-(2-trimethylsilanyl-ethoxymethyl)-3H-thiazol-(2Z)-ylidene]-amide Example 200A and 2,4-difluorophenylboronic acid were processed using the method described in Example 131C to afford the title compound. MS (ESI) m/z 505 (M+H)$^+$.

Example 200C

N-[5-(2,4-difluorophenyl)-1,3-thiazol-2-yl]adamantane-1-carboxamide

A solution of Example 200B in trifluoroacetic acid was heated at 50° C. for 3 hours then concentrated. The residue was diluted with saturated aqueous NaHCO$_3$, and extracted with ethyl acetate. The organic extract was dried (Na$_2$SO$_4$), filtered and concentrated to afford the title compound. MS (ESI) m/z 375 (M+H)$^+$.

Example 200D

N-[(2Z)-5-(2,4-difluorophenyl)-3-(tetrahydrofuran-2-ylmethyl)-1,3-thiazol-2(3H)-ylidene]adamantane-1-carboxamide Example 200C and 2-(bromomethyl)tetrahydrofuran were processed using the method described in Example 131B to afford the title compound. $^1$H NMR (500 MHz, dimethylsulfoxide-d$_6$) δ ppm 1.63-1.75 (m, 7H) 1.80-1.85 (m, 2H) 1.85-1.89 (m, 6H) 1.91-1.98 (m, 1H) 1.98-2.03 (m, 3H) 3.66 (q, J=14.95, 7.02 Hz, 1H) 3.79 (q, J=6.71 Hz, 1H) 4.22-4.34 (m, 3H) 7.21 (td, J=16.78, 8.24, 2.44 Hz, 1H) 7.40-7.46 (m, 1H) 7.67 (td, J=8.85, 6.41 Hz, 1H) 7.86-7.87 (m, 1H); MS (ESI) m/z 459 (M+H)$^+$.

Example 201

N-[(2Z)-5-(2,4-difluorophenyl)-3-(tetrahydro-2H-pyran-2-ylmethyl)-1,3-thiazol-2(3H)-ylidene]adamantane-1-carboxamide A mixture of Example 200C (120 mg, 0.32 mmol), 2-(bromomethyl)tetrahydro-2H-pyran (62 mg, 0.35 mmol) and sodium hydride (60% dispersion in oil) (16 mg, 0.38 mmol) in tetrahydrofuran/N,N-dimethylformamide (2:1) (1 mL) was heated at 150° C. in a microwave (Emrys Personal Chemistry) for 30 minutes. The mixture was diluted with water, and extracted with ethyl acetate. The organic extract was dried (Na$_2$SO$_4$), filtered and concentrated. Purification by preparative high pressure liquid chromatography on a Waters Symmetry C8 column (40 mm×100 mm, 7 µm particle size) using a gradient of 10% to 100% acetonitrile: ammonium acetate (10 mM) over 15 minutes at a flow rate of 70 mL/minutes afforded the title compound. $^1$H NMR (400 MHz, dimethylsulfoxide-d$_6$) δ ppm 1.17-1.30 (m, 1H) 1.40-1.51 (m, 3H) 1.60 (d, J=13.50 Hz, 1H) 1.64-1.76 (m, 7H) 1.76-1.83 (m, 1H) 1.85-1.89 (m, 6H) 1.96-2.03 (m, 3H) 3.74-3.83 (m, 1H) 3.88 (d, J=11.66 Hz, 1H) 4.18-4.28 (m, 2H) 7.20 (td, J=7.98, 2.76, 2.15 Hz, 1H) 7.38-7.45 (m, 1H) 7.66 (td, J=6.14 Hz, 1H) 7.80 (s, 1H); MS (ESI) m/z 473 (M+H)$^+$.

Example 202

N-[(2Z)-5-(2,4-difluorophenyl)-3-ethyl-1,3-thiazol-2(3H)-ylidene]adamantane-1-carboxamide Example 200C and iodoethane were processed using the method described in Example 201 to afford the title compound. $^1$H NMR (400 MHz, dimethylsulfoxide-d$_6$) δ ppm 1.36 (t, J=7.06 Hz, 3H) 1.64-1.76 (m, 6H) 1.85-1.91 (m, 6H) 1.96-2.04 (m, 3H) 4.23 (q, J=7.06 Hz, 2H) 7.21 (td, J=8.29, 3.07, 1.84 Hz, 1H) 7.37-7.46 (m, 1H) 7.68 (td, J=8.90, 6.44 Hz, 1H) 7.95 (s, 1H); MS (ESI) m/z 403 (M+H)$^+$.

Example 203

N-[(2Z)-5-(2,4-difluorophenyl)-3-methyl-1,3-thiazol-2(3H)-ylidene]adamantane-1-carboxamide Example 200C and iodomethane were processed using the method described in Example 201 to afford the title compound. $^1$H NMR (400 MHz, dimethylsulfoxide-d$_6$) δ ppm 1.64-1.77 (m, 6H) 1.86-1.92 (m, 6H) 2.00 (brs, 3H) 3.72 (s, 3H) 7.21 (td, J=7.67, 2.76, 1.84 Hz, 1H) 7.38-7.47 (m, 1H) 7.66 (td, J=15.04, 6.44 Hz, 1H) 7.89-7.93 (m, 1H); MS (ESI) m/z 389 (M+H)$^+$.

Example 204

3-fluoro-N-[(2Z)-3-(2-methoxyethyl)-4,5-dimethyl-1,3-thiazol-2(3H)-ylidene]adamantane-1-carboxamide

Example 204A

3-Hydroxy-adamantane-1-carboxylic acid[3-(2-methoxy-ethyl)-4,5-dimethyl-3H-thiazol-(2Z)-ylidene]-amide A mixture of Example 46A (268 mg, 1.00 mmol), 3-hydroxy-adamantane-1-carboxylic acid (189 mg, 1.05 mmol), O-(7-azabenzotriazol-1-yl)-N,N,N',N'-tetramethyluronium hexafluorophosphate (570 mg, 1.50 mmol) and triethylamine (417 ul, 3.00 mmol) in N,N-dimethylformamide (15 mL) was stirred at room temperature for 12 hours. The mixture was diluted with water, and extracted with ethyl acetate. The organic extract was dried (Na$_2$SO$_4$), filtered and concentrated. Purification by chromatography (silica gel, 100% ethyl acetate) afforded the title compound. MS (ESI) m/z 365.

Example 204B 3-fluoro-N-[(2Z)-3-(2-methoxyethyl)-4,5-dimethyl-1,3-thiazol-2(3H)-ylidene]adamantane-1-carboxamide To a solution of Example 204A (200 mg, 0.55 mmol) in CHCl$_3$ (40 mL) at room temperature was treated with (diethylamino)sulfur trifluoride (177 mg, 1.10 mmol). The reaction mixture was heated at reflux for 2 hours. After cooling to ambient temperature, the mixture was quenched with water and extracted with ethyl acetate. The organic extract was dried (Na$_2$SO$_4$), filtered and concentrated. Purification by preparative high pressure liquid chromatography on a Waters Symmetry C8 column (40 mm×100 mm, 7 µm particle size) using a gradient of 10% to 100% acetonitrile:ammonium acetate (10 mM) over 15 minutes at a flow rate of 70 mL/minutes afforded the title compound. $^1$H NMR (500 MHz, dimethylsulfoxide-d$_6$) δ ppm 1.56 (d, J=2.44 Hz, 2H) 1.67-1.81 (m, 4H) 1.81 (t, J=4.88, 3.36 Hz, 3H) 1.95 (d, J=5.80 Hz, 2H) 2.15 (s, 3H) 2.21 (s, 3H) 2.26-2.31 (m, 2H) 3.24 (s, 3H) 3.65 (t, J=5.49 Hz, 2H) 4.25 (t, J=5.49 Hz, 2H); MS (ESI) m/z 367 (M+H)$^+$.

Example 205

3-chloro-N-[(2Z)-3-(2-methoxyethyl)-5-methyl-1,3-thiazol-2(3H)-ylidene]adamantane-1-carboxamide A mixture of 3-chloro-adamantane-1-carboxylic acid and Example 15A were processed as described in Example 3B to afford the title compound. $^1$H NMR (500 MHz, dimethylsulfoxide-d$_6$) δ ppm 1.61 (q, J=32.34, 14.04, 12.51 Hz, 2H) 1.78 (dd, J=13.12, 11.90 Hz, 4H) 2.01-2.12 (m, 4H) 2.17-2.26 (m, 7H) 3.26 (s, 3H) 3.68 (t, J=5.49 Hz, 2H) 4.26 (t, J=5.49 Hz, 2H) 7.15 (s, 1H); MS (ESI) m/z 369 (M+H)$^+$.

Example 206

3,5-dichloro-N-[(2Z)-3-(2-methoxyethyl)-5-methyl-1,3-thiazol-2(3H)-ylidene]adamantane-1-carboxamide

Example 206A 3,5-Dichloro-adamantane-1-carboxylic acid

To a solution of adamantane-1-carboxylic acid (2.0 g, 15 mmol) in ethyl acetate (15 mL) was added ruthenium chloride (100 mg) and H$_2$O (2.5 g) followed by 12% sodium hypochlorite (20.6 g, 57.5 mmol). The mixture was heated at 80° C. for 12 hours, cooled to ambient temperature, then quenched by the addition of saturated sodium thiosulfate. The pH was adjusted to slightly less than 7 with 1 N aqueous HCl, and extracted with 2-propanol/CH$_2$Cl$_2$ (1:3). The organic extract was dried (Na$_2$SO$_4$), filtered and concentrated to afford the title compound.

Example 206B 3,5-dichloro-N-[(2Z)-3-(2-methoxyethyl)-5-methyl-1,3-thiazol-2(3H)-ylidene]adamantane-1-carboxamide A mixture of the product from Example 206A and the product from Example 15A were processed using the method described in Example 3B to afford the title compound. $^1$H NMR (400 MHz, dimethylsulfoxide-d$_6$) δ ppm 1.71-1.76 (m, 2H) 1.95-2.10 (m, 4H) 2.18 (s, 3H) 2.21-2.25 (m, 4H) 2.34-2.40 (m, 1H) 2.42-2.45 (m, 2H) 3.26 (s, 3H) 3.68 (t, J=5.52 Hz, 2H) 4.26 (t, J=5.22 Hz, 2H) 7.18 (s, 1H); MS (ESI) m/z 403 (M+H)$^+$.

Example 207

3-fluoro-N-[(2Z)-3-(2-methoxyethyl)-5-methyl-1,3-thiazol-2(3H)-ylidene]adamantane-1-carboxamide The product from Example 205 (50 mg, 0.14 mmol) in CH$_2$Cl$_2$/ether (3:2) (5 mL) was treated with silver tetrafluoroborate (272 mg, 1.4 mmol) for 48 hours. Purification by preparative high pressure liquid chromotography on a Waters Symmetry C8 column (40 mm×100 mm, 7 μm particle size) using a gradient of 10% to 100% acetonitrile:ammonium acetate (10 mM) over 15 minutes at a flow rate of 70 mL/minutes afforded the title compound. $^1$H NMR (400 MHz, dimethylsulfoxide-d$_6$) δ ppm 1.53-1.58 (m, 2H) 1.64-1.79 (m, 4H) 1.79-1.83 (m, 4H) 1.95 (d, J=5.83 Hz, 2H) 2.21 (s, 3H) 2.25-2.32 (brs, 2H) 3.25 (s, 3H) 3.68 (t, J=5.22 Hz, 2H) 4.25 (t, J=4.91 Hz, 2H) 7.14 (s, 1H); MS (ESI) m/z 353 (M+H)$^+$.

Example 208

3,5-difluoro-N-[(2Z)-3-(2-methoxyethyl)-5-methyl-1,3-thiazol-2(3H)-ylidene]adamantane-1-carboxamide The product from 206B was processed using the method described in Example 207 to afford the title compound. $^1$H NMR (400 MHz, CDCl$_3$) δ ppm 1.76-1.81 (m, 2H) 1.83-1.88 (m, 4H) 2.09 (t, J=3.99 Hz, 4H) 2.11-2.16 (m, 2H) 2.30 (d, J=1.23 Hz, 3H) 2.50-2.58 (m, 1H) 3.35 (s, 3H) 3.70 (t, J=5.22, 4.60 Hz, 2H) 4.35 (t, J=4.91 Hz, 2H) 6.84 (s, 1H); MS (ESI) m/z 371 (M+H)$^+$.

Example 209

3-hydroxy-N-[(2Z)-3-(2-methoxyethyl)-3,4,5,6-tetrahydro-2H-cyclopenta[d][1,3]thiazol-2-ylidene]adamantane-1-carboxamide

Example 209A 5,6-dihydro-4H-cyclopenta[d]thiazol-2-amine hydrochloride

A mixture of 2-chlorocyclopentanone (5.00 g, 39.5 mmol) and thiourea (3.00 g, 39.5 mmol) was heated at 80° C. for 3-4 minutes. After cooling to room temperature, the mixture was triturated with ethanol and the solid was collected by filtration to afford the title compound. MS (ESI) m/z 141 (M+H)$^+$.

Example 209B 3-hydroxy-adamantane-1-carboxylic acid (5,6-dihydro-4H-cyclopentathiazol-2-yl)-amide A mixture of Example 209A (921 mg, 5.19 mmol), 3-hydroxy-adamantane-1-carboxylic acid (1.22 g, 6.2 mmol), 1-ethyl-3-[3-(dimethylamino)propyl]-carbodiimide hydrochloride (2.0 g, 10.4 mmol), 1-hydroxybenzotriazole hydrate (846 mg, 10.4 mmol) and 4-dimethylaminopyridine (196 mg, 1.04 mmol) in pyridine (20 mL) was stirred at room temperature for 12 hours. The solvent was removed and the residue was diluted with water and extracted with ethyl acetate. The organic extract was dried (Na$_2$SO$_4$), filtered and concentrated. Purification by flash chromatography (silica gel, 50% ethyl acetate/hexanes) afforded the title compound. MS (ESI) m/z 319 (M+H)$^+$.

Example 209C 3-hydroxy-N-[(2Z)-3-(2-methoxyethyl)-3,4,5,6-tetrahydro-2H-cyclopenta[d][1,3]thiazol-2-ylidene]adamantane-1-carboxamide The product of 209B and 1-bromo-2-methoxyethane were processed using the method described in Example 131B to afford the title compound. $^1$H NMR (400 MHz, dimethylsulfoxide-d$_6$) δ ppm 1.50 (brs, 2H) 1.56 (brs, 4H) 1.69 (brs, 6H) 2.14 (brs, 2H) 2.29-2.40 (m, 2H) 2.68-2.84 (m, 4H) 3.24 (s, 3H) 3.66 (t, J=5.22 Hz, 2H) 4.17 (t, J=5.22 Hz, 2H) 4.37 (s, 1H); MS (ESI) m/z 377 (M+H)$^+$.

Example 210

N-[(2Z)-3-butyl-3,4,5,6-tetrahydro-2H-cyclopenta[d] [1,3]thiazol-2-ylidene]-3-hydroxyadamantane-1-carboxamide The product of 209B and 1-bromobutane were processed using the method described in Example 131B to afford the title compound. $^1$H NMR (400 MHz, dimethylsulfoxide-d$_6$) δ ppm 0.91 (t, J=7.06 Hz, 3H) 1.22-1.35 (m, 2H) 1.48-1.53 (m, 2H) 1.53-1.59 (m, 4H) 1.63-1.75 (m, 8H) 2.09-2.19 (m, 2H) 2.32-2.42 (m, 2H) 2.70-2.76 (m, 2H) 2.76-2.83 (m, 2H) 4.04 (t, J=7.06 Hz, 2H) 4.37 (s, 1H); MS (ESI) m/z 375 (M+H)$^+$.

Example 211

3-hydroxy-N-[(2Z)-3-(tetrahydrofuran-2-ylmethyl)-3,4,5,6-tetrahydro-2H-cyclopenta[d][1,3]thiazol-2-ylidene]adamantane-1-carboxamide The product of 209B and 2-(bromomethyl)tetrahydrofuran were processed using the method described in Example 131B to afford the title compound. $^1$H NMR (400 MHz, dimethylsulfoxide-d$_6$) δ ppm 1.48-1.53 (m, 2H) 1.56 (d, J=2.76 Hz, 4H) 1.60-1.69 (m, 1H) 1.67-1.72 (m, 6H) 1.77-1.88 (m, 2H) 1.88-1.99 (m, 1H) 2.15 (t, J=2.45 Hz, 2H) 2.30-2.41 (m, 2H) 2.68-2.88 (m, 4H) 3.63 (dd, J=14.73, 7.06 Hz, 1H) 3.76 (dd, J=13.20, 7.06 Hz, 1H) 3.97 (dd, J=13.50, 7.36 Hz, 1H) 4.14 (dd, J=13.81, 3.99 Hz, 1H) 4.19-4.27 (m, 1H) 4.37 (s, 1H); MS (ESI) m/z 403 (M+H)$^+$.

Example 212

N-[(2Z)-3-(2-methoxyethyl)-5-methyl-1,3-thiazol-2 (3H)-ylidene]-3-methylene-7-oxobicyclo[3.3.1] nonane-1-carboxamide Example 212A 3,5-Dihydroxy-adamantane-1-carboxylic acid To a mixture of potassium hydroxide (130 mg, 2.0 mmol) and potassium permanganate (350 mg, 2.2 mmol) in H$_2$O (10 mL) at 50° C. was added 3-bromo-adamantane-1-carboxylic acid (512 mg, 2.0 mmol). The reaction mixture was heated at 98° C. for 18 hours. After cooling to ambient temperature, the mixture was acidified by the addition of 6 N aqueous HCl, then saturated aqueous sodium bisulfite was added. The mixture was extracted with 2-propanol/CH$_2$Cl$_2$ (1:3). The organic extract was concentrated to afford the title compound.

Example 212B 3,5-dihydroxy-N-[(2Z)-3-(2-methoxyethyl)-5-methyl-1,3-thiazol-2(3H)-ylidene]adamantane-1-carboxamide A mixture of Example 15A and Example 212A were processed using the method described in Example 3B to afford the title compound. MS (ESI) m/z 367 (M+H)$^+$.

Example 212C

N-[(2Z)-3-(2-methoxyethyl)-5-methyl-1,3-thiazol-2 (3H)-ylidene]-3-methylene-7-oxobicyclo[3.3.1] nonane-1-carboxamide Example 212B (390 mg, 1.06 mmol) in CHCl$_3$ was treated with (diethylamino)sulfur trifluoride (256 mg, 1.59 mmol) and the mixture was heated at reflux for 2 hours. Purification by preparative high pressure liquid chromotography on a Waters Symmetry C8 column (40 mm×100 mm, 7 μm particle size) using a gradient of 10% to 100% acetonitrile:ammonium acetate (10 mM) over 15 minutes at a flow rate of 70 mL/minutes afforded the title compound. $^1$H NMR (400 MHz, dimethylsulfoxide-d$_6$) δ ppm 1.97-2.22 (m, 5H) 2.24 (d, J=1.53 Hz, 3H) 2.26-2.35 (m, 3H) 2.41-2.49 (m, 2H) 2.70 (dd, J=16.57, 1.84 Hz, 1H) 3.25 (s, 3H) 3.68 (t, J=5.22 Hz, 2H) 4.27 (t, J=5.22 Hz, 2H) 4.73 (t, J=1.84 Hz, 2H) 7.17 (s, 1H); MS (ESI) m/z 349 (M+H)$^+$.

Example 213

3-hydroxy-N-[(2Z)-3-(tetrahydro-2H-pyran-4-ylmethyl)-3,4,5,6-tetrahydro-2H-cyclopenta[d][1,3]thiazol-2-ylidene]adamantane-1-carboxamide Example 209B and 4-(bromomethyl)tetrahydro-2H-pyran were processed using the method described in Example 131B to afford the title compound. $^1$H NMR (500 MHz, dimethylsulfoxide-d$_6$) δ ppm 1.25-1.36 (m, 2H) 1.43 (dd, J=12.51, 1.83 Hz, 2H) 1.49-1.53 (m, 2H) 1.53-1.60 (m, 4H) 1.70 (d, J=3.05 Hz, 6H) 2.12-2.17 (m, 3H) 2.32-2.42 (m, 2H) 2.77 (dt, J=26.55, 6.71 Hz, 4H) 3.23 (td, J=11.60, 1.83 Hz, 2H) 3.84 (dd, J=11.60, 2.44 Hz, 2H) 3.94 (d, J=7.32 Hz, 2H) 4.42 (s, 1H); MS (ESI) m/z 417 (M+H)$^+$.

Example 214

N-[(2Z)-3-(2-methoxyethyl)-5-methyl-1,3-thiazol-2 (3H)-ylidene]-4-oxo adamantane-1-carboxamide A mixture of 4-oxo-adamantane-1-carboxylic acid (Apin Chemicals) and Example 15A were processed using the method described in Example 3B to afford the title compound. $^1$H NMR (500 MHz, dimethylsulfoxide-d$_6$) δ ppm 1.89 (d, J=12.21 Hz, 2H) 1.97-2.17 (m, 8H) 2.22 (d, J=1.22 Hz, 3H) 2.41-2.47 (m, 2H) 2.47-2.53 (m, 1H) 3.25 (s, 3H) 3.67 (t, J=5.19 Hz, 2H) 4.25 (t, J=5.19 Hz, 2H) 7.15 (d, J=1.22 Hz, 1H) MS (ESI) m/z 349 (M+H)$^+$ Example 215

3-fluoro-5-hydroxy-N-[(2Z)-3-(2-methoxyethyl)-5-methyl-1,3-thiazol-2(3H)-ylidene]adamantane-1-carboxamide 3-Fluoro-5-hydroxy-adamantane-1-carboxylic acid (prepared as described by Jasys, V. J.; et al., *J. Am. Chem. Soc.* 2000, 122, 466-473) and the product from Example 15A were processed using the method described in Example 204A to afford the title compound. $^1$H NMR (400 MHz, dimethylsulfoxide-d$_6$) δ ppm 1.49-1.65 (m, 5H) 1.65-1.77 (m, 6H) 1.85-1.90 (m, 2H) 2.21 (d, J=1.53 Hz, 3H) 2.29-2.38 (m, 1H) 3.25 (s, 3H) 3.67 (t, J=5.52 Hz, 2H) 4.25 (t, J=5.22 Hz, 2H) 7.15 (d, J=1.53 Hz, 1H); MS (ESI) m/z 369 (M+H)$^+$

Example 216

4,4-difluoro-N-[(2Z)-3-(2-methoxyethyl)-5-methyl-1,3-thiazol-2(3H)-ylidene]adamantane-1-carboxamide The product from Example 214 was processed using the method described in Example 204B to afford the title compound. $^1$H NMR (300 MHz, dimethylsulfoxide-$d_6$) δ ppm 1.70-1.94 (m, 8H) 1.94-2.07 (m, 3H) 2.18-2.24 (m, 2H) 2.22 (d, J=1.36 Hz, 3H) 3.25 (s, 3H) 3.67 (t, J=5.43 Hz, 2H) 4.25 (t, J=5.09 Hz, 2H) 7.15 (d, J=1.36 Hz, 1H); MS (ESI) m/z 371 (M+H)$^+$.

Example 217

N-[(2Z)-3-(2-methoxyethyl)-5-methyl-1,3-thiazol-2(3H)-ylidene]-1-methyl-2-oxatricyclo[3.3.1.1$^{3,7}$]decane-5-carboxamide A solution of Example 212C (50 mg, 0.14 mmol) in tetrahydrofuran (10 mL) was treated with a 2.0 M solution of LiBH$_4$ (430 ul, 0.86 mmol) in tetrahydrofuran. To this mixture was added methanol (0.10 mL, 2.5 mmol) dropwise. The reaction mixture was stirred at room temperature for 48 hours. The mixture was diluted with methanol and 1 N aqueous HCl, then extracted with 2-propanol/CH$_2$Cl$_2$ (1:3). The organic extract was dried and concentrated. Purification by preparative high pressure liquid chromotography on a Waters Symmetry C8 column (40 mm×100 mm, 7 μm particle size) using a gradient of 10% to 100% acetonitrile:ammonium acetate (10 mM) over 15 minutes at a flow rate of 70 mL/minutes afforded the title compound and the compound of Example 218. $^1$H NMR (400 MHz, dimethylsulfoxide-$d_6$) δ ppm 1.04 (s, 3H) 1.47-1.63 (m, 3H) 1.64-1.79 (m, 4H) 1.81-1.92 (m, 3H) 2.14-2.19 (m, 1H) 2.21 (s, 3H) 3.25 (s, 3H) 3.67 (t, J=5.52 Hz, 2H) 4.01-4.07 (m, 1H) 4.25 (t, J=5.22 Hz, 2H) 7.12 (s, 1H); MS (ESI) m/z 351 (M+H)$^+$.

Example 218

(1S,3R,5R)-3-hydroxy-N-[(2Z)-3-(2-methoxyethyl)-5-methyl-1,3-thiazol-2(3H)-ylidene]-7-methylenebicyclo[3.3.1]nonane-1-carboxamide Example 217 describes preparation and chromatography. $^1$H NMR (300 MHz, CD$_3$OD) δ ppm 1.43 (td, J=12.89, 4.41 Hz, 2H) 1.55-1.67 (m, 2H) 1.82-1.88 (m, 2H) 1.91-1.99 (m, 1H) 2.19 (dd, J=12.55, 5.76 Hz, 1H) 2.28 (d, J=1.36 Hz, 3H) 2.34-2.40 (m, 2H) 2.49-2.65 (m, 2H) 3.34 (s, 3H) 3.73 (t, J=5.43 Hz, 2H) 4.34 (t, J 5.09 Hz, 2H) 4.54-4.68 (m, 1H) 4.73 (brs, 2H) 7.00 (s, 1H); MS (ESI) m/z 351 (M+H)$^+$.

Example 219

3,5,7-trifluoro-N-[(2Z)-3-(2-methoxyethyl)-5-methyl-1,3-thiazol-2(3H)-ylidene]adamantane-1-carboxamide 3,5,7-Trifluoro-adamantane-1-carboxylic acid (prepared as described by Jasys, V. J.; et al., *J. Am. Chem. Soc.* 2000, 122, 466-473) and Example 15A were processed using the method described in Example 3B to afford the title compound. $^1$H NMR (300 MHz, CDCl$_3$) δ ppm 1.81-1.96 (m, 4H) 2.12-2.24 (m, 6H) 2.27 (d, J=1.36 Hz, 3H) 2.40-2.53 (m, 2H) 3.34 (s, 3H) 3.68 (t, J=5.42, 4.75 Hz, 2H) 4.26 (t, J=5.09 Hz, 2H) 6.73 (d, J=1.36 Hz, 1H); MS (ESI) m/z 389 (M+H)$^+$.

Example 220

N-[(2Z)-3-(2-methoxyethyl)-5-methyl-1,3-thiazol-2(3H)-ylidene]-1-oxohexahydro-2,5-methanopentalene-3a(1H)-carboxamide Example 15A and 1-oxo-hexahydro-2,5-methano-pentalene-3a-carboxylic acid (prepared as described in European patent application EP619316(A1)) were processed using the method described in Example 3B to afford the title compound. $^1$H NMR (500 MHz, dimethylsulfoxide-$d_6$) δ ppm 1.75-1.83 (m, 2H) 1.84-2.05 (m, 4H) 2.23 (s, 3H) 2.28-2.34 (m, 4H) 2.59-2.64 (m, 2H) 3.26 (s, 3H) 3.68 (t, J=5.19 Hz, 2H) 4.26 (t, J=5.19 Hz, 2H) 7.16 (s, 1H); MS (ESI) m/z 335 (M+H)$^+$.

Example 221

N-[(2Z)-3-(2-methoxyethyl)-5-(1-methylcyclopropyl)-1,3-thiazol-2(3H)-ylidene]hexahydro-2,5-methanopentalene-3a(1H)-carboxamide

Example 221A 5-bromo-3-(2-methoxyethyl)thiazol-2(3H)-imine hydrobromide

2-Amino-5-bromothiazole (Aldrich) and 2-bromoethyl methyl ether were processed as described in Example 2A to afford the title compound. MS (DCI/NH$_3$) m/z 238 (M+H)$^+$.

Example 221B

Hexahydro-2,5-methano-pentalene-3a-carboxylic acid[5-bromo-3-(2-methoxy-ethyl)-3H-thiazol-(2Z)-ylidene]-amide The product of Example 221A and the product of Example 14A were processed as described in Example 122B to afford the title compound. MS (DCI/NH$_3$) m/z 387 (M+H)$^+$.

Example 221C

Hexahydro-2,5-methano-pentalene-3a-carboxylic acid[5-isopropenyl-3-(2-methoxy-ethyl)-3H-thiazol-(2Z)-ylidene]-amide The product of Example 221B and prop-1-en-2-ylboronic acid were processed using the method described in Example 131C to afford the title compound. MS (ESI) m/z 347 (M+H)$^+$.

Example 221D

N-[(2Z)-3-(2-methoxyethyl)-5-(1-methylcyclopropyl)-1,3-thiazol-2(3H)-ylidene]hexahydro-2,5-methanopentalene-3a(1H)-carboxamide A 20 mL vial was charged with 1 mL of CH$_2$Cl$_2$ and dimethoxyethane (78 μL, 0.75 mmol). The solution was cooled to −10° C. and diethylzinc (89 mg, 0.72 mmol) was added. To this solution was added diiodomethane (402 mg, 1.5 mmol) dropwise. After the addition was complete, the resulting clear solution was stirred for 10 minutes at −10° C.

then a solution of Example 221C (65 mg, 0.19 mmol) in CH$_2$Cl$_2$ (0.5 mL) was added. The reaction mixture was stirred overnight at room temperature then quenched with water, and extracted with CH$_2$Cl$_2$. The organic extract was dried (Na$_2$SO$_4$), filtered and concentrated. Purification by preparative high pressure liquid chromatography on a Waters Symmetry C8 column (40 mm×100 mm, 7 µm particle size) using a gradient of 10% to 100% acetonitrile:ammonium acetate (10 mM) over 15 minutes at a flow rate of 70 mL/minutes afforded the title compound. $^1$H NMR (500 MHz, CDCl$_3$) δ ppm 0.82 (t, J=6.71, 4.58 Hz, 2H) 0.91 (t, J=5.80, 5.19 Hz, 2H) 1.41 (s, 3H) 1.60-1.67 (m, 4H) 1.81-1.88 (m, 2H) 1.90 (dd, J=10.68, 2.75 Hz, 2H) 2.16 (dd, J=10.37, 0.92 Hz, 2H) 2.29-2.36 (m, 2H) 2.72 (t, J=6.71 Hz, 1H) 3.36 (s, 3H) 3.74 (t, J=4.88 Hz, 2H) 4.41 (t, J=4.88 Hz, 2H) 6.88 (s, 1H); MS (ESI) m/z 361 (M+H)$^+$.

Example 222

(1R,4S)—N-[(2Z)-3-(2-methoxyethyl)-4,5-dimethyl-1,3-thiazol-2(3H)-ylidene]-4,7,7-trimethyl-2-oxabicyclo[2.2.1]heptane-1-carboxamide Example 222A (1R)-1-hydroxy-3-(hydroxymethyl)-2,2,3-trimethyl-cyclopentanecarboxylic acid To a solution of (R)-(+)-camphanic acid (1.019 g, 5.14 mmol) in tetrahydrofuran (10 mL) at 0° C. under N$_2$ was added slowly a solution of 1.0 M lithium triethylhydroborate/tetrahydrofuran (25 mL), then the reaction was allowed to warm to room temperature and stirred for 4.5 hours. The reaction was cooled to 0° C. and quenched by slow addition of H$_2$O (0.5 mL). 6N HCl (5 mL) was added and the reaction was concentrated on a rotary evaporator. Acetonitrile was added and evaporated repeatedly until excess water was removed. Methanol was added and evaporated (5×) to remove boronic acid esters. The white residue was triturated with toluene and acetonitrile and filtered to remove an insoluble solid. The filtrate was concentrated, dissolved in ethyl acetate, dried (MgSO$_4$), filtered and evaporated. The residue was treated with ether, filtered through a short cotton plug to remove the solids and the solvent was evaporated to afford the title compound. $^1$H NMR (dimethylsulfoxide-d$_6$, 300 MHz) δ ppm 0.74 (s, 3H), 0.82 (s, 3H), 0.87 (s, 3H), 1.26-1.35 (m, 1H), 1.50-1.60 (m, 1H), 1.84-1.93 (m, 1H), 2.41-2.50 (m, 1H), 3.07 (d, 1H), 3.3 (br s, 1H), 3.58 (d, 1H).

Example 222B (1R)-4,7,7-trimethyl-2-oxabicyclo[2.2.1]heptane-1-carboxylic acid

To a solution of Example 222A (125 mg) and triphenylphosphine (366 mg) in tetrahydrofuran (10 mL) at 0° C. was added dropwise diisopropylazodicarboxylate (0.27 mL). The reaction mixture was allowed to warm to room temperature and stirred overnight. The mixture was partitioned between 1 N aqueous NaOH (10 mL) and ether (20 mL) and the layers separated. The aqueous phase was extracted twice with ether to remove non-polar organic extracts, then acidified with 1 N aqueous HCl and extracted with ether (3×). The organic extracts were dried (MgSO$_4$), filtered and solvent evaporated to afford the title compound. $^1$H NMR (CDCl$_3$, 300 MHz) δ ppm 0.93 (s, 3H), 0.95 (s, 3H), 1.04 (s, 3H), 1.5-1.6 (m, 1H), 1.73-1.85 (m, 1H), 1.88-1.97 (m, 1H), 2.24-2.35 (m, 1H), 3.60 (d, 1H), 3.76 (dd, 1H).

Example 222C (1R,4S)—N-[(2Z)-3-(2-methoxyethyl)-4,5-dimethyl-1,3-thiazol-2(3H)-ylidene]-4,7,7-trimethyl-2-oxabicyclo[2.2.1]heptane-1-carboxamide A mixture of Example 46A (84 mg), Example 222B (50 mg), 1-hydroxybenzotriazole hydrate (38 mg), 1-ethyl-3-[3-(dimethylamino)propyl]-carbodiimide hydrochloride (55 mg) and triethylamine (75 µL) in tetrahydrofuran (3 mL) was heated to 70° C. for 24 hours in a closed vessel with mixing, then quenched in water and extracted with ethyl acetate (2×). The organic extracts were dried (Na$_2$SO$_4$), filtered and solvent evaporated. The crude was chromatographed using an Analogix® IT280™ gradient eluting from 0% to 100% ethyl acetate/hexane. After chromatography, the product was dissolved in ether and washed with 0.2 N NaOH to remove polar co-eluting byproducts. The organic layer was dried (Na$_2$SO$_4$), filtered and the solvent was evaporated to afford the title compound. $^1$H NMR (CDCl$_3$, 300 MHz) δ ppm 0.90 (s, 3H), 0.92 (s, 3H), 1.06 (s, 3H), 1.47-1.57 (m, 1H), 1.70-1.80 (m, 1H), 1.88-1.98 (m, 1H), 2.20 (s, 3H), 2.25 (s, 3H), 2.34-2.44 (m, 1H), 3.29 (s, 3H), 3.57 (d, 1H), 3.69-3.77 (m, 3H), 4.33 (br s, 2H); MS (DCI/NH$_3$) m/z 353 (M+H)$^+$.

Example 223

(1R,6S)—N-[(2Z)-3-(2-methoxyethyl)-4,5-dimethyl-1,3-thiazol-2(3H)-ylidene]-6,9,9-trimethyl-2,4-dioxabicyclo[4.2.1]nonane-1-carboxamide Example 223A (1R)-6,9,9-trimethyl-2,4-dioxabicyclo[4.2.1]nonane-1-carboxylic acid A mixture of Example 222A (131.6 mg), dimethoxymethane (0.575 mL) and para-toluenesulfonic acid monohydrate (catalytic) in benzene (15 mL) was stirred and heated to reflux with a Dean-Stark trap overnight. An additional 0.5 mL dimethoxymethane was added and heating continued 24 hours. The reaction mixture was evaporated to dryness and flash chromatographed over silica gel eluting with 10% methanol/CH$_2$Cl$_2$ to afford the title compound. $^1$H NMR (CDCl$_3$, 300 MHz) δ ppm 0.88 (s, 3H), 0.94 (s, 3H), 1.15 (s, 3H), 1.88-2.05 (m, 3H), 2.7-2.85 (m, 1H), 3.59 (s, 2H), 5.00 (AB q, J=26.3, 7.9 Hz, 2H).

Example 223B (1R,6S)—N-[(2Z)-3-(2-methoxyethyl)-4,5-dimethyl-1,3-thiazol-2(3H)-ylidene]-6,9,9-trimethyl-2,4-dioxabicyclo[4.2.1]nonane-1-carboxamide A mixture of Example 223A (55 mg), Example 46A (70 mg), 1-hydroxybenzotriazole hydrate (35 mg), 1-ethyl-3-[3-(dimethylamino)propyl]-carbodiimide hydrochloride (51 mg), triethylamine (0.08 mL) in tetrahydrofuran (2 mL) was heated to 70° C. for 24 hours on a shaker, cooled, poured into saturated aqueous NaHCO$_3$, extracted with ethyl acetate (2×), the organic extracts dried (Na$_2$SO$_4$), filtered and solvent evaporated. The residue was purified by reverse phase preparative high pressure liquid chromatography on a Waters Symmetry C8 column (25 mm×100 mm, 7 µm particle size)

using a gradient of 10% to 100% acetonitrile:0.1% aqueous trifluoroacetic acid over 8 minutes (10 minutes run time) at a flow rate of 40 mL/min) to afford the title compound. $^1$H NMR (CDCl$_3$, 300 MHz) δ ppm 0.76 (s, 3H), 0.83 (s, 3H), 1.32 (s, 3H), 1.8-2.0 (m, 3H), 2.19 (s, 3H), 2.22 (s, 3H), 3.0-3.17 (m, 1H), 3.30 (s, 3H), 3.58 (AB qu, J=10.1, 11.9 Hz, 2H), 3.70 (t, 2H), 4.18 (dt, 1H), 4.43 (dt, 1H), 5.00 (AB qu, J=17.8, 7.8 Hz, 2H); MS (DCI/NH$_3$) m/z 383 (M+H)$^+$.

Example 224

(1aR,2R,2aS,5aR,6S,6aS)—N-[(2Z)-3-(2-methoxyethyl)-4,5-dimethyl-1,3-thiazol-2(3H)-ylidene]decahydro-2,6-methanocyclopropa[f]indene-1-carboxamide To a solution of tetracyclo[5.3.1.0$^{2,6}$.0$^{8,10}$]undecane-9-carboxylic acid (0.43 g, 2.2 mmol, Bennani, Y. L., et al., US2004077617) in dichloromethane (11 mL) was added oxalyl chloride 0.21 mL, 2.4 mmol) and a catalytic amount of dimethylformamide (2 drops). The mixture was stirred for 2 hours and then concentrated under reduced pressure to afford tetracyclo[5.3.1.0$^{2,6}$.0$^{8,10}$]undecane-9-carbonyl chloride. To a suspension of the product of Example 46A (0.30 g, 1.1 mmol) and triethylamine (0.46 mL, 3.3 mmol) in tetrahydrofuran (5 mL) was added a solution of tetracyclo[5.3.1.0$^{2,6}$.0$^{8,10}$]undecane-9-carbonyl chloride (0.23 g, 1.2 mmol) in tetrahydrofuran (1 mL). The mixture was heated at reflux for 14 hours, then cooled to room temperature and diluted with water and CH$_2$Cl$_2$. The layers were separated and the organic extract was washed with water and brine, dried (Na$_2$SO$_4$), and concentrated. Purification by column chromatography (SiO$_2$, 10-35% ethyl acetate/hexanes gradient) afforded the title compound. $^1$H NMR (CDCl$_3$, 300 MHz) δ ppm 0.94 (d, J=10.5 Hz, 1H), 1.22 (d, J=11.9 Hz, 1H), 1.45-1.76 (m, 6H), 1.87-1.98 (m, 2H), 2.17 (s, 3H), 2.20 (s, 3H), 2.32 (s, 2H), 2.35-2.43 (m, 3H), 3.30 (s, 3H), 3.70 (t, J=5.3 Hz, 2H), 4.20-4.33 (m, 2H); MS (DCI/NH$_3$) m/z 361 (M+H)$^+$. Anal. Calculated for C$_{20}$H$_{28}$N$_2$O$_2$S: C, 66.63; H, 7.83; N, 7.77. Found: C, 66.49; H, 7.91; N, 7.53.

In Vitro Methods

The CB$_1$ and CB$_2$ radioligand binding assays described herein can be utilized to ascertain the selectivity of compounds of the present invention for binding to CB$_2$ relative to CB$_1$ receptors.

Human CB$_2$ Radioligand Binding Assays:

HEK293 cells stably expressing human CB$_2$ receptors were grown until a confluent monolayer was formed. Briefly, the cells were harvested and homogenized in TE buffer (50 mM Tris-HCl, 1 mM MgCl$_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM MgCl$_2$, and 1 mM EDTA and 10% sucrose) and frozen at −78° C. until used. Saturation binding reactions were initiated by the addition of membrane preparation (protein concentration of 5 μg/well for human CB$_2$) into wells of a deep well plate containing ([$^3$H]CP-55,940 (120 Ci/mmol, a nonselective CB agonist commercially available from Tocris) in assay buffer (50 mM Tris, 2.5 mM EDTA, 5 mM MgCl$_2$, and 0.5 mg/mL fatty acid free BSA, pH 7.4). After 90 minutes incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations (1 nM to 10 μM) of displacing ligands. The addition of 10 unlabeled CP-55,940 (Tocris, Ellisville, Mo.) was used to assess nonspecific binding.

The majority of the compounds of the present invention bound (K$_i$) to CB$_2$ receptors with a K$_i$ less than about 10,000 nM. In a more preferred embodiment, compounds of the present invention bound to CB$_2$ receptors with a K$_i$ less than about 200 nM.

Human CB$_1$ Radioligand Binding Assay:

HEK293 human CB$_1$ membranes were purchased from Perkin Elmer. Binding was initiated by the addition of membranes (8-12 μg per well) into wells (Scienceware 96-well DeepWell plate, VWR, West Chester, Pa.) containing [$^3$H]CP-55,940 (120 Ci/mmol, Perkin Elmer, Boston, Mass.) and a sufficient volume of assay buffer (50 mM Tris, 2.5 mM EDTA, 5 mM MgCl$_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding. The majority of the compounds of the present application tested for CB$_1$ binding, bound to CB$_1$ receptors with a K$_i$ 10×-1000× higher than the K$_i$ for CB$_2$. These results show that the compounds of the present application preferably bind to CB$_2$ receptors, therefore are selective ligands for the CB$_2$ receptor.

In Vivo Methods:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

Incision Model of Postoperative Pain

A skin incision model of postoperative pain was produced using the procedures previously described (Brennan et al., 1996, Pain, 64, 493). All rats were anesthetized with isoflurane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as previously described (Chaplan, S. R., F. W. Bach, J. W. Pogrel, J. M. Chung and T. L. Yaksh, 1994, Quantitative assessment of tactile allodynia in the rat paw, J. Neurosci. Methods, 53, 55) Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol. 20, 441).

Representative compounds of the present application showed a statistically significant change in paw withdrawal latency versus a saline vehicle at less than about 300 micromoles/kg in the incision model of postoperative pain. In a more preferred embodiment, compounds of the present application showed efficacy at less than about 50 micromoles/kg in the incision model of postoperative pain.

Complete Freund's Adjuvant (CFA) Model of Inflammatory Pain

Chronic inflammatory thermal hyperalgesia was induced by injection of 150 μl of a 50% solution of CFA in phosphate buffered saline (PBS) into the plantar surface of the right hind paw in rats; control animals received only PBS treatment. Thermal hyperalgesia was assessed 48 hours post CFA injection. Thermal hyperalgesia was determined using a commercially available thermal paw stimulator (University Anesthesiology Research and Development Group (UARDG), University of California, San Diego, Calif.) described by Hargreaves et al. (Hargreaves, et. al., 1988, Pain 32, 77). Rats were placed into individual plastic cubicles mounted on a glass surface maintained at 30° C., and allowed a 20 minutes habituation period. A thermal stimulus, in the form of radiant heat emitted from a focused projection bulb, was then applied to the plantar surface of each hind paw. The stimulus current was maintained at 4.50±0.05 amp, and the maximum time of exposure was set at 20.48 sec to limit possible tissue damage. The elapsed time until a brisk withdrawal of the hind paw from the thermal stimulus was recorded automatically using photodiode motion sensors. The right and left hind paw of each rat was tested in three sequential trials at approximately 5-minute intervals. Paw withdrawal latency (PWL) was calculated as the mean of the two shortest latencies.

Representative compounds of the present invention showed a statistically significant change in paw withdrawal latency versus a saline vehicle at less than about 300 micromoles/kg in the Complete Freund's Adjuvant (CFA) model of inflammatory pain. In a more preferred embodiment, compounds of the present invention showed efficacy at less than about 50 micromoles/kg in the Complete Freund's Adjuvant (CFA) model of inflammatory pain.

Spinal Nerve Ligation Model of Neuropathic Pain

A model of spinal nerve ligation-induced (SNL model) neuropathic pain was produced using the procedure originally described by Kim and Chung (Kim, S. H. and J. M. Chung, 1992, An experimental model for peripheral neuropathy produced by segmental spinal nerve ligation in the rat, Pain 50, 355). The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as previously described (Chaplan, S. R., F. W. Bach, J. W. Pogrel, J. M. Chung and T. L. Yaksh, 1994, Quantitative assessment of tactile allodynia in the rat paw, J. Neurosci. Methods 53, 55). Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol. 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals a well as in the contralateral paws of nerve-injured rats.

Representative compounds of the present invention showed efficacy at less than about 300 micromoles/kg in the spinal nerve ligation model of neuropathic pain. In a more preferred embodiment, compounds of the present invention showed efficacy at less than about 100 micromoles/kg in the spinal nerve ligation model of neuropathic pain.

The data contained herein demonstrates that compounds of the present invention bind to the $CB_2$ receptor. Certain compounds of the present invention were shown to have an analgesic effect in two types of animal pain models relating to neuropathic and nociceptive pain.

In addition to the data contained herein, several lines of evidence support the assertion that $CB_2$ receptors play a role in analgesia. For example, Zimmer et al. have reported that the nonselective cannabinoid agonist $\Delta^9$-THC retains some analgesic efficacy in $CB_1$ receptor knockout mice (Zimmer, A., et al., Proc. Nat. Acad. Sci., 1999, 96, 5780-5785). HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260). The analgesic effects induced by these $CB_2$-selective ligands are blocked by $CB_2$ and not by $CB_1$ receptor antagonists. Furthermore, at fully efficacious doses, AM-1241 and GW405833 are devoid of typical $CB_1$ receptor-mediated CNS side effects, providing evidence that modulation of $CB_2$ receptors can produce broad-spectrum pain relief with reduced side-effect liability.

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators are useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. They are quiescent and resting having a ramified morphology as long as the CNS is healthy. Microglia express a variety of receptors enabling them to survey the CNS and respond to pathological events. Insult or injury to the CNS leads to microglial cell activation, which is characterized by various morphological changes allowing response to the lesion. Ramifications are retracted and microglia are transformed into amoeboid-like cells with phagocytic function. They can proliferate, rapidly migrate to the site of injury, and produce and release cytokines, chemokines and complement components (Watkins L. R., et al., Trends in Neuroscience, 2001, 24(8), 450; Kreutzberg, G. W., Trends Neurosci., 1996, 19, 312-318). $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. It is conceivable that $CB_2$ receptors may be more susceptible to pharmacological effects during neuroinflammation (Walter, L., Stella, N., Br. J. Pharmacol. 2004, 141, 775-785). Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

$CB_2$ receptor expression has been detected in perivascular microglial cells within normal, healthy human cerebellum (Nunez, E., et al., Synapse, 2004, 58, 208-213). Perivascular cells are immunoregulatory cells located adjacent to CNS blood vessels and, along with parenchymal microglia and astrocytes, they play a pivotal role in maintaining CNS homeostasis and blood-brain barrier functionality (Williams, K., et al., Glia, 2001, 36, 156-164). $CB_2$ receptor expression has also been detected on cerebromicrovascular endothelial cells, which represent a main component of the blood-brain barrier (Golech, S. A., et al., Mol. Brain. Res., 2004, 132, 87-92). A recent report demonstrated that $CB_2$ receptor expression is up-regulated in the brains of macaques with simian immunodeficiency virus-induced encephalitis (Benito, C., et al., J. Neurosci. 2005, 25(10), 2530-2536). Thus, compounds that affect $CB_2$ signaling may protect the blood-brain barrier and be clinically useful in the treatment of neuroinflammation and a variety of neuroinflammatory disorders including retroviral encephalitis, which occurs with human immunodeficiency virus (HIV) infection in the CNS.

Multiple sclerosis is a common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators represents a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators represents a unique approach for the treatment of liver fibrosis.

$CB_2$ receptors are involved in the neuroprotective and anti-inflammatory mechanisms induced by the interleukin-1 receptor antagonist (IL-1ra) (Molina-Holgado, F., et al., J. Neurosci., 2003, 23(16), 6470-6474). IL-lra is an important anti-inflammatory cytokine that protects against ischemic, excitotoxic, and traumatic brain insults. $CB_2$ receptors play a role in mediating these neuroprotective effects indicating that $CB_2$ ligands are useful in the treatment of traumatic brain injury, stroke, and in mitigating brain damage.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators have utility as antitussive agents for the treatment pulmonary inflammation, chronic cough, and a variety of airway inflammatory diseases including but not limited to asthma, chronic obstructive pulmonary disease, and pulmonary fibrosis.

Recent studies indicate the presence of both cannabinoid $CB_1$ and $CB_2$ receptor immunoreactivity in rat pancreatic (3- and non-β-cells, adding the endocrine pancreas to adipose tissue and the liver as potential sites for endocannabinoid regulation of glucose homeostasis, indicating that $CB_2$-selective modulators have utility in the treatment of diabetes and obesity (Bermudez-Silva et al., Eur. Journal of Pharmacology, 2007).

Osteoporosis is a disease characterized by reduced bone mass, which leads to deterioration of bone microstructure and increased susceptibility to fracture. Age is associated with bone loss and it is estimated that 50% of all Caucasian women will have osteoporosis by the age of 80 (Ralston, S. H., Curr. Opin. Pharmacol., 2003, 3, 286-290). There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators are useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor are clinically useful for the treatment of atherosclerosis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators have utility for the treatment or prophylaxis of cardiovascular disease and the development of myocardial infarction.

The present invention also provides pharmaceutical compositions that comprise compounds of the present invention. The pharmaceutical compositions comprise compounds of the present invention formulated together with one or more non-toxic pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration that include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants, which may be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutically acceptable salt," as used herein, means acid addition or basic addition salts. The salts can be prepared in situ during the final isolation and purification of compounds of the invention or separately by reacting the free base of a compound of the invention with an inorganic or organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, malate, maleate, fumarate, methanesulfonate, nicotinate, 2-naphthalenesulfonate, oxalate, pamoate, pectinate, persulfate, 3-phenylpropionate, picrate, pivalate, propionate, succinate, sulfate, (L) tartrate, (D) tartrate, (DL) tartrate, thiocyanate, phosphate, glutamate, bicarbonate, p-toluenesulfonate, and undecanoate.

The present invention contemplates compounds of the invention formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others, are equivalent to the unsolvated forms for the purposes of the invention.

The total daily dose of the compounds of this invention administered to a human or lower animal may range from about 0.003 to about 30 mg/kg/day. For purposes of oral administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

What is claimed is:

1. A method of treating inflammatory disorders in a mammal in need of such treatment, comprising administering to the mammal a therapeutically effective amount of a compound having formula (I)

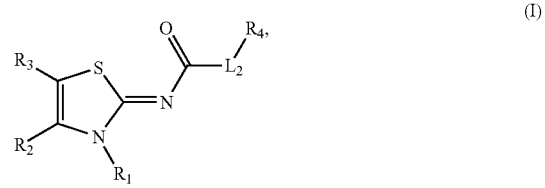

or a pharmaceutically acceptable salt, or a combination thereof, wherein
  $R_1$ is alkyl, alkenyl, alkoxyalkyl, alkoxyalkoxyalkyl, alkoxycarbonylalkyl, alkynyl, arylalkoxyalkyl, arylalkyl, aryloxyalkyl, carboxyalkyl, cycloalkyl, cycloalkylalkyl, haloalkyl, haloalkoxyalkyl, heteroarylalkyl, heteroaryloxyalkyl, heterocycle, heterocyclealkyl, heterocycleoxyalkyl, hydroxyalkyl, or $R_aR_bN$-alkylene-;
  $R_2$ and $R_3$, together with the carbon atoms to which they are attached, form a 4-, 5-, 6-, or 7-membered monocyclic ring, optionally fused to a benzo or a monocyclic heteroaryl, said monocyclic ring contains zero or one additional double bonds, one oxygen atom, and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, alkylsulfonyl, halo, —OH, —O(alkyl), and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl;
  $R_4$ is a bridged cycloalkyl or a bridged heterocycle; optionally substituted with 1, 2, 3, 4, 5, or 6 substituents selected from the group consisting of alkyl, —$OR_p$, —$NR_cR_d$, oxo, halo, haloalkyl, carboxy and =$CH_2$;
  $R_a$ and $R_b$ are each independently hydrogen, alkyl, alkylcarbonyl, alkylsulfonyl, aryl, arylalkyl, arylcarbonyl, arylsulfonyl, cycloalkylalkyl, heteroaryl, heteroarylalkyl, heteroarylcarbonyl, heteroarylsulfonyl, heterocycle, heterocyclealkyl, heterocyclecarbonyl or heterocyclesulfonyl;
  $R_c$ and $R_d$, at each occurrence, are each independently hydrogen, alkoxycarbonyl, alkyl, alkylcarbonyl, alkylsulfonyl or arylalkyl;

L₂ is a single bond, alkylene, —NR$_g$- or —NR$_g$-alkylene- wherein the alkylene moiety is attached to R₄ of formula (I);

R$_g$ is hydrogen or alkyl, the aryl, cycloalkyl, cycloalkenyl, heterocycle, and heteroaryl moieties, as substituents or part of a substituent, represented by R₁, R₂, R₃, R$_a$, R$_b$, R$_c$, and R$_d$, are each independently unsubstituted or substituted with 1, 2, 3, 4, 5, or 6 substituents independently selected from the group consisting of alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halo, haloalkyl, haloalkoxy, oxo, hydroxy, hydroxyalkyl, —SH, —NO₂, —NZ₁Z₂, and (NZ₃Z₄)carbonyl;

Z₁ and Z₂ are each independently hydrogen, alkyl, haloalkyl, alkylcarbonyl, or formyl;

Z₃ and Z₄ are each independently hydrogen, alkyl, or haloalkyl; and

R$_p$, at each occurrence, is independently hydrogen, alkyl, or haloalkyl.

2. The method of claim 1 wherein the compound is selected from the group consisting of N-[(2Z)-3-(2-methoxyethyl)-4,6-dihydrofuro[3,4-d][1,3]thiazol-2(3H)-ylidene]adamantane-1-carboxamide;

N-[(2Z)-3-(2-methoxyethyl)-4,6-dihydrofuro[3,4-d][1,3]thiazol-2(3H)-ylidene]hexahydro-2,5-methanopentalene-3a(1H)-carboxamide;

N-[(2Z)-1-(2-methoxyethyl)-1,4,6,7-tetrahydro-2H-pyrano[4,3-d][1,3]thiazo-l-2 ylidene]hexahydro-2,5-methanopentalene-3a(1H)-carboxamide; and N-[(2Z)-3-(2-methoxyethyl)-4,6-dihydrofuro[3,4-d][1,3]thiazol-2 (3H)-ylidene]-2-oxatricyclo[3.3.1.1$^{3,7}$]decane-1-carboxamide;

or a pharmaceutically acceptable salt thereof.

* * * * *